(12) United States Patent
Chen et al.

(10) Patent No.: US 10,875,894 B2
(45) Date of Patent: Dec. 29, 2020

(54) MULTIMERIC BICYCLIC PEPTIDE LIGANDS

(71) Applicant: BicycleTx Limited, Cambridge (GB)

(72) Inventors: Liuhong Chen, Cambridge (GB); Rachid Lani, Cambridge (GB); Kevin McDonnell, Lexington, MA (US); Gemma Elizabeth Mudd, Cambridge (GB); Peter U. Park, Lincoln, MA (US); Punit Upadhyaya, Lexington, MA (US)

(73) Assignee: BicycleTx Limited, Cambridge (GB)

( * ) Notice: Subject to any disclaimer, the term of this patent is extended or adjusted under 35 U.S.C. 154(b) by 0 days.

(21) Appl. No.: 16/282,877

(22) Filed: Feb. 22, 2019

(65) Prior Publication Data
US 2019/0263866 A1     Aug. 29, 2019

(30) Foreign Application Priority Data

Feb. 23, 2018 (GB) ............................ 1802931.4
Apr. 9, 2018 (GB) ............................ 1805848.7
Nov. 7, 2018 (GB) ............................ 1818158.6

(51) Int. Cl.
| | | |
|---|---|---|
| C07K 4/00 | (2006.01) |
| A61K 38/00 | (2006.01) |
| C07K 7/08 | (2006.01) |
| C07K 2/00 | (2006.01) |
| A61K 47/64 | (2017.01) |
| A61K 47/66 | (2017.01) |
| A61P 35/00 | (2006.01) |
| C07K 7/64 | (2006.01) |
| C07K 17/02 | (2006.01) |
| A61K 47/60 | (2017.01) |
| C07K 17/14 | (2006.01) |
| A61K 47/59 | (2017.01) |
| C07K 14/705 | (2006.01) |
| A61K 47/54 | (2017.01) |

(52) U.S. Cl.
CPC ............. *C07K 7/08* (2013.01); *A61K 47/59* (2017.08); *A61K 47/60* (2017.08); *A61K 47/64* (2017.08); *A61K 47/66* (2017.08); *A61P 35/00* (2018.01); *C07K 2/00* (2013.01); *C07K 7/64* (2013.01); *C07K 14/70575* (2013.01); *C07K 17/02* (2013.01); *C07K 17/14* (2013.01); *A61K 47/54* (2017.08); *C07K 2319/00* (2013.01)

(58) Field of Classification Search
CPC ........ A61K 47/54; A61K 47/59; A61K 47/60; A61K 47/64; A61K 47/66; A61P 35/00; C07K 14/70575; C07K 17/02; C07K 17/14; C07K 2319/00; C07K 2/00; C07K 7/08; C07K 7/64
See application file for complete search history.

(56) References Cited

FOREIGN PATENT DOCUMENTS

| WO | WO2004/077062 | 9/2004 |
| WO | WO2012/057624 | 5/2012 |
| WO | WO2017/191460 | 11/2017 |
| WO | WO2019/025811 | 2/2019 |

OTHER PUBLICATIONS

Chen et al., "Peptide Ligands Stabilized by Small Molecules", Angew. Chem. Int. Ed. 2014, vol. 53, pp. 1602-1606.
Loktev et al., "Multicyclic Peptides as Scaffolds for the Development of Tumor Targeting Agents", Current Medicinal Chemistry, 2017, vol. 24, pp. 2141-2155.
Morrison, "Chemical Strategies for Bicyclic Peptide Formation", Univ. of Leeds, Sep. 2015, pp. 1-160.
Mulder et al., "Scaffold optimization in discontinuous epitope containing protein mimics of gp120 using smart libraries", Org. Biomol. Chem. 2013, vol. 11, pp. 2676-2684.
Pickens et al., "Practical Considerations, Challenges, and Limitations of Bioconjugation via Azide-Alkyne Cycloaddition", Bioconjugate Chem. 2018, vol. 29, pp. 686-701.
Smeenk et al., "Reconstructing the Discontinuous and Conformational β1/β3-Loop Binding Site on hFSH/hCG by Using Highly Constrained Multicyclic Peptides", ChemBioChem 2015, vol. 16, pp. 91-99.
International Search Report for PCT/GB2019/050485.

*Primary Examiner* — Thomas S Heard
(74) *Attorney, Agent, or Firm* — Andrea L. C. Reid; Paul R. Fleming; Dechert LLP

(57) ABSTRACT

The present invention relates to multimers of polypeptides which are covalently bound to molecular scaffolds such that two or more peptide loops are subtended between attachment points to the scaffold. The invention also describes the multimerization of polypeptides through various chemical linkers and hinges of various lengths and rigidity using different sites of attachments within polypeptides. In particular, the invention describes multimers of peptides which are high affinity binders and activators of CD137. The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by CD137.

29 Claims, 15 Drawing Sheets
Specification includes a Sequence Listing.

(A)

(B)

(A)

(B)

MULTIMERIC BICYCLIC PEPTIDE LIGANDS

FIELD OF THE INVENTION

The present invention relates to multimers of polypeptides which are covalently bound to molecular scaffolds such that two or more peptide loops are subtended between attachment points to the scaffold. The invention also describes the multimerization of polypeptides through various chemical linkers and hinges of various lengths and rigidity using different sites of attachments within polypeptides. In particular, the invention describes multimers of peptides which are high affinity binders and activators of CD137. The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by CD137.

BACKGROUND OF THE INVENTION

Protein-protein interactions are important regulators of cellular functions. These interactions typically involve large surface areas and as such can neither be easily inhibited nor mimicked using typical small molecule therapeutic agents. Additionally, many important receptor classes (receptor tyrosine kinases, cytokine receptors, tumor necrosis factor (TNF) receptors, T-cell receptors and G-protein coupled receptors) require oligomerization of receptor monomer units in a particular orientation to activate the receptor signaling pathway. Recombinant proteins such as monoclonal antibodies and fusion proteins (e.g. ligand-Fc fusions) are able to bind and induce oligomerization of such receptors due to high affinity and large interaction surface areas with the potential for multivalent binding. However, large proteins are inefficient at penetrating into tissues and may not be an ideal therapeutic modality for modulating receptors, especially those found on cells that are poorly vascularized or surrounded by barriers to penetration, such as the stromal barrier found in pancreatic cancer. Small synthetic and modular therapeutic modalities with a larger interaction surface than small molecules will be ideal for bypassing the penetration barrier and activating target receptors by oligomerization.

The recent success of immune checkpoint inhibitors, such as anti-PD-1 and anti-PD-L1 antibodies in treating various types of cancers have boosted the interest in molecules that activate co-stimulatory targets, including CD137 on T cells. CD137 (4-1BB/TNFRSF9) belongs to the TNF receptor superfamily and provides costimulatory signaling for T cells.

Inducible CD137 expression is found on activated T-, B-, dendritic and natural killer (NK) cells. Stimulation of CD137 by its natural ligand, CD137L, or by agonistic antibody induces vigorous T-cell proliferation and prevents activation-induced cell death. 4-1BB forms a heterotrimer complex consisting of two TNF-receptor associated factor TRAF-2 complexes in conjunction with TRAF-1. This interaction, through leukocyte specific protein-1 (LSP-1), potentiates signaling through JNK and ERK pathways as well as through β-catenin and AKT. These signaling pathways converge on the master transcription factor NF-κB to regulate 4-1BB signaling, as well as effector immune responses.

Agonistic anti-CD137 antibodies have shown potent, often curative anti-tumor activity in mouse models. Its anti-tumor activity is even further boosted in combination with an anti-PD-1 or anti-CTLA-4 antibody. These effects are mainly mediated by cytotoxic T cells and generate long lasting, memory responses. Two human anti-CD137 antibodies are currently undergoing clinical testing: urelumab has shown single agent, partial responses in melanoma, however hepatoxicity was observed at doses ≥1 mg/kg and as a result, it is being combined with other immunotherapies at a suboptimal dose of 0.1 mg/kg; utolimumab is also being evaluated in solid tumors in combination with other immunotherapies, but while hepatotoxicity was not observed up to 5 mg/kg, it has little or no single agent activity.

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred-square angstrom, as for example the cyclic peptide CXCR4 antagonist CVX15 (400 Å$_2$; Wu et al. (2007), Science 330, 1066-71), a cyclic peptide with the Arg-Gly-Asp motif binding to integrin αVβ3 (355 Å$_2$) (Xiong et al. (2002), Science 296 (5565), 151-5) or the cyclic peptide inhibitor upain-1 binding to urokinase-type plasminogen activator (603 Å$_2$; Zhao et al. (2007), J Struct Biol 160 (1), 1-10).

Bicycles® are a novel therapeutic class of fully synthetic, constrained bicyclic peptides that have high affinity and exquisite target specificity unachievable with conventional small molecule approaches. The Bicycle® platform uses phage display to rapidly identify and optimize binders that can then be readily chemically optimized to tune affinity and physicochemical properties. Their small size (1.5-2 kDa) delivers advantages in tumor penetration and rapid renal elimination avoids liver and gastrointestinal toxicity often associated with other drug modalities, including certain antibodies. Bicycle® CD137 agonists with rapid renal clearance and lacking Fc receptor interaction could induce anti-tumor activity while avoiding liver toxicity.

There is a need to provide alternative bicyclic peptides which bind and activate their targets with a wide range of potency and efficacy.

SUMMARY OF THE INVENTION

According to a first aspect of the invention, there is provided a multimeric binding complex which comprises at least two bicyclic peptide ligands, wherein said peptide ligands may be the same or different, each of which comprises a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a further aspect of the invention, there is provided a drug conjugate comprising a multimeric binding complex as defined herein conjugated to one or more effector and/or functional groups.

According to a further aspect of the invention, there is provided a pharmaceutical composition comprising a multimeric binding complex or a drug conjugate as defined herein in combination with one or more pharmaceutically acceptable excipients.

According to a further aspect of the invention, there is provided a multimeric binding complex or drug conjugate as defined herein for use in preventing, suppressing or treating a disease or disorder, such as a disease or disorder mediated by CD137.

DETAILED DESCRIPTION OF THE INVENTION

Figure 1:
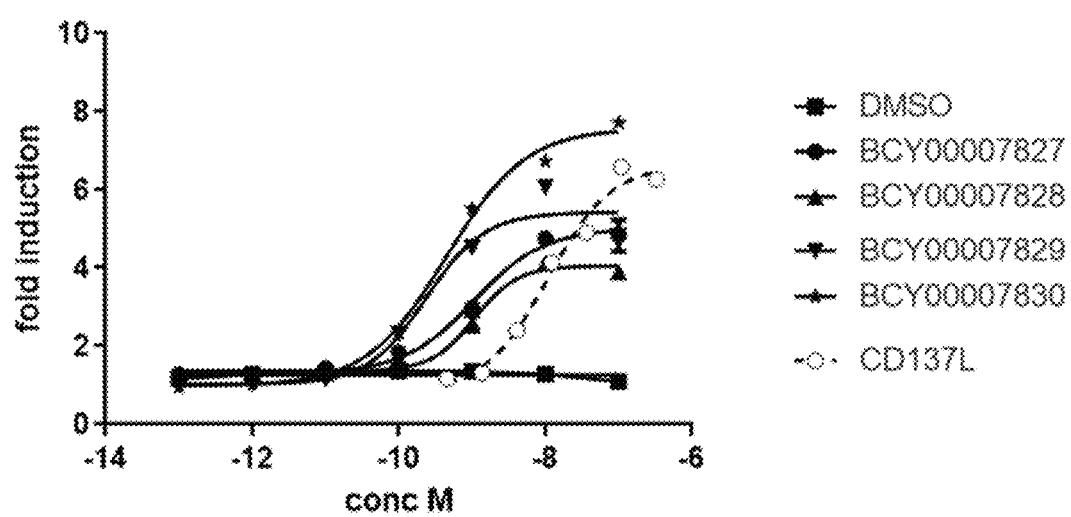
FIG. 1: Reporter cell activity assay data obtained for trimers BCY7827 and BCY7828 and tetramers BCY7829 and BCY7830 compared with CD137L.

According to a first aspect of the invention, there is provided a multimeric binding complex which comprises at least two bicyclic peptide ligands, wherein said peptide ligands may be the same or different, each of which comprises a polypeptide comprising at least three reactive groups, separated by at least two loop sequences, and a molecular scaffold which forms covalent bonds with the reactive groups of the polypeptide such that at least two polypeptide loops are formed on the molecular scaffold.

The present invention describes a series of multimerized bicyclic peptides with various chemical linkers and hinges of various lengths and rigidity using different sites of attachments within said bicyclic peptide which bind and activate targets (such as CD137) with a wide range of potency and efficacy.

It will be appreciated by the skilled person that the concept of the invention is the recognition that multiply arranged (multimeric) bicyclic peptides provide a synergistic benefit by virtue of the resultant properties of said multimeric binding complexes compared to the corresponding monomeric binding complexes which contain a single bicyclic peptide. For example, the multimeric binding complexes of the invention typically have greater levels of binding potency or avidity (as measured herein by Kd values) than their monomeric counterparts. Furthermore, the multimeric binding complexes of the invention are designed to be sufficiently small enough to be cleared by the kidneys.

The complexes of the present invention find particular utility in the treatment of cancer. Thus, in one embodiment, one of said peptide ligands is specific for an epitope present on a T cell or a cancer cell. In a further embodiment, each of said peptide ligands is specific for an epitope present on a T cell or a cancer cell.

Without being bound by theory it is believed that multimerized bicyclic peptides are able to activate receptors by homo-crosslinking more than one of the same receptor. Thus, in one embodiment, said bicyclic peptide ligands are specific for the same target. In a further embodiment, the multimeric binding complex comprises at least two identical bicyclic peptide ligands. By "identical" it is meant bicyclic peptides having the same amino acid sequence, most critically the same amino acid sequence refers to the binding portion of said bicyclic peptide (for example, the sequence may vary in attachment position). In this embodiment, each of the bicyclic peptides within the multimeric binding complex will bind exactly the same epitope upon the same target—the resultant target bound complex will therefore create a homodimer (if the multimeric complex comprises two identical bicyclic peptides), homotrimer (if the multimeric complex comprises three identical bicyclic peptides) or homotetramer (if the multimeric complex comprises four identical bicyclic peptides), etc.

In an alternative embodiment, the multimeric binding complex comprises at least two differing bicyclic peptide ligands. By "differing" it is meant bicyclic peptides having a different amino acid sequence. In this embodiment, the differing bicyclic peptide ligands within the multimeric binding complex will bind to different epitopes on the same target—the resultant target bound complex will therefore create a biparatopic (if the multimeric complex comprises two differing bicyclic peptides), triparatopic (if the multimeric complex comprises three differing bicyclic peptides) or tetraparatopic (if the multimeric complex comprises four differing bicyclic peptides), etc.

Without being bound by theory it is believed that multimerized bicyclic peptides are able to activate receptors by hetero-crosslinking differing targets, such as differing target receptors. Thus, in one embodiment, said bicyclic peptide ligands are specific for different targets. It will be appreciated that in this embodiment, the multimeric binding complex comprises at least two differing bicyclic peptide ligands (i.e. bicyclic peptide ligands having differing amino acid sequences). In this embodiment, each of the bicyclic peptides within the multimeric binding complex will bind a differing epitope upon a different target—the resultant target bound complex will therefore create a bispecific multimeric binding complex (if the multimeric complex comprises two differing bicyclic peptides), trispecific multimeric binding complex (if the multimeric complex comprises three differing bicyclic peptides), tetraspecific multimeric binding complex (if the multimeric complex comprises four differing bicyclic peptides), etc.

It will be appreciated that the multimeric binding complexes of the invention may be designed to be capable of binding to a range of different targets, such as receptors. Suitable examples include any target (i.e. receptor) involved in a cancer, such as members of the TNF receptor superfamily (i.e. CD137), receptor tyrosine kinase (RTK), Ig domain receptors (immune checkpoint) etc. It will be appreciated that for the bi-, tri- and tetra-specific multimeric binding complexes referred to hereinbefore the bicyclic peptides may bind to targets on at least two differing cells (such as T, NK or other immune cells).

The bicyclic peptides within the multimeric binding complexes of the invention may be assembled via a number of differing options. For example, there may be a central hinge or branching moiety with spacer or arm elements radiating from said hinge or branch point each of which will contain a bicyclic peptide. Alternatively, it could be envisaged that a circular support member may hold a number of inwardly or outwardly projecting bicyclic peptides.

In one embodiment, each bicyclic peptide ligand is connected to a central hinge moiety by a spacer group.

It will be appreciated that the spacer group may be linear and connect a single bicyclic peptide with the central hinge moiety. Thus, in one embodiment, the multimeric binding complex comprises a compound of formula (I):

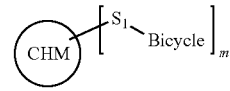

(I)

wherein CHM represents a central hinge moiety;
$S_1$ represents a spacer group;
Bicycle represents a bicyclic peptide ligand as defined herein; and
m represents an integer selected from 2 to 10.

In one embodiment, m represents an integer selected from 3 to 10. In a further embodiment, m represents an integer selected from 3 or 4. Data is presented herein which shows that optimal results were achieved with the trimers (m=3) and tetramers (m=4). When m represents 4, it will be appreciated that the central hinge moiety will require 4 points of attachment. Thus, in one embodiment, m represents 4 and CHM is a motif of formula (A):

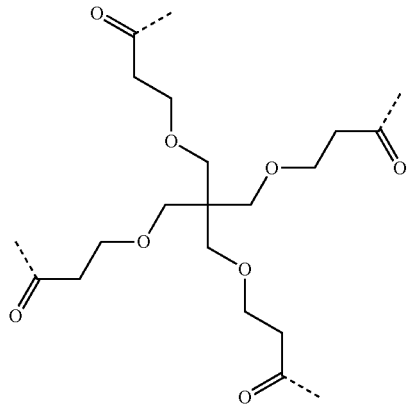

(A)

wherein "-----" represents the point of attachment to each $S_1$ group.

When m represents 3, it will be appreciated that the central hinge moiety will require 3 points of attachment. Thus, in one embodiment, m represents 3 and CHM is a motif of formula (B):

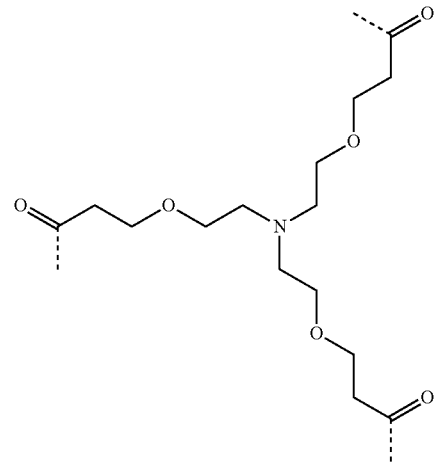

(B)

wherein "-----" represents the point of attachment to each S₁ group.

In an alternative embodiment, m represents 3 and CHM is a motif of formula (C):

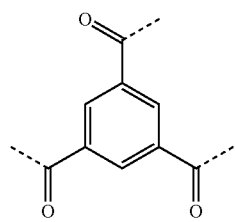

(C)

wherein "-----" represents the point of attachment to each S₁ group.

In an alternative embodiment, m represents 3 and CHM is a motif of formula (D):

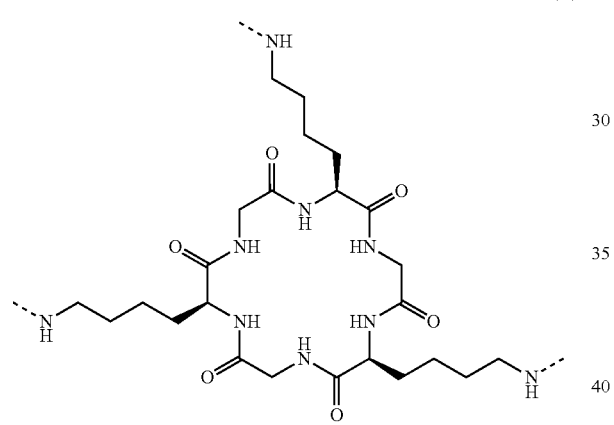

(D)

wherein "-----" represents the point of attachment to each S₁ group.

It will be readily apparent to the skilled person how alternative central hinge moieties may be constructed depending upon the value of m.

It will be appreciated that the spacer ($S_1$) may be any suitable construction to link the bicyclic peptide central hinge moiety to the bicyclic peptide. In one embodiment, the spacer ($S_1$) comprises a triazolyl moiety. The advantage of this embodiment is that the triazolyl moiety may be incorporated within the synthesis using commonly available "click" chemistry. Examples of suitable spacer ($S_1$) groups include one or more PEG moieties, peptide sequences, carbohydrates, lipids and the like.

In a further embodiment, the spacer ($S_1$) comprises one or more PEG moieties. References herein to "PEG" refer to a linear polymer with a regular repeat unit of the general structure: $(CH_2CH_2O)_n$— (where n represents any number, such as 1 to 30).

Thus, in a further embodiment, the spacer ($S_1$) is selected from any one of spacers $S_1A$, $S_1B$, $S_1C$, $S_1D$, $S_1E$, $S_1F$, $S_1G$ and $S_1H$:

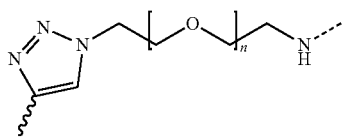

$S_1A$ n = 5, 10 and 23

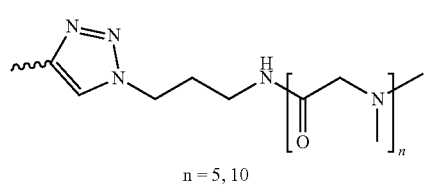

$S_1B$ n = 5, 10

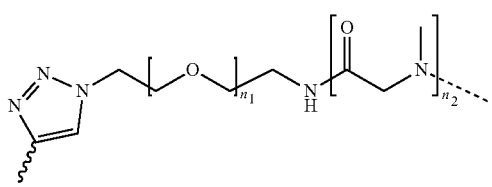

$S_1C$ $n_1 = 5, n_2 = 5$
$n_1 = 10, n_2 = 10$

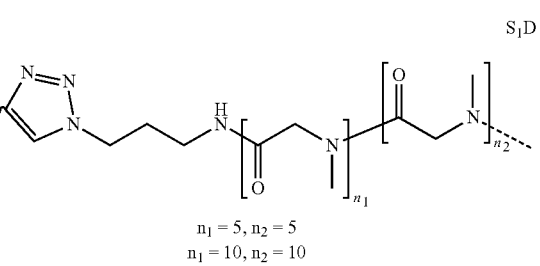

$S_1D$ $n_1 = 5, n_2 = 5$
$n_1 = 10, n_2 = 10$

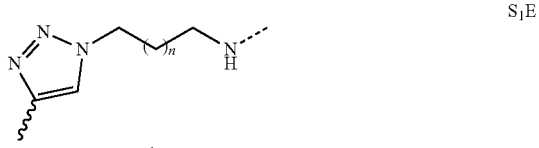

$S_1E$ n = 1

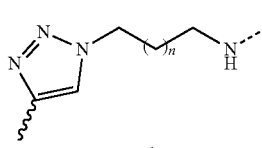

$S_1F$ n = 1

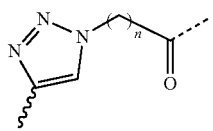

$S_1G$ n = 5 and 10

S₁H

[chemical structure diagram]

n₁ = 5, n₂ = 5
n₁ = 10, n₂ = 10 wherein "-----" represents the point of attachment to the CHM group; and "∼∼∼" represents the point of attachment to the Bicycle group.

In a yet further embodiment, the spacer ($S_1$) is $S_1A$.

In an alternative arrangement the spacer group may be branched and thus a single spacer group may connect multiple bicyclic peptides with the central hinge moiety. Thus, in an alternative embodiment, the multimeric binding complex comprises a compound of formula (II):

$$\text{CHM} - S_1 - [\text{Bicycle}]_m \quad \text{(II)}$$

wherein CHM represents a central hinge moiety;
$S_1$ represents a spacer group;
Bicycle represents a bicyclic peptide ligand as defined herein; and
m represents an integer selected from 2 to 10.

It will be appreciated that the bicyclic peptide ligand may be attached to the spacer via a number of means. In one embodiment, the bicyclic peptide ligand is conjugated to one half of a binding pair and said other half of said binding pair links each of the bicyclic peptides to the spacer.

In one embodiment, said binding pair comprises biotin and streptavidin. Thus, each bicyclic peptide ligand is conjugated to biotin and linked to the spacer via streptavidin.

Bicyclic Peptides

It will be appreciated that the multimeric binding complexes herein will comprise a plurality of monomeric bicyclic peptides. In one embodiment, each of said peptide ligands (i.e. monomers) is specific for CD137.

CD137 Bicyclic Peptide Monomers

In one embodiment, said loop sequences comprise 5 or 6 amino acids.

In a further embodiment, said loop sequences comprise three cysteine residues separated by two loop sequences both of which consist of 6 amino acids.

In a yet further embodiment, said peptide ligand comprises a core amino acid sequence selected from:

$C_i$IEEGQYC$_{ii}$FADPY(Nle)C$_{iii}$;   (SEQ ID NO: 23)

$C_i$IKEGQYC$_{ii}$FADPY(Nle)C$_{iii}$;   (SEQ ID NO: 24)

$C_i$IEKGQYC$_{ii}$FADPY(Nle)C$_{iii}$;   (SEQ ID NO: 25)

$C_i$IEE(D-K)QYC$_{ii}$FADPY(Nle)C$_{iii}$;   (SEQ ID NO: 26)

$C_i$IEEGKYC$_{ii}$FADPY(Nle)C$_{iii}$;   (SEQ ID NO: 27)

$C_i$IEEGQYC$_{ii}$KADPY(Nle)C$_{iii}$;   (SEQ ID NO: 28)

$C_i$IEEGQYC$_{ii}$FADKY(Nle)C$_{iii}$;   (SEQ ID NO: 29)
and $C_i$IEEGQYC$_{ii}$FADPYKC$_{iii}$;   (SEQ ID NO: 30)

wherein $C_i$, $C_{ii}$ and $C_{iii}$ represent first, second and third cysteine residues, respectively and Nle represents norleucine, or a pharmaceutically acceptable salt thereof.

In a yet further embodiment, said peptide ligand comprises N and C terminal modifications and comprises an amino acid sequence selected from:

A-$C_i$IEEGQYC$_{ii}$FADPY(Nle)C$_{iii}$-A (SEQ ID NO: 31; herein referred to as Monomer 1 and BCY3814);

Ac-A-$C_i$IEEGQYC$_{ii}$FADPY(Nle)C$_{iii}$-Dap (SEQ ID NO: 32; herein referred to as Monomer 2 and BCY7732);

Ac-A-$C_i$IKEGQYC$_{ii}$FADPY(Nle)C$_{iii}$-A (SEQ ID NO: 33; herein referred to as Monomer 3 and BCY7733);

Ac-A-$C_i$IEKGQYC$_{ii}$FADPY(Nle)C$_{iii}$-A (SEQ ID NO: 34; herein referred to as Monomer 4 and BCY7734);

Ac-A-$C_i$IEE(D-K)QYC$_{ii}$FADPY(Nle)$_{iii}$-A (SEQ ID NO: 35; herein referred to as Monomer 5 and BCY7735);

Ac-A-$C_i$IEEGKYC$_{ii}$FADPY(Nle)C$_{iii}$-A (SEQ ID NO: 36; herein referred to as Monomer 6 and BCY7736);

Ac-A-$C_i$IEEGQYC$_{ii}$KADPY(Nle)C$_{iii}$-A (SEQ ID NO: 37; herein referred to as Monomer 7 and BCY7737);

Ac-A-$C_i$IEEGQYC$_{ii}$FADKY(Nle)C$_{iii}$-A (SEQ ID NO: 38; herein referred to as Monomer 8 and BCY7738);

Ac-A-$C_i$IEEGQYC$_{ii}$FADPYKC$_{iii}$-A (SEQ ID NO: 39; herein referred to as Monomer 9 and BCY7739);

A-$C_i$IEEGQYC$_{ii}$F[D-A]DPY[Nle]C$_{iii}$-A (SEQ ID NO: 58; herein referred to as Monomer 10 and BCY8217);

Ac-$C_i$[tBuAla]PK[D-A]PYC$_{ii}$FADPY[Nle]C$_{iii}$-A (SEQ ID NO: 59; herein referred to as Monomer 11 and BCY8919);

Ac-$C_i$[tBuAla]PE[D-K]PYC$_{ii}$FADPY[Nle]C$_{iii}$-A (SEQ ID NO: 60; herein referred to as Monomer 12 and BCY8920);

Ac-A-$C_i$IE[D-K]GQYC$_{ii}$F[D-A]DPY[Nle]C$_{iii}$-A (SEQ ID NO: 61; herein referred to as Monomer 13 and BCY8914);

Ac-A-$C_i$IE[D-K]GQYC$_{ii}$F[D-A]DPY[Nle]C$_{iii}$-A (SEQ ID NO: 62; herein referred to as Monomer 14 and BCY8915);
and

[Ac]-[D-A]-[D-C$_i$][D-I][D-E][D-E]K[D-Q][D-Y][D-C$_{ii}$][D-F][D-A][D-D][D-P][D-Y][D-Nle][D-C$_{iii}$][D-A] (SEQ ID NO: 63; herein referred to as Monomer 15 and BCY11072);

wherein $C_i$, $C_{ii}$ and $C_{iii}$ represent first, second and third cysteine residues, respectively, Ac represents an N-terminal acetyl group, Dap represents diaminopropionic acid, tBuAla represents t-butyl-alanine and Nle represents norleucine, or a pharmaceutically acceptable salt thereof.

In a still yet further embodiment, said peptide ligand comprises N and C terminal modifications and comprises an amino acid sequence selected from:

A-$C_i$IEEGQYC$_{ii}$FADPY(Nle)C$_{iii}$-A (SEQ ID NO: 31; herein referred to as Monomer 1 and BCY3814);

Ac-A-$C_i$IEEGQYC$_{ii}$FADPY(Nle)C$_{iii}$-Dap (SEQ ID NO: 32; herein referred to as Monomer 2 and BCY7732);

Ac-A-$C_i$IKEGQYC$_{ii}$FADPY(Nle)C$_{iii}$-A (SEQ ID NO: 33; herein referred to as Monomer 3 and BCY7733);

Ac-A-$C_i$IEKGQYC$_{ii}$FADPY(Nle)C$_{iii}$-A (SEQ ID NO: 34; herein referred to as Monomer 4 and BCY7734);

Ac-A-$C_i$IEE(D-K)QYC$_{ii}$FADPY(Nle)C$_{iii}$-A (SEQ ID NO: 35; herein referred to as Monomer 5 and BCY7735);

Ac-A-$C_i$IEEGKYC$_{ii}$FADPY(Nle)C$_{iii}$-A (SEQ ID NO: 36; herein referred to as Monomer 6 and BCY7736);

Ac-A-$C_i$IEEGQYC$_{ii}$KADPY(Nle)C$_{iii}$-A (SEQ ID NO: 37; herein referred to as Monomer 7 and BCY7737);

Ac-A-$C_i$IEEGQYC$_{ii}$FADKY(Nle)C$_{iii}$-A (SEQ ID NO: 38; herein referred to as Monomer 8 and BCY7738); and Ac-A-$C_i$IEEGQYC$_{ii}$FADPYKC$_{iii}$-A (SEQ ID NO: 39; herein referred to as Monomer 9 and BCY7739);

wherein $C_i$, $C_{ii}$ and $C_{iii}$ represent first, second and third cysteine residues, respectively, Ac represents an N-terminal acetyl group, Dap represents diaminopropionic acid and Nle represents norleucine, or a pharmaceutically acceptable salt thereof.

In a yet further embodiment, said peptide ligand comprises attachment of a PYA moiety at the N-terminus, C-terminus or Lysine residues within said sequence and comprises an amino acid sequence selected from:

(PYA)-A-$C_i$IEEGQYC$_{ii}$FADPY(Nle)C$_{iii}$-A (SEQ ID NO: 40; herein referred to as Monomer 1A and BCY7740);

Ac-A-$C_i$IEEGQYC$_{ii}$FADPY(Nle)C$_{iii}$-Dap(PYA) (SEQ ID NO: 41; herein referred to as Monomer 2A and BCY7741);

Ac-A-$C_i$IK(PYA)EGQYC$_{ii}$FADPY(Nle)C$_{iii}$-A (SEQ ID NO: 42; herein referred to as Monomer 3A and BCY7742);

Ac-A-$C_i$IEK(PYA)GQYC$_{ii}$FADPY(Nle)C$_{iii}$-A (SEQ ID NO: 43; herein referred to as Monomer 4A and BCY7743);

Ac-A-$C_i$IEE(D-K)(PYA)QYC$_{ii}$FADPY(Nle)C$_{iii}$-A (SEQ ID NO: 44; herein referred to as Monomer 5A and BCY7744);

Ac-A-$C_i$IEEGK(PYA)YC$_{ii}$FADPY(Nle)C$_{iii}$-A (SEQ ID NO: 45; herein referred to as Monomer 6A and BCY7745);

Ac-A-$C_i$IEEGQYC$_{ii}$K(PYA)ADPY(Nle)C$_{iii}$-A (SEQ ID NO: 46; herein referred to as Monomer 7A and BCY7746);

Ac-A-$C_i$IEEGQYC$_{ii}$FADK(PYA)Y(Nle)C$_{iii}$-A (SEQ ID NO: 47; herein referred to as Monomer 8A and BCY7747);

Ac-A-$C_i$IEEGQYC$_{ii}$FADPYK(PYA)C$_{iii}$-A (SEQ ID NO: 48; herein referred to as Monomer 9A and BCY7748);

(PYA)-A-$C_i$IEEGQYC$_{ii}$F[D-A]DPY[Nle]C$_{iii}$-A (SEQ ID NO: 64; herein referred to as Monomer 10A and BCY8935);

Ac-$C_i$[tBuAla]PK(PYA)[D-A]PYC$_{ii}$FADPY[Nle]C$_{iii}$-A (SEQ ID NO: 65; herein referred to as Monomer 11A and BCY8927);

Ac-$C_i$[tBuAla]PE[D-K(PYA)]PYC$_{ii}$FADPY[Nle]C$_{iii}$-A (SEQ ID NO: 66; herein referred to as Monomer 12A and BCY8928);

Ac-A-CiIE[D-K(PYA)]GQYC$_{ii}$F[D-A]DPY[Nle]C$_{iii}$-A (SEQ ID NO: 67; herein referred to as Monomer 13A and BCY8925);

Ac-A-CiIE[K(PYA)]GQYC$_{ii}$F[D-A]DPY[Nle]C$_{iii}$-A (SEQ ID NO: 68; herein referred to as Monomer 14A and BCY8926); and

[Ac]-[D-A][D-$C_i$][D-I][D-E][D-E][K(PYA)][D-Q][D-Y][D-$C_{ii}$][D-F][D-A][D-D][D-P][D-Y][D-Nle][D-$C_{iii}$][D-A]

(SEQ ID NO: 69; herein referred to as Monomer 15A and BCY11506);

wherein $C_i$, $C_{ii}$ and $C_{iii}$ represent first, second and third cysteine residues, respectively, Ac represents an N-terminal acetyl group, Dap represents diaminopropionic acid, PYA represents propargyl-acid, tBuAla represents t-butyl-alanine and Nle represents norleucine, or a pharmaceutically acceptable salt thereof.

In a still yet further embodiment, said peptide ligand comprises attachment of a PYA moiety at the N-terminus, C-terminus or Lysine residues within said sequence and comprises an amino acid sequence selected from:

(PYA)-A-$C_i$IEEGQYC$_{ii}$FADPY(Nle)C$_{iii}$-A (SEQ ID NO: 40; herein referred to as Monomer 1A and BCY7740);

Ac-A-$C_i$IEEGQYC$_{ii}$FADPY(Nle)C$_{iii}$-Dap(PYA) (SEQ ID NO: 41; herein referred to as Monomer 2A and BCY7741);

Ac-A-$C_i$IK(PYA)EGQYC$_{ii}$FADPY(Nle)C$_{iii}$-A (SEQ ID NO: 42; herein referred to as Monomer 3A and BCY7742);

Ac-A-$C_i$IEK(PYA)GQYC$_{ii}$FADPY(Nle)C$_{iii}$-A (SEQ ID NO: 43; herein referred to as Monomer 4A and BCY7743);

Ac-A-$C_i$IEE(D-K)(PYA)QYC$_{ii}$FADPY(Nle)C$_{iii}$-A (SEQ ID NO: 44; herein referred to as Monomer 5A and BCY7744);

Ac-A-$C_i$IEEGK(PYA)YC$_{ii}$FADPY(Nle)C$_{iii}$-A (SEQ ID NO: 45; herein referred to as Monomer 6A and BCY7745);

Ac-A-$C_i$IEEGQYC$_{ii}$K(PYA)ADPY(Nle)C$_{iii}$-A (SEQ ID NO: 46; herein referred to as Monomer 7A and BCY7746);

Ac-A-$C_i$IEEGQYC$_{ii}$FADK(PYA)Y(Nle)C$_{iii}$-A (SEQ ID NO: 47; herein referred to as Monomer 8A and BCY7747);

Ac-A-$C_i$IEEGQYC$_{ii}$FADPYK(PYA)C$_{iii}$-A (SEQ ID NO: 48; herein referred to as Monomer 9A and BCY7748);

wherein $C_i$, $C_{ii}$ and $C_{iii}$ represent first, second and third cysteine residues, respectively, Ac represents an N-terminal acetyl group, Dap represents diaminopropionic acid, PYA represents propargyl-acid and Nle represents norleucine, or a pharmaceutically acceptable salt thereof.

In a yet further embodiment, said peptide ligand comprises attachment of a BCN moiety at the N-terminus or Lysine residues within said sequence and comprises an amino acid sequence selected from:

(BCN)-A-C$_i$IEEGQYC$_{ii}$FADPY(Nle)C$_{iii}$-A (SEQ ID NO: 49; herein referred to as Monomer 1-BCN and BCY8141);

Ac-A-C$_i$IK(BCN)EGQYC$_{ii}$FADPY(Nle)C$_{iii}$-A (SEQ ID NO: 50; herein referred to as Monomer 3-BCN and BCY8095);

Ac-A-C$_i$IEK(BCN)GQYC$_{ii}$FADPY(Nle)C$_{iii}$-A (SEQ ID NO: 51; herein referred to as Monomer 4-BCN and BCY8142);

Ac-A-C$_i$IEE[(D-K)(BCN)]QYC$_{ii}$FADPY(Nle)C$_{iii}$-A (SEQ ID NO: 52; herein referred to as Monomer 5-BCN and BCY8096);

Ac-A-C$_i$IEEGK(BCN)YC$_{ii}$FADPY(Nle)C$_{iii}$-A (SEQ ID NO: 53; herein referred to as Monomer 6-BCN and BCY8143);

Ac-A-C$_i$IEEGQYC$_{ii}$K(BCN)ADPY(Nle)C$_{iii}$-A (SEQ ID NO: 54; herein referred to as Monomer 7-BCN and BCY8144); and Ac-A-C$_i$IEEGQYC$_{ii}$FADPYK(BCN)C$_{iii}$-A (SEQ ID NO: 55; herein referred to as Monomer 9-BCN and BCY8097);

wherein C$_i$, C$_{ii}$ and C$_{iii}$ represent first, second and third cysteine residues, respectively, Ac represents an N-terminal acetyl group, Nle represents norleucine and BCN represents:

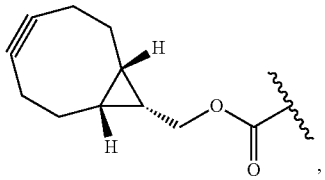 [SMILES: *C(=O)OC[C@@H]1[C@@H]2CCC#CCC[C@@H]21]

or a pharmaceutically acceptable salt thereof.

In an alternative embodiment, said loop sequences comprise three cysteine residues separated by two loop sequences one of which consists of 5 amino acids and the other of which consists of 6 amino acids.

Examples of further monomer sequences which may be used in the present invention are described in the following embodiments.

In one embodiment, said peptide ligand comprises an amino acid sequence selected from:

C$_i$-E-E-G-Q-Y-C$_{ii}$-X$_1$-X$_2$-D-X$_3$-Y/Q-X4-C$_{iii}$; (SEQ ID NO: 20)

C$_i$-D-I-G-P-P-T-C$_{ii}$-Y-R/A-D-M/P-Y-M-C$_{iii}$; (SEQ ID NO: 21)

C$_i$-D-E-W-G-L-F/Y-C$_{ii}$-I/F-P/A-H-S/P-D-C$_{iii}$; and (SEQ ID NO: 22)

C$_i$IEPGPFC$_{ii}$YADPYMC$_{iii}$; (SEQ ID NO: 19)

wherein X$_1$-X$_4$ represent any amino acid residue and C$_i$, C$_{ii}$ and C$_{iii}$ represent first, second and third cysteine residues, respectively or a pharmaceutically acceptable salt thereof.

In one embodiment, said loop sequences comprise three cysteine residues separated by two loop sequences both of which consist of 6 amino acids, and said peptide ligand comprises an amino acid sequence selected from:

C$_i$-E-E-G-Q-Y-C$_{ii}$-X$_1$-X$_2$-D-X$_3$-Y/Q-X4-C$_{iii}$; (SEQ ID NO: 20)

C$_i$-D-I-G-P-P-T-C$_{ii}$-Y-R/A-D-M/P-Y-M-C$_{iii}$; (SEQ ID NO: 21)

C$_i$IEPGPFC$_{ii}$YADPYMC$_{iii}$; (SEQ ID NO: 19)

wherein X$_1$-X$_4$ represent any amino acid residue and C$_i$, C$_{ii}$ and C$_{iii}$ represent first, second and third cysteine residues, respectively or a pharmaceutically acceptable salt thereof.

In one embodiment, X$_1$ is selected from Y, F and H.
In one embodiment, X$_2$ is selected from R, A and S.
In one embodiment, X$_3$ is selected from M, P and H.
In one embodiment, X$_4$ is selected from M, Y, L and F.
In one embodiment, said loop sequences comprise three cysteine residues separated by two loop sequences the first of which consists of 6 amino acids and the second of which consists of 5 amino acids, and said peptide ligand comprises an amino acid sequence selected from:

C$_i$-D-E-W-G-L-F/Y-C$_{ii}$-I/F-P/A-H-S/P-D-C$_{iii}$ (SEQ ID NO: 22);

wherein C$_i$, C$_{ii}$ and C$_{iii}$ represent first, second and third cysteine residues, respectively or a pharmaceutically acceptable salt thereof.

In a further embodiment, the peptide ligand of C$_i$-I-E-E-G-Q-Y-C$_{ii}$-X$_1$-X$_2$-D-X$_3$-Y/Q-X$_4$-C$_{iii}$ (SEQ ID NO: 20) comprises an amino acid sequence selected from:

C$_i$IEEGQYCIIYRDMYMC$_{iii}$; (SEQ ID NO: 1)

C$_i$IEEGQYCIIYADPYMC$_{iii}$; (SEQ ID NO: 2)

C$_i$IEEGQYCIIYADPYYC$_{iii}$; (SEQ ID NO: 3)

C$_i$IEEGQYCIIYSDPYYC$_{iii}$; (SEQ ID NO: 4)

C$_i$IEEGQYCIIFADPYMC$_{iii}$; (SEQ ID NO: 5)

C$_i$IEEGQYCIIYADHQLC$_{iii}$; (SEQ ID NO: 6)

C$_i$IEEGQYCIIHADPYYC$_{iii}$; (SEQ ID NO: 7)

C$_i$IEEGQYCIIHADPYFC$_{iii}$; (SEQ ID NO: 8)

C$_i$IEEGQYCIIYADHYMC$_{iii}$; (SEQ ID NO: 9)

C$_i$IEEGQYCIIYADPYLC$_{iii}$; (SEQ ID NO: 10)

C$_i$IEEGQYCIIYSDPYLC$_{iii}$; (SEQ ID NO: 11)

C$_i$IEEGQYCIIFADPYLC$_{iii}$; (SEQ ID NO: 12)

C$_i$IEEGQYCIIHADPYMC$_{iii}$; and (SEQ ID NO: 13)

C$_i$IEEGQYCIIHADPQMC$_{iii}$; (SEQ ID NO: 14)

wherein C$_i$, C$_{ii}$ and C$_{iii}$ represent first, second and third cysteine residues, respectively, or a pharmaceutically acceptable salt thereof.

In a further embodiment, the peptide ligand of $C_i$-I-E-E-G-Q-Y-$C_{ii}$-$X_1$-$X_2$-D-$X_3$-Y/Q-$X_4$-$C_{iii}$ (SEQ ID NO: 20) comprises an amino acid sequence selected from:
- A-(SEQ ID NO: 1)-A (herein referred to as 74-01-00-N004);
- A-(SEQ ID NO: 2)-A (herein referred to as 74-01-01-N001);
- A-(SEQ ID NO: 3)-A (herein referred to as 74-01-02-N001);
- A-(SEQ ID NO: 4)-A (herein referred to as 74-01-03-N001);
- A-(SEQ ID NO: 5)-A (herein referred to as 74-01-04-N001);
- A-(SEQ ID NO: 6)-A (herein referred to as 74-01-05-N001);
- A-(SEQ ID NO: 7)-A (herein referred to as 74-01-06-N001);
- A-(SEQ ID NO: 8)-A (herein referred to as 74-01-07-N001);
- A-(SEQ ID NO: 9)-A (herein referred to as 74-01-08-N001);
- A-(SEQ ID NO: 10)-A (herein referred to as 74-01-09-N001);
- A-(SEQ ID NO: 10)-SVG (herein referred to as 74-01-09-T03-N002);
- A-(SEQ ID NO: 11)-A (herein referred to as 74-01-10-N001);
- A-(SEQ ID NO: 12)-A (herein referred to as 74-01-11-N001);
- A-(SEQ ID NO: 13)-A (herein referred to as 74-01-13-N001); and
- A-(SEQ ID NO: 14)-A (herein referred to as 74-01-14-N001).

In a further embodiment, the peptide ligand of $C_i$-D-I-G-P—P-Y-$C_{ii}$-Y-R/A-D-M/P-Y-M-$C_{iii}$ (SEQ ID NO: 21) comprises an amino acid sequence selected from:

$$C_i DIGPPYC_{ii}YRDMYMC_{iii}; \quad \text{(SEQ ID NO: 15)}$$
and
$$C_i DIGPPYC_{ii}YADPYMC_{iii}; \quad \text{(SEQ ID NO: 16)}$$

wherein $C_i$, $C_{ii}$ and $C_{iii}$ represent first, second and third cysteine residues, respectively, or a pharmaceutically acceptable salt thereof.

In a further embodiment, the peptide ligand of $C_i$-D-I-G-P—P-Y-$C_{ii}$-Y-R/A-D-M/P-Y-M-$C_{iii}$ (SEQ ID NO: 21) comprises an amino acid sequence selected from:
- A-(SEQ ID NO: 15)-A (herein referred to as 74-01-16-N001); and
- A-(SEQ ID NO: 16)-A (herein referred to as 74-01-17-N001).

In a further embodiment, the peptide ligand of $C_i$-D-E-W-G-L-F/Y-$C_{ii}$-I/F-P/A-H-S/P-D-$C_{iii}$ (SEQ ID NO: 22) comprises an amino acid sequence selected from:

$$C^i DEWGLFC^{ii}IPHSDC^{iii}; \quad \text{(SEQ ID NO: 17)}$$
and
$$C^i DEWGLYC^{ii}FAHPDC^{iii}; \quad \text{(SEQ ID NO: 18)}$$

wherein $C_i$, $C_{ii}$ and $C_{iii}$ represent first, second and third cysteine residues, respectively, or a pharmaceutically acceptable salt thereof.

In a further embodiment, the peptide ligand of $C_i$-D-E-W-G-L-F/Y-$C_{ii}$-I/F-P/A-H-S/P-D-$C_{iii}$ (SEQ ID NO: 22) comprises an amino acid sequence selected from:
- Ac-A-(SEQ ID NO: 17)-A (herein referred to as 74-02-00-N004); and
- A-(SEQ ID NO: 18)-A (herein referred to as 74-02-01-N001).

In one embodiment, the peptide ligand of $C_i$IEPGPF$C_{ii}$-YADPYM$C_{iii}$ (SEQ ID NO: 19) comprises an amino acid sequence of:
- A-(SEQ ID NO: 19)-NRV (herein referred to as 74-19-00-T01-N002).

In one embodiment, the molecular scaffold is 1,1',1"-(1,3,5-triazinane-1,3,5-triyl)triprop-2-en-1-one (TATA).

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4th ed., John Wiley & Sons, Inc.), which are incorporated herein by reference.

Numbering

When referring to amino acid residue positions within peptides of the invention, cysteine residues ($C_i$, $C_{ii}$ and $C_{iii}$) are omitted from the numbering as they are invariant, therefore, the numbering of amino acid residues within the peptides of the invention is referred to as below:

$$\text{(SEQ ID NO: 1)}$$
$$C_i\text{-I-E-E-G-Q-Y-}C_{ii}\text{-Y-R-D-M-Y-M-}C_{iii}.$$

For the purpose of this description, all bicyclic peptides are assumed to be cyclised with TBMB (1,3,5-tris(bromomethyl)benzene) or 1,1',1"-(1,3,5-triazinane-1,3,5-triyl)triprop-2-en-1-one (TATA) and yielding a tri-substituted structure. Cyclisation with TBMB and TATA occurs on $C_i$, $C_{ii}$, and $C_{iii}$.

Molecular Format

N- or C-terminal extensions to the bicycle core sequence are added to the left or right side of the sequence, separated by a hyphen. For example, an N-terminal βAla-$Sar_{10}$-Ala tail would be denoted as:

$$\text{(SEQ ID NO: X)}$$
$$\beta\text{Ala-Sar}_{10}\text{-A-.}$$

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus becomes C-terminus and vice versa) and their stereochemistry is likewise also reversed (i.e. D-amino acids become L-amino acids and vice versa).

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as $C_i$, $C_{ii}$ and $C_{iii}$), and form at least two loops on the scaffold.

Multimeric Binding Complexes

Trimers

In one embodiment, the multimeric binding complex comprises a trimeric binding complex described in the following Table 1:

TABLE 1

Exemplified Trimeric Binding Complexes of the Invention

| Multimer Compound Number | Corresponding Monomer | Number of Monomers | Central Hinge Moiety | Spacer Molecule | Attachment Point |
|---|---|---|---|---|---|
| BCY7750 | BCY7741 | 3 | B (TCA) | $S_1A$: n = 10 | C-terminal Dap (PYA) |
| BCY7749 | BCY7741 | 3 | B (TCA) | $S_1A$: n = 23 | C-terminal Dap (PYA) |
| BCY7827 | BCY7740 | 3 | B (TCA) | $S_1A$: n = 10 | N-terminal PYA |
| BCY7828 | BCY7740 | 3 | B (TCA) | $S_1A$: n = 23 | N-terminal PYA |
| BCY7831 | BCY7742 | 3 | B (TCA) | $S_1A$: n = 10 | Lys(PYA)$_2$ |
| BCY7832 | BCY7742 | 3 | B (TCA) | $S_1A$: n = 23 | Lys(PYA)$_2$ |
| BCY7835 | BCY7743 | 3 | B (TCA) | $S_1A$: n = 10 | Lys(PYA)$_3$ |
| BCY7836 | BCY7743 | 3 | B (TCA) | $S_1A$: n = 23 | Lys(PYA)$_3$ |
| BCY7839 | BCY7744 | 3 | B (TCA) | $S_1A$: n = 10 | D-Lys(PYA)$_4$ |
| BCY7840 | BCY7744 | 3 | B (TCA) | $S_1A$: n = 23 | D-Lys(PYA)$_4$ |
| BCY7843 | BCY7745 | 3 | B (TCA) | $S_1A$: n = 10 | Lys(PYA)$_5$ |
| BCY7844 | BCY7745 | 3 | B (TCA) | $S_1A$: n = 23 | Lys(PYA)$_5$ |
| BCY7847 | BCY7746 | 3 | B (TCA) | $S_1A$: n = 10 | Lys(PYA)$_7$ |
| BCY7848 | BCY7746 | 3 | B (TCA) | $S_1A$: n = 23 | Lys(PYA)$_7$ |
| BCY7851 | BCY7747 | 3 | B (TCA) | $S_1A$: n = 10 | Lys(PYA)$_{10}$ |
| BCY7852 | BCY7747 | 3 | B (TCA) | $S_1A$: n = 23 | Lys(PYA)$_{10}$ |
| BCY7855 | BCY7748 | 3 | B (TCA) | $S_1A$: n = 10 | Lys(PYA)$_{12}$ |
| BCY7856 | BCY7748 | 3 | B (TCA) | $S_1A$: n = 23 | Lys(PYA)$_{12}$ |
| BCY8102 | BCY8096 | 3 | B (TCA) | $S_1A$: n = 10 | D-Lys(BCN)$_4$ |
| BCY8103 | BCY8096 | 3 | B (TCA) | $S_1A$: n = 23 | D-Lys(BCN)$_4$ |
| BCY8106 | BCY8097 | 3 | B (TCA) | $S_1A$: n = 10 | Lys(BCN)$_{12}$ |
| BCY8107 | BCY8097 | 3 | B (TCA) | $S_1A$: n = 23 | Lys(BCN)$_{12}$ |
| BCY8098 | BCY8095 | 3 | B (TCA) | $S_1A$: n = 10 | Lys(BCN)$_2$ |
| BCY8099 | BCY8095 | 3 | B (TCA) | $S_1A$: n = 23 | Lys(BCN)$_2$ |
| BCY8145 | BCY8144 | 3 | B (TCA) | $S_1A$: n = 10 | Lys(BCN)$_7$ |
| BCY8146 | BCY8144 | 3 | B (TCA) | $S_1A$: n = 23 | Lys(BCN)$_7$ |
| BCY8151 | BCY8143 | 3 | B (TCA) | $S_1A$: n = 10 | Lys(BCN)$_5$ |
| BCY8581 | BCY8935 | 3 | B (TCA) | $S_1A$: n = 10 | N-terminal PYA |
| BCY8582 | BCY8935 | 3 | B (TCA) | $S_1A$: n = 23 | N-terminal PYA |
| BCY8948 | BCY8928 | 3 | B (TCA) | $S_1A$: n = 10 | D-Lys(PYA)$_4$ |
| BCY8957 | BCY7743 | 3 | B (TCA) | $S_1B$: n = 5 | Lys(PYA)$_3$ |
| BCY8958 | BCY7743 | 3 | B (TCA) | $S_1A$: n = 5 | Lys(PYA)$_3$ |
| BCY8961 | BCY7743 | 3 | B (TCA) | $S_1C$: $n_1$ = 5, $n_2$ = 5 | Lys(PYA)$_3$ |
| BCY8962 | BCY7743 | 3 | B (TCA) | $S_1D$: $n_1$ = 5, $n_2$ = 5 | Lys(PYA)$_3$ |
| BCY8965 | BCY7743 | 3 | B (TCA) | $S_1B$: n = 10 | Lys(PYA)$_3$ |
| BCY9573 | BCY7743 | 3 | B (TCA) | $S_1C$: $n_1$ = 10, $n_2$ = 10 | Lys(PYA)$_3$ |
| BCY9595 | BCY7743 | 3 | B (TCA) | $S_1D$: $n_1$ = 10, $n_2$ = 10 | Lys(PYA)$_3$ |
| BCY9775 | BCY7744 | 3 | C (Trimesic acid) | $S_1A$: n = 10 | D-Lys(PYA)$_4$ |
| BCY9776 | BCY7744 | 3 | C (Trimesic acid) | $S_1A$: n = 23 | D-Lys(PYA)$_4$ |
| BCY10046 | BCY7744 | 3 | D (c(KGKGKG)) (cyclic (SEQ ID NO: 57)) | $S_1G$: n = 5 | D-Lys(PYA)$_4$ |
| BCY10047 | BCY7744 | 3 | D (c(KGKGKG)) (cyclic (SEQ ID NO: 57)) | $S_1G$: n = 10 | D-Lys(PYA)$_4$ |
| BCY11194 | BCY7744, BCY8928 | 2 × BCY7744 and 1 × BCY8928 | B (TCA) | $S_1A$: n = 10 | D-Lys(PYA)$_4$ |

TABLE 1-continued

Exemplified Trimeric Binding Complexes of the Invention

| Multimer Compound Number | Corresponding Monomer | Number of Monomers | Central Hinge Moiety | Spacer Molecule | Attachment Point |
|---|---|---|---|---|---|
| BCY11195 | BCY8925, BCY8928 | 2 × BCY8925 and 1 × BCY8928 | B (TCA) | $S_1A$: n = 10 | D-Lys(PYA)$_4$ |
| BCY11196 | BCY8925, BCY7744 | 2 × BCY8925 and 1 × BCY7744 | B (TCA) | $S_1A$: n = 10 | D-Lys(PYA)$_4$ |
| BCY11382 | BCY7744 | 3 | C (Trimesic acid) | $S_1E$: n = 1 | D-Lys(PYA)$_4$ |
| BCY11383 | BCY7744 | 3 | D (c(KGKGKG)) (cyclic (SEQ ID NO: 57)) | $S_1F$: n = 1 | D-Lys(PYA)$_4$ |
| BCY11450 | BCY11072 | 3 | B (TCA) | $S_1A$: n = 10 | L-Lys(PYA)$_4$ |

Data is presented herein which demonstrates that certain trimeric binding complexes of Table 1 displayed EC50 improvement relative to the CD137 ligand (see Table 4A).

In a further embodiment, the multimeric binding complex comprises a trimer comprising three bicyclic peptides each of which are BCY7741 as defined herein, which is linked via the C-terminal DAP(PYA) moiety to a spacer molecule ($S_1A$) wherein n represents 23 and wherein ($S_1A$) is linked to a central hinge moiety which is (B) as defined herein. This multimeric binding complex is referred to herein as BCY7749. Data is presented herein in FIG. 2 which shows high levels of CD137 agonism compared with the corresponding monomer (BCY7741) which demonstrated no agonism. Data is also presented in FIG. 6 which shows the stability of BCY7749 to mouse plasma.

In an alternative further embodiment, the multimeric binding complex comprises a trimer comprising three bicyclic peptides each of which are BCY7741 as defined herein, which is linked via the C-terminal DAP(PYA) moiety to a spacer molecule ($S_1A$) wherein n represents 10 and wherein ($S_1A$) is linked to a central hinge moiety which is (B) as defined herein. This multimeric binding complex is referred to herein as BCY7750. Data is presented herein in FIG. 2 which shows high levels of CD137 agonism compared with the corresponding monomer (BCY7741) which demonstrated no agonism.

In an alternative further embodiment, the multimeric binding complex comprises a trimer comprising three bicyclic peptides each of which are BCY7743 as defined herein, which is linked via a Lys(PYA)$_3$ moiety to a spacer molecule ($S_1A$) wherein n represents 10 and wherein ($S_1A$) is linked to a central hinge moiety which is (B) as defined herein. This multimeric binding complex is referred to herein as BCY7835. Data is presented in FIG. 5B which demonstrated that the multimeric bicycle conjugate BCY7835 retained the property of rapid systemic elimination characteristic of monomeric bicyclic peptides and bicyclic peptide drug conjugates (BDCs). Data is also presented in FIG. 6 which shows the stability of BCY7835 to mouse plasma. Data is also presented in FIG. 7 wherein it can be seen that BCY7835 elicits a range of anti-tumor activities as compared to a CD137 monoclonal antibody agonist that has previously been shown to elicit a CD137 dependent anti-tumour activity.

Figure 12:
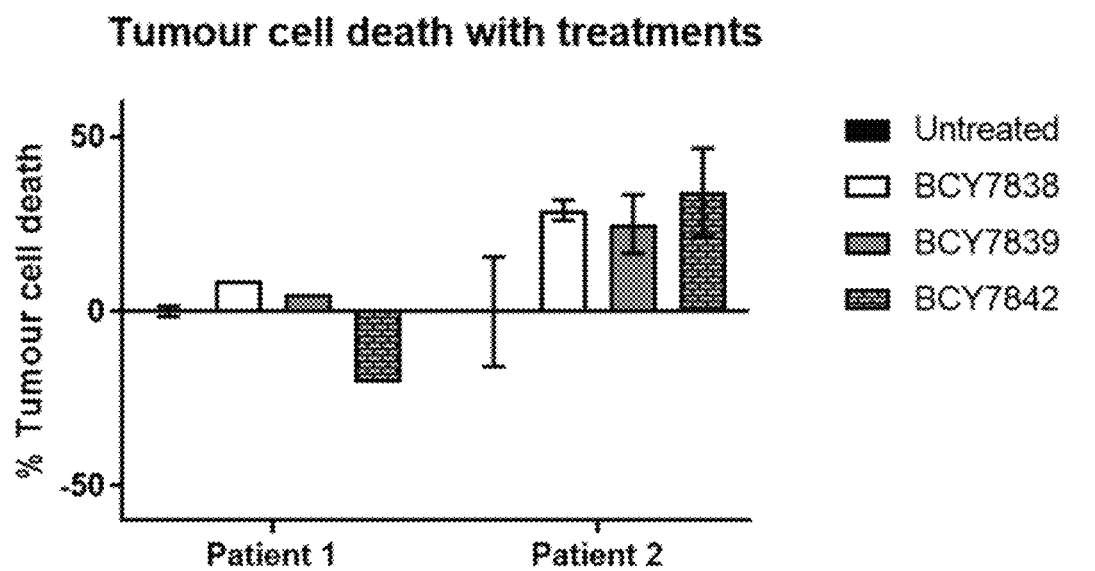
FIG. 12: Percentage of cell death, normalized to untreated control, after 2 days in 3D spheroid culture of two melanoma tumours. (A) Tumour cells are the live CD45 negative population and (B) lymphocytes are the live CD45 positive population as determined by flow cytometry. Significance is calculated using a 2-way ANOVA multiple comparison, $p<0.05$.
Figure 12:
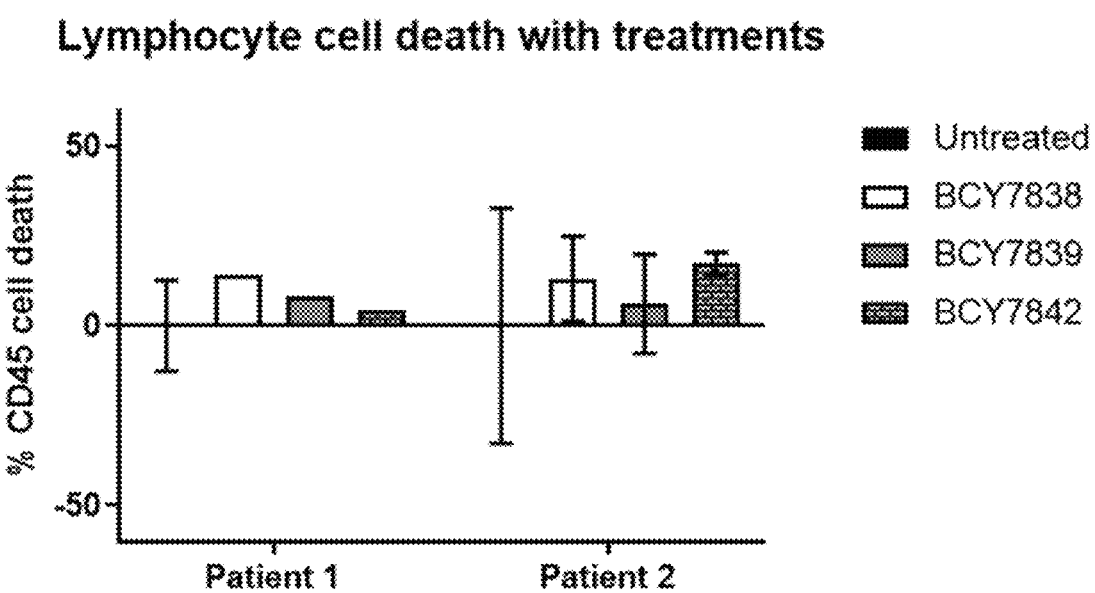

In a further alternative embodiment, the multimeric binding complex comprises a trimer comprising three bicyclic peptides each of which are BCY7744 as defined herein, which is linked via a D-Lys(PYA)$_4$ moiety to a spacer molecule ($S_1A$) wherein n represents 10 and wherein ($S_1A$) is linked to a central hinge moiety which is (B) as defined herein. This multimeric binding complex is referred to herein as BCY7839. Data is presented herein in FIG. 12 which demonstrates significant tumour cell death in response to treatment with BCY7839 in one melanoma patient sample, but not the other (FIG. 12A) and with no significant difference between treatments on lymphocyte numbers (FIG. 12B). Data is also presented herein in FIG. 13 which demonstrates that BCY7839 maintains cell activity after washout which is consistent with a molecule having high avidity to the trimeric CD137 receptor complex. Data is also presented herein in FIG. 14 which demonstrates that T-cells secrete pro-inflammatory cytokines in response to BCY7839. Data is also presented herein in FIG. 15 which demonstrates that BCY7839 activates CD137 on the surface of Jurkat reporter cells.

In one embodiment which may be mentioned, the multimeric binding complex is a trimer selected from BCY7749, BCY7750, BCY7835 and BCY7839, such as BCY7839.

Tetramers

In one embodiment, the multimeric binding complex comprises a tetrameric binding complex described in the following Table 2:

TABLE 2

Exemplified Tetrameric Binding Complexes of the Invention

| Multimer Compound Number | Corresponding Monomer | Number of Monomers | Central Hinge Moiety | Spacer Molecule | Attachment Point |
|---|---|---|---|---|---|
| BCY7751 | BCY7741 | 4 | A (TET) | $S_1A$: n = 10 | C-terminal Dap(PYA) |
| BCY7752 | BCY7741 | 4 | A (TET) | $S_1A$: n = 23 | C-terminal Dap(PYA) |
| BCY7829 | BCY7740 | 4 | A (TET) | $S_1A$: n = 10 | N-terminal PYA |
| BCY7830 | BCY7740 | 4 | A (TET) | $S_1A$: n = 23 | N-terminal PYA |
| BCY7833 | BCY7742 | 4 | A (TET) | $S_1A$: n = 10 | $Lys(PYA)_2$ |
| BCY7834 | BCY7742 | 4 | A (TET) | $S_1A$: n = 23 | $Lys(PYA)_2$ |
| BCY7837 | BCY7743 | 4 | A (TET) | $S_1A$: n = 10 | $Lys(PYA)_3$ |
| BCY7838 | BCY7743 | 4 | A (TET) | $S_1A$: n = 23 | $Lys(PYA)_3$ |
| BCY7841 | BCY7744 | 4 | A (TET) | $S_1A$: n = 10 | $D-Lys(PYA)_4$ |
| BCY7842 | BCY7744 | 4 | A (TET) | $S_1A$: n = 23 | $D-Lys(PYA)_4$ |
| BCY7845 | BCY7745 | 4 | A (TET) | $S_1A$: n = 10 | $Lys(PYA)_5$ |
| BCY7846 | BCY7745 | 4 | A (TET) | $S_1A$: n = 23 | $Lys(PYA)_5$ |
| BCY7849 | BCY7746 | 4 | A (TET) | $S_1A$: n = 10 | $Lys(PYA)_7$ |
| BCY7850 | BCY7746 | 4 | A (TET) | $S_1A$: n = 23 | $Lys(PYA)_7$ |
| BCY7853 | BCY7747 | 4 | A (TET) | $S_1A$: n = 10 | $Lys(PYA)_{10}$ |
| BCY7854 | BCY7747 | 4 | A (TET) | $S_1A$: n = 23 | $Lys(PYA)_{10}$ |
| BCY7857 | BCY7748 | 4 | A (TET) | $S_1A$: n = 10 | $Lys(PYA)_{12}$ |
| BCY7858 | BCY7748 | 4 | A (TET) | $S_1A$: n = 23 | $Lys(PYA)_{12}$ |
| BCY8104 | BCY8096 | 4 | A (TET) | $S_1A$: n = 10 | $D-Lys(BCN)_4$ |
| BCY8105 | BCY8096 | 4 | A (TET) | $S_1A$: n = 23 | $D-Lys(BCN)_4$ |
| BCY8108 | BCY8097 | 4 | A (TET) | $S_1A$: n = 10 | $Lys(BCN)_{12}$ |
| BCY8109 | BCY8097 | 4 | A (TET) | $S_1A$: n = 23 | $Lys(BCN)_{12}$ |
| BCY8100 | BCY8095 | 4 | A (TET) | $S_1A$: n = 10 | $Lys(BCN)_2$ |
| BCY8101 | BCY8095 | 4 | A (TET) | $S_1A$: n = 23 | $Lys(BCN)_2$ |
| BCY8147 | BCY8144 | 4 | A (TET) | $S_1A$: n = 10 | $Lys(BCN)_7$ |
| BCY8148 | BCY8144 | 4 | A (TET) | $S_1A$: n = 23 | $Lys(BCN)_7$ |
| BCY8149 | BCY8141 | 4 | A (TET) | $S_1A$: n = 23 | N-terminal BCN |
| BCY8150 | BCY8142 | 4 | A (TET) | $S_1A$: n = 10 | $Lys(BCN)_3$ |
| BCY8583 | BCY8935 | 4 | A (TET) | $S_1A$: n = 10 | N-terminal PYA |
| BCY8584 | BCY8935 | 4 | A (TET) | $S_1A$: n = 23 | N-terminal PYA |
| BCY8937 | BCY8926 | 4 | A (TET) | $S_1A$: n = 23 | $Lys(PYA)_3$ |
| BCY8945 | BCY8927 | 4 | A (TET) | $S_1A$: n = 23 | $Lys(PYA)_3$ |
| BCY8946 | BCY8927 | 4 | A (TET) | $S_1A$: n = 10 | $Lys(PYA)_3$ |
| BCY8947 | BCY8928 | 4 | A (TET) | $S_1A$: n = 10 | $D-Lys(PYA)_4$ |
| BCY8959 | BCY7743 | 4 | A (TET) | $S_1B$: n = 5 | $Lys(PYA)_3$ |
| BCY8960 | BCY7743 | 4 | A (TET) | $S_1A$: n = 5 | $Lys(PYA)_3$ |
| BCY8963 | BCY7743 | 4 | A (TET) | $S_1C$: $n_1$ = 5, $n_2$ = 5 | $Lys(PYA)_3$ |
| BCY8964 | BCY7743 | 4 | A (TET) | $S_1D$: $n_1$ = 5, $n_2$ = 5 | $Lys(PYA)_3$ |
| BCY8966 | BCY7743 | 4 | A (TET) | $S_1B$: n = 10 | $Lys(PYA)_3$ |
| BCY9113 | BCY8926 | 4 | A (TET) | $S_1A$: n = 10 | $Lys(PYA)_3$ |
| BCY9767 | BCY7743 | 4 | A (TET) | $S_1H$: $n_1$ = 10, $n_2$ = 10 | $Lys(PYA)_3$ |
| BCY10388 | BCY8928 | 4 | A (TET) | $S_1A$: n = 23 | $D-Lys(PYA)_4$ |
| BCY11451 | BCY11506 | 4 | A (TET) | $S_1A$: n = 23 | $L-Lys(PYA)_4$ |

Data is presented herein which demonstrates that certain tetrameric binding complexes of Table 2 displayed EC50 improvement relative to the CD137 ligand (see Table 4A).

In a further embodiment, the multimeric binding complex comprises a tetramer comprising four bicyclic peptides each of which are BCY7741 as defined herein, which is linked via the C-terminal DAP(PYA) moiety to a spacer molecule ($S_1A$) wherein n represents 10 and wherein ($S_1A$) is linked to a central hinge moiety which is (A) as defined herein. This multimeric binding complex is referred to herein as BCY7751. Data is presented herein in FIG. 2 which shows high levels of CD137 agonism compared with the corresponding monomer (BCY7741) which demonstrated no agonism.

In a further alternative embodiment, the multimeric binding complex comprises a tetramer comprising four bicyclic peptides each of which are BCY7741 as defined herein, which is linked via the C-terminal DAP(PYA) moiety to a spacer molecule ($S_1A$) wherein n represents 23 and wherein ($S_1A$) is linked to a central hinge moiety which is (A) as defined herein. This multimeric binding complex is referred to herein as BCY7752. Data is presented herein in FIG. 2 which shows high levels of CD137 agonism compared with the corresponding monomer (BCY7741) which demonstrated no agonism.

In a further alternative embodiment, the multimeric binding complex comprises a tetramer comprising four bicyclic peptides each of which are BCY7745 as defined herein, which is linked via the Lysine5 amino acid residue to a spacer molecule ($S_1A$) wherein n represents 10 and wherein ($S_1A$) is linked to a central hinge moiety which is (A) as defined herein. This multimeric binding complex is referred to herein as BCY7845. Data is presented herein in FIG. 3 which shows high levels of CD137 agonism compared with the corresponding monomer (BCY7741) which demonstrated no agonism. Data is also presented in FIG. 6 which shows the stability of BCY7845 to mouse plasma.

In a further alternative embodiment, the multimeric binding complex comprises a tetramer comprising four bicyclic peptides each of which are BCY7745 as defined herein, which is linked via the Lysine5 amino acid residue to a spacer molecule ($S_1A$) wherein n represents 23 and wherein ($S_1A$) is linked to a central hinge moiety which is (A) as defined herein. This multimeric binding complex is referred to herein as BCY7846. Data is presented herein in FIG. 3 which shows high levels of CD137 agonism compared with the corresponding monomer (BCY7741) which demonstrated no agonism.

In a further alternative embodiment, the multimeric binding complex comprises a tetramer comprising four bicyclic peptides each of which are BCY7740 as defined herein, which is linked via an N-terminal PYA moiety to a spacer molecule ($S_1A$) wherein n represents 10 and wherein ($S_1A$) is linked to a central hinge moiety which is (A) as defined herein. This multimeric binding complex is referred to herein as BCY7829. Data is presented herein in FIG. 1 which shows high levels of CD137 agonism. Data is also presented herein in FIG. 4 which shows the stability of BCY7829 to human, cyno, rat and mouse plasma. Data is also presented in FIG. 5A which demonstrated that the multimeric bicycle conjugate BCY7829 retained the property of rapid systemic elimination characteristic of monomeric bicyclic peptides and bicyclic peptide drug conjugates (BDCs). Data is also presented in FIG. 6 which shows the stability of BCY7829 to mouse plasma. Data is also presented in FIG. 7 wherein it can be seen that BCY7829 elicits a range of anti-tumor activities as compared to a CD137 monoclonal antibody agonist that has previously been shown to elicit a CD137 dependent anti-tumour activity.

In a further alternative embodiment, the multimeric binding complex comprises a tetramer comprising four bicyclic peptides each of which are BCY7743 as defined herein, which is linked via a Lys(PYA)$_3$ moiety to a spacer molecule ($S_1A$) wherein n represents 23 and wherein ($S_1A$) is linked to a central hinge moiety which is (A) as defined herein. This multimeric binding complex is referred to herein as BCY7838. Data is presented herein in FIG. 5B which demonstrated that the multimeric bicycle conjugate BCY7838 retained the property of rapid systemic elimination characteristic of monomeric bicyclic peptides and bicyclic peptide drug conjugates (BDCs). Data is also presented in FIG. 6 which shows the stability of BCY7838 to mouse plasma. Data is also presented in FIG. 7 wherein it can be seen that BCY7838 elicits a range of anti-tumor activities as compared to a CD137 monoclonal antibody agonist that has previously been shown to elicit a CD137 dependent anti-tumour activity. Data is also presented herein in FIG. 12 which demonstrates significant tumour cell death in response to treatment with BCY7838 in one melanoma patient sample, but not the other (FIG. 12A) and with no significant difference between treatments on lymphocyte numbers (FIG. 12B). Data is also presented herein in FIG. 13 which demonstrates that BCY7838 maintains cell activity after washout which is consistent with a molecule having high avidity to the trimeric CD137 receptor complex. Data is also presented herein in FIG. 14 which demonstrates that T-cells secrete pro-inflammatory cytokines in response to BCY7838.

In a further alternative embodiment, the multimeric binding complex comprises a tetramer comprising four bicyclic peptides each of which are BCY7744 as defined herein, which is linked via a D-Lys(PYA)$_4$ moiety to a spacer molecule ($S_1A$) wherein n represents 23 and wherein ($S_1A$) is linked to a central hinge moiety which is (A) as defined herein. This multimeric binding complex is referred to herein as BCY7842. Data is presented in FIG. 8 wherein it can be seen that BCY7842 elicits anti-tumour activity in syngeneic mouse models. Data is also presented in FIGS. 9 and 10 wherein it can be seen that BCY7842 elicits a range of increase in T-cell and CD8+ T-cell percentage, respectively, in the tumor tissue as compared to the CD137 monoclonal antibody agonist. Data is also presented in FIG. 11 wherein it can be seen that BCY7842 elicits a range of decease in T-cell percentage in the tumor tissue as compared to the CD137 monoclonal antibody agonist that has previously been shown to elicit a CD137 dependent anti-tumour activity. Data is also presented herein in FIG. 12 which demonstrates significant tumour cell death in response to treatment with BCY7842 in one melanoma patient sample, but not the other (FIG. 12A) and with no significant difference between treatments on lymphocyte numbers (FIG. 12B). Data is also presented herein in FIG. 13 which demonstrates that BCY7842 maintains cell activity after washout which is consistent with a molecule having high avidity to the trimeric CD137 receptor complex. Data is also presented herein in FIG. 14 which demonstrates that T-cells secrete pro-inflammatory cytokines in response to BCY7842. Data is also presented herein in FIG. 15 which demonstrates that BCY7842 activates CD137 on the surface of Jurkat reporter cells.

In a further alternative embodiment, the multimeric binding complex comprises a tetramer comprising four bicyclic peptides each of which are BCY8927 as defined herein, which is linked via a Lys(PYA)$_3$ moiety to a spacer molecule ($S_1A$) wherein n represents 23 and wherein ($S_1A$) is linked to a central hinge moiety which is (A) as defined herein. This multimeric binding complex is referred to herein as BCY8945. Data is presented in FIG. 8 wherein it can be seen that BCY8945 elicits anti-tumour activity in syngeneic mouse models. Data is also presented in FIGS. 9 and 10 wherein it can be seen that BCY8945 elicits a range of increase in T-cell and CD8+ T-cell percentage, respectively, in the tumor tissue as compared to the CD137 monoclonal antibody agonist. Data is also presented in FIG. 11 wherein it can be seen that BCY8945 elicits a range of decease in T-cell percentage in the tumor tissue as compared to the CD137 monoclonal antibody agonist that has previously been shown to elicit a CD137 dependent anti-tumour activity. Data is also presented herein in FIG. 13 which demonstrates that BCY8945 maintains cell activity after washout which is consistent with a molecule having high avidity to the trimeric CD137 receptor complex. Data is also presented herein in FIG. 14 which demonstrates that T-cells secrete pro-inflammatory cytokines in response to BCY8945. Data is also presented herein in FIG. 15 which demonstrates that BCY8945 activates CD137 on the surface of Jurkat reporter cells.

In a further alternative embodiment, the multimeric binding complex comprises a tetramer comprising four bicyclic peptides each of which are BCY8928 as defined herein, which is linked via a D-Lys(PYA)$_4$ moiety to a spacer molecule ($S_1A$) wherein n represents 10 and wherein ($S_1A$) is linked to a central hinge moiety which is (A) as defined herein. This multimeric binding complex is referred to herein as BCY8947. Data is presented in FIG. 8 wherein it can be seen that BCY8947 elicits anti-tumour activity in syngeneic mouse models. Data is also presented in FIGS. 9 and 10 wherein it can be seen that BCY8947 elicits a range of increase in T-cell and CD8+ T-cell percentage, respectively, in the tumor tissue as compared to the CD137 monoclonal antibody agonist. Data is also presented in FIG. 11 wherein it can be seen that BCY8947 elicits a range of decease in T-cell percentage in the tumor tissue as compared to the CD137 monoclonal antibody agonist that has previously been shown to elicit a CD137 dependent anti-tumour activity. Data is also presented herein in FIG. 13 which demonstrates that BCY8947 maintains cell activity after washout which is consistent with a molecule having high avidity to the trimeric CD137 receptor complex. Data is also presented herein in FIG. 14 which demonstrates that T-cells secrete pro-inflammatory cytokines in response to BCY8947. Data is also presented herein in FIG. 15 which demonstrates that BCY8947 activates CD137 on the surface of Jurkat reporter cells.

In one embodiment, the multimeric binding complex is a tetramer selected from BCY7751, BCY7752, BCY7845, BCY7846, BCY7829, BCY7838, BCY7842, BCY8945 and BCY8947.

In one embodiment which may be mentioned, the multimeric binding complex is a tetramer selected from BCY7751, BCY7752, BCY7845, BCY7846, BCY7829, BCY7838 and BCY7842.

In a further embodiment, the multimeric binding complex is as a tetramer selected from BCY7842, BCY8945 and BCY8947.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acet-amidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the peptides of the invention contain an amine function, these may form quaternary ammonium salts, for example by reaction with an alkylating agent according to methods well known to the skilled person. Such quaternary ammonium compounds are within the scope of the peptides of the invention.

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group (the group referred to herein as $C_{iii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, $C_\alpha$-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labelled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I, and $^{131}$I, nitrogen, such as $^{13}$N and $^{15}$N, oxygen, such as $^{15}$O, $^{17}$O and $^{18}$O, phosphorus, such as $^{32}$P, sulphur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled peptide ligands of the invention, for example, those incorporating a radioactive isotope, are useful in drug and/or substrate tissue distribution studies, and to clinically assess the presence and/or absence of the CD137 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labelled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of hexahydro-1,3,5-triazine, especially 1,3,5-triacryloylhexahydro-1,3,5-triazine (TATA), or a derivative thereof.

In one embodiment, the molecular scaffold is 2,4,6-tris(bromomethyl)mesitylene. This molecule is similar to 1,3,5-tris(bromomethyl)benzene (TBMB) but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene or iodoacetamide. Other scaffold reactive groups that are used to selectively couple compounds to cysteines in proteins are maleimides, αβ unsaturated carbonyl containing compounds and α-halomethylcarbonyl containing compounds. Examples of maleimides which may be used as molecular scaffolds in the invention include: tris-(2-maleimidoethyl)amine, tris-(2-maleimidoethyl)benzene, tris-(maleimido)benzene. An example of an αβ unsaturated carbonyl containing compound is 1,1',1''-(1,3,5-triazinane-1,3,5-triyl)triprop-2-en-1-one (TATA) (Angewandte Chemie, International Edition (2014), 53(6), 1602-1606). An example of an α-halomethylcarbonyl containing compound is N,N',N''-(benzene-1,3,5-triyl)tris(2-bromoacetamide). Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Effector and Functional Groups

According to a further aspect of the invention, there is provided a drug conjugate comprising a peptide ligand as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of Drosophila (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from Drosophila Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half-life in the range 12 to 60 hours. In a further embodiment, it will have a tβ half-life of a day or more. In a further embodiment still, it will be in the range 12 to 26 hours.

In one particular embodiment of the invention, the functional group is selected from a metal chelator, which is suitable for complexing metal radioisotopes of medicinal relevance.

Possible effector groups also include enzymes, for instance such as carboxypeptidase G2 for use in enzyme/prodrug therapy, where the peptide ligand replaces antibodies in ADEPT.

In one embodiment, the multimeric binding complexes of the invention contain a cleavable bond, such as a disulphide bond or a protease sensitive bond. Without being bound by theory it is believed that such a cleavable moiety deactivates the complex until it reaches the tumour microenvironment. The benefit of this embodiment provides for the complex to be reduced in size following binding to the target. In a further embodiment, the groups adjacent to the disulphide bond are modified to control the hindrance of the disulphide bond, and by this the rate of cleavage and concomitant release of the binding agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on the targeting entity (here, the bicyclic peptide).

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to the manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TATA) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulphide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a multimeric binding complex or a drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringers dextrose, dextrose and sodium chloride and lactated Ringers. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringers dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counterindications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as CD137 binding agents.

CD137 is a member of the tumour necrosis factor (TNF) receptor family. Its alternative names are tumour necrosis factor receptor superfamily member 9 (TNFRSF9), 4-IBB and induced by lymphocyte activation (ILA). CD137 can be expressed by activated T cells, but to a larger extent on CD8+ than on CD4+ T cells. In addition, CD137 expression is found on dendritic cells, follicular dendritic cells, natural killer cells, granulocytes and cells of blood vessel walls at sites of inflammation. One characterized activity of CD137 is its costimulatory activity for activated T cells. Crosslinking of CD137 enhances T cell proliferation, IL-2 secretion, survival and cytolytic activity. Further, it can enhance immune activity to eliminate tumours in mice.

CD137 is a T-cell costimulatory receptor induced on TCR activation (Nam et al., Curr. Cancer Drug Targets, 5:357-363 (2005); Waits et al., Annu. Rev, Immunol., 23:23-68 (2005)). In addition to its expression on activated CD4+ and CD8+ T cells, CD137 is also expressed on CD4+CD25+ regulatory T cells, natural killer (NK) and NK-T cells, monocytes, neutrophils, and dendritic cells. Its natural ligand, CD137L, has been described on antigen-presenting cells including B cells, monocyte/macrophages, and dendritic cells (Watts et al. Annu. Rev. Immunol, 23:23-68 (2005)). On interaction with its ligand, CD137 leads to increased TCR-induced T-cell proliferation, cytokine production, functional maturation, and prolonged CD8+ T-cell survival (Nam et al, Curr. Cancer Drug Targets, 5:357-363 (2005), Watts et al., Annu. Rev. Immunol, 23:23-68 (2005)).

Signalling through CD137 by either CD137L or agonistic monoclonal antibodies (mAbs) against CD137 leads to increased TCR-induced T cell proliferation, cytokine production and functional maturation, and prolonged CD8+ T cell survival. These effects result from: (1) the activation of the NF-κB, c-Jun $NH_2$-terminal kinase/stress-activated protein kinase (JNK/SAPK), and p38 mitogen-activated protein kinase (MAPK) signalling pathways, and (2) the control of anti-apoptotic and cell cycle-related gene expression.

Experiments performed in both CD137 and CD137L-deficient mice have additionally demonstrated the importance of CD137 costimulation in the generation of a fully competent T cell response.

IL-2 and IL-15 activated NK cells express CD137, and ligation of CD137 by agonistic mAbs stimulates NK cell proliferation and IFN-γ secretion, but not their cytolytic activity.

Furthermore, CD137-stimulated NK cells promote the expansion of activated T cells in vitro.

In accordance with their costimulatory function, agonist mAbs against CD137 have been shown to promote rejection of cardiac and skin allografts, eradicate established tumours, broaden primary antiviral CD8+ T cell responses, and increase T cell cytolytic potential. These studies support the view that CD137 signalling promotes T cell function which may enhance immunity against tumours and infection.

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

According to a further aspect of the invention, there is provided a multimeric binding complex or a drug conjugate as defined herein, for use in preventing, suppressing or treating a disease or disorder mediated by CD137.

According to a further aspect of the invention, there is provided a method of preventing, suppressing or treating a disease or disorder mediated by CD137, which comprises administering to a patient in need thereof an effector group and drug conjugate of the multimeric binding complex as defined herein.

In one embodiment, the CD137 is mammalian CD137. In a further embodiment, the mammalian CD137 is human CD137 (hCD137).

In one embodiment, the disease or disorder mediated by CD137 is selected from cancer, infection and inflammation. In a further embodiment, the disorder or disease mediated by CD137 is selected from cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the oesophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukaemias, lymphomas) and premalignant haematological disorders and disorders of borderline malignancy including haematological malignancies and related conditions of lymphoid lineage (for example acute lymphocytic leukaemia [ALL], chronic lymphocytic leukaemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukaemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In a further embodiment, the cancer is selected from a hematopoietic malignancy such as selected from: non-Hodgkin's lymphoma (NHL), Burkitt's lymphoma (BL), multiple myeloma (MM), B chronic lymphocytic leukaemia (B-CLL), B and T acute lymphocytic leukaemia (ALL), T cell lymphoma (TCL), acute myeloid leukaemia (AML), hairy cell leukaemia (HCL), Hodgkin's Lymphoma (HL), and chronic myeloid leukaemia (CML).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Materials and Methods
Peptide Synthesis

Peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with appropriate side chain protecting groups: where applicable standard coupling conditions were used in each case, followed by deprotection using standard methodology. Peptides were purified using HPLC and following isolation they were modified with 1,3,5-Triacryloylhexahydro-1,3,5-triazine (TATA, Sigma). For this, linear peptide was diluted with 50:50 MeCN:H$_2$O up to ~35 mL, ~500 μL of 100 mM TATA in acetonitrile was added, and the reaction was initiated with 5 mL of 1 M NH$_4$HCO$_3$ in H$_2$O. The reaction was allowed to proceed for ~30-60 min at RT, and lyophilised once the reaction had completed (judged by MALDI-MS). Once completed, 1 ml of 1M L-cysteine hydrochloride monohydrate (Sigma) in H$_2$O was added to the reaction for ~60 min at RT to quench any excess TATA.

Following lyophilisation, the modified peptide was purified as above, while replacing the Luna C8 with a Gemini C18 column (Phenomenex), and changing the acid to 0.1% trifluoroacetic acid. Pure fractions containing the correct TATA-modified material were pooled, lyophilised and kept at −20° C. for storage.

All amino acids, unless noted otherwise, were used in the L-configurations.

Multimer Synthesis

General Procedure for Preparation of Compound 3

To a solution of compound 1 (500 mg, 5.10 mmol, 1.0 eq) in DCM (25 mL) were added compound 2 (645.2 mg, 5.61 mmol, 1.1 eq) and EDCl (1.95 g, 10.19 mmol, 2.0 eq). The mixture was stirred at 20° C. for 1 hr. TLC (PE: DCM=0:1, R$_f$=0.43, Color Developing Reagent: Bromocresol green) indicated compound 1 was consumed completely and one new spot was formed. The reaction was clean according to TLC. The reaction mixture was concentrated under reduced pressure to give a residue. The residue was purified by column chromatography (SiO$_2$, Petroleum ether/Ethyl acetate=2/1 to 1:1) to give compound 3 (620 mg, 3.18 mmol, 62.33% yield) as a white solid.

$^1$H NMR: 400 MHz CDCl$_3$

δ 2.80-2.95 (m, 6H), 2.55-2.70 (m, 2H), 2.05-2.10 (t, 1H)

General Procedure for Preparation of Compound 5

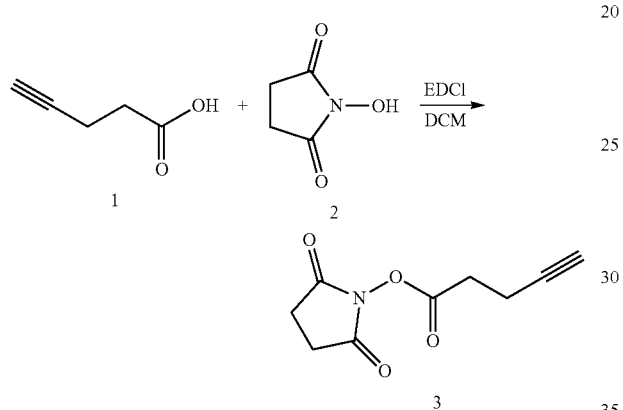

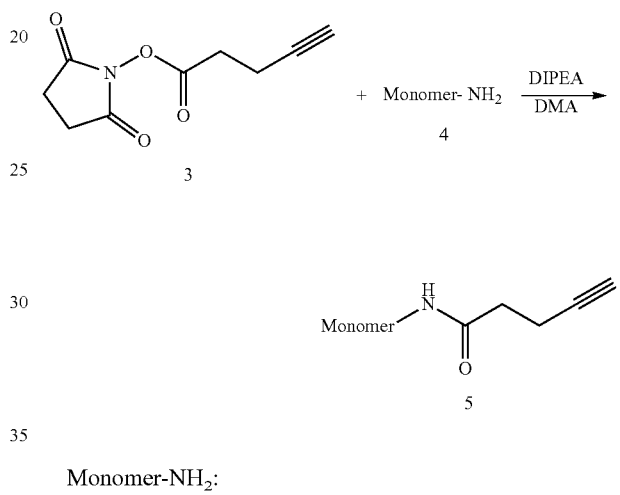

Monomer-NH$_2$:

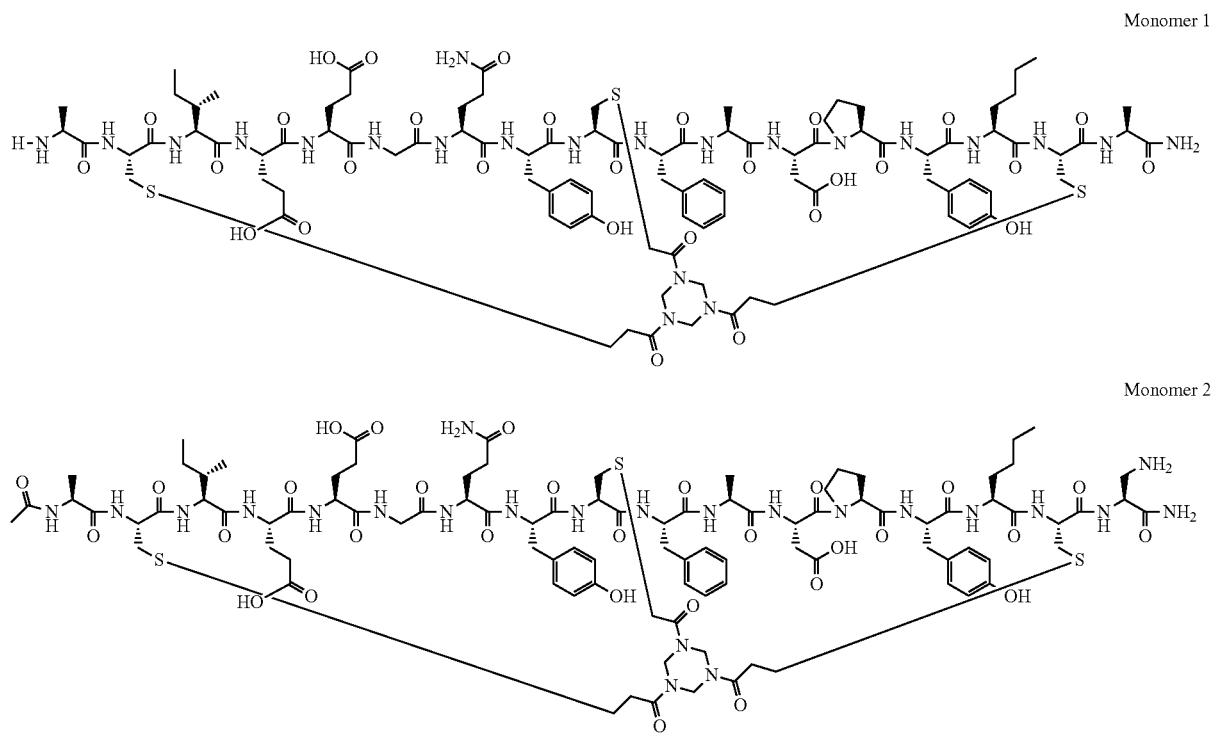

-continued
Monomer 3
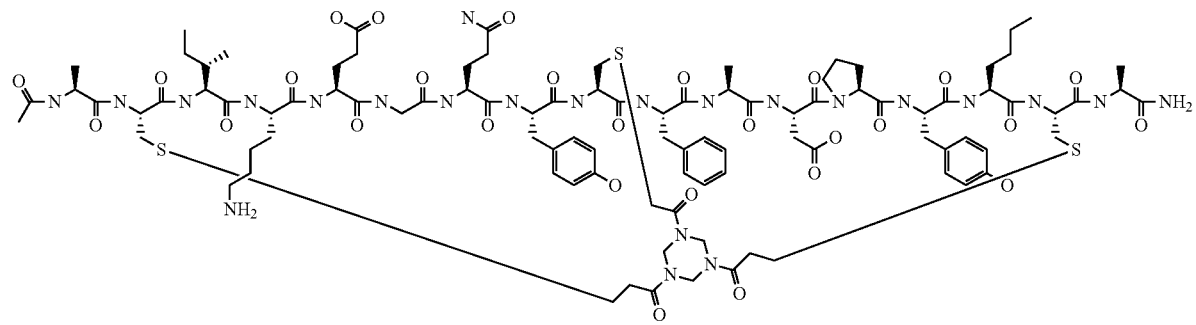
Monomer 4
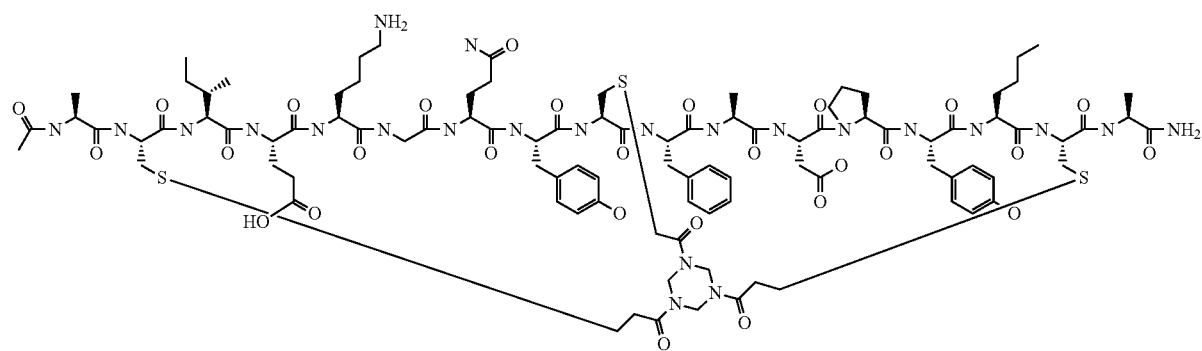
Monomer 5
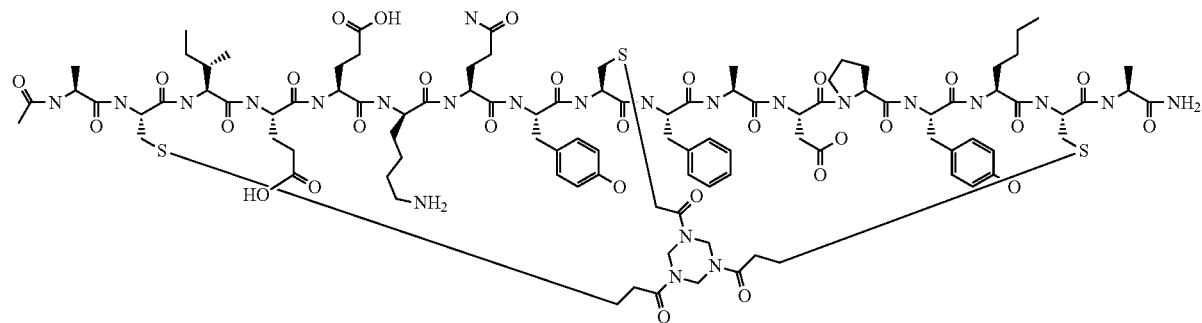
Monomer 6
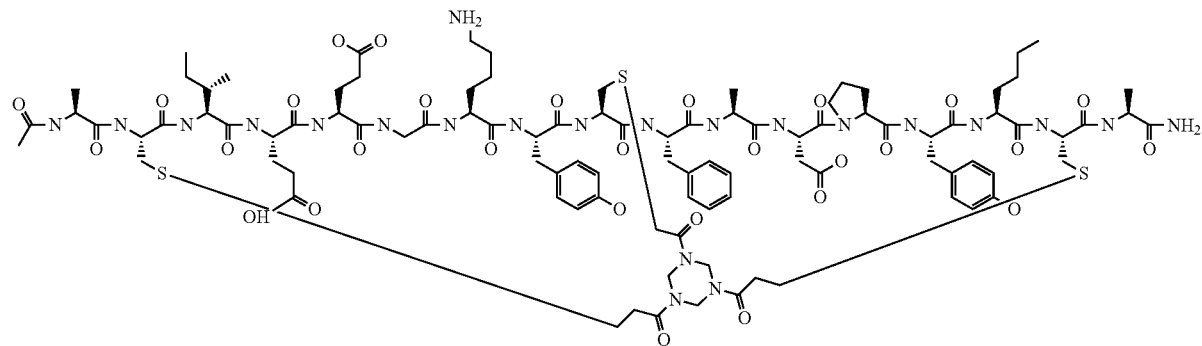

Monomer 7
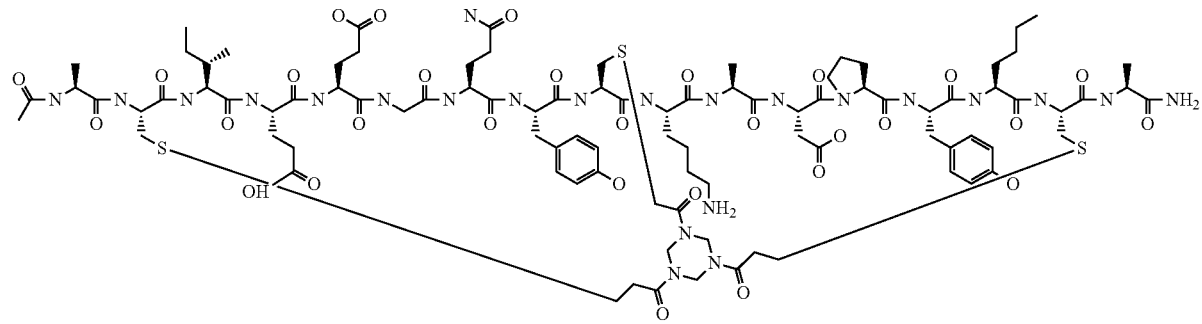
Monomer 8
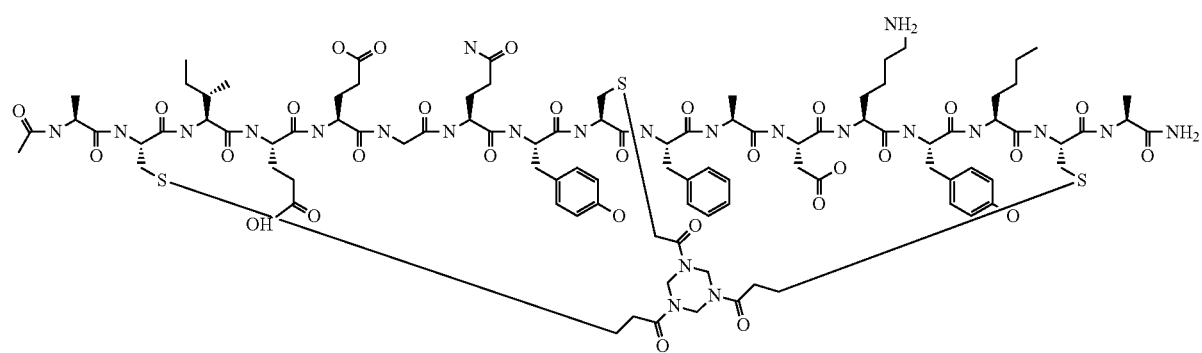
Monomer 9
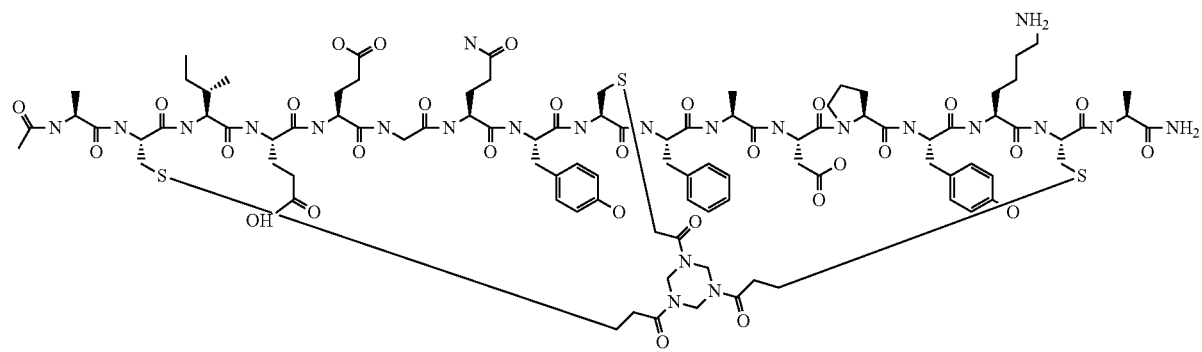
Monomer 10
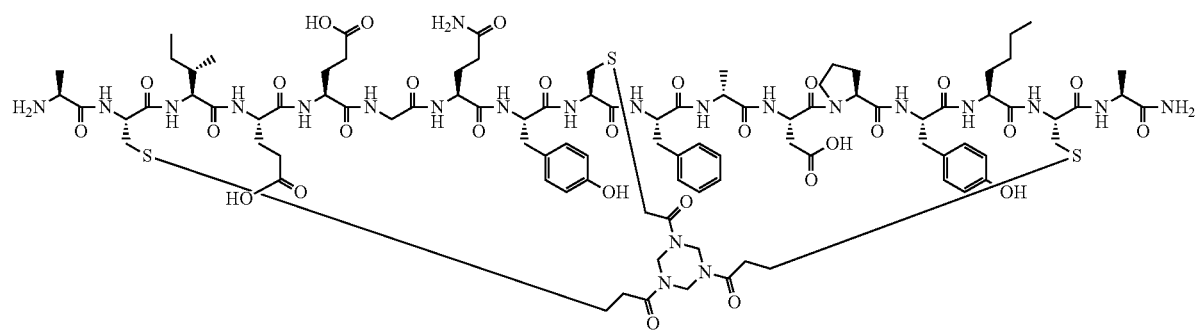

Monomer 11
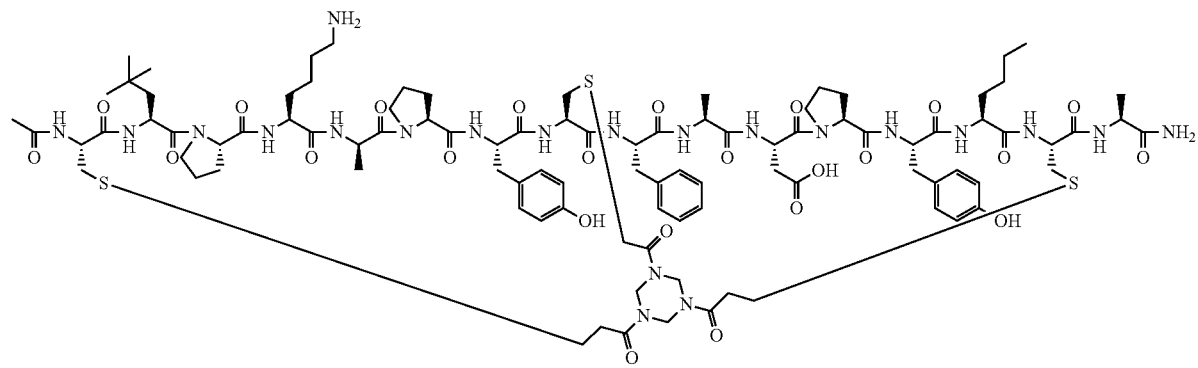
Monomer 12
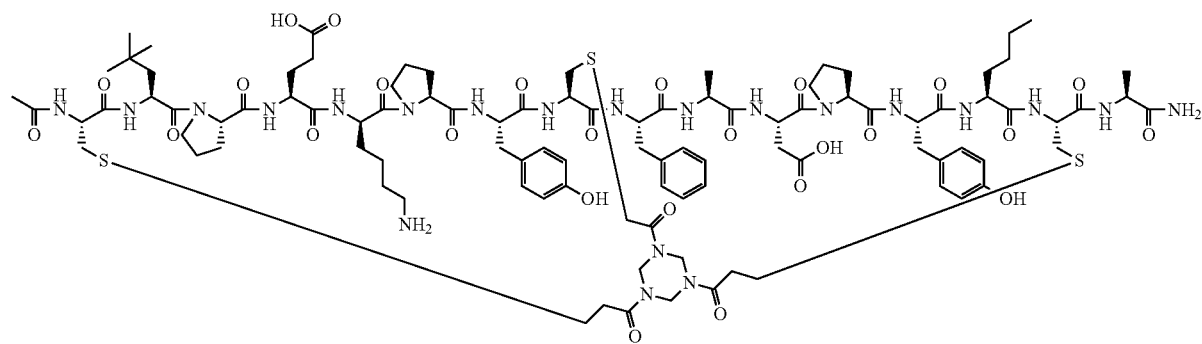
Monomer 13
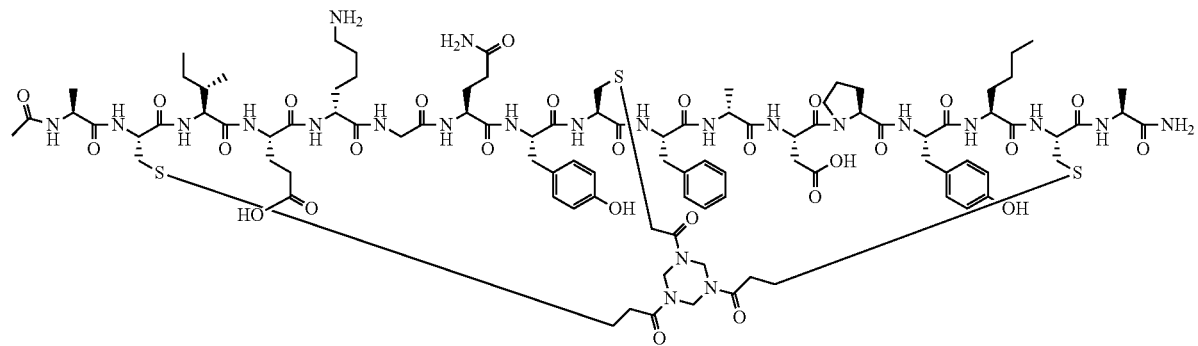
Monomer 14
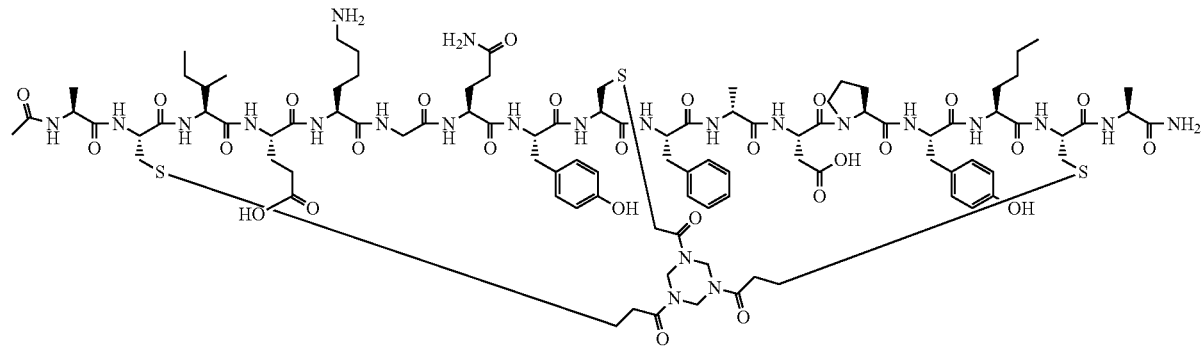

Monomer 15
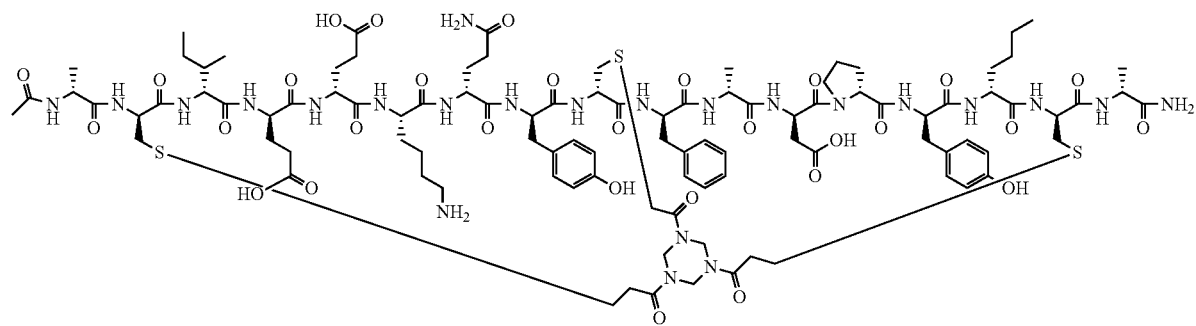
Compound 5:
Monomer 1A
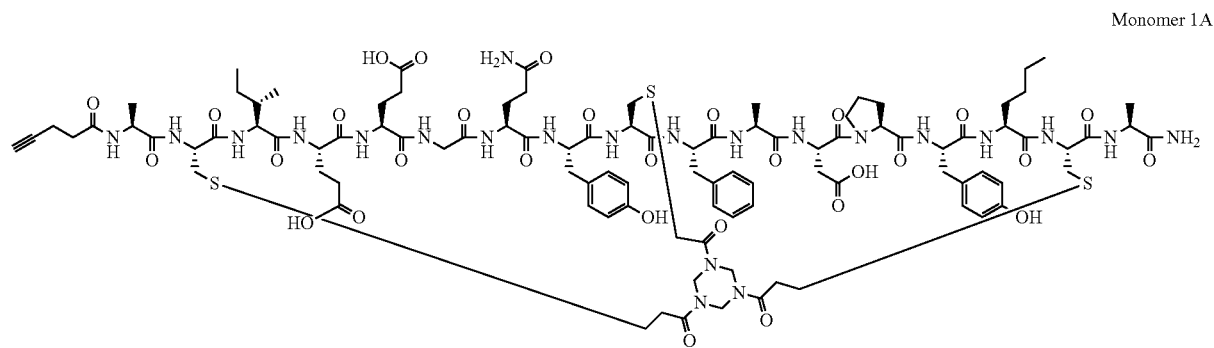
Monomer 2A
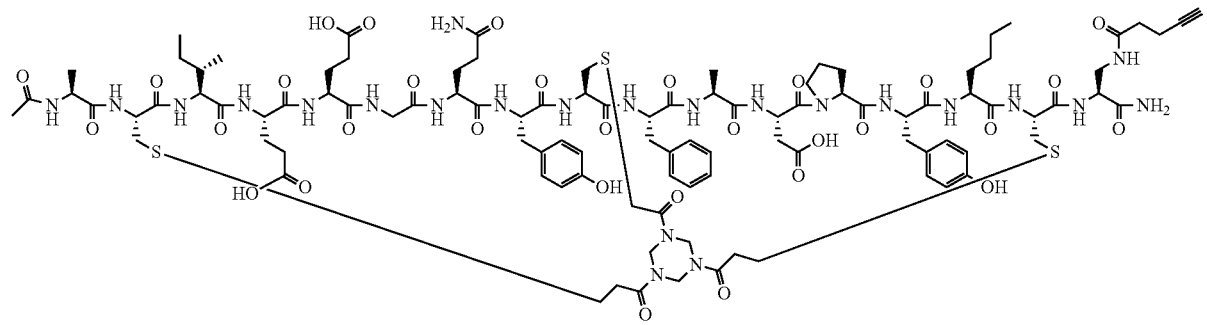
Monomer 3A
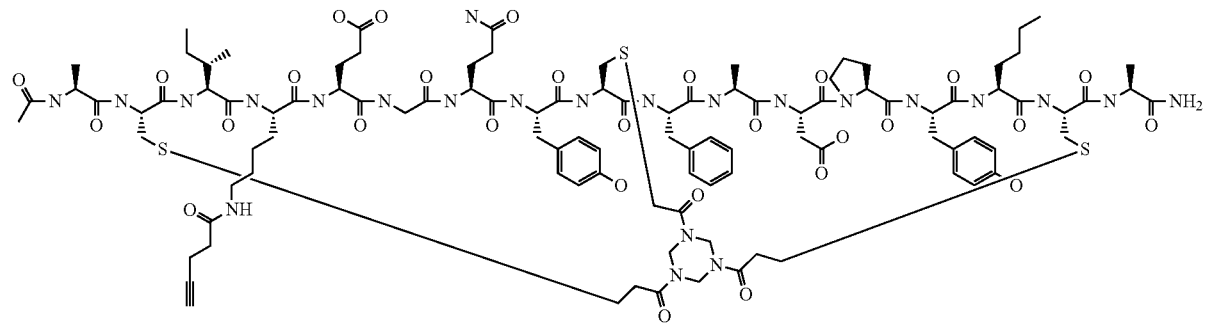

Monomer 4A
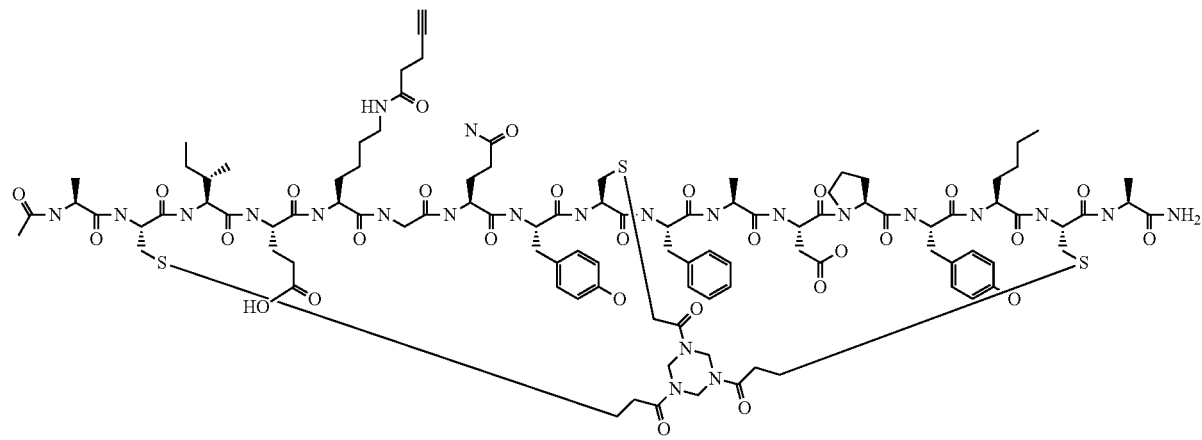
Monomer 5A
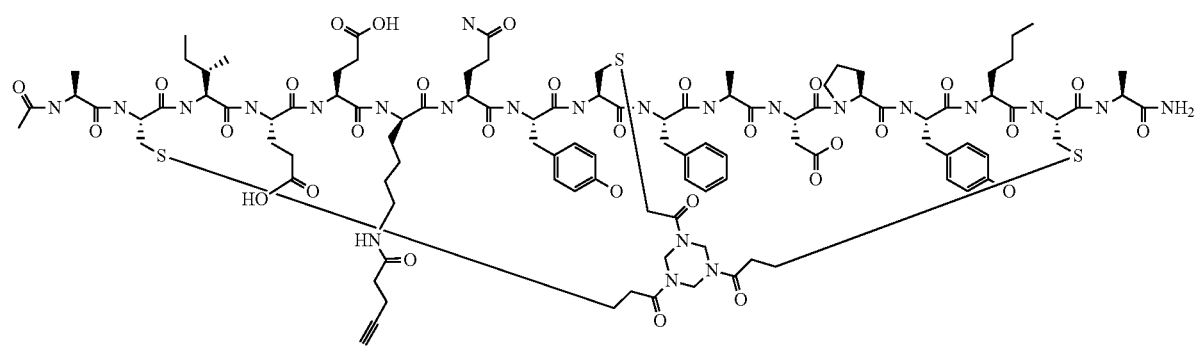
Monomer 6A
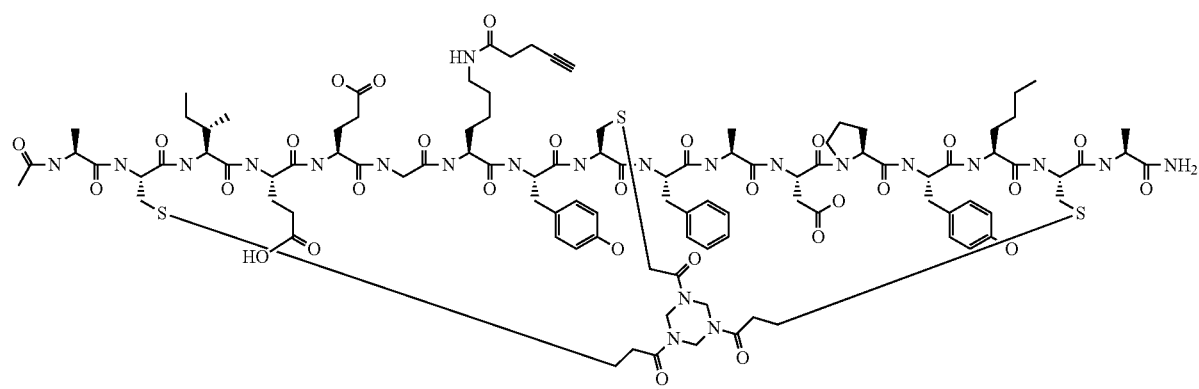
Monomer 7A
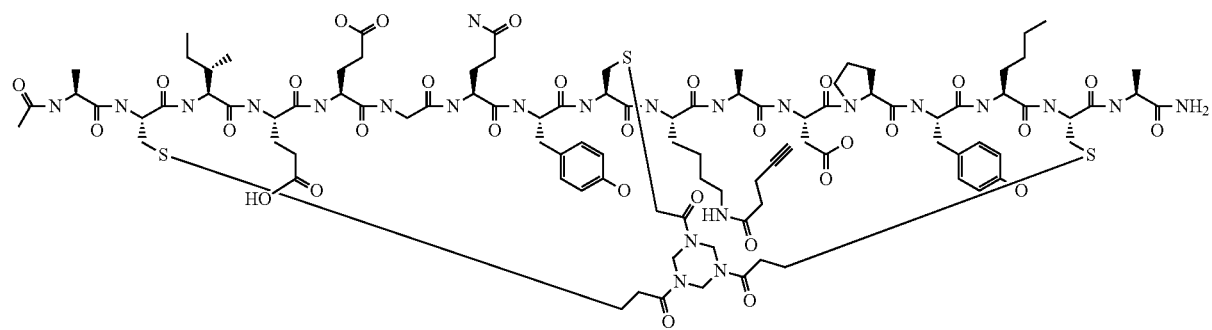

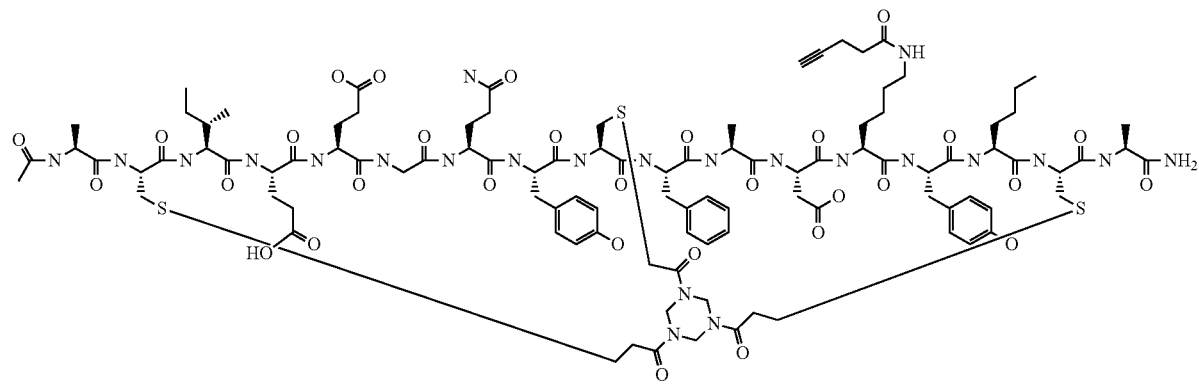
Monomer 8A
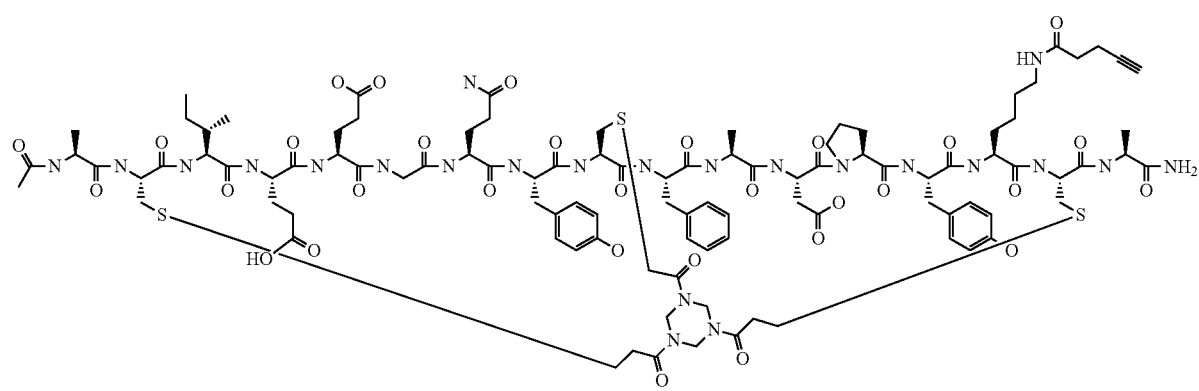
Monomer 9A
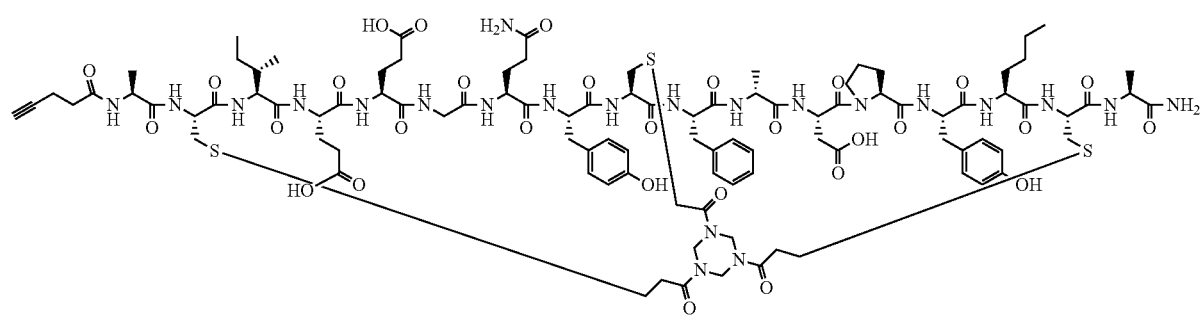
Monomer 10A
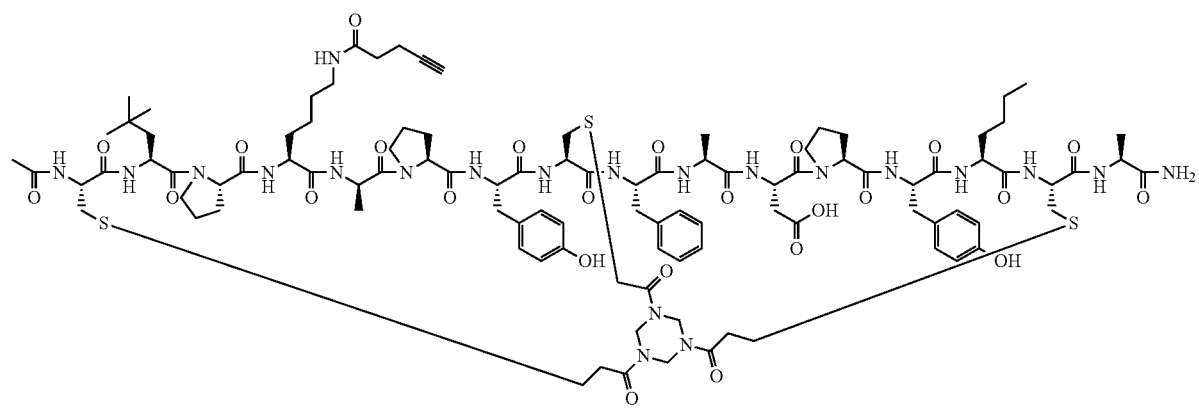
Monomer 11A Monomer 12A
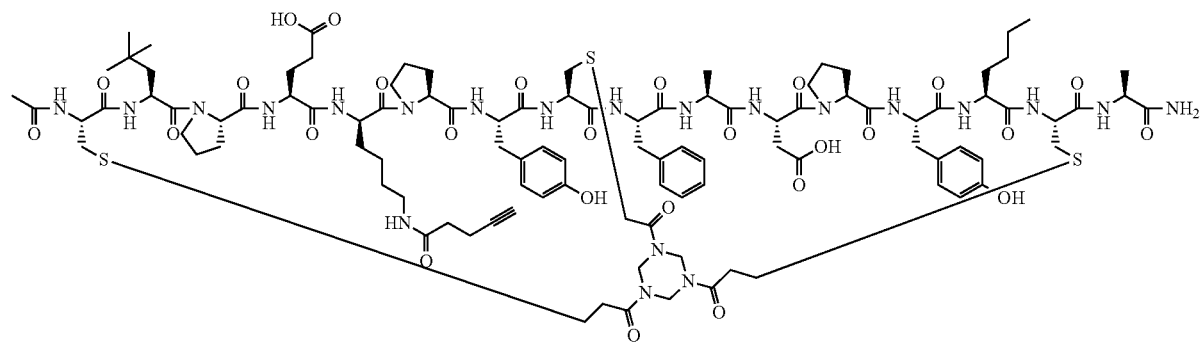
Monomer 13A
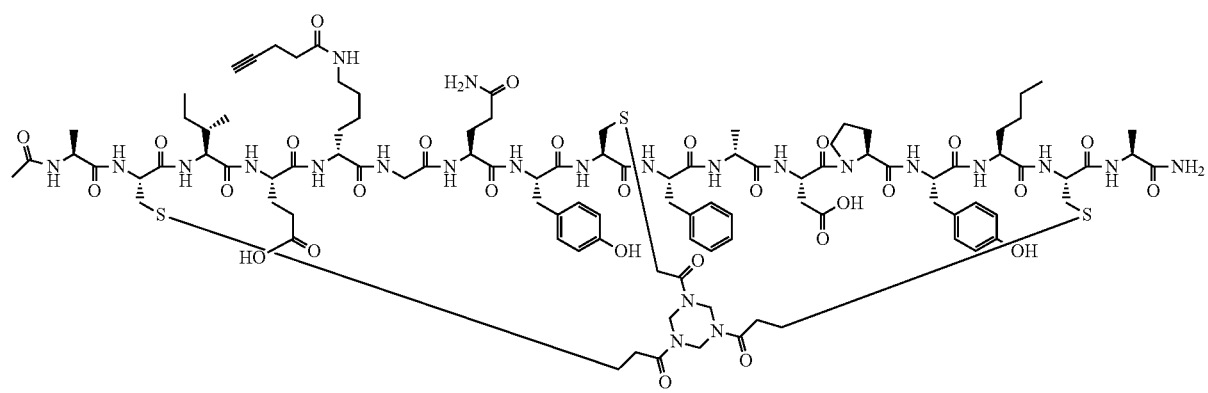
Monomer 14A
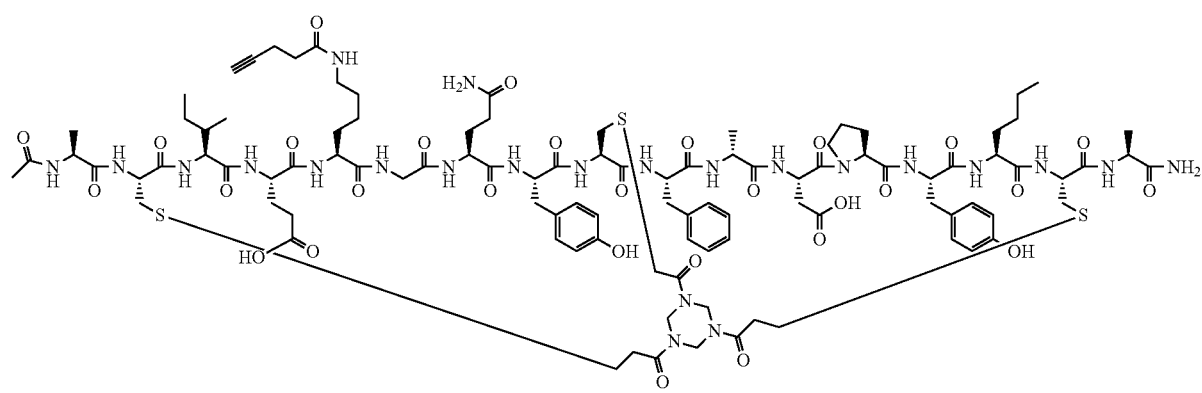
Monomer 15A
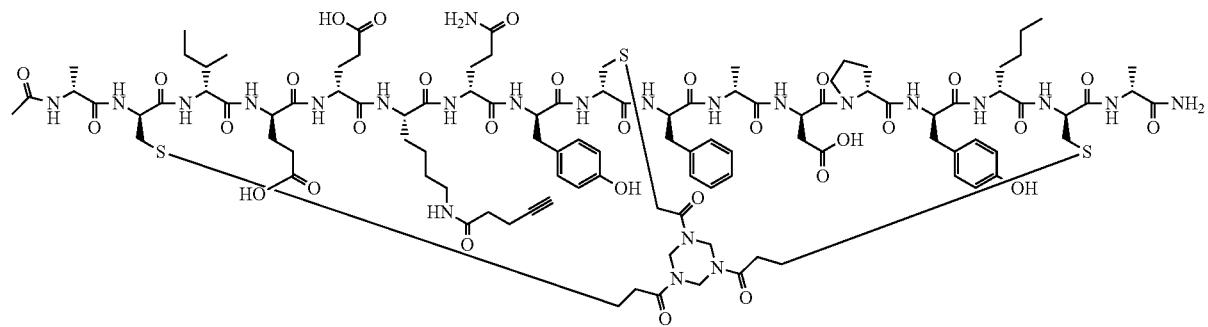

Monomer 1A:

To a solution of Monomer 1 (350.0 mg, 163.22 µmol, 1.0 eq) and compound 3 (63.71 mg, 326.43 µmol, 2.0 eq) in DMA (10 mL) was added DIPEA (105.47 mg, 816.08 µmol, 142.15 µL, 5.0 eq). The mixture was stirred at 20° C. for 2 hr. LC-MS showed Monomer 1 was consumed completely and one main peak with desired MS was detected. The mixture was purified by prep-HPLC (neutral condition) to give Monomer 1A (254 mg, 69.96% yield) as a white solid.

Monomer 2A:

To a solution of Monomer 2 (350 mg, 158.99 µmol, 1 eq) and compound 3 (62.0 mg, 317.97 µmol, 2 eq) in DMA (3 mL) was added DIPEA (103.0 mg, 794.93 µmol, 138.46 µL, 5 eq). The mixture was stirred at 20° C. for 2 hr. LC-MS showed Monomer 2 was consumed completely and one main peak with desired MS was detected. The mixture was purified by prep-HPLC (neutral condition) to give Monomer 2A (304 mg, 130.58 µmol, 82.13% yield, 98% purity) as a white solid.

Monomer 3A:

To a solution of Monomer 3 (0.3 g, 137.27 µmol, 1.0 eq) and compound 3 (54 mg, 276.68 µmol, 2.0 eq) in DMA (3 mL) was added DIPEA (89 mg, 688.63 µmol, 119.95 µL, 5.0 eq). The mixture was stirred at 25-30° C. for 2 hr. LC-MS and HPLC showed Monomer 3 was consumed completely and one main peak with desired MS was detected. The mixture was purified by prep-HPLC (neutral condition) to give Monomer 3A (272 mg, 110.21 µmol, 80.29% yield, 91.8% purity) as a white solid.

Monomer 4A:

To a solution of Monomer 4 (0.3 g, 137.27 µmol, 1 eq) and compound 3 (54 mg, 276.68 µmol, 2.02 eq) in DMA (3 mL) was added DIPEA (89 mg, 688.63 µmol, 119.95 µL, 5.02 eq). The mixture was stirred at 25-30° C. for 2 hr. LC-MS and HPLC showed Monomer 4 was consumed completely and one main peak with desired MS was detected. The mixture was purified by prep-HPLC (neutral condition) to give Monomer 4A (204 mg, 85.36 µmol, 62.19% yield, 94.8% purity) as a white solid.

Monomer 5A:

To a solution of Monomer 5 (0.3 g, 132.89 µmol, 1 eq) and compound 3 (52.0 mg, 266.43 µmol, 2.0 eq) in DMA (3 mL) was added DIPEA (86.0 mg, 665.41 µmol, 115.90 µL, 5.0 eq). The mixture was stirred at 25-30° C. for 2 hr. LC-MS and HPLC showed Monomer 5 was consumed completely and one main peak with desired MS was detected. The mixture was purified by prep-HPLC (neutral condition) to give Monomer 5A (194 mg, 74.69 µmol, 56.21% yield, 90.0% purity) as a white solid.

Monomer 6A:

To a solution of Monomer 6 (0.3 g, 137.21 µmol, 1.0 eq) and compound 3 (54 mg, 276.68 µmol, 2.0 eq) in DMA (3 mL) was added DIPEA (89 mg, 688.63 µmol, 119.95 µL, 5.02 eq). The mixture was stirred at 25-30° C. for 2 hr. LC-MS and HPLC showed Monomer 6 was consumed completely and one main peak with desired MS was detected. The mixture was purified by prep-HPLC (neutral condition) to give Monomer 6A (204 mg, 83.25 µmol, 60.68% yield, 92.5% purity) as a white solid.

Monomer 7A:

To a solution of Monomer 7 (0.3 g, 138.41 µmol, 1.0 eq) and compound 3 (54.00 mg, 276.82 µmol, 2.0 eq) in DMA (3 mL) was added DIPEA (89 mg, 688.63 µmol, 119.95 µL, 5.0 eq). The mixture was stirred at 25-30° C. for 2 hr. LC-MS and HPLC showed Monomer 7 was consumed completely and one main peak with desired MS was detected. The mixture was purified by prep-HPLC (neutral condition) to give Monomer 7A (183 mg, 73.69 µmol, 53.24% yield, 90.5% purity) as a white solid.

Monomer 8A:

A mixture of Monomer 8 (400 mg, 180.38 µmol, 1.0 eq), compound 3 (70.41 mg, 360.77 µmol, 2.0 eq) and DIPEA (118.72 mg, 918.58 µmol, 160.00 µL, 5.0 eq) in DMSO (5 mL) was degassed and purged with N2 for 3 times. And then the mixture was stirred at 30° C. for 2 hrs under N2 atmosphere. LC-MS and HPLC showed Monomer 8 was consumed completely and one main peak with desired MS was detected. The mixture was purified by prep-HPLC (neutral condition) to give Monomer 8A (300 mg, 118.82 µmol, 65.87% yield, 91.74% purity) as a white solid.

Monomer 9A:

To a solution of Monomer 9 (0.3 g, 136.27 µmol, 1.0 eq) and compound 3 (53.0 mg, 272.55 µmol, 2.0 eq) in DMA (3 mL) was added DIPEA (88.0 mg, 681.37 µmol, 118.68 µL, 5.0 eq). The mixture was stirred at 25-30° C. for 2 hr. LC-MS and HPLC showed Monomer 9 was consumed completely and one main peak with desired MS was detected. The mixture was purified by prep-HPLC (neutral condition) to give Monomer 9A (249 mg, 100.41 µmol, 73.68% yield, 92.0% purity) as a white solid.

Monomer 10A (260 mg, 90% purity), Monomer 11A (123 mg, 97.10% purity), Monomer 12A (131 mg, 97.5% purity), Monomer 13A (780 mg, 98.0% purity), Monomer 14A (710 mg, 92.40% purity) and Monomer 15A (820 mg, 96.9% purity) was synthesized as described above and purified using prep-HPLC to give a white solid.

General Procedure for Preparation of Compound 7

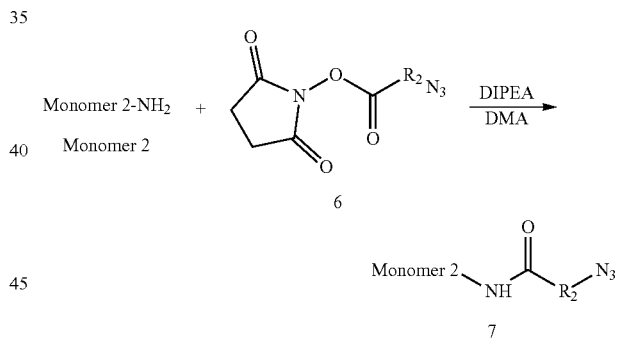

Compound 6:

Compound 7:

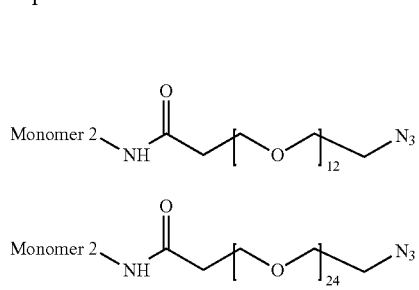

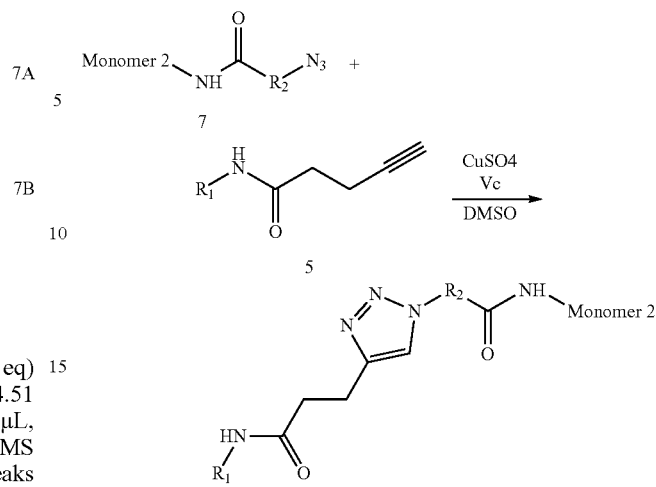

Compound 7A:

To a solution of Monomer 2 (120 mg, 54.51 µmol, 1.0 eq) in DMA (4 mL) was added compound 6A (40.38 mg, 54.51 µmol, 1.0 eq) and DIPEA (35.22 mg, 272.55 µmol, 47.47 µL, 5 eq). The mixture was stirred at 20° C. for 12 hrs. LC-MS showed no Monomer 2 was remained. Several new peaks were shown on LC-MS and ~80% of desired compound was detected. The mixture was purified by prep-HPLC (TFA condition) to give compound 7A (89 mg, 31.48 µmol, 57.75% yield) as a white solid.

Compound 7B:

To a solution of Monomer 2 (75.0 mg, 34.07 µmol, 1.0 eq) in DMA (3 mL) was added compound 6B (43.25 mg, 34.07 µmol, 1.0 eq) and DIPEA (22.02 mg, 170.34 µmol, 29.67 µL, 5.0 eq). The mixture was stirred at 20° C. for 12 hrs. LC-MS showed no Monomer 2 was remained. Several new peaks were shown on LC-MS and ~80% of desired compound was detected. The mixture was purified by prep-HPLC (TFA condition) to give compound 7B about (73 mg, 21.75 µmol, 63.85% yield) as a white solid.

General Procedure for Preparation of Dimeric Bicycle Conjugates:

Compound 7:

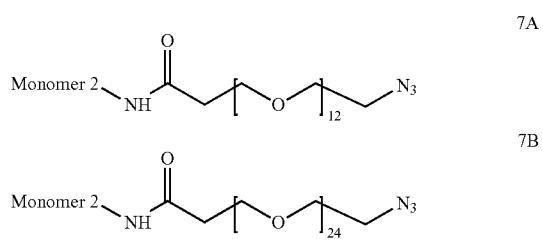

Compound 5:

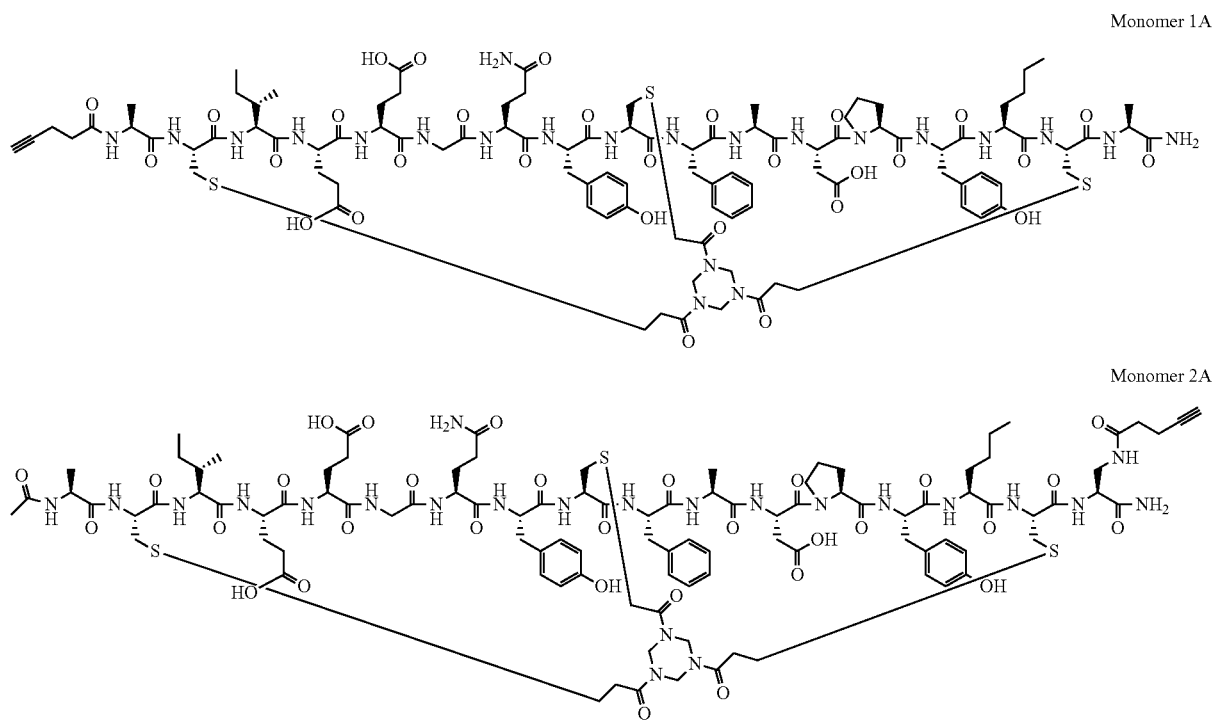

Monomer 3A
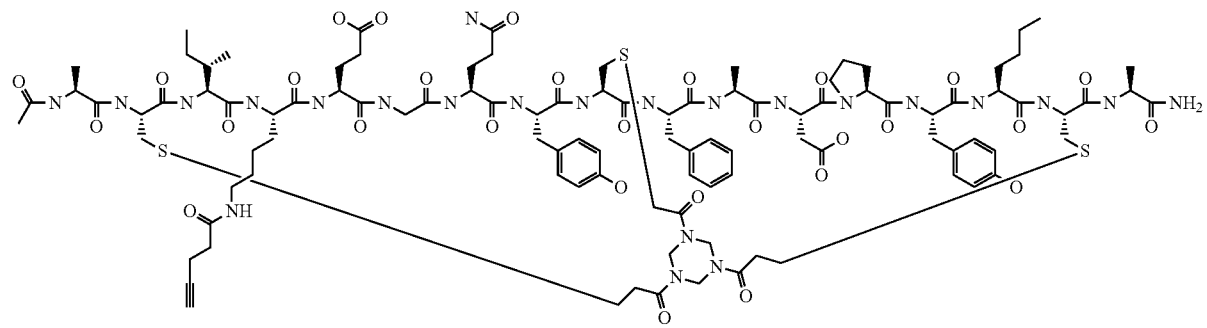
Monomer 4A
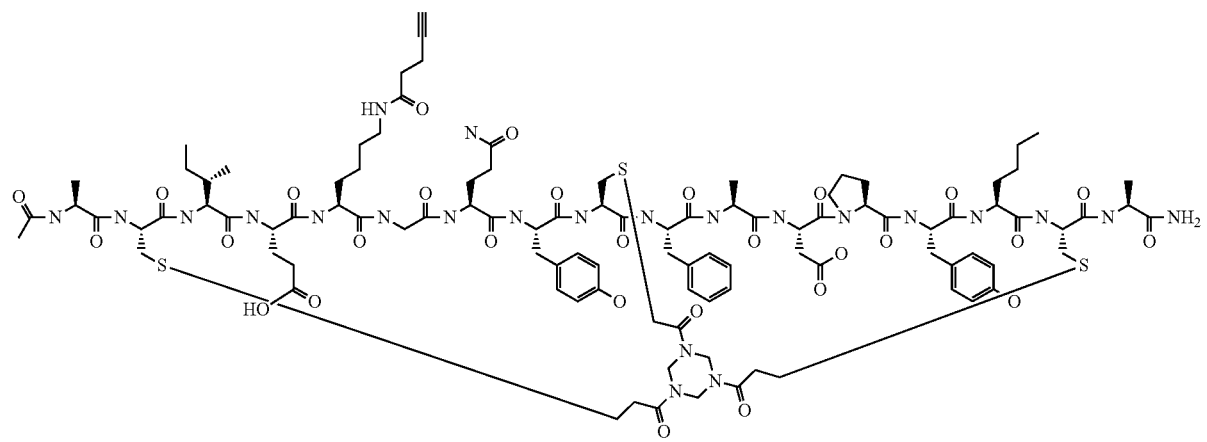
Monomer 5A
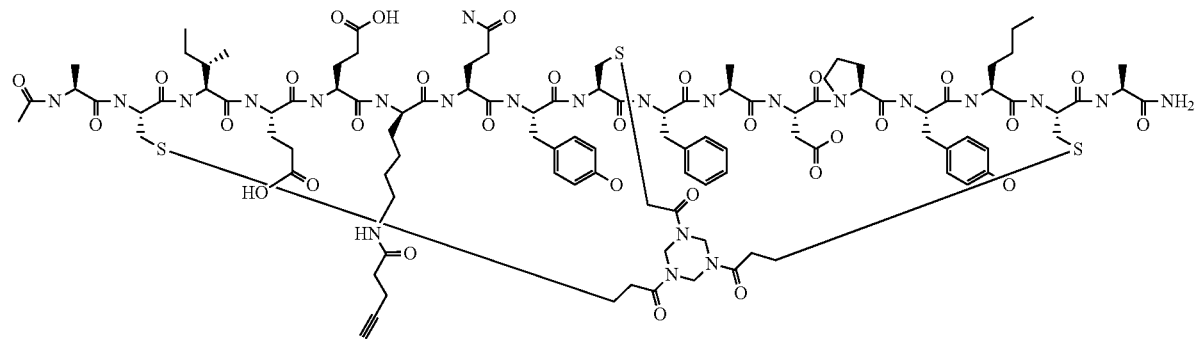
Monomer 6A
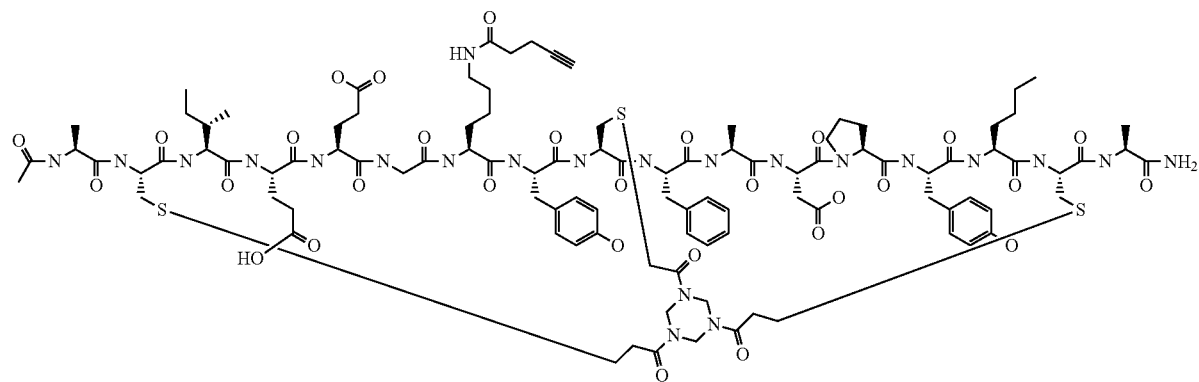

-continued
Monomer 7A
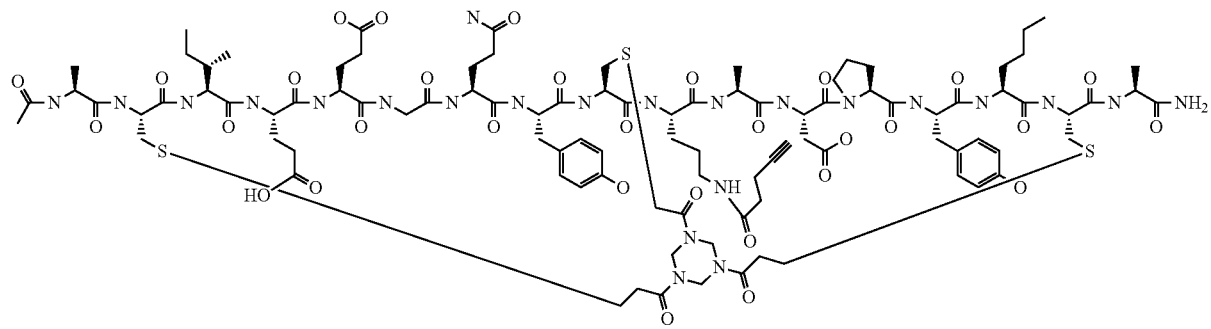
Monomer 8A
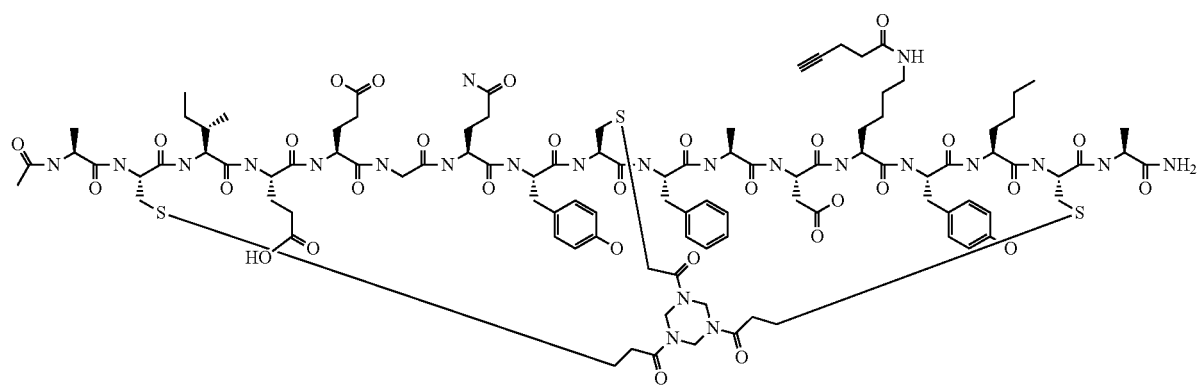
Monomer 9A
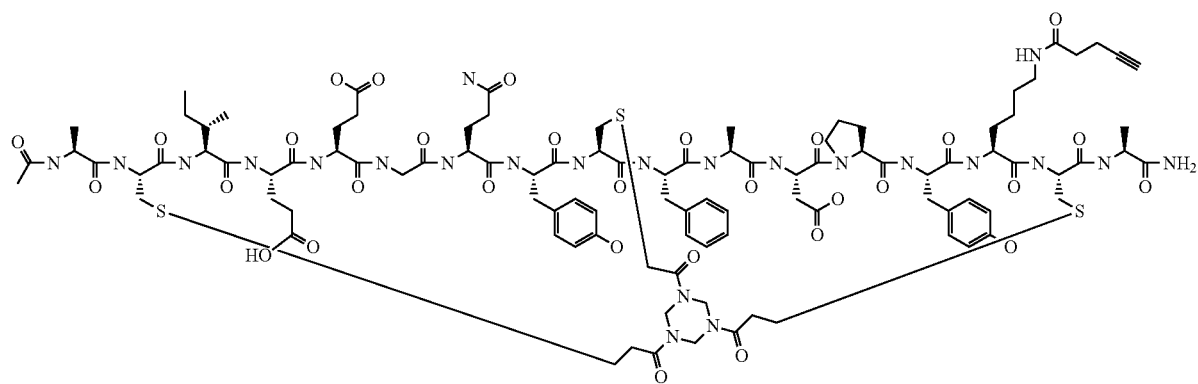
Compound 8:
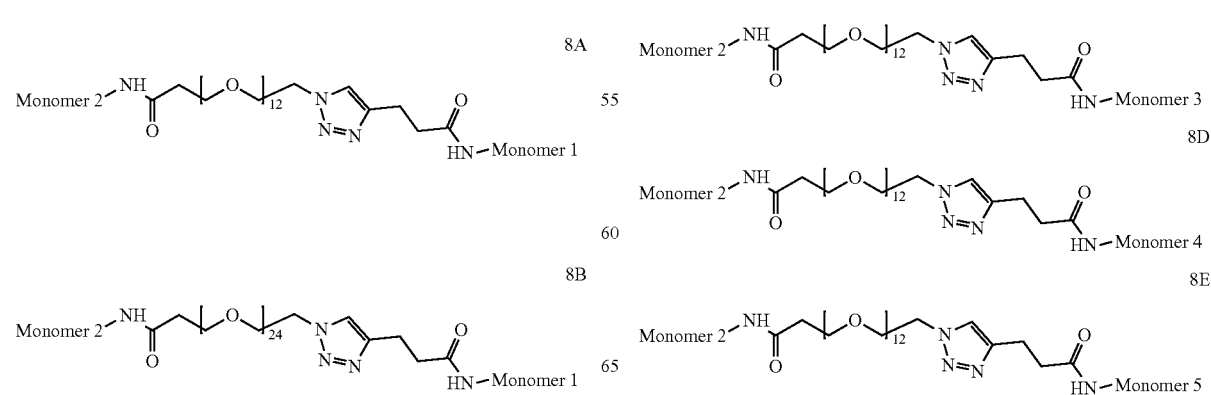

-continued

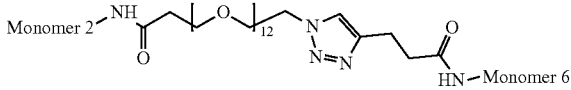

8F

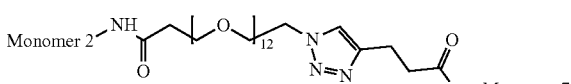

8G

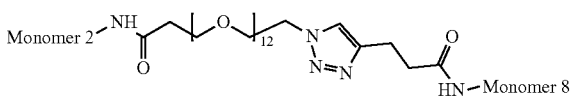

8H

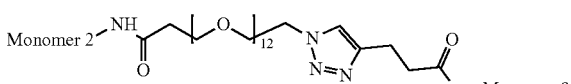

8I

Compound 8A:

To a solution of compound 7A (12 mg, 4.24 µmol, 1 eq) and Monomer 1A (9.44 mg, 4.24 µmol, 1 eq) in DMF (1 mL) was added $CuSO_4·5H_2O$ (0.4 M, 31.83 µL, 3 eq) and ascorbic acid (0.4 M, 106.11 µL, 10 eq) under nitrogen. The mixture was stirred at 20° C. for 1 hr. LC-MS showed no compound 7A was remained. Several new peaks were shown on LC-MS and ~80% of desired compound was detected. The residue was purified by prep-HPLC (TFA condition) to give compound 8A (8.1 mg, 1.49 µmol, 35.11% yield, 92.94% purity) as a white solid.

Compound 8B:

To a solution of compound 7B (14 mg, 4.17 µmol, 1 eq) and Monomer 1A (9.28 mg, 4.17 µmol, 1 eq) in DMF (1 mL) was added $CuSO_4·5H_2O$ (0.4 M, 31.29 µL, 3 eq) and ascorbic acid (0.4 M, 104.30 µL, 10 eq) under nitrogen. The mixture was stirred at 20° C. for 1 hr. LC-MS showed no compound 7B was remained. Several new peaks were shown on LC-MS and ~80% of desired compound was detected. The residue was purified by prep-HPLC (TFA condition) to give compound 8B (5.2 mg, 0.86 µmol, 20.62% yield, 92.31% purity) as a white solid.

Compound 8C:

To a solution of compound 7A (10 mg, 3.54 µmol, 1 eq) and Monomer 3A (12.02 mg, 5.31 µmol, 1.5 eq) in DMF (1 mL) was added $CuSO_4·5H_2O$ (0.4 M, 26.53 µL, 3 eq) and ascorbic acid (0.4 M, 88.43 µL, 10 eq) under nitrogen. The mixture was stirred at 20° C. for 1 hr. LC-MS showed no compound 7A was remained. Several new peaks were shown on LC-MS and ~40% of desired compound was detected. The residue was purified by prep-HPLC (TFA condition) to give compound 8C (2.8 mg, 5.04e-1 µmol, 14.24% yield, 91.6% purity) as a white solid.

Compound 8D:

To a solution of compound 7A (10 mg, 3.54 µmol, 1 eq) and Monomer 4A (12.02 mg, 5.31 µmol, 1.5 eq) in DMF (1 mL) was added $CuSO_4·5H_2O$ (0.4 M, 26.53 µL, 3 eq) and ascorbic acid (0.4 M, 88.43 µL, 10 eq) under nitrogen. The mixture was stirred at 20° C. for 1 hr. LC-MS showed no compound 7A was remained. Several new peaks were shown on LC-MS and ~40% of desired compound was detected. The residue was purified by prep-HPLC (TFA condition) to give compound 8O (2.1 mg, 3.76e-1 µmol, 10.62% yield, 91.1% purity) as a white solid.

Compound 8E:

To a solution of compound 7A (10 mg, 3.54 µmol, 1 eq) and Monomer 5A (12.40 mg, 5.31 µmol, 1.5 eq) in DMF (1 mL) was added $CuSO_4·5H_2O$ (0.4 M, 26.53 µL, 3 eq) and ascorbic acid (0.4 M, 88.43 µL, 10 eq) under nitrogen. The mixture was stirred at 20° C. for 1 hr. LC-MS showed no compound 7A was remained. Several new peaks were shown on LC-MS and ~20% of desired compound was detected. The residue was purified by prep-HPLC (TFA condition) to give compound 8E (1.2 mg, 2.01e-1 µmol, 5.69% yield, 86.6% purity) as a white solid.

Compound 8F:

To a solution of compound 7A (10 mg, 3.54 µmol, 1 eq) and Monomer 6A (12.03 mg, 5.31 µmol, 1.5 eq) in DMF (1 mL) was added $CuSO_4·5H_2O$ (0.4 M, 26.53 µL, 3 eq) and ascorbic acid (0.4 M, 88.43 µL, 10 eq) under nitrogen. The mixture was stirred at 20° C. for 1 hr. LC-MS showed no compound 7A was remained. Several new peaks were shown on LC-MS and ~40% of desired compound was detected. The residue was purified by prep-HPLC (TFA condition) to give compound 8F (3.4 mg, 3.93e-1 µmol, 11.12% yield, 58.9% purity) as a white solid.

Compound 8G:

To a solution of compound 7A (10 mg, 3.54 µmol, 1 eq) and Monomer 7A (11.92 mg, 5.31 µmol, 1.5 eq) in DMSO (1 mL) was added $CuSO_4·5H_2O$ (0.4 M, 26.53 µL, 3 eq) and ascorbic acid (0.4 M, 88.43 µL, 10 eq) under nitrogen. The mixture was stirred at 25-30° C. for 1 hr. LC-MS showed no compound 7A was remained. Several new peaks were shown on LC-MS and ~40% of desired compound was detected. The residue was purified by prep-HPLC (TFA condition) to give compound 8G (7.2 mg, 1.33 mmol, 37.78% yield, 94.2% purity) as a white solid.

Compound 8H:

To a solution of compound 7A (10 mg, 3.54 µmol, 1 eq) and Monomer 8A (11.19 mg, 5.31 µmol, 1.5 eq) in DMSO (1 mL) was added $CuSO_4·5H_2O$ (0.4 M, 26.53 µL, 3 eq) and ascorbic acid (0.4 M, 88.43 µL, 10 eq) under nitrogen. The mixture was stirred at 25-30° C. for 1 hr. LC-MS showed no compound 7A was remained. Several new peaks were shown on LC-MS and ~40% of desired compound was detected. The residue was purified by prep-HPLC (TFA condition) to give compound 8H (9.0 mg, 1.73 mmol, 49.15% yield, 99.0% purity) as a white solid.

Compound 8I:

To a solution of compound 7A (10 mg, 3.54 µmol, 1 eq) and Monomer 9A (12.11 mg, 5.31 µmol, 1.5 eq) in DMF (1 mL) was added $CuSO_4·5H_2O$ (0.4 M, 26.53 µL, 3 eq) and ascorbic acid (0.4 M, 88.43 µL, 10 eq) under nitrogen. The mixture was stirred at 20° C. for 1 hr. LC-MS showed no compound 7A was remained. Several new peaks were shown on LC-MS and ~40% of desired compound was detected. The residue was purified by prep-HPLC (TFA condition) to afford compound 8I (3.8 mg, 6.81e-1 µmol, 19.24% yield, 91.5% purity) as a white solid.

General procedure for preparation of trimeric azide linker

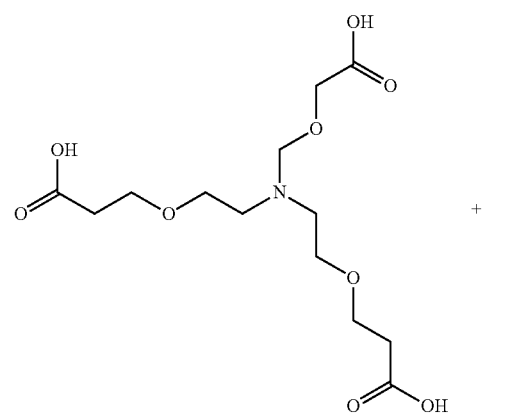

9A

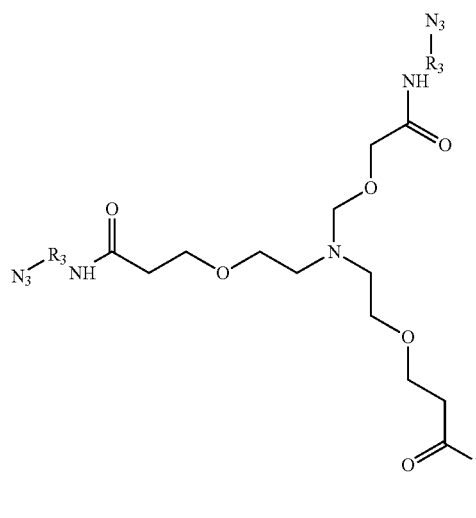

11

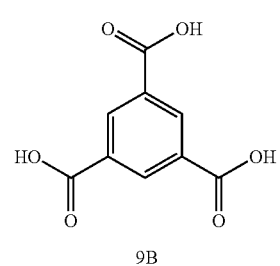

9B

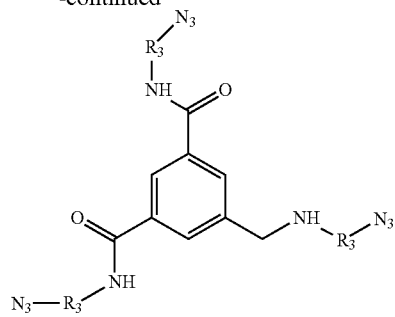

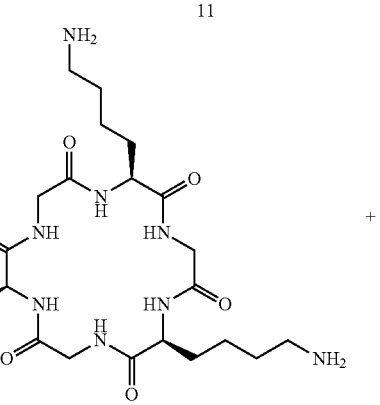

9C

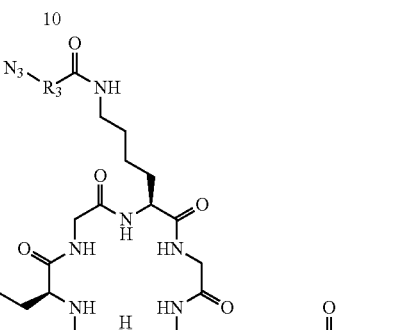

11

Compound 9C: c(KGKGKG) (cyclic (SEQ ID NO: 57))

Linear peptide NH$_2$-Lys-Gly-Lys-Gly-Lys-Gly-COOH (NH$_2$-(SEQ ID NO: 57)-COOH) was synthesized on 2-Cl-Trt chloride resin (CTC resin) using standard Fmoc chemistry. The peptide was then cleaved by treatment with 20% HFIP in DCM (30 min×2), and the solution was combined, evaporated under vacuum, and lyophilized to dry, resulting in linear crude product. The crude peptide was then dissolved in DMF, following by addition of coupling reagents (DIC and HOAt, 1 eq and 1 eq, respectively). The mixture was stirred at room temperature for 16 hr, until LCMS indicated no linear peptide remained. Subsequently, the cyclisation crude was dried under vacuum and purified by FLASH C18 chromatography. The purified cyclic peptide was then lyophilized, and all protecting groups were removed by treatment with HCl/dioxane (4 M, 1 hour, room temperature). The precipitates were collected, washed with methyl tert-butyl ether, and dried under vacuum to give final product as a white solid (HCl salt).

Compound 10:

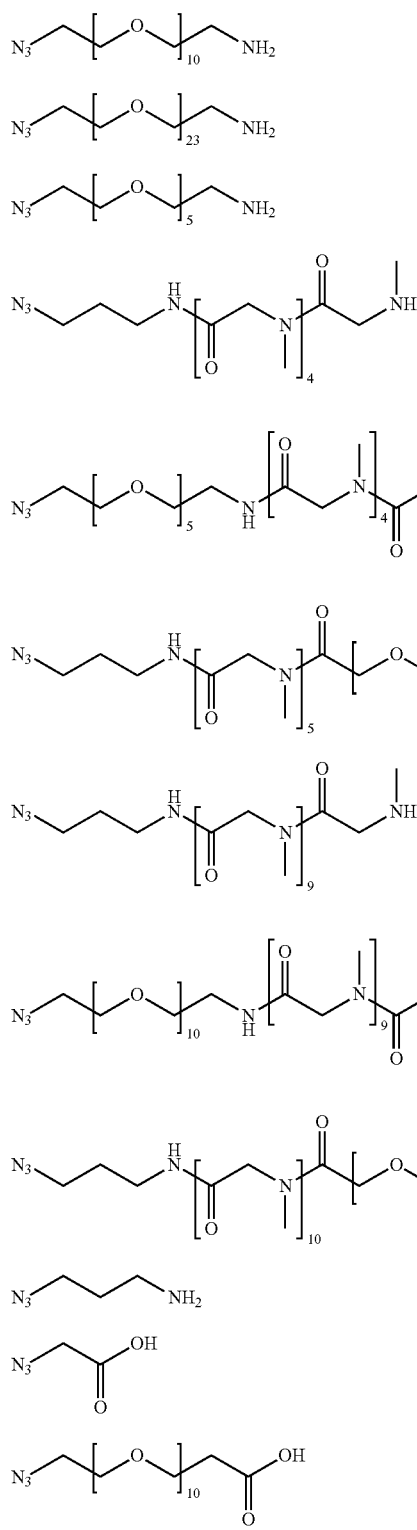

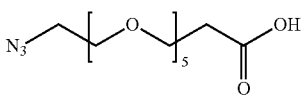

Compound 10D:

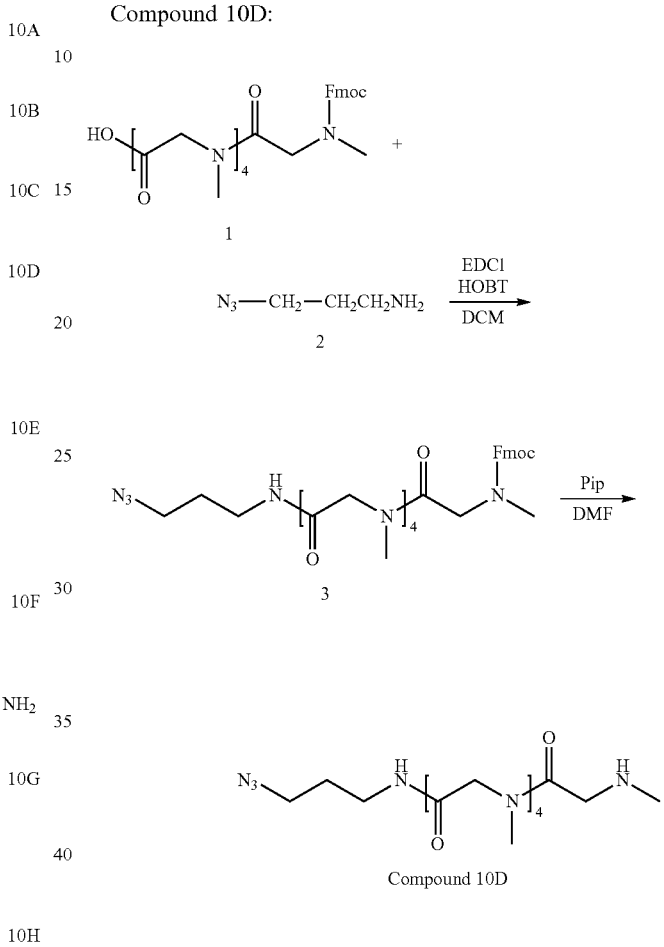

A mixture of compound 1 (700.0 mg, 1.18 mmol, 1.0 eq) (obtained from solid phase peptide synthesis), 3-azidopropan-1-amine (compound 2, 117.7 mg, 1.18 mmol, 1.0 eq), HOBt (190.6 mg, 1.41 mmol, 1.2 eq), EDCl (270.4 mg, 1.41 mmol, 1.2 eq) was dissolved in DCM (20 mL, pre-degassed and purged with N2 for 3 times), and then the mixture was stirred at 25-30° C. for 2 hr under $N_2$ atmosphere. LC-MS showed compound 1 was consumed completely and one main peak with desired m/z (calculated MW: 677.75, observed m/z: 678.2 ([M+H]$^+$)) was detected. The reaction mixture was treated with a few drops of 1 M HCl and the organic layer was collected and evaporated to remove solvent. Compound 3 (600.0 mg, crude) was obtained as a white solid. Compound 3 (600.0 mg, 885.3 μmol, 1.0 eq) was dissolved in DMF (3 mL, pre-degassed and purged with $N_2$ for 3 times), and then piperidine (1.29 g, 15.19 mmol, 1.50 mL, 17.2 eq) was added and the mixture was stirred at 25-30° C. for 2 hr under $N_2$ atmosphere. LC-MS showed compound 3 was consumed completely and one main peak with desired m/z (MW: 455.51 observed m/z: 456.3 ([M+H]$^+$)) was detected. The residue was purified by prep-HPLC (TFA condition). Compound 10D (400.0 mg, 879.1 μmol) was obtained as colorless oil.

Compound 10E:

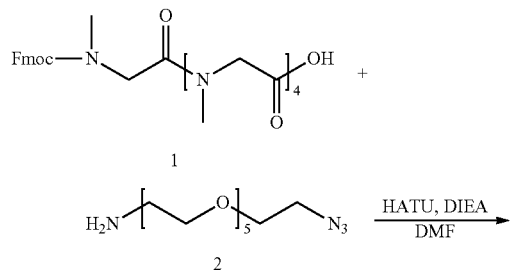

stirred at 25° C. for 30 min. TLC (DCM: CH₃OH=10:1, $R_f=0.18$) showed compound 1 was consumed completely and one new spot formed. The solvent was evaporated to produce compound 3 (1 g, 1.13 mmol, 67.38% yield) as a white solid, which was directly used in next step without further purification. Compound 3 (1 g, 1.13 mmol, 1.0 eq) was dissolved in DMF (8 mL), following by addition of piperidine (2 mL). The mixture was stirred for 15 mins at 25° C. LC-MS showed compound 3 was consumed completely and one main peak with desired m/z (calculated MW: 661.75, observed m/z: 663.1 ([M+H]⁺)) was detected. The residue was purified by prep-HPLC (TFA condition). Compound 10E (800 mg, 1.09 mmol, 96.18% yield,) was obtained as colorless oil.

Compound 10F:

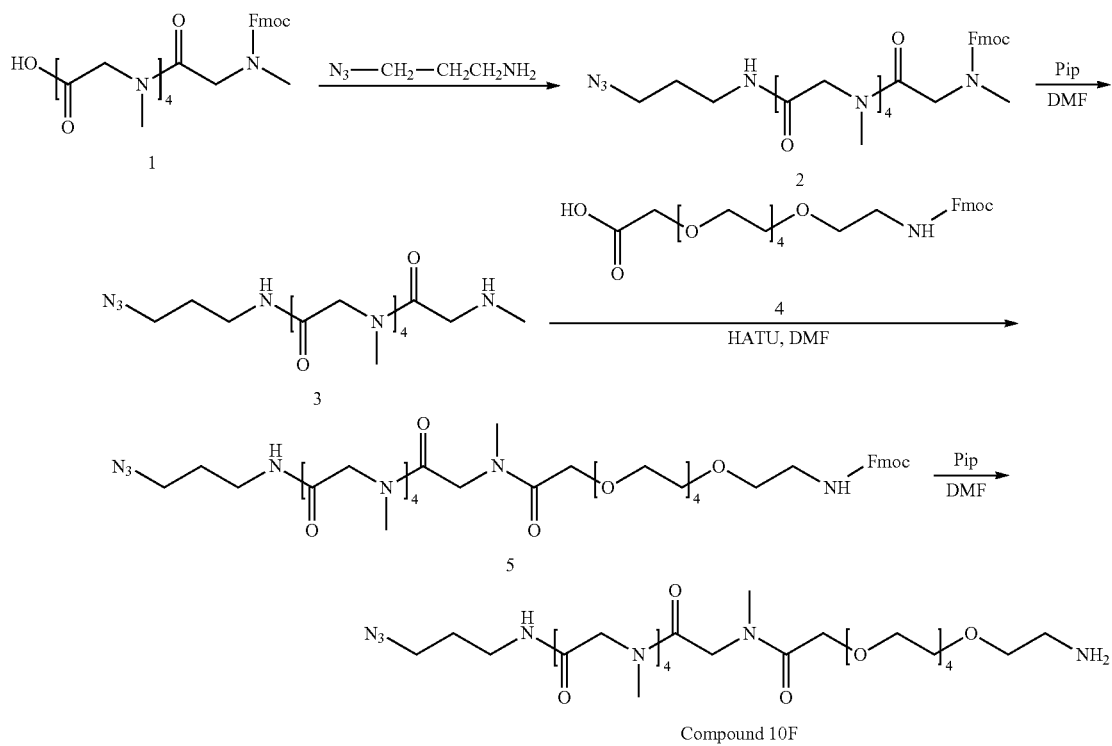

-continued

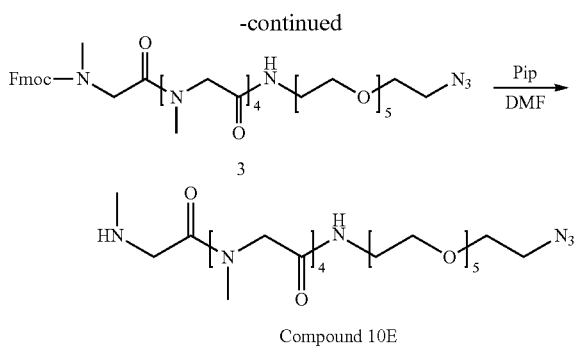

A mixture of compound 1 (1 g, 1.68 mmol, 1.0 eq), compound 2 (411.5 mg, 1.34 mmol, 0.8 eq) and DIEA (217.0 mg, 1.68 mmol, 292.4 µL, 1.0 eq) was dissolved in DMF (2 mL), following by addition of HATU (638.4 mg, 1.68 mmol, 1.0 eq) as one portion at 25° C. The mixture was A mixture of compound 1 (700.0 mg, 1.18 mmol, 1.0 eq), 3-azidopropan-1-amine (117.7 mg, 1.18 mmol, 1.0 eq), HOBt (190.6 mg, 1.41 mmol, 1.2 eq), EDCl (270.4 mg, 1.41 mmol, 1.2 eq) was dissolved in DCM (20 mL, pre-degassed and purged with N₂ for 3 times), and then the mixture was stirred at 25-30° C. for 2 hr under N₂ atmosphere. LC-MS showed compound 1 was consumed completely and one main peak with desired m/z (calculated MW: 677.75, observed m/z: 678.2 ([M+H]⁺)) was detected. The reaction mixture was treatment with a few drops of 1 M HCl, and the organic layer was collected and evaporated under reduced pressure. Compound 2 (600.0 mg, crude) was obtained as a white solid.

Compound 2 (600.0 mg, 885.2 µmol, 1.0 eq) was dissolved in DMF (3 mL, pre-degassed and purged with N₂ for 3 times), and then piperidine (1.29 g, 15.19 mmol, 1.50 mL, 17.2 eq) was added and the mixture was stirred at 25-30° C. for 2 hr under N₂ atmosphere. LC-MS showed compound 2 was consumed completely and one main peak with desired m/z (calculated MW: 455.51 observed m/z: 456.3 ([M+H]⁺)) was detected. The reaction mixture was purified by prep-HPLC (TFA condition), and compound 3 (400.0 mg, 879.1 µmol) was obtained as colorless oil.

A mixture of compound 3 (250.0 mg, 548.83 µmol, 1.0 eq), compound 4 (284.1 mg, 548.83 µmol, 1 eq), HATU (229.6 mg, 603.72 µmol, 1.1 eq), DIEA (141.9 mg, 1.10 mmol, 191.19 µL, 2.0 eq) in DCM (20 mL, pre-degassed and purged with $N_2$ for 3 times), and then the mixture was stirred at 25-30° C. for 2 hr under $N_2$ atmosphere. LC-MS showed compound 3 was consumed completely and one main peak with desired m/z (calculated MW: 955.06, observed m/z: 955.6 ([M+H]⁺)) was detected. The residue was purified by prep-HPLC (TFA condition). Compound 5 (400.0 mg, 419.1 µmol) was obtained as a white solid.

A mixture of Compound 5 (400.0 mg, 418.82 µmol, 1.0 eq) was dissolved in DMF (4 mL, pre-degassed and purged with $N_2$ for 3 times), and then piperidine (862.2 mg, 10.13 mmol, 1 mL, 24.2 eq) was added and the mixture was stirred at 25-30° C. for 2 hr under $N_2$ atmosphere. LC-MS showed Compound 5 was consumed completely and one main peak with desired m/z (MW: 732.83 observed m/z: 733.3 ([M+H]⁺)) was detected. The residue was purified by prep-HPLC (TFA condition). Compound 10F (200 mg, 272.9 µmol) was obtained as colorless oil.

Compound 10G:

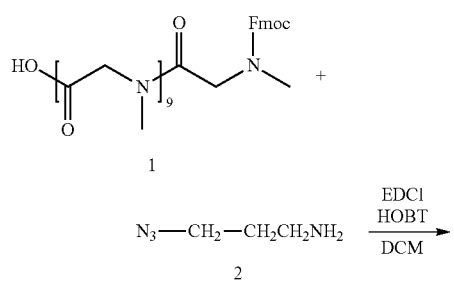

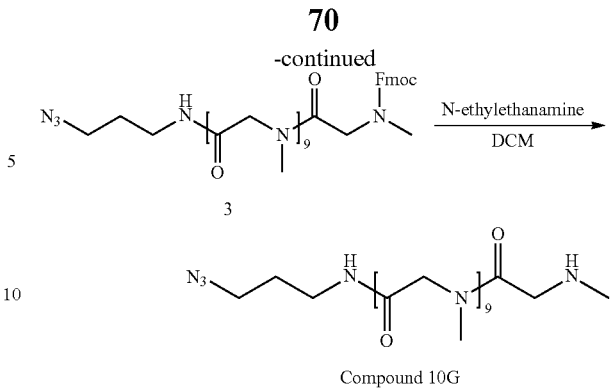

Compound 10G

A mixture of compound 1 (700.0 mg, 736.04 µmol, 1.0 eq) (obtained from solid phase peptide synthesis), 3-azidopropan-1-amine (73.7 mg, 736.04 µmol, 1.0 eq), EDCl (282.2 mg, 1.47 mmol, 2.0 eq), HOBt (119.4 mg, 883.25 µmol, 1.2 eq) was dissolved in DCM (5 mL, pre-degassed and purged with $N_2$ for 3 times), and then the mixture was stirred at 25-30° C. for 2 hr under $N_2$ atmosphere. LC-MS showed compound 1 was consumed completely and one main peak with desired (calculated MW: 1033.14, observed m/z: 1033.2 ([M+H]⁺)) was detected. The reaction mixture was treated with a few drops of 1 M HCl, and the organic layer was collected and evaporated under reduced pressure to remove solvent. Compound 3 (700.0 mg, crude) was obtained as a white solid.

A mixture of compound 3 (700.0 mg, 677.6 µmol, 1.0 eq), N-ethylethanamine (2.48 g, 33.88 mmol, 3.49 mL, 50.0 eq) was dissolved in DCM (5 mL, pre-degassed and purged with $N_2$ for 3 times), and then the mixture was stirred at 25-30° C. for 2 hr under $N_2$ atmosphere. LC-MS showed compound 3 was consumed completely and one main peak with desired m/z (calculated MW: 810.90, observed m/z: 811.1 ([M+H]⁺)) was detected. The reaction mixture was concentrated under reduced pressure to remove solvent. Compound 10G (400.0 mg, crude) was obtained as a white solid.

Compound 10H:

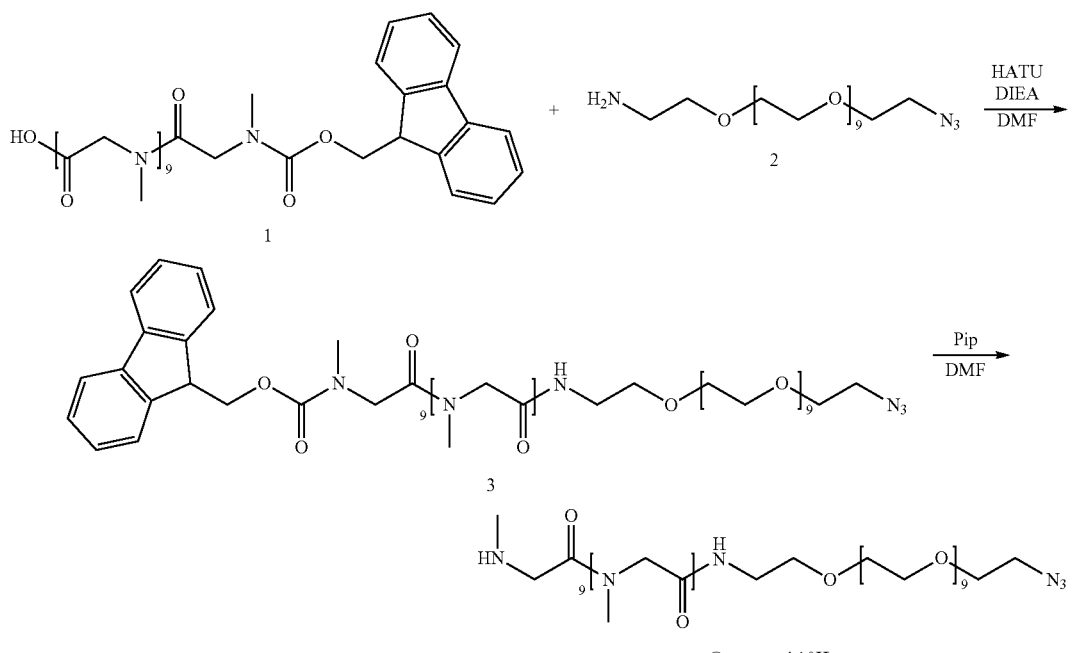

Compound 10H

A mixture of compound 1 (1 g, 1.05 mmol, 1.0 eq) (obtained from solid phase peptide synthesis), compound 2 (553.7 mg, 1.05 mmol, 1.0 eq) was dissolved in DMF (2 mL), following by addition of HATU (399.8 mg, 1.05 mmol, 1.0 eq) and DIEA (135.9 mg, 1.05 mmol, 183.2 µL, 1.0 eq). The mixture was stirred at 25-30° C. for 2 hr under $N_2$ atmosphere. TLC (Dichloromethane:Methanol=10:1, $R_f$=0.28) showed the compound 1 was consumed completely. The crude product was then directly used for next step without purification.

To a solution of compound 3 (1 g, 685.11 µmol, 1 eq) in DMF (8 mL) was added piperidine (2 mL, 714.05 µmol, 24 eq) in one portion at 25° C. The mixture was stirred for 15 mins at 25° C. LC-MS showed compound 3 was consumed completely and one main peak with desired m/z (calculated MW: 1237.4, observed m/z: 1238.4 ([M+H]$^+$)) was detected. The reaction mixture was purified by prep-HPLC (TFA condition). Compound 10H (757 mg, 611.77 µmol, 89.30% yield) was obtained as a white solid.

Compound 10I:

organic layer was evaporated under reduced pressure to remove solvent. Compound 2 (1.1 g, crude) was obtained as yellow oil.

A mixture of compound 2 (1.1 g, 1.06 mmol, 1 eq), N-ethylethanamine (3.89 g, 53.24 mmol, 5.48 mL, 50 eq) was dissolved in DCM (5 mL, pre-degassed and purged with $N_2$ for 3 times), and then the mixture was stirred at 20-25° C. for 1 hr under $N_2$ atmosphere. LC-MS showed compound 2 was consumed completely and one main peak with desired m/z (calculated MW: 810.90, observed m/z: 810.9 ([M+H]$^+$)) was detected. The reaction mixture was evaporated under reduced pressure and compound 3 (810 mg, crude) was obtained as a white solid.

A mixture of compound 3 (810.0 mg, 998.9 µmol, 1.0 eq), compound 4 (810.7 mg, 1.10 mmol, 1.1 eq), HATU (455.8 mg, 1.20 mmol, 1.2 eq), DIEA (258.2 mg, 2.00 mmol, 348.0 µL, 2.0 eq) was dissolved in DMF (2 mL, pre-degassed and purged with $N_2$ for 3 times), and then the mixture was stirred at 25-30° C. for 2 under $N_2$ atmosphere. LC-MS showed compound 3 was consumed completely and one main peak

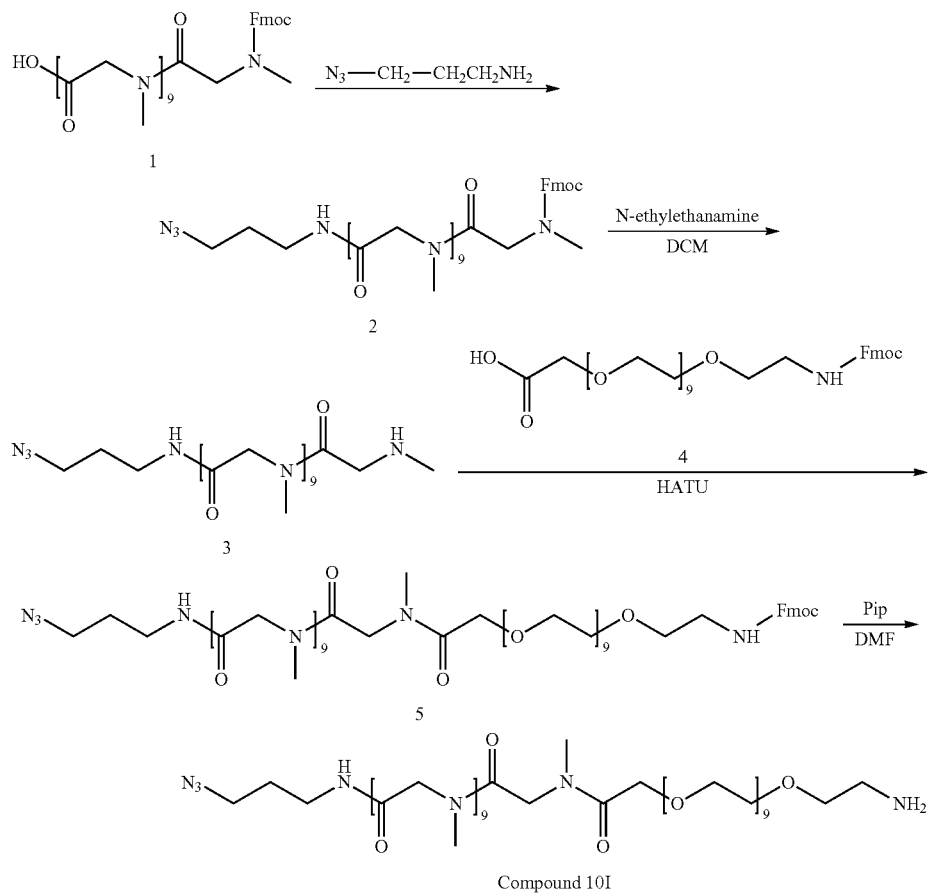

Compound 10I

A mixture of compound 1 (1.4 g, 1.47 mmol, 1.0 eq), 3-azidopropan-1-amine (162.1 mg, 1.62 mmol, 1.1 eq), EDCl (338.6 mg, 1.77 mmol, 1.2 eq), HOBt (238.7 mg, 1.77 mmol, 1.2 eq) was dissolved in DCM (5 mL, pre-degassed and purged with $N_2$ for 3 times), and then the mixture was stirred at 20-25° C. for 1 hr under $N_2$ atmosphere. LC-MS showed compound 1 was consumed completely and one main peak with desired m/z (calculated MW: 1033.14, observed m/z: 1033.2 ([M+H]$^+$)) was detected. The reaction mixture was treated with a few drops of 1 M HCl, and the with desired m/z (calculated MW: 1530.72, observed m/z: 765.5 ([M/2+H]$^+$)) was detected. The reaction mixture was treated with a few drops of 1 M HCl, and the organic layer was collected and evaporated under reduced pressure to remove solvent. Compound 5 (1.1 g, crude) was obtained as a yellow solid.

Compound 5 (1 g, 653.29 µmol, 1 eq) was dissolved in DCM (10 mL, pre-degassed and purged with $N_2$ for 3 times), following by addition of piperidine (2.39 g, 32.66 mmol, 3.36 mL, 50 eq), and then the mixture was stirred at 25-30°

C. for 2 hr under N₂ atmosphere. LC-MS showed Compound 5 was consumed completely and one main peak with desired m/z (calculated MW: 1308.47, observed m/z: 1308.4 ([M+H]⁺)) was detected. The residue was purified by prep-HPLC (TFA condition). Compound 10I (700 mg, 463.72 μmol, 70.98% yield) was obtained as a yellow solid.
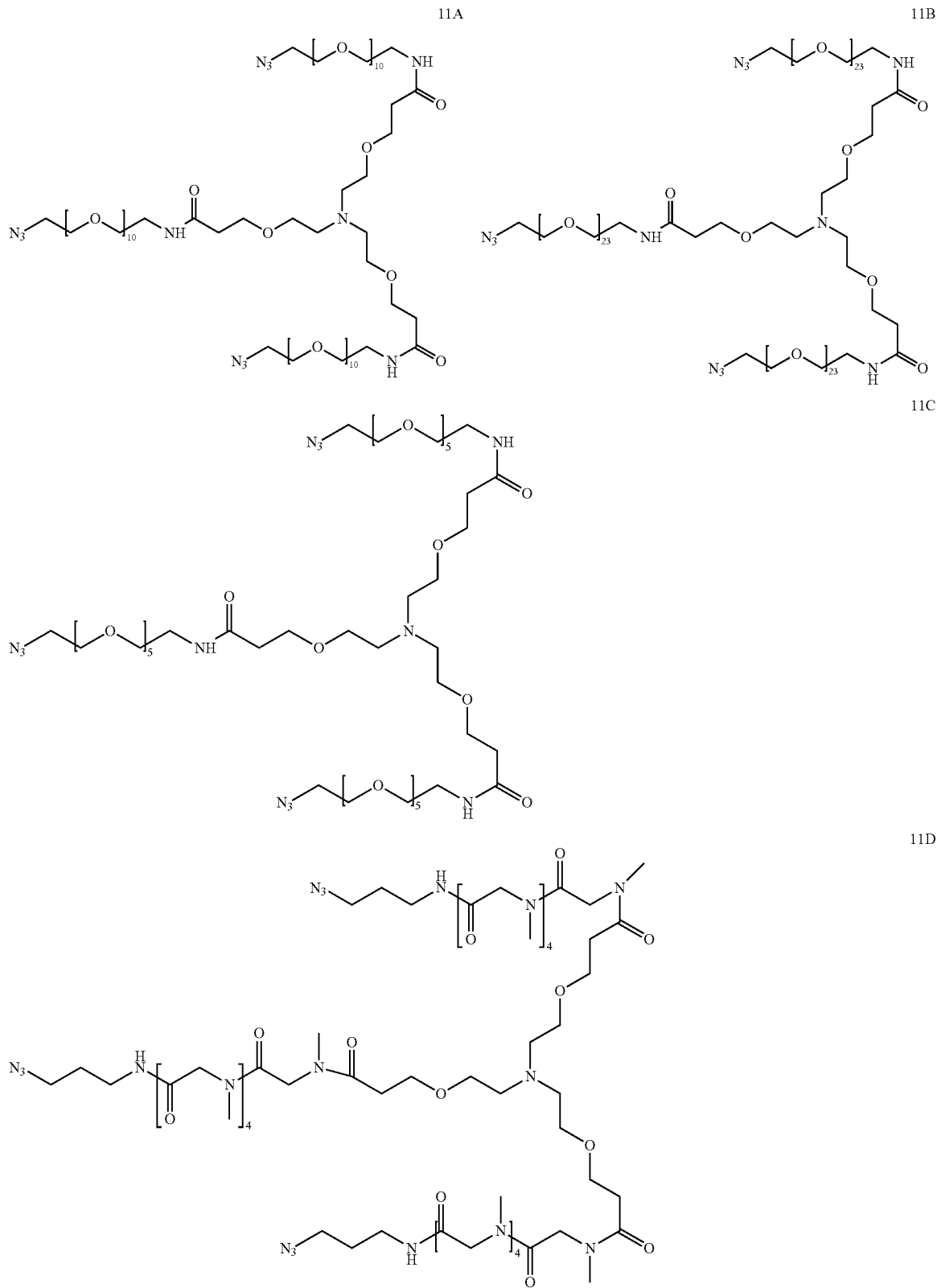

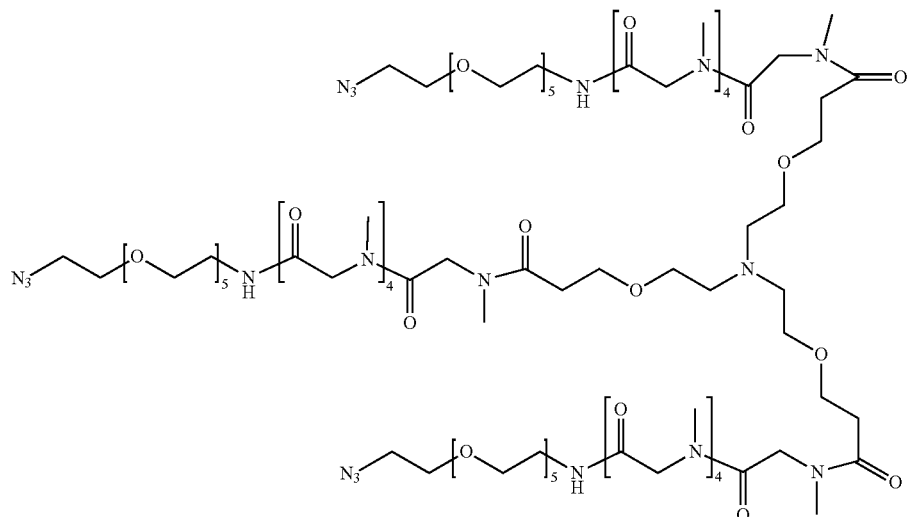
11E
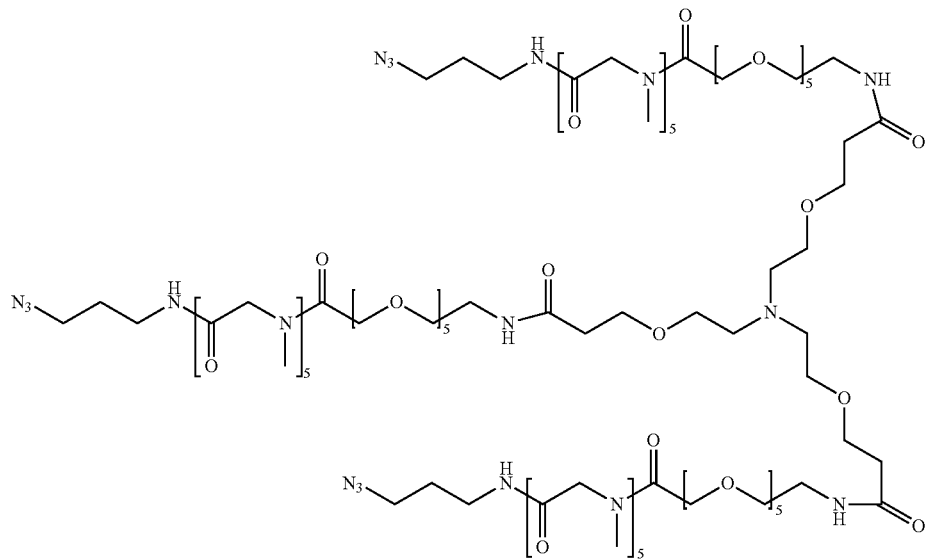
11F
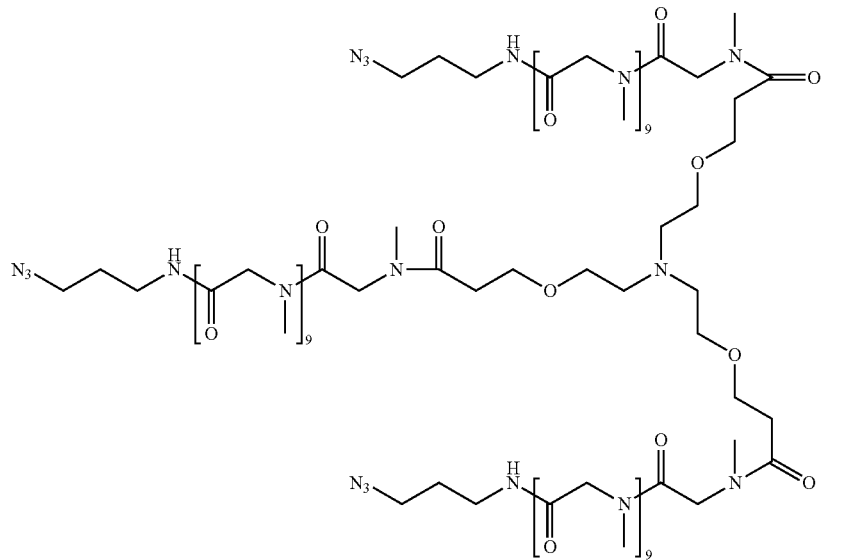
11G

-continued
11H
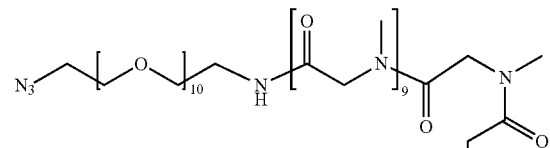
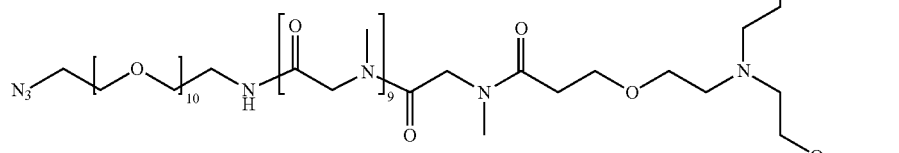
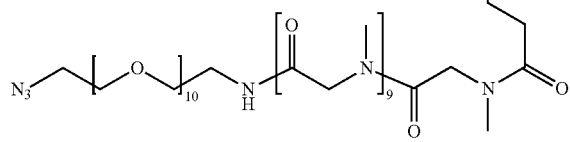
11I
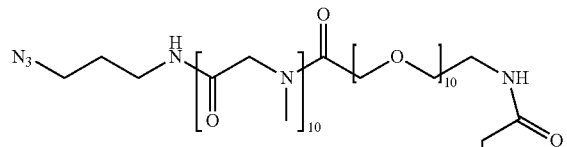
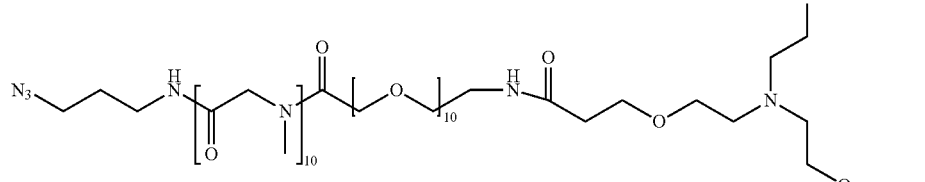
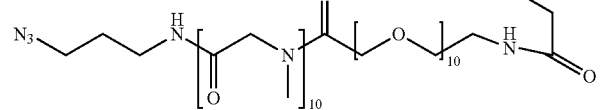
11J 11K
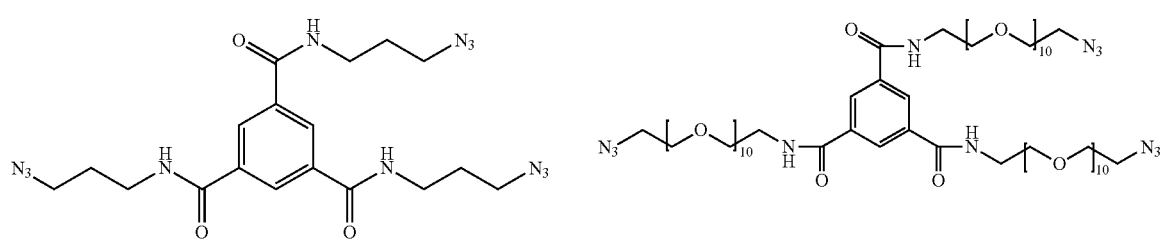
11L
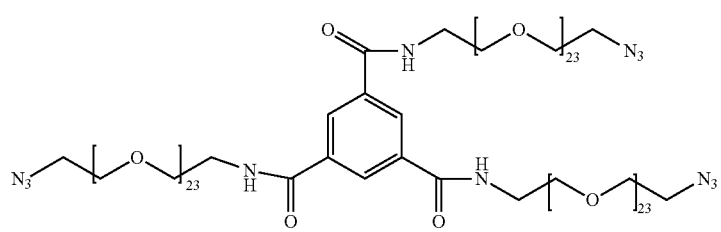

-continued
11M
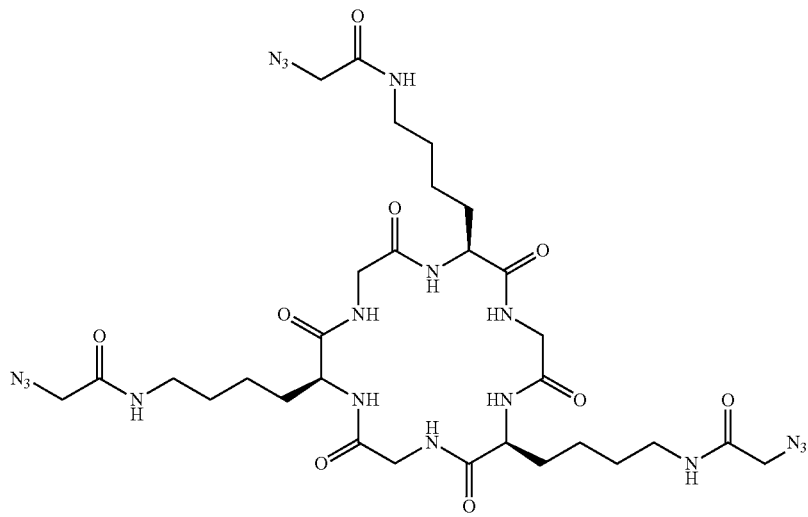
11N
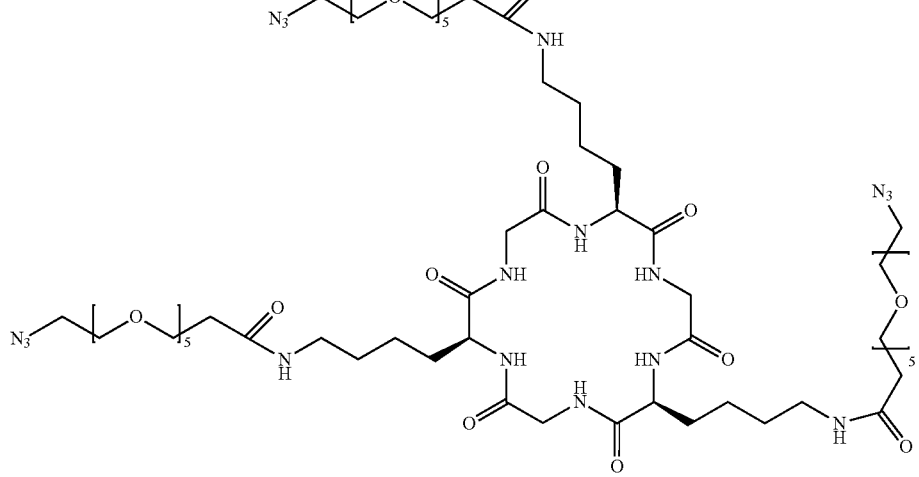
11O
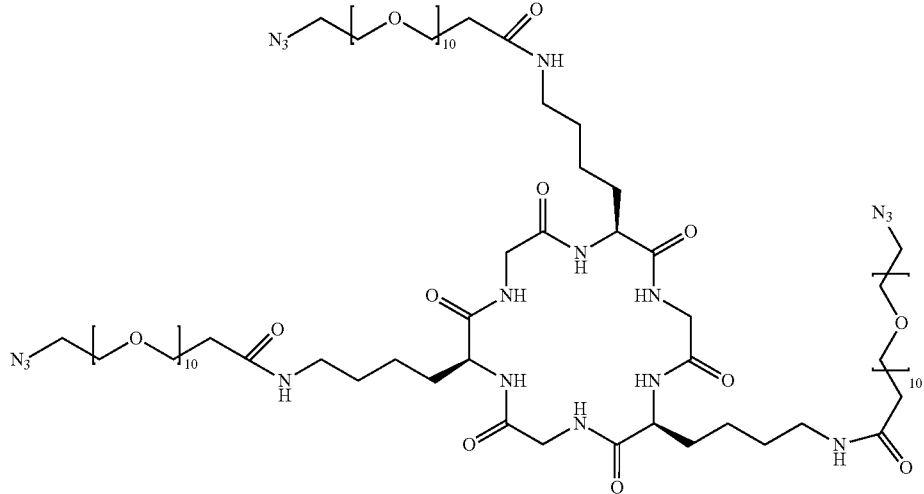

Compound 11A:

To a solution of compound 9A (100 mg, 248.86 μmol, 1 eq, HCl) in DMF (1 mL) was added EDCl (160 mg, 834.63 μmol, 3.35 eq) and HOBt (110 mg, 814.07 μmol, 3.27 eq) and DIPEA (192.98 mg, 1.49 mmol, 260.08 μL, 6.0 eq), then compound 10A (400 mg, 759.56 μmol, 3.05 eq) in DMF (1 mL) was added dropwise. The mixture was stirred at 25-30° C. for 12 hrs. LC-MS showed Reactant 1 was consumed completely and one main peak with desired m/z was detected. The reaction mixture was purified by prep-HPLC (TFA condition) to give compound 11A (128 mg, 64.30 μmol, 25.84% yield, 95% purity) as a colorless oil.

Compound 11B:

To a solution of compound 9A (50 mg, 124.43 μmol, 1.0 eq, HCl) in DMF (1 mL) was added HOBt (56 mg, 414.44 μmol, 3.33 eq), EDCl (80 mg, 417.31 μmol, 3.35 eq) and DIPEA (96.49 mg, 746.57 μmol, 130.04 μL, 6.0 eq) then compound 10B (420 mg, 382.06 μmol, 3.07 eq) in DMF (1 mL) was added dropwise. The mixture was stirred at 25-30° C. for 12 hrs. LC-MS showed Reactant 1 was consumed completely and one main peak with desired m/z was detected. The reaction mixture was purified by prep-HPLC (TFA condition) to give compound 11B (257 mg, 67.65 μmol, 54.37% yield, 95.0% purity) as a colorless oil.

Compounds 11C, 11D, 11E, 11F, 11G, 11H and 11I were synthesized in an analogous manner to that described above for Compound 11B using Compound 9A and one of Compounds 10C, 10D, 10E, 10F, 10G, 10H and 10I as starting materials, EDCl as the coupling reagent and DIPEA as the base.

Compound 11K:

To a solution of compound 9B (20.0 mg, 95.2 μmol, 1.0 eq), compound 10A (320.0 mg, 291.1 μmol, 3.06 eq) in DMF (5 mL) was added EDCl (60.0 mg, 313.0 μmol, 3.29 eq), HOBt (40.0 mg, 296.0 μmol, 3.11 eq), DMAP (10.0 mg, 81.8 μmol, 0.86 eq) and DIEA (44.5 mg, 344.5 μmol, 60 μL, 3.62 eq). The mixture was stirred at 30° C. for 12 hr. LC-MS showed compound 9B was consumed completely and one main peak with desired m/z (calculated MW: 3454.01, observed m/z: 1168.4000 ([M/3+H$_2$O]$^+$)) was detected. The reaction mixture was concentrated under reduced pressure to remove solvent to give a residue. The residue was purified by prep-HPLC (TFA condition). Compound 11K (200.0 mg, 57.9 μmol, 60.84% yield, 100% purity) was obtained as a white solid.

Compound 11J was synthesized in an analogous manner to that described above for Compound 11K using Compound 9B and Compound 10J as starting materials, EDCl as coupling reagent and DIPEA as base.

Compound 11L:

To a solution of compound 9B (20.0 mg, 95.2 μmol, 1.0 eq), compound 10B (152.0 mg, 288.6 μmol, 3.03 eq) in DMF (5 mL) was added EDCl (60.0 mg, 313.0 μmol, 3.29 eq), HOBt (40.0 mg, 296.0 μmol, 3.11 eq), DMAP (12.0 mg, 98.2 μmol, 1.03 eq) and DIEA (41.6 mg, 321.5 μmol, 56 μL, 3.38 eq). The mixture was stirred at 30° C. for 12 hr. LC-MS showed compound 9B was consumed completely and one main peak with desired m/z (calculated MW: 1735.96, observed m/z: 867.87 ([M/2+H]$^+$)) was detected. The reaction mixture was concentrated under reduced pressure to remove solvent to give a residue. The residue was purified by prep-HPLC (TFA condition). Compound 11L (140.0 mg, 79.8 μmol, 83.86% yield, 98.97% purity) was obtained as a colorless oil.

Compound 11M was synthesized in an analogous manner to that described below for Compound 11N using Compound 9C and Compound 10M as starting materials, EDCl as coupling reagent and DIPEA as base.

Compound 11N:

To a solution of compound 9C (20.0 mg, 36.0 μmol, 1.0 eq), compound 10M (40.0 mg, 119.3 μmol, 3.3 eq) in DMF (2 mL) was added EDCl (26.0 mg, 135.6 μmol, 3.8 eq), HOBt (18.0 mg, 133.2 μmol, 3.7 eq), DMAP (4.4 mg, 36.0 μmol, 1.0 eq) and DIEA (23.7 mg, 183.7 μmol, 32 μL, 5.1 eq). The mixture was stirred at 30° C. for 12 hr. LC-MS showed compound 9C was consumed completely and one main peak with desired m/z (calculated MW: 1507.68, observed m/z: 753.77 ([M/2+H]$^+$)) was detected. The reaction mixture was concentrated under reduced pressure to remove solvent to give a residue. The residue was purified by prep-HPLC (TFA condition). Compound 11N (40.0 mg, 26.5 μmol, 73.71% yield, 100% purity) was obtained as a colorless oil.

Compound 11O:

To a solution of compound 9C (10.0 mg, 18.0 μmol, 1.0 eq), compound 10L (30.0 mg, 54.0 μmol, 3.0 eq) in DMF (2 mL) was added EDCl (28.0 mg, 144.0 μmol, 8.0 eq), HOBt (13.0 mg, 90.0 μmol, 5.0 eq), DMAP (5.0 mg, 36.0 μmol, 2.0 eq) and DIEA (19 mg, 144.0 μmol, 25 μL, 8.0 eq). The mixture was stirred at 30° C. for 12 hr. LC-MS showed compound 9C was consumed completely and one main peak with desired m/z (calculated MW: 2168.47, observed m/z: 1183.88 ([M/2+H]$^+$)) was detected. The reaction mixture was concentrated under reduced pressure to remove solvent to give a residue. The residue was purified by prep-HPLC (TFA condition). Compound 11O (17.8 mg, 8.2 μmol, 45.61% yield, 100% purity) was obtained as a white oil.

General Procedure for Preparation of Tetrameric Azide Linker

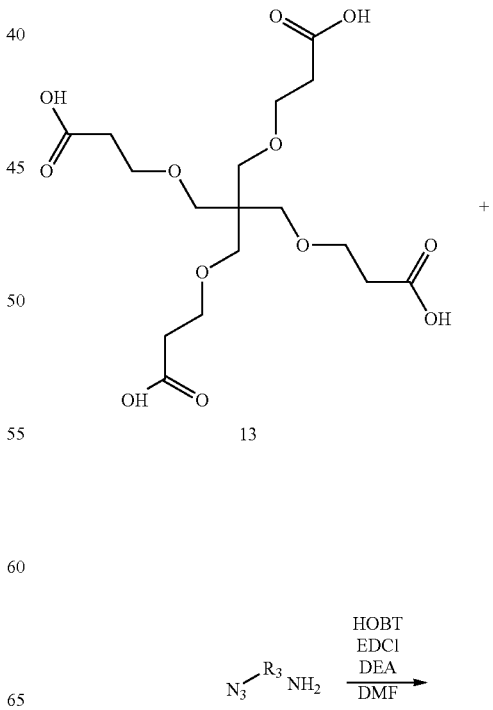

Compound 10:

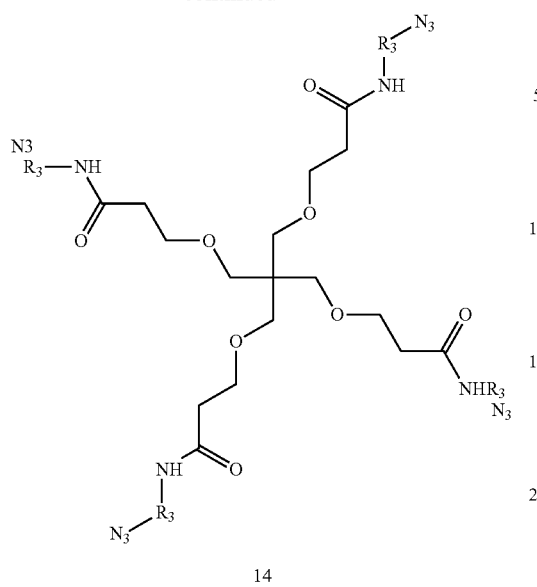

Compound 10N:

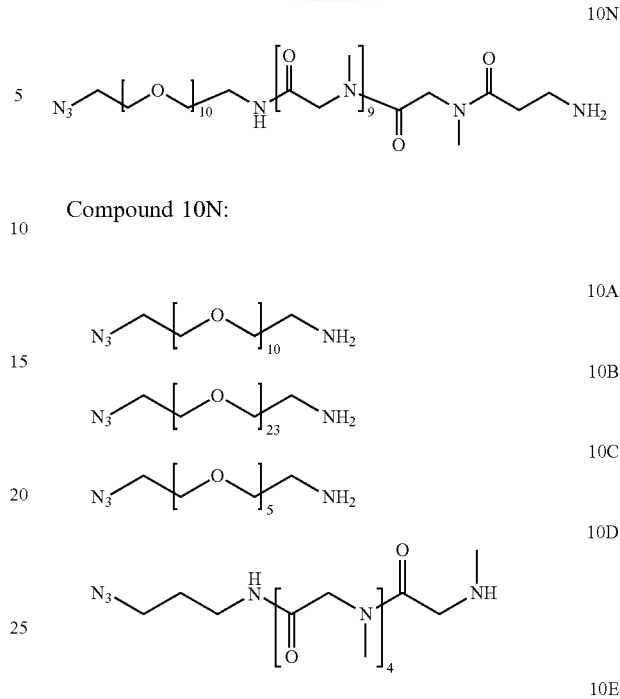

A mixture of compound 1 (900 mg, 1.23 mmol, 1.0 eq) and compound 2 (1.0 g, 3.21 mmol, 2.6 eq) was dissolved in DCM (20 mL), following by addition of (284.0 mg, 1.48 mmol, 1.2 eq), HOBt (200.2 mg, 1.48 mmol, 1.2 eq). The mixture was stirred at 25° C. for 2 hr. LC-MS showed compound 1 was consumed completely and one peak with desired m/z (calculated MW: 1021.49, observed m/z: 1022.2 ([M+H]$^+$)) was detected. The reaction mixture was concentrated under reduced pressure to remove solvent. The residue was purified by prep-HPLC (TFA condition). Compound 3 (0.900 g, 880.53 μmol, 71.30% yield) was obtained as a white solid.

A mixture of compound 3 (500.0 mg, 489.19 μmol, 1.0 eq), compound 4 (257.6 mg, 489.19 μmol, 1.0 dissolved in DCM (5 mL), following by addition of HOBt (132.2 mg, 978.37 µmol, 2.0 eq), EDCl (187.6 mg, 978.37 µmol, 2.0 eq). The mixture was stirred at 25-30° C. for 2 hrs. LC-MS showed compound 3 was consumed completely and one main peak with desired m/z (MW: 1529.80 observed m/z: 765.9 ([M/2+H]$^+$) was detected. The reaction mixture was concentrated under reduced pressure to remove solvent to give a residue. The residue was purified by prep-HPLC (neutral condition). Compound 3 (420 mg, 246.94 µmol, 50.48% yield) was obtained as colorless oil.

Compound 5 (420 mg, 274.38 µmol, 1.0 eq) was dissolved in DMF (4 mL), following by addition of piperidine (865.2 mg, 10.16 mmol, 1 mL, 37 eq). The mixture was stirred at 25-30° C. for 2 hr. LC-MS showed compound 5 was consumed completely and one main peak with desired m/z (calculated MW: 1308.48, observed m/z: 654.8 ([M/2+H]$^+$) was detected. The crude product was purified by prep-HPLC (TFA condition). Compound 10N (386 mg, 265.50 µmol, 96.76% yield) was obtained as colorless oil.

Compound 14:

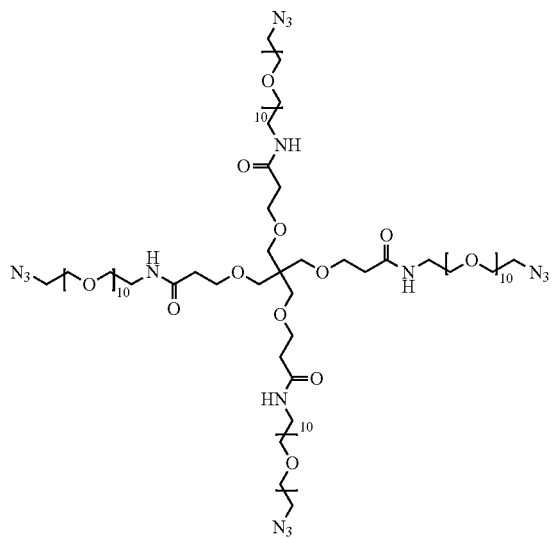

14A

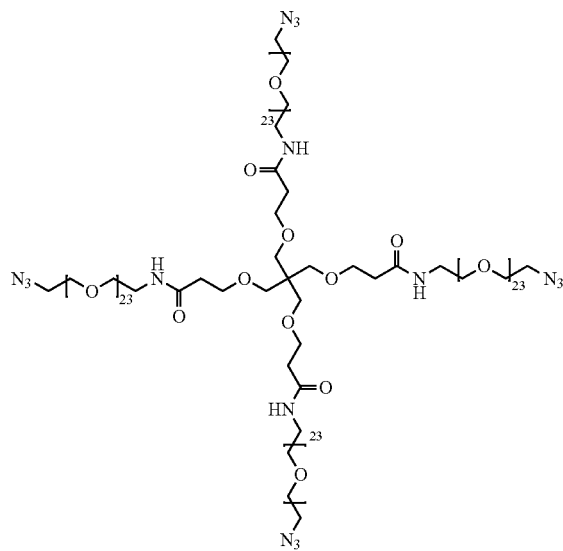

14B

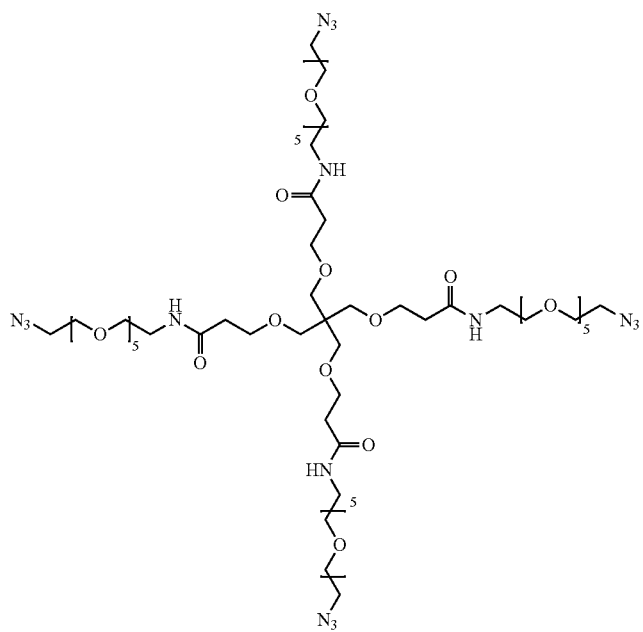

14C

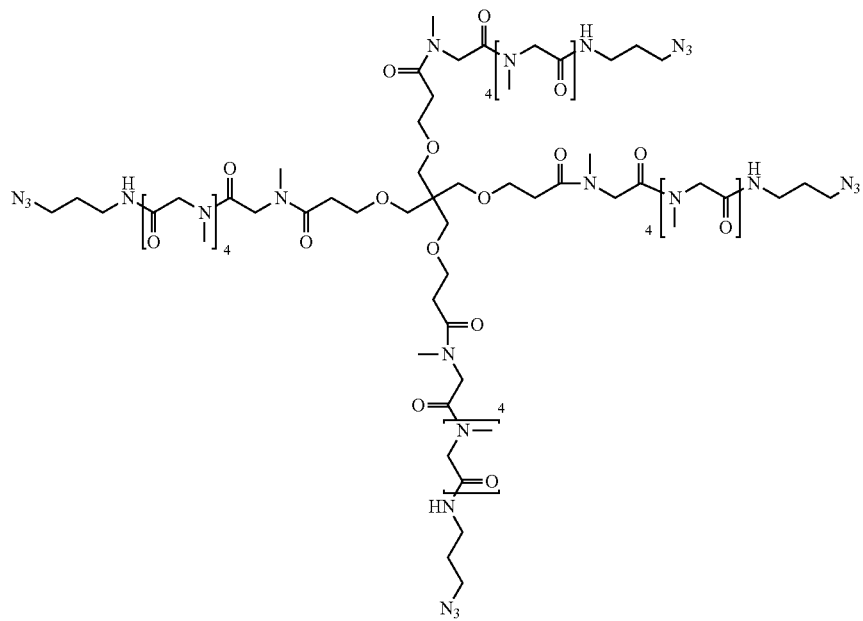
14D
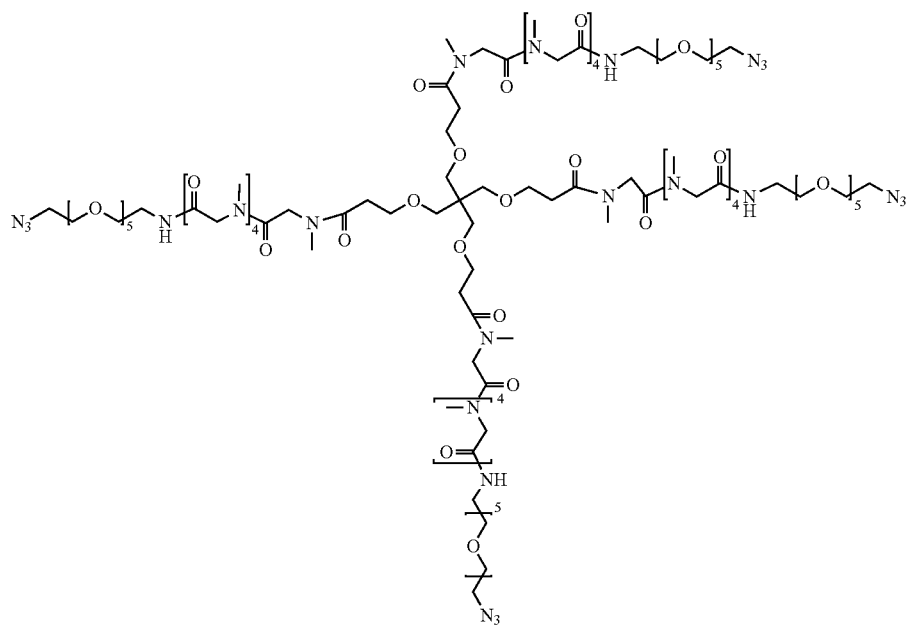
14E

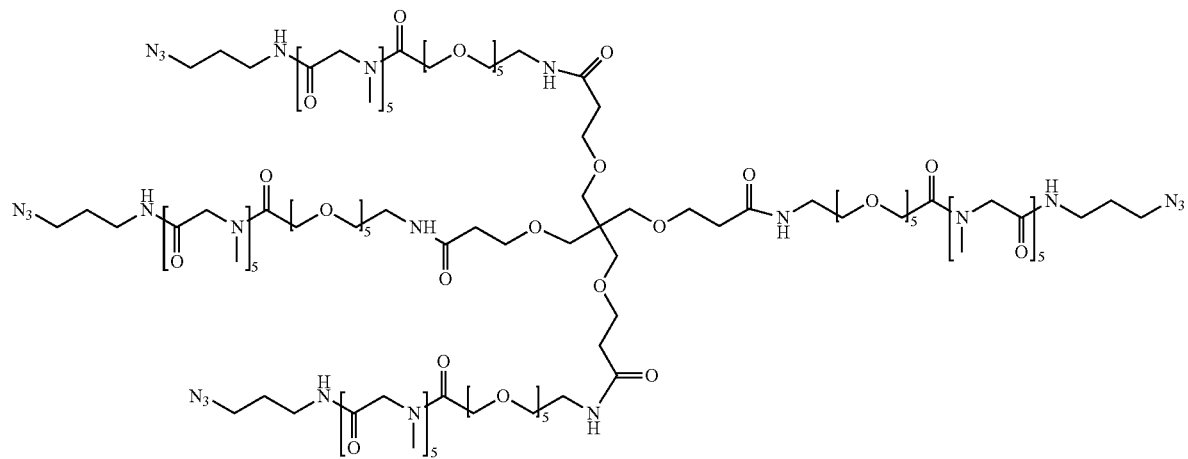
14F
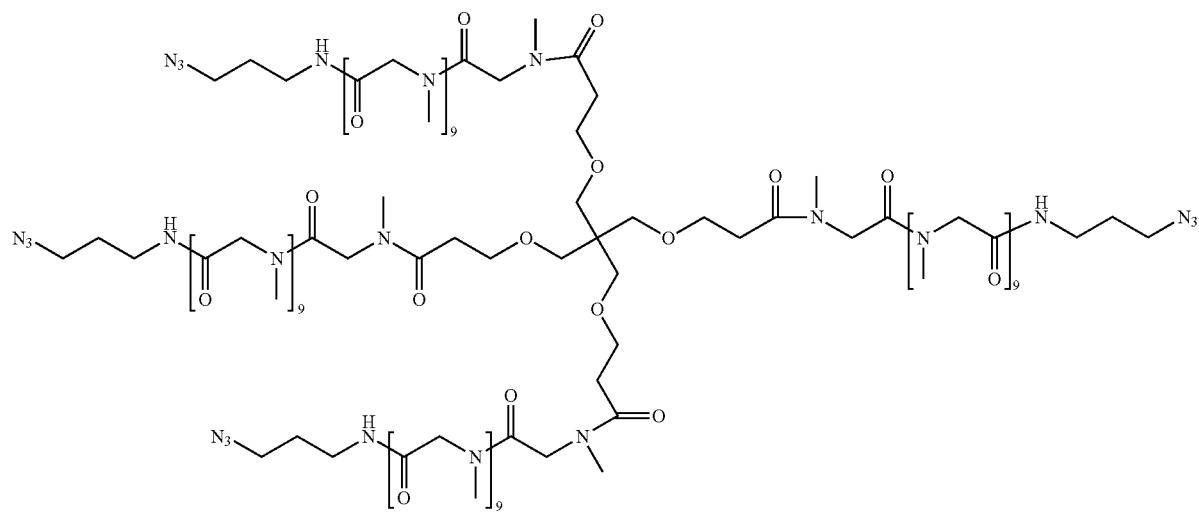
14G

-continued

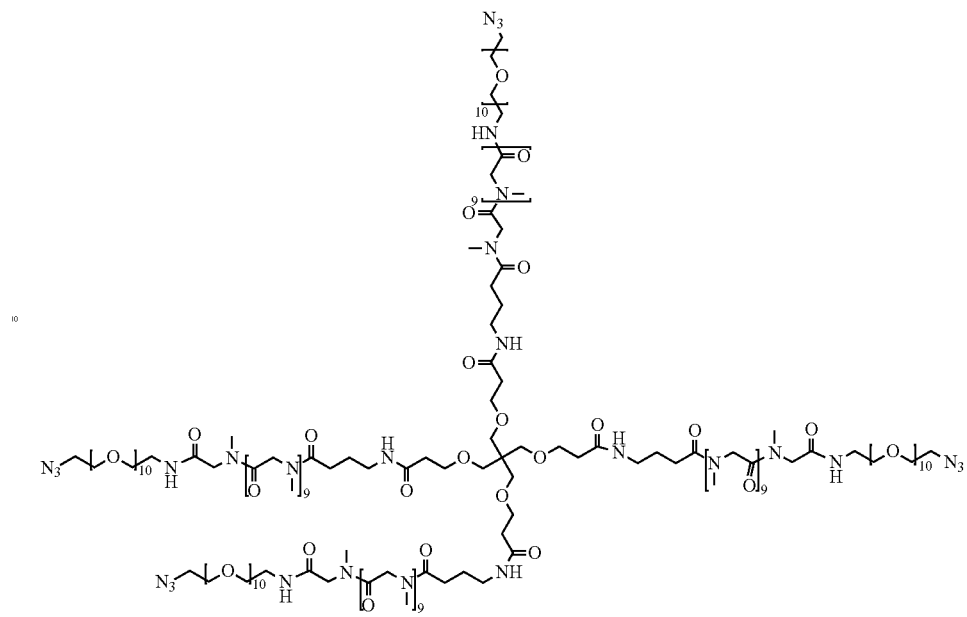

14H

Compound 14A:

To a solution of compound 13 (100 mg, 235.63 μmol, 1 eq) in DMF (1 mL) was added EDCl (200 mg, 1.04 mmol, 4.43 eq) and HOBt (140 mg, 1.04 mmol, 4.4 eq) and DIPEA (185.50 mg, 1.44 mmol, 0.25 mL, 6.09 eq), then compound 10A (500 mg, 949.45 μmol, 4.03 eq) in DMF (1 mL) was added dropwise. The mixture was stirred at 25-30° C. for 12 hrs. LC-MS showed LC-MS showed no Reactant 1 was remained. Several new peaks were shown on LC-MS and ~50% of desired compound was detected. The reaction mixture was purified by prep-HPLC (TFA condition) to give compound 14A (385 mg, 148.75 μmol, 63.13% yield, 95% purity) as a light yellow oil.

Compound 14B:

To a solution of compound 13 in DMF (1 mL) was added HOBt (56 mg, 414.45 μmol, 4.40 eq) and EDCl (80 mg, 417.32 μmol, 4.43 eq) and DIEA (73.09 mg, 565.51 μmol, 98.50 μL, 6.0 eq) then compound 10B (420 mg, 382.06 μmol, 4.05 eq) in DMF (1 mL) was added dropwise. The mixture was stirred at 20° C. for 12 hrs. LC-MS showed no compound 13 was remained. Several new peaks were shown on LC-MS and 50% of desired compound was detected. The mixture was purified by prep-HPLC (TFA condition) to give compound 14B (225 mg, 47.37 μmol, 50.26% yield, 100% purity) as a white solid.

Compounds 14C, 14D, 14E, 14F, 14G, and 14H were synthesized in an analogous manner to that described above for Compound 14B using Compound 13, and one of Compounds 10A, 10B, 10C, 10D, 10E, 10F, 10G and 10N as starting materials, EDCl as the coupling reagent and DIPEA as the base.

General Procedure for Preparation of Compound Trimeric Bicycle Conjugates

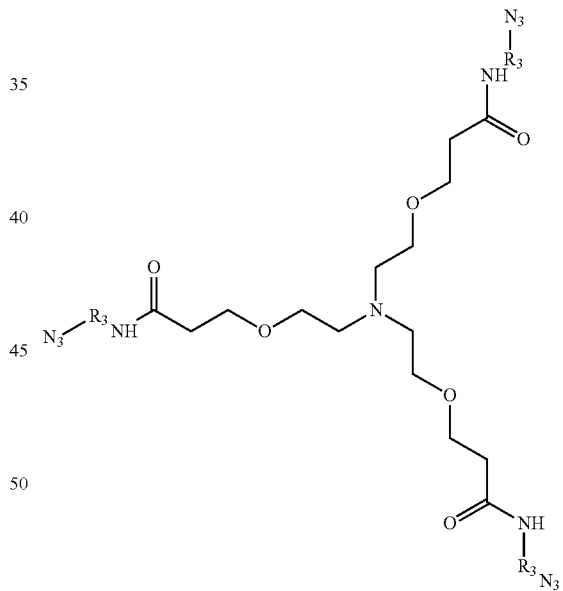

11

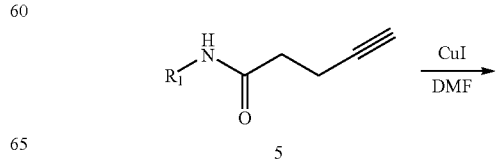

5

-continued
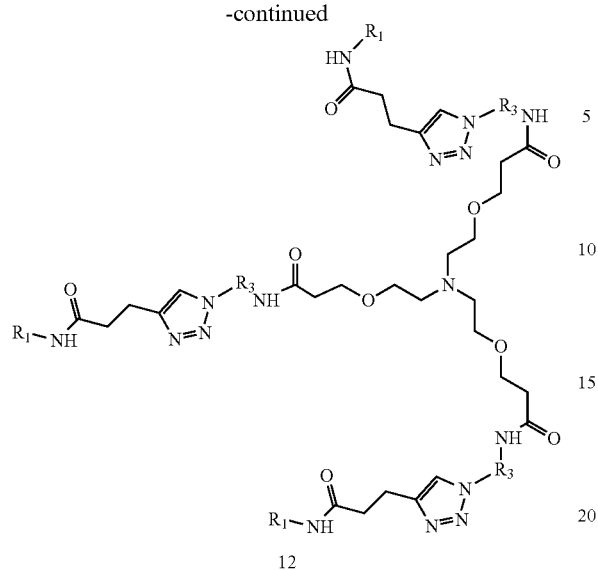
12
Compound 11:
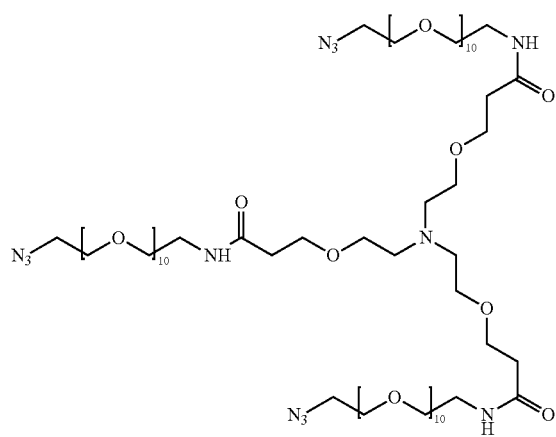
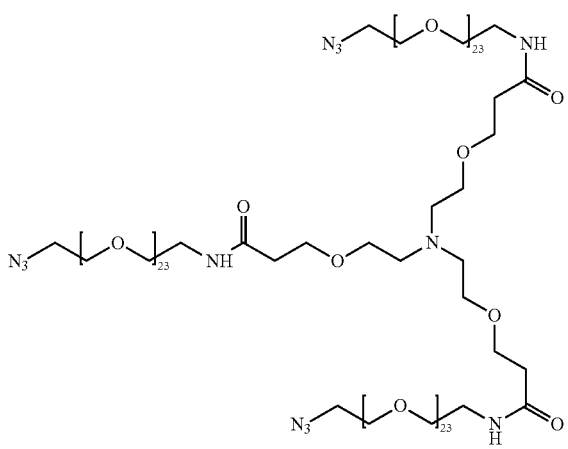
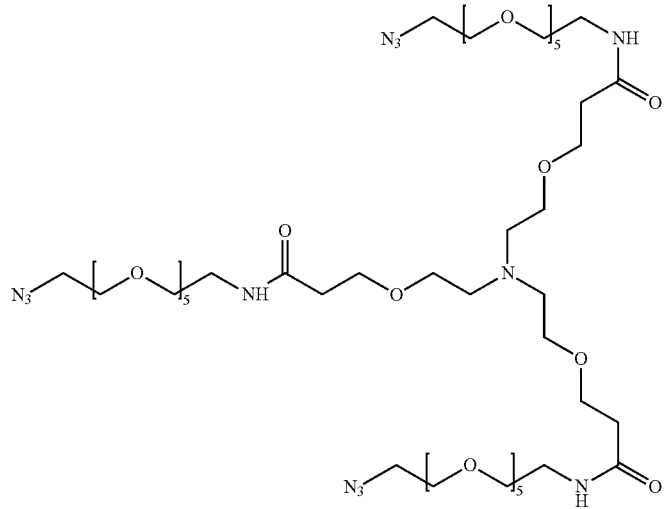

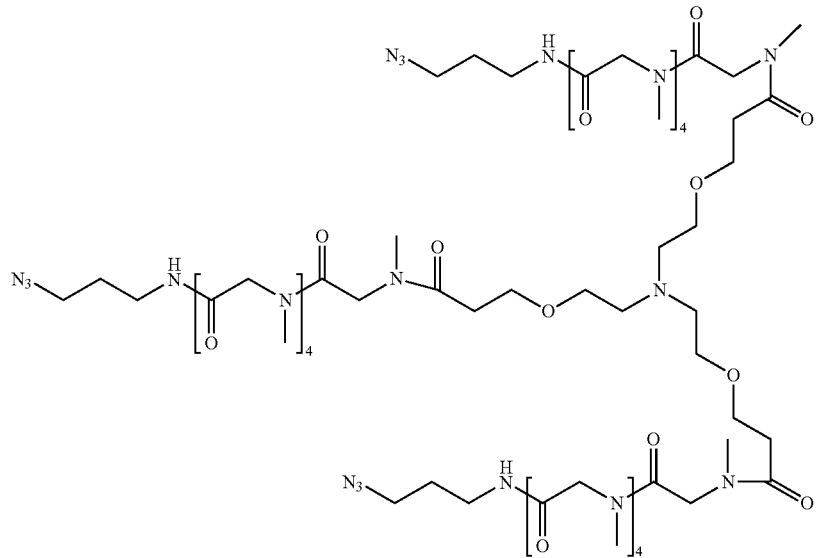
11D
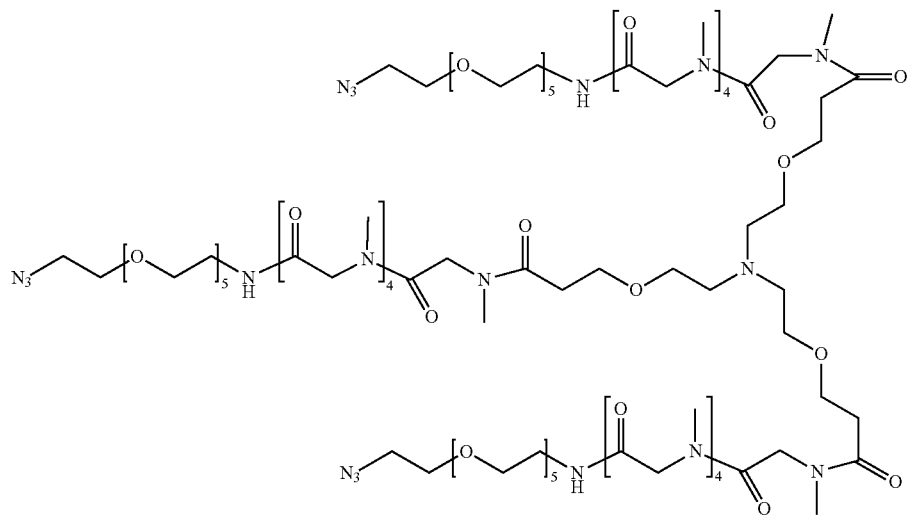
11E
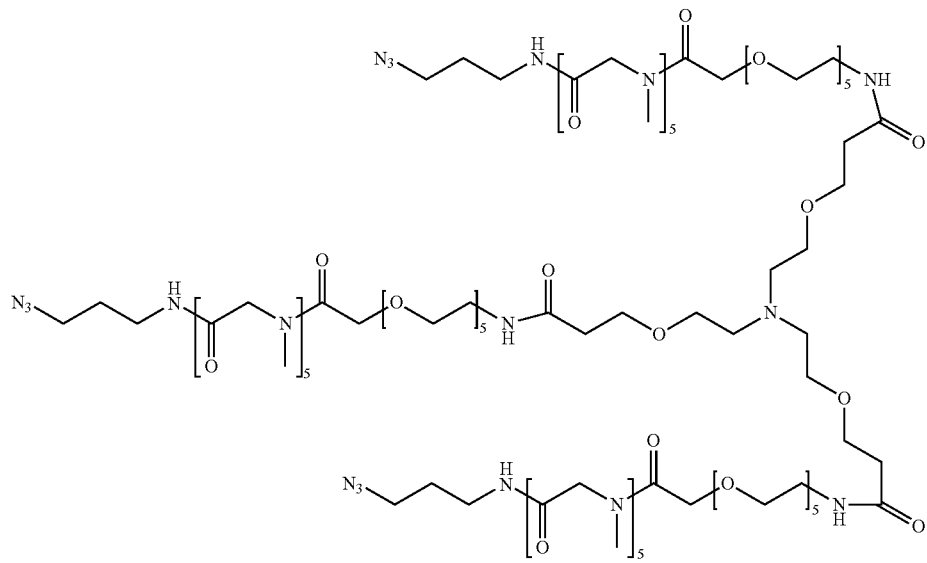
11F

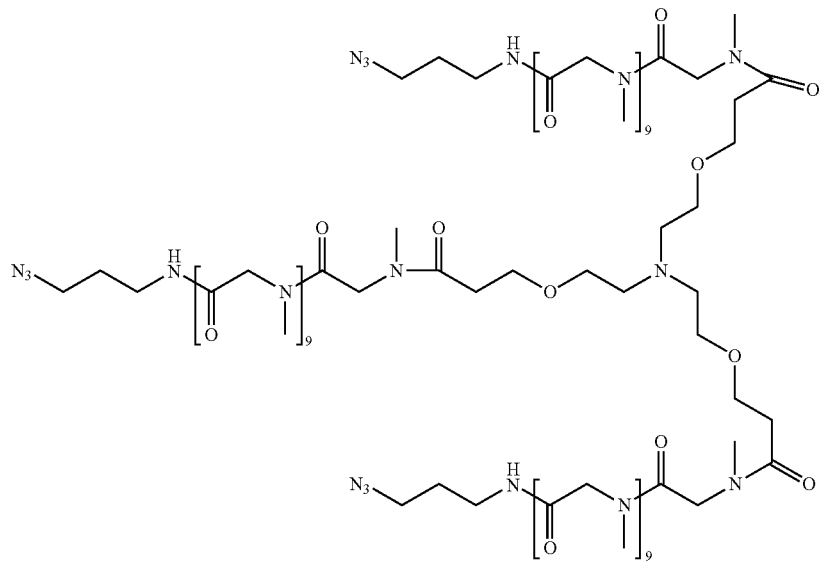
11G
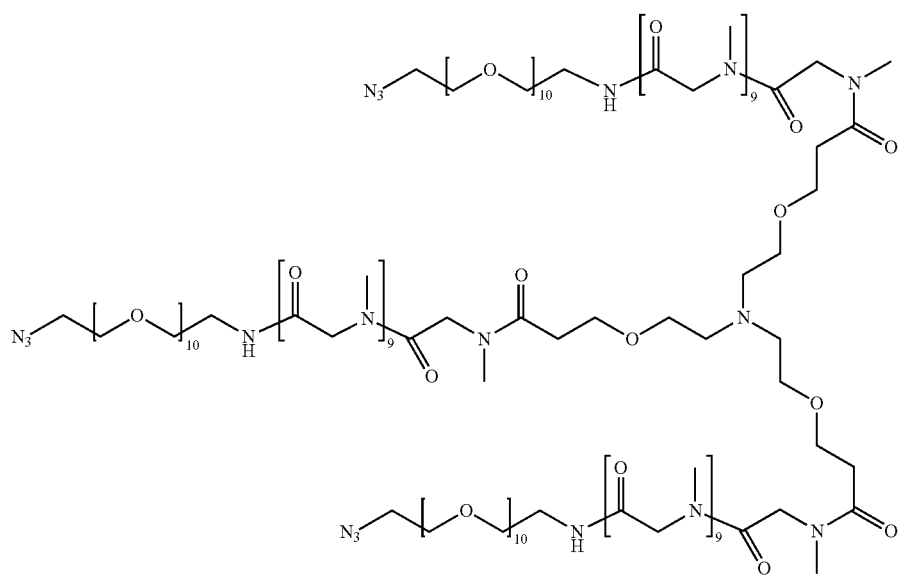
11H

-continued
11I
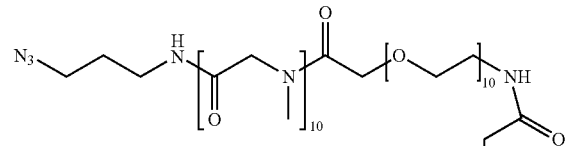
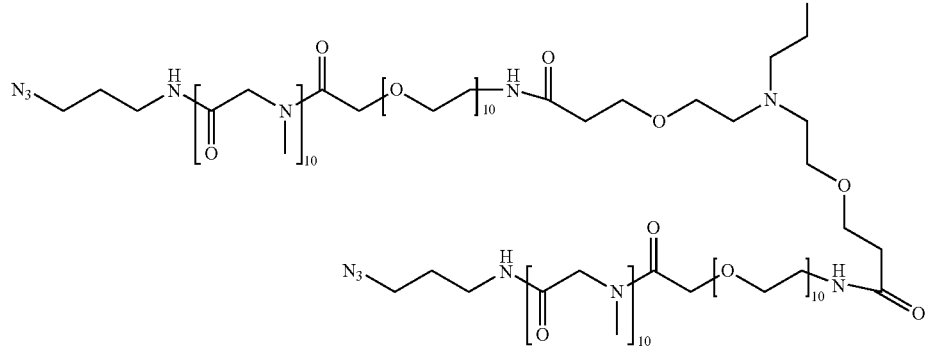
11J
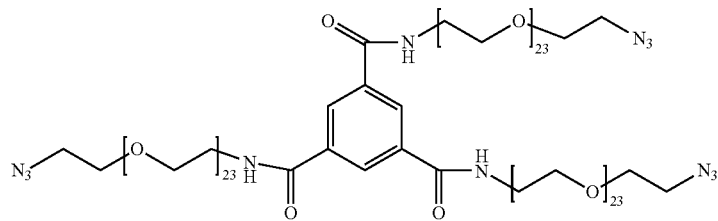
11K
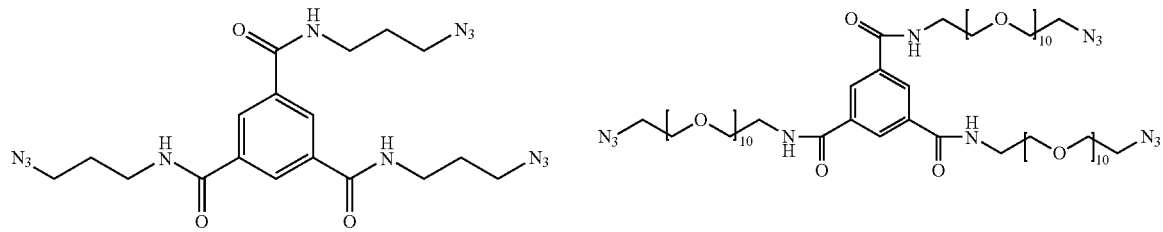
11L
11M
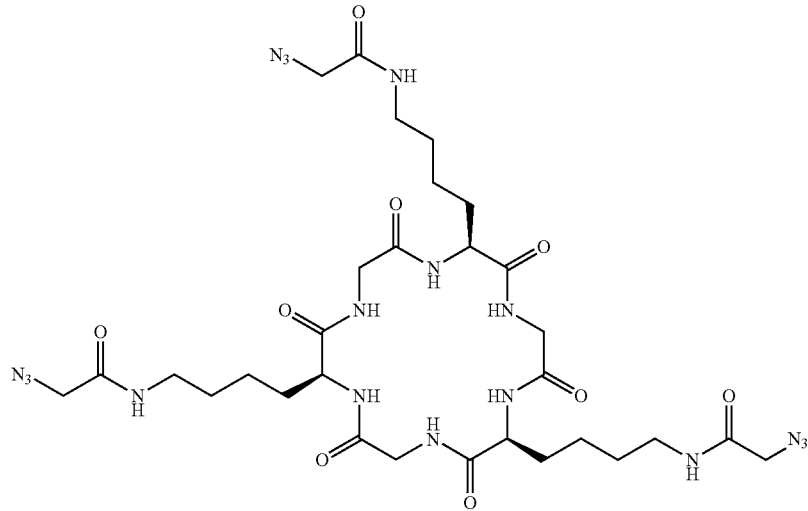

-continued
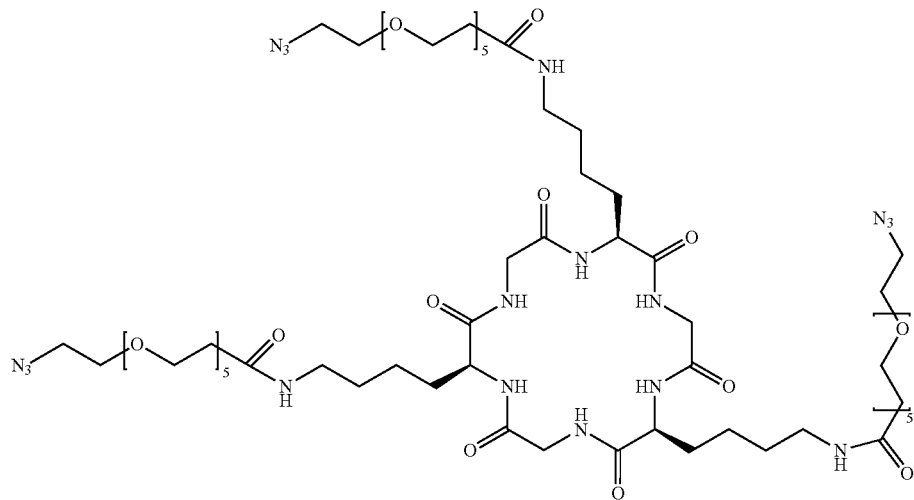
11N
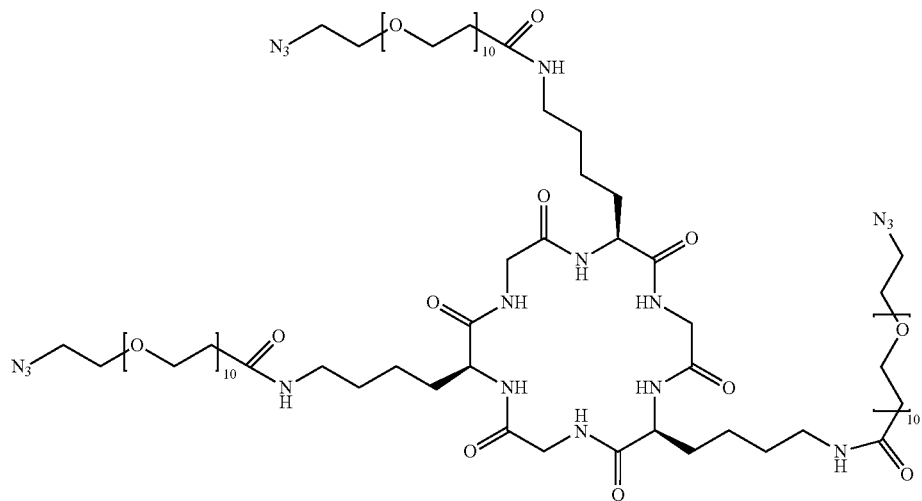
11O
Compound 5:
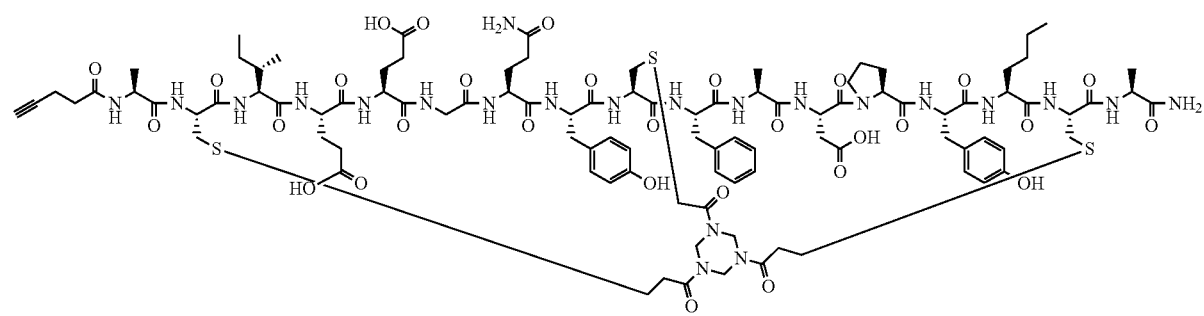
Monomer 1A

Monomer 2A
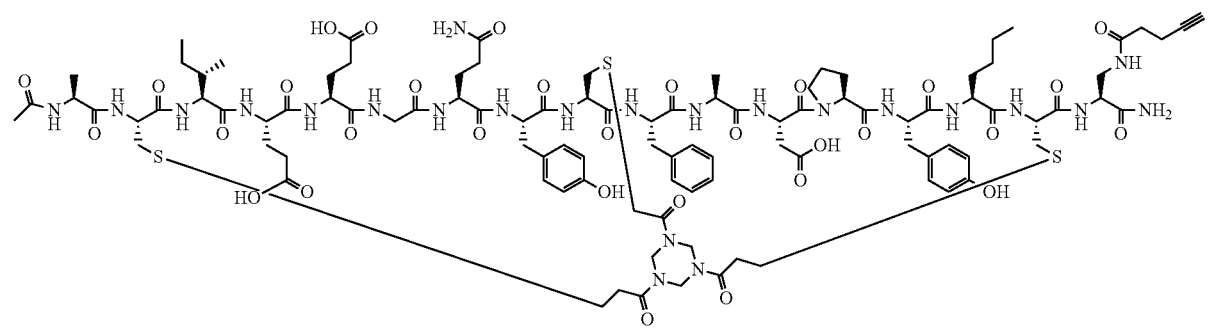
Monomer 3A
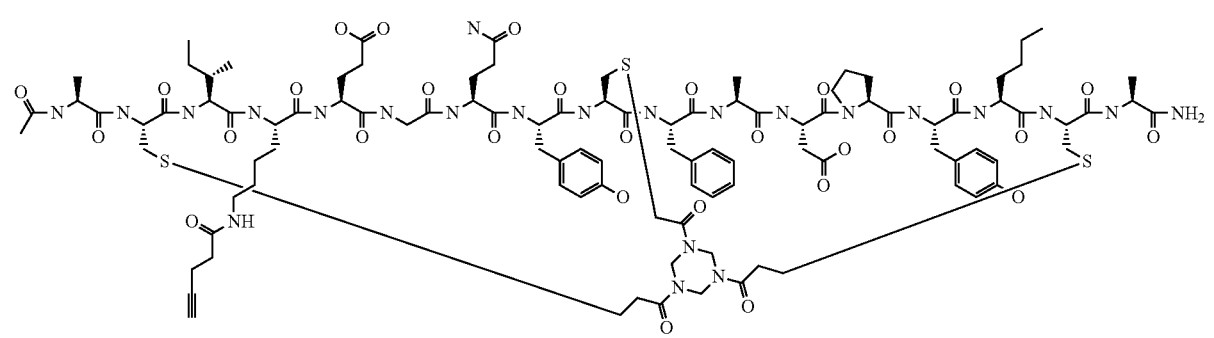
Monomer 4A
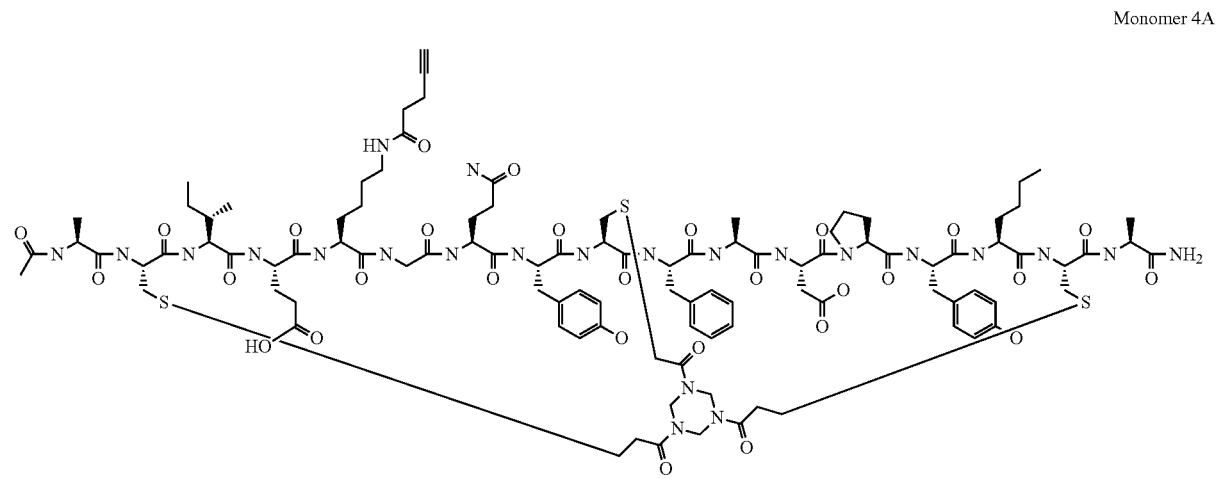
Monomer 5A
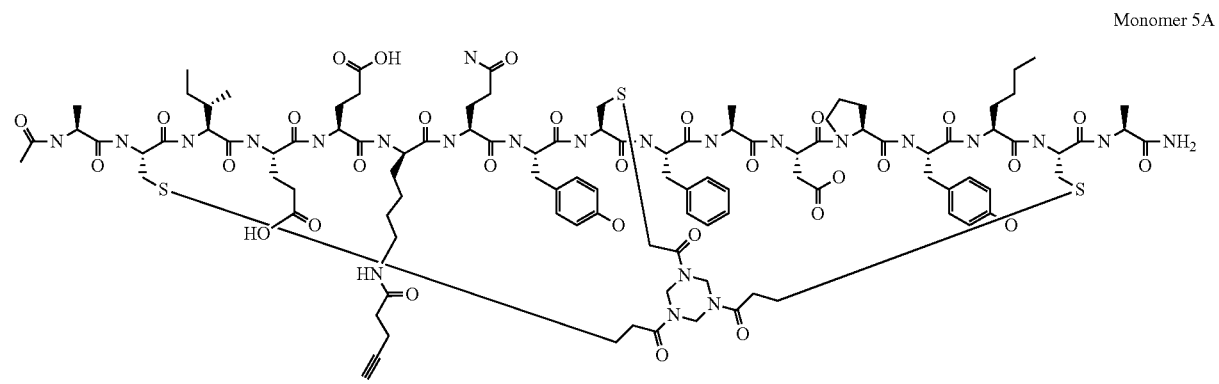

Monomer 6A
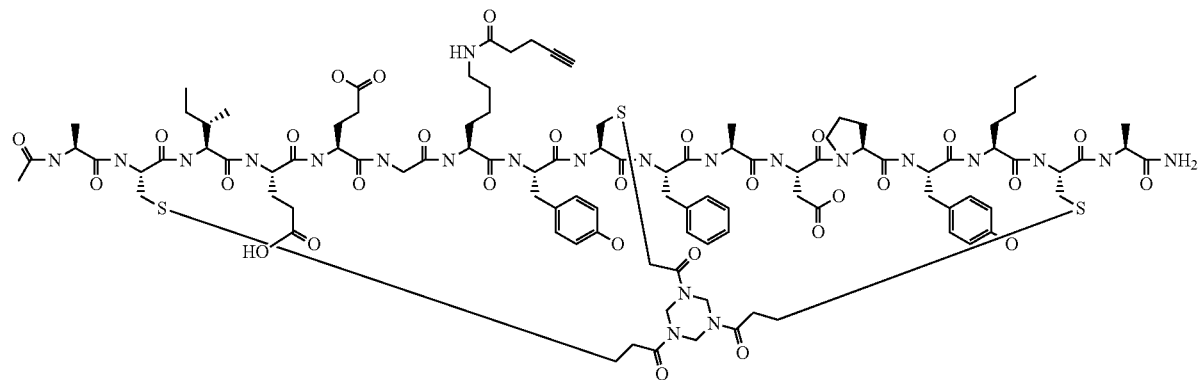
Monomer 7A
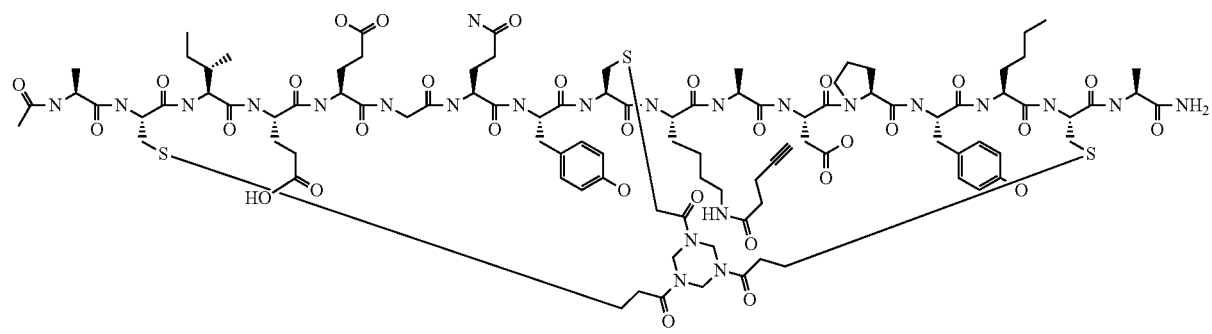
Monomer 8A
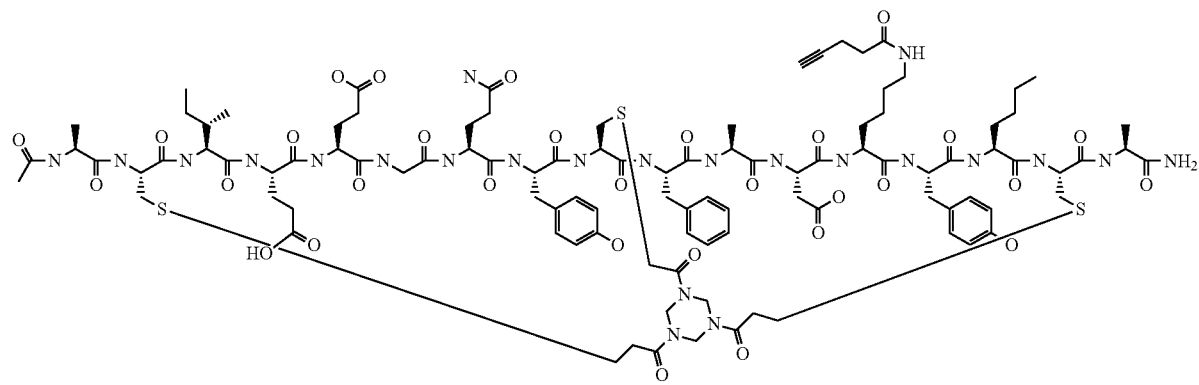
Monomer 9A
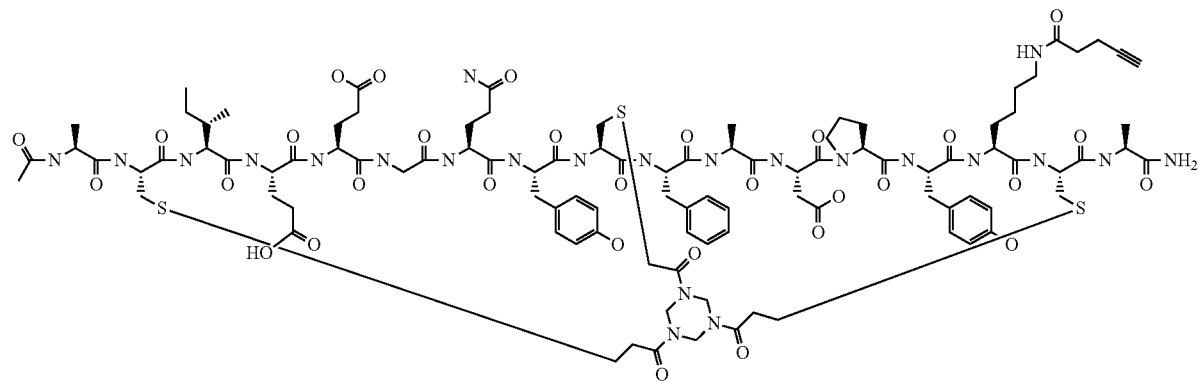

Monomer 10A
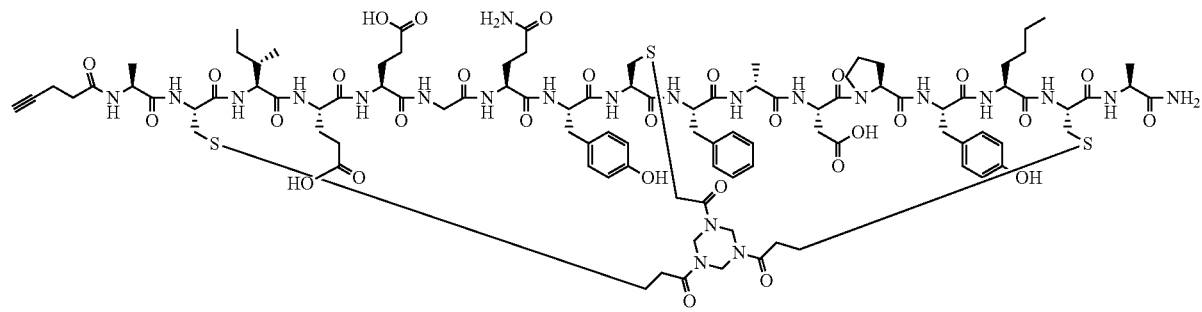
Monomer 11A
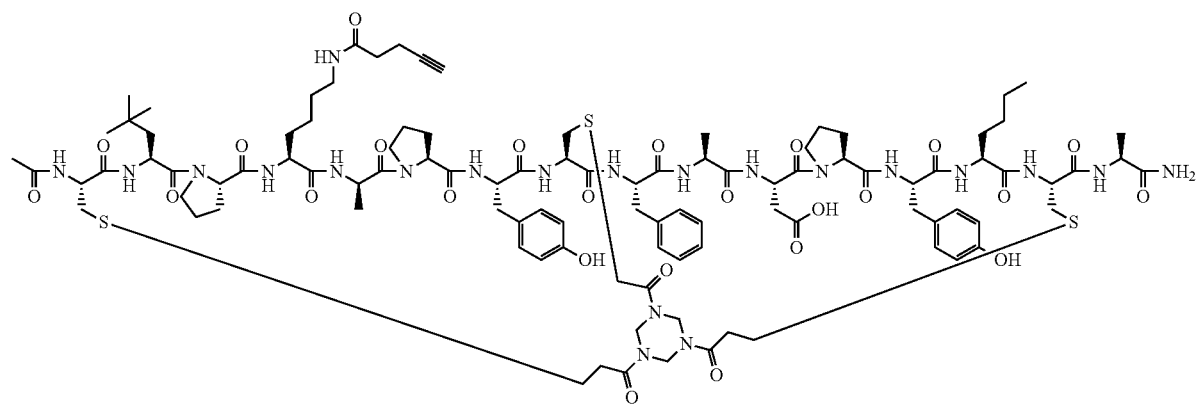
Monomer 12A
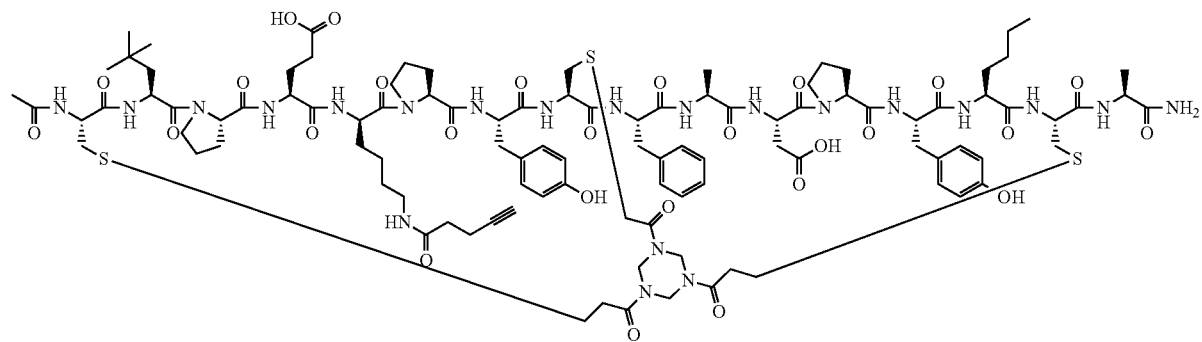
Monomer 13A
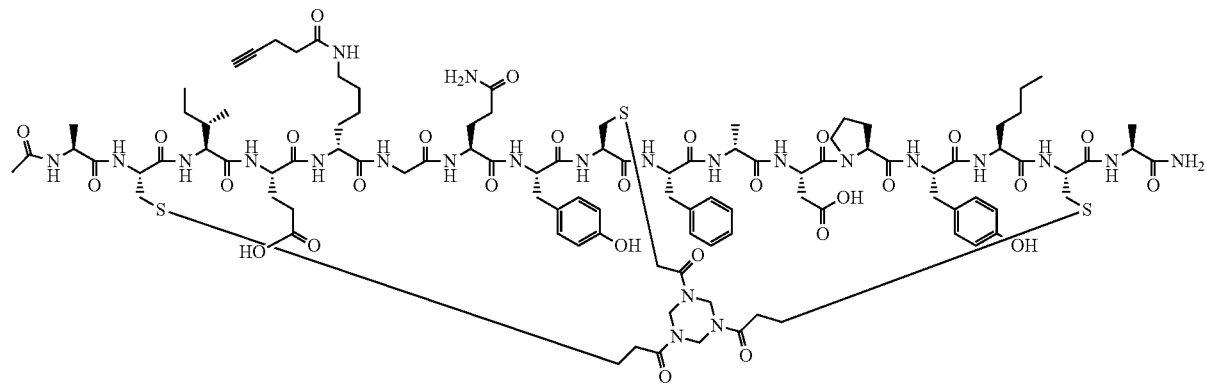

Monomer 14A
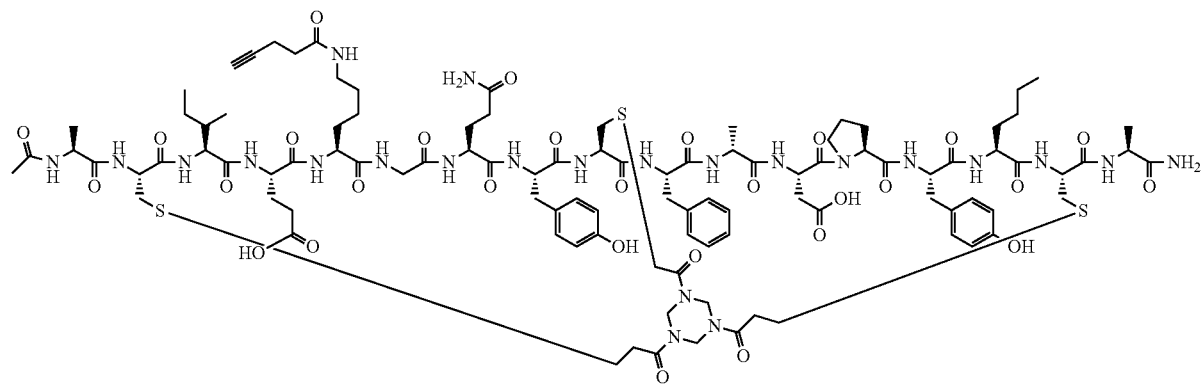
Monomer 15A
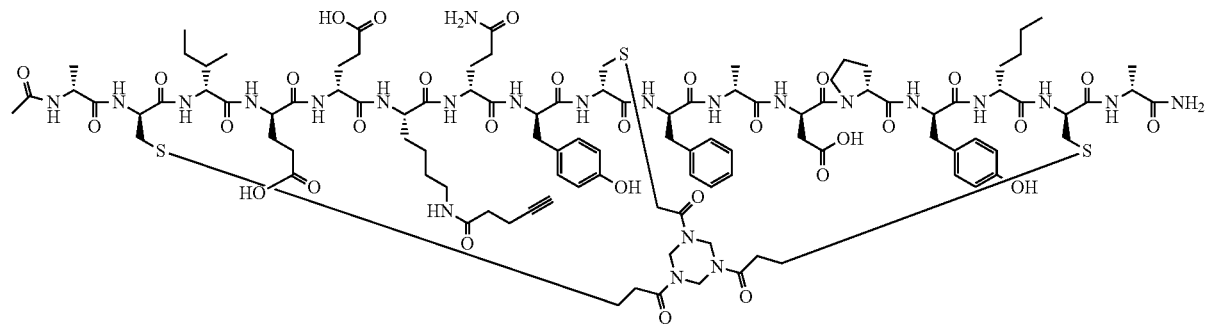
Compound 12:
BCY7827
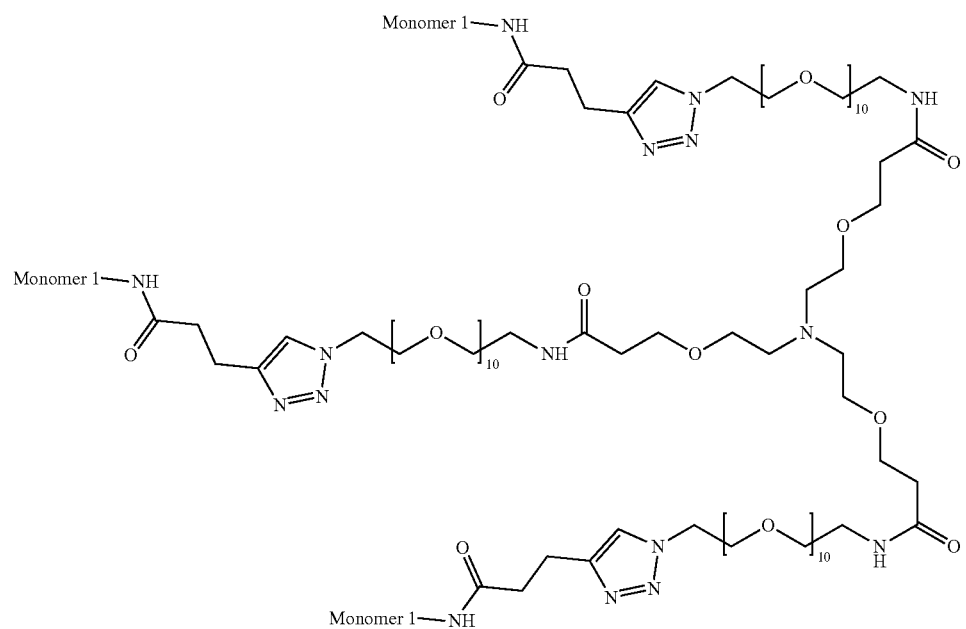

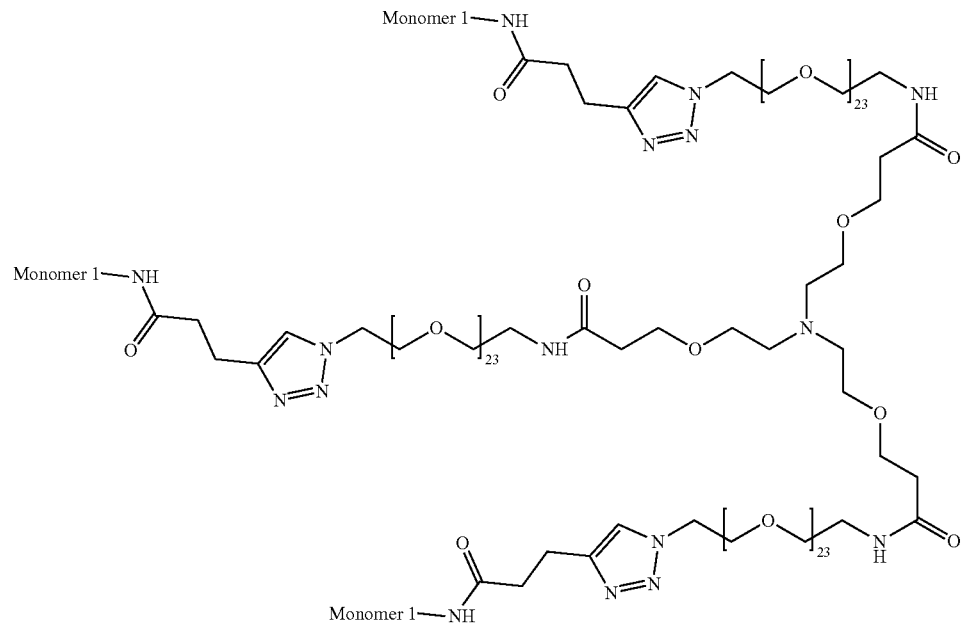
BCY7828
BCY7750

BCY7749
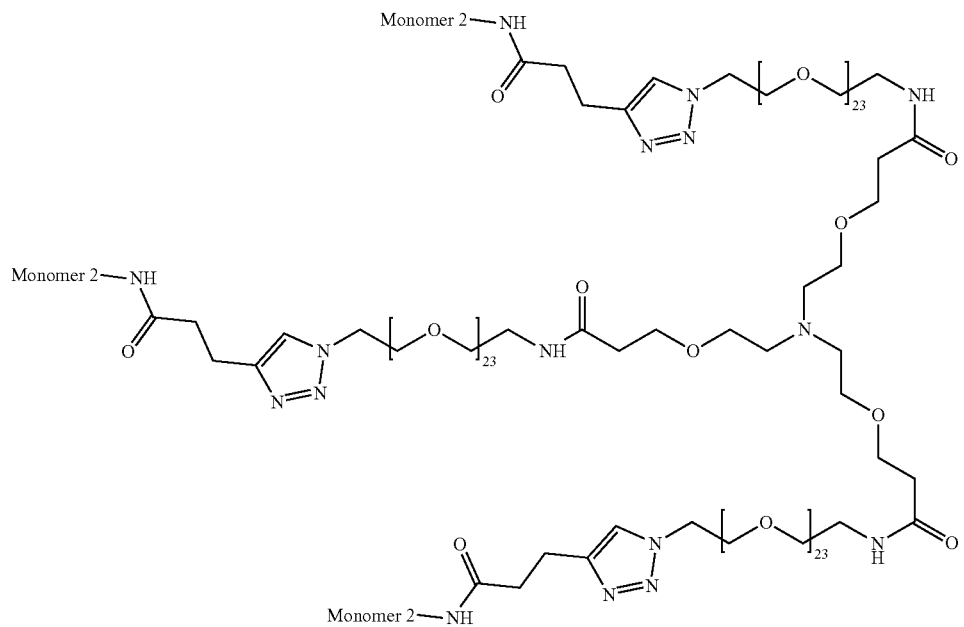
BCY7831
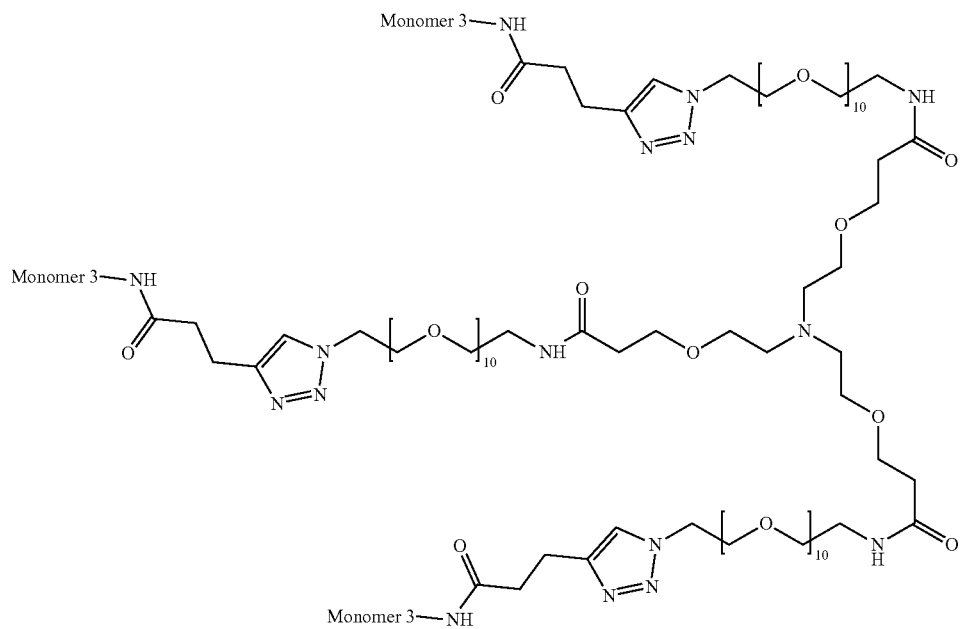

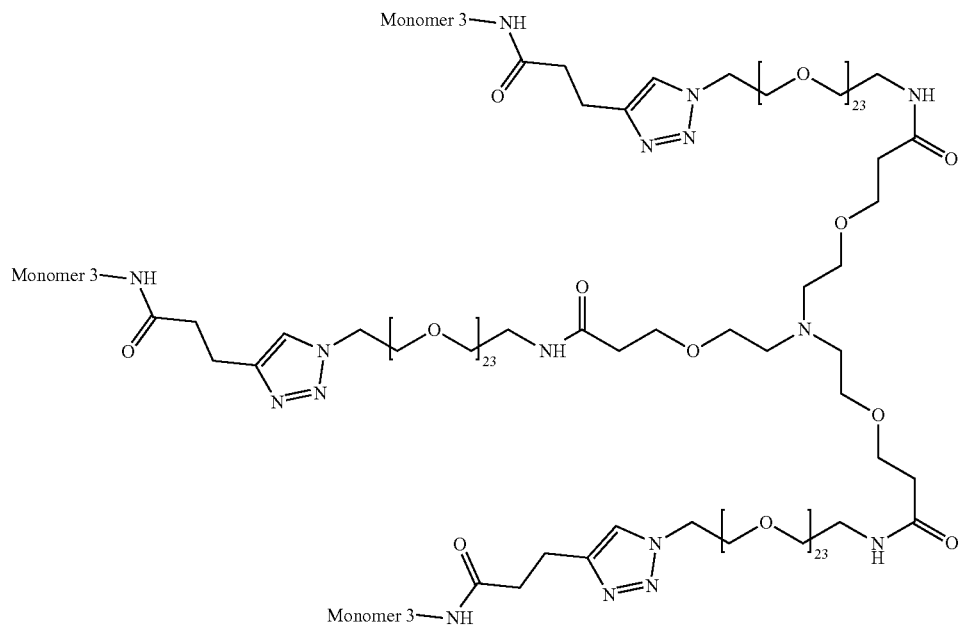
BCY7832
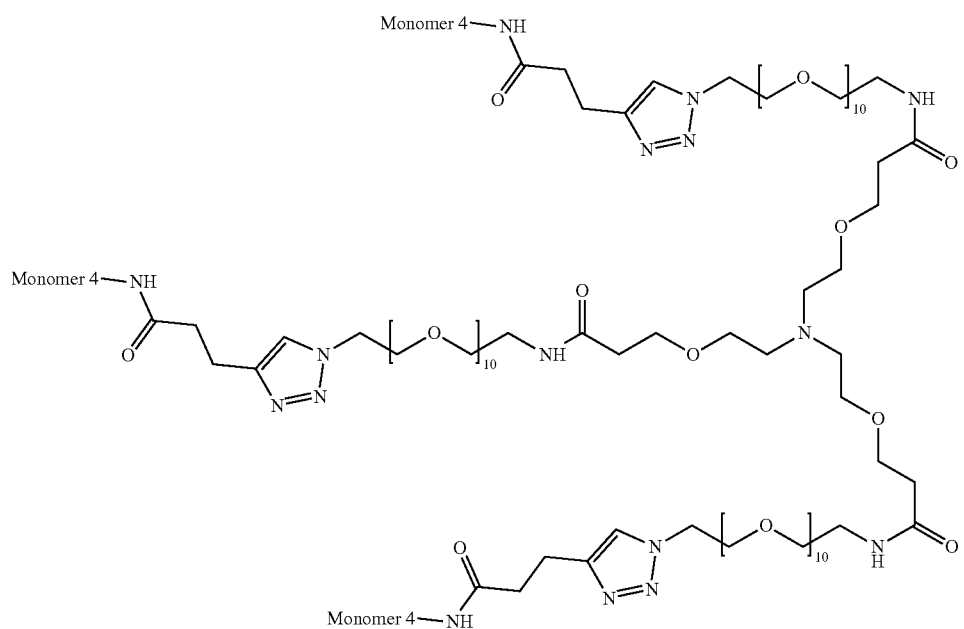
BCY7835

-continued
BCY7836
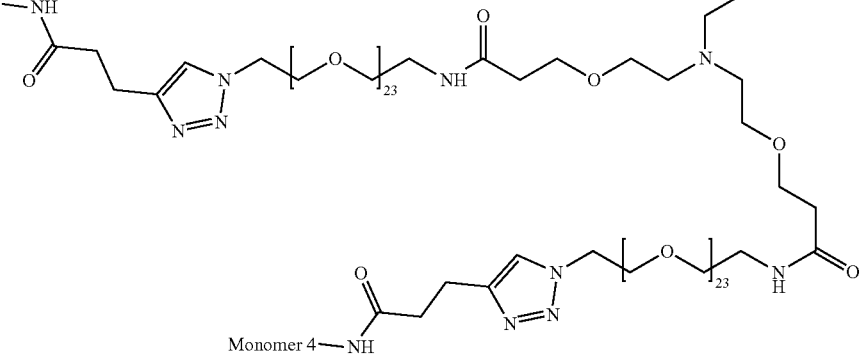
BCY7839
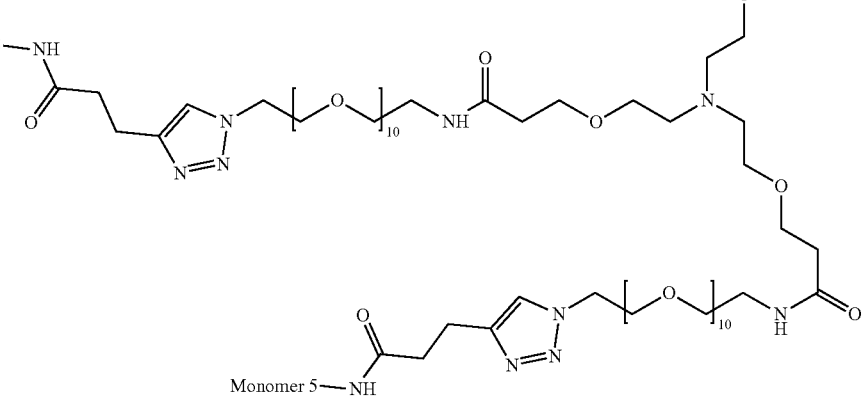

BCY7840
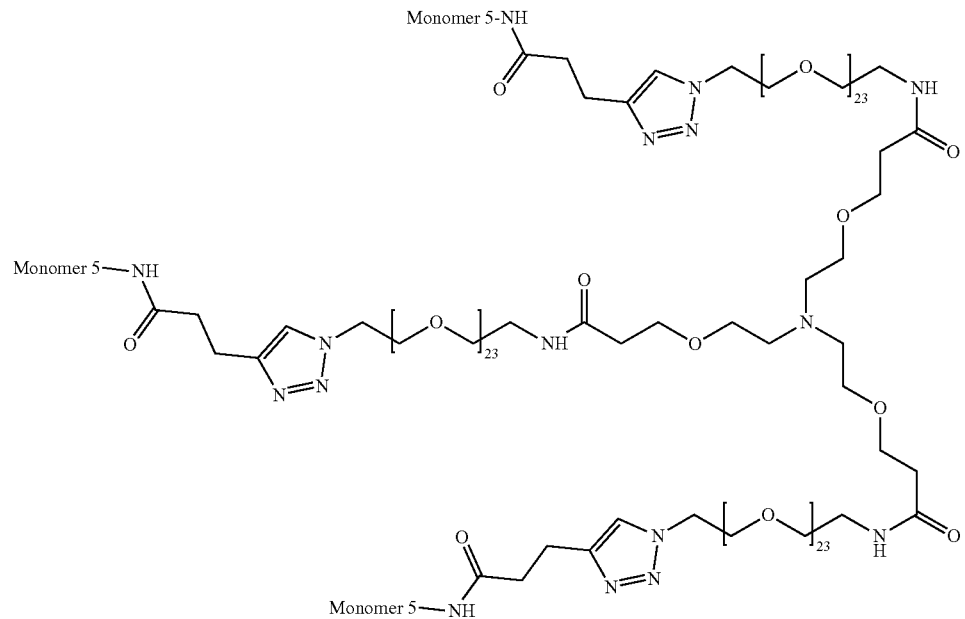
BCY7843
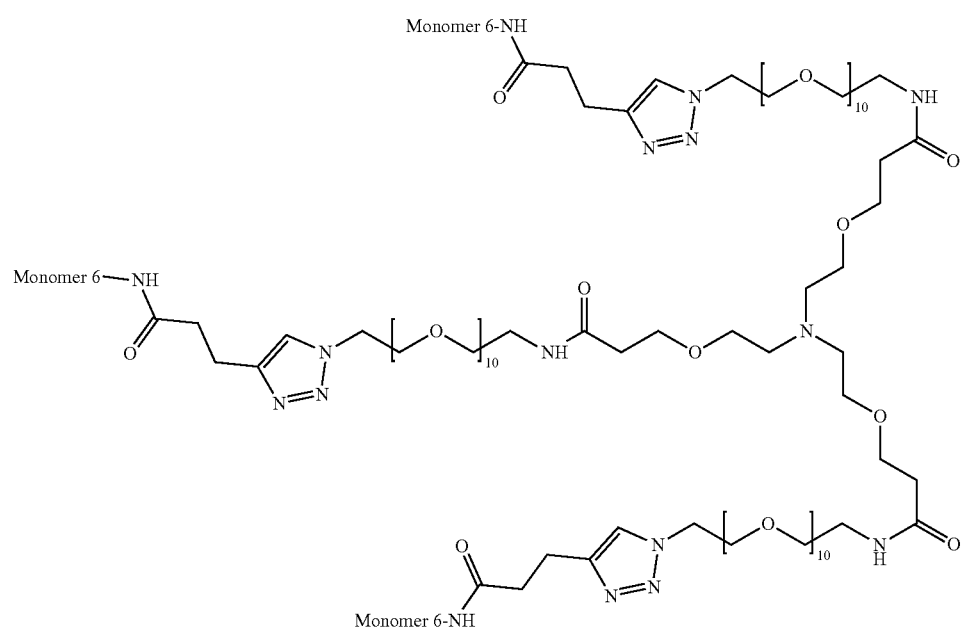

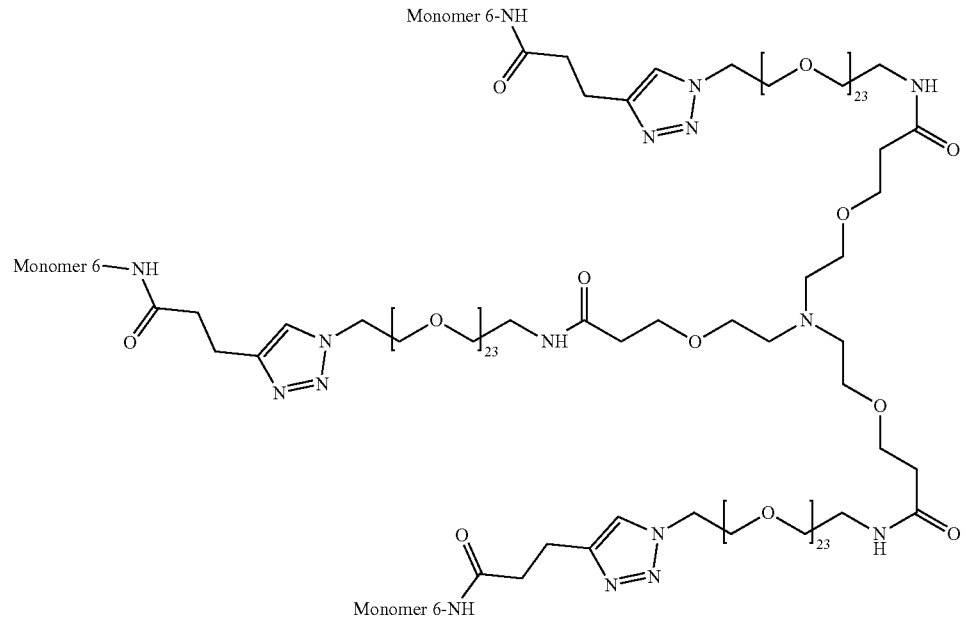
BCY7844
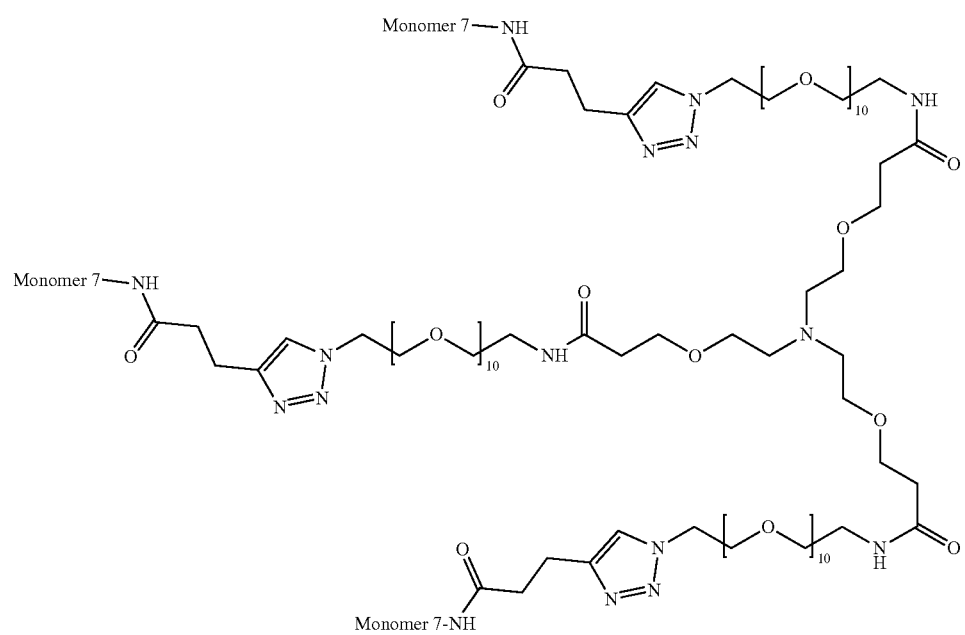
BCY7847

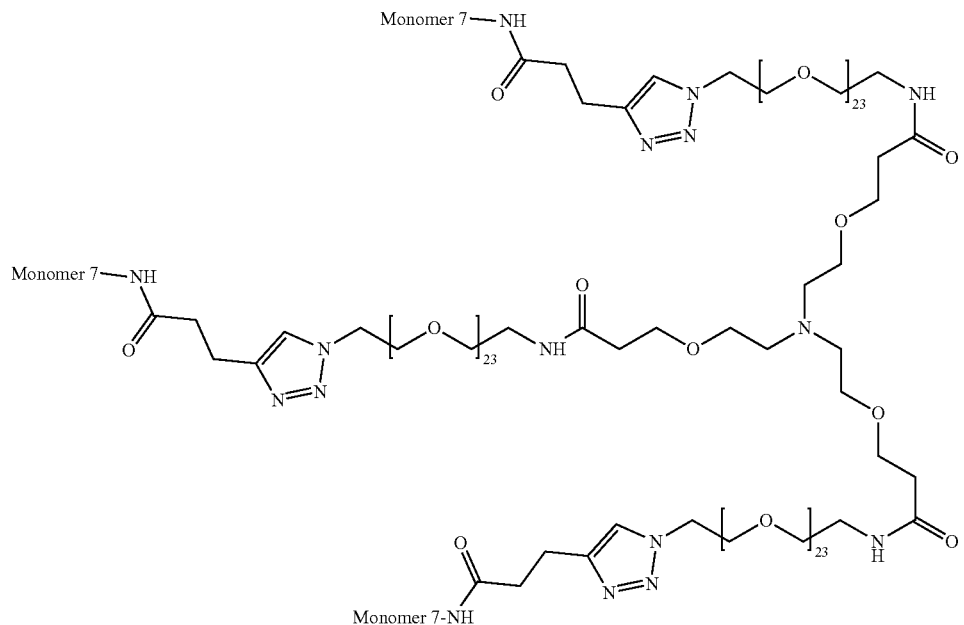
BCY7848
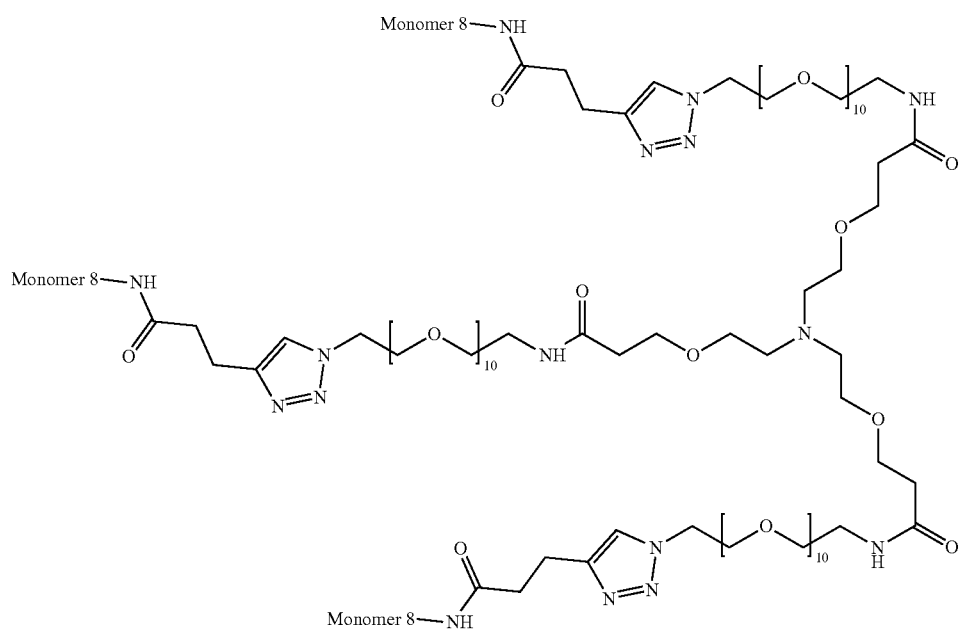
BCY7851

-continued
BCY7852
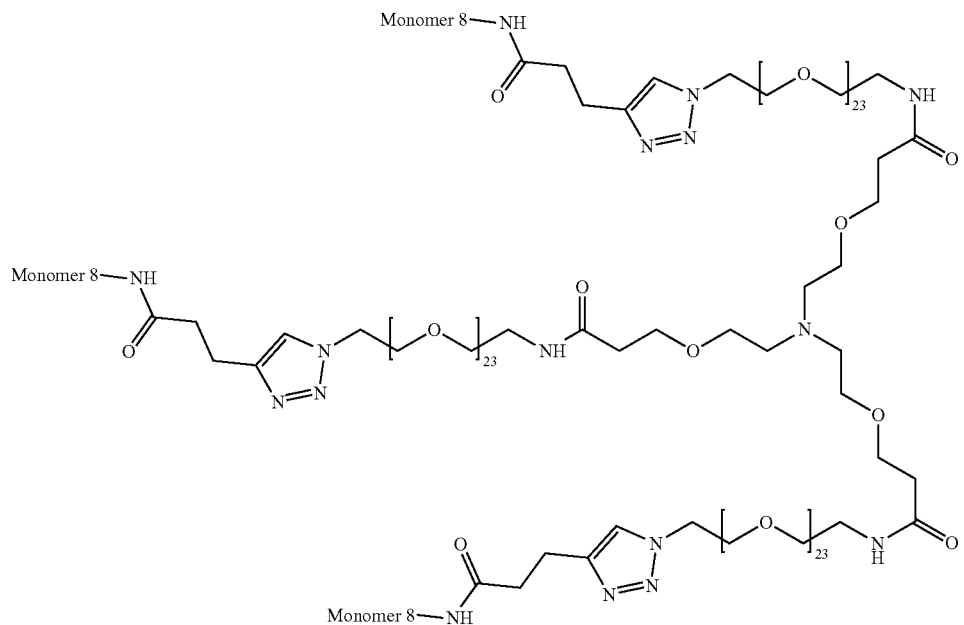
BCY7855
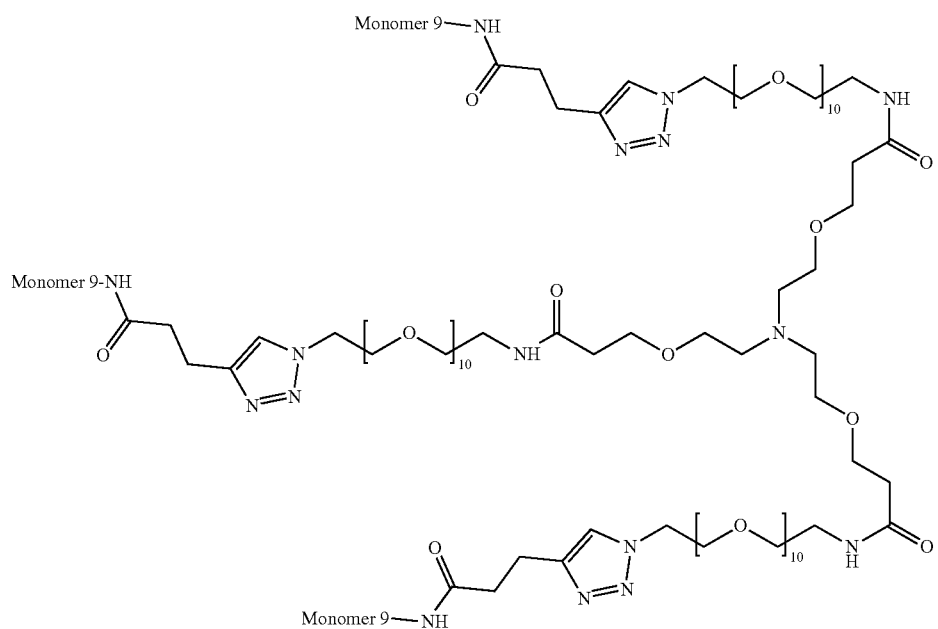

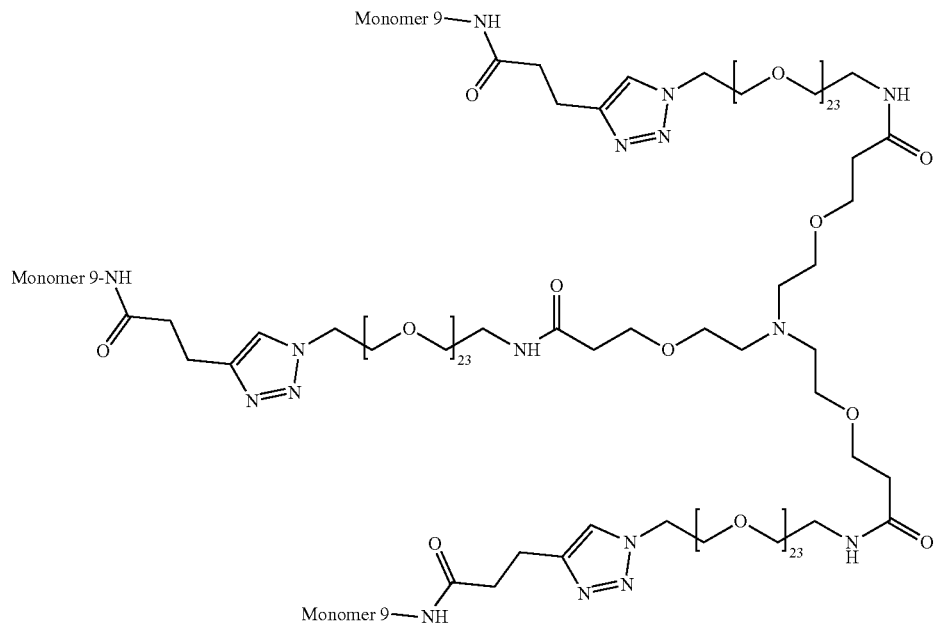
BCY7856
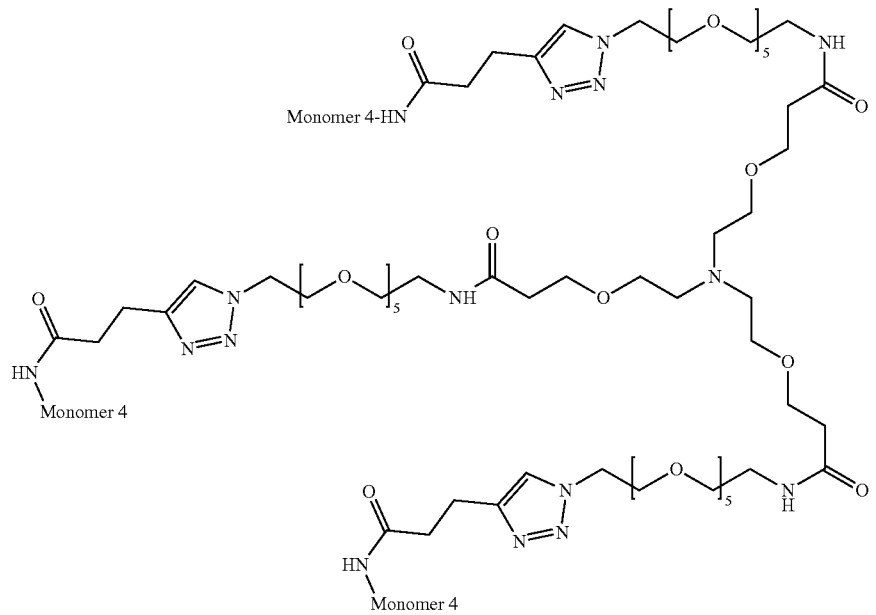
BCY8958

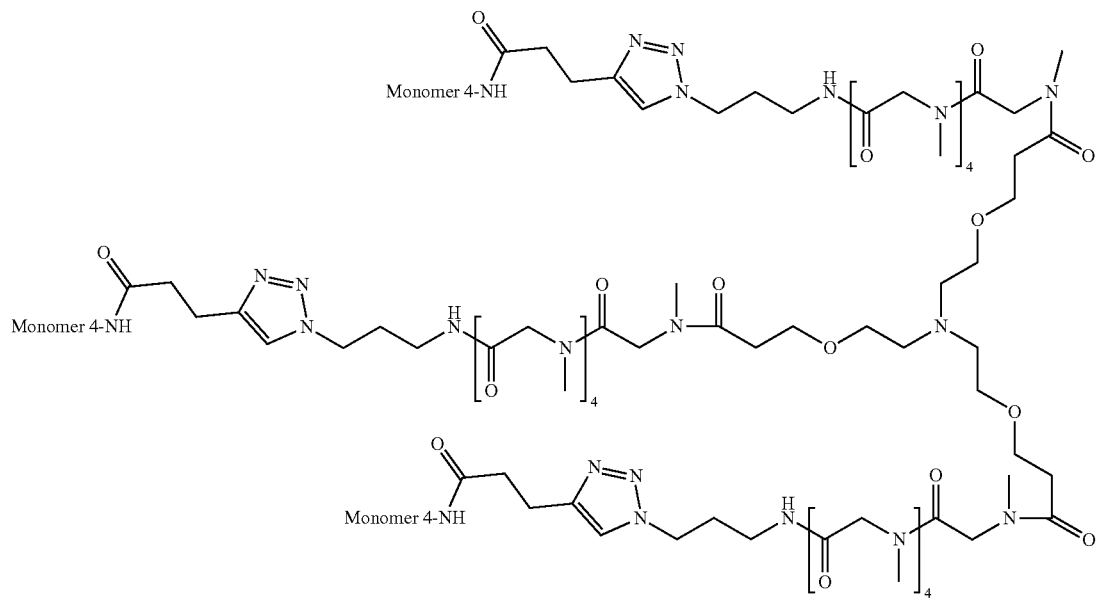
BCY8957
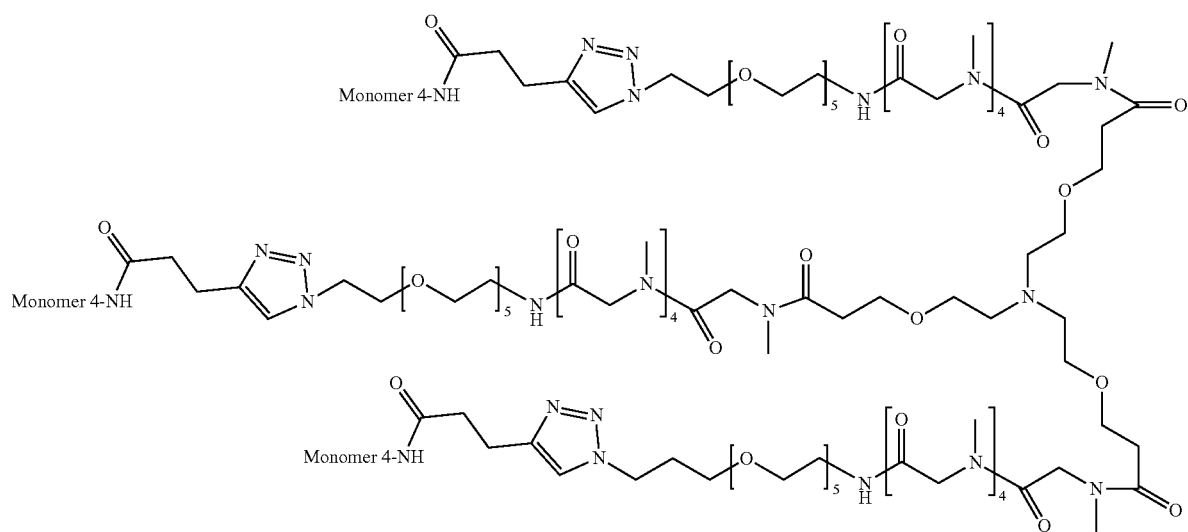
BCY8961

-continued
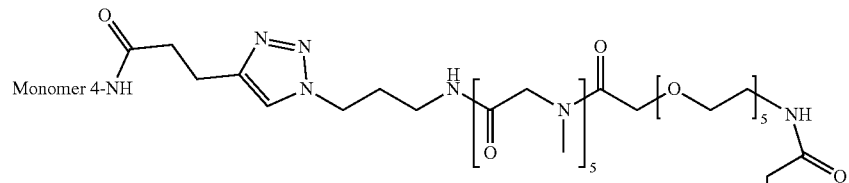
BCY8962
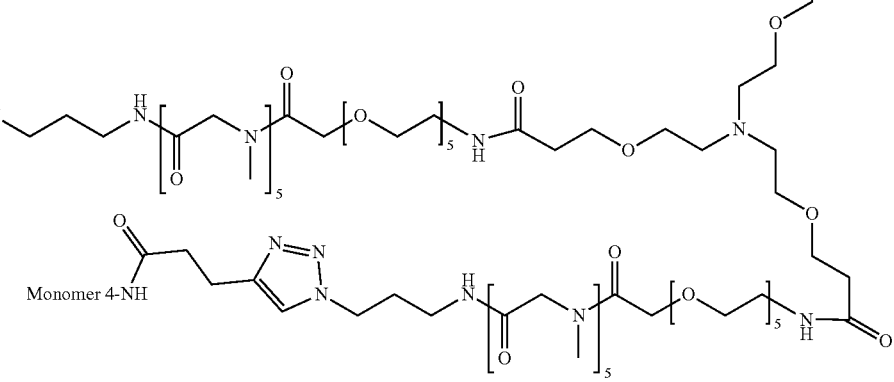
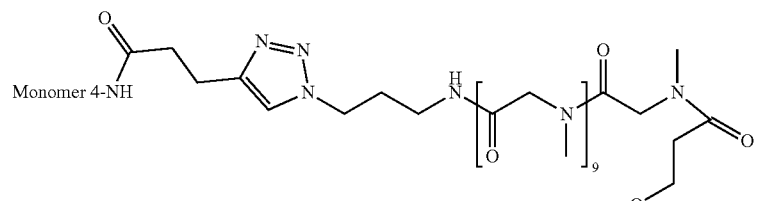
BCY8965
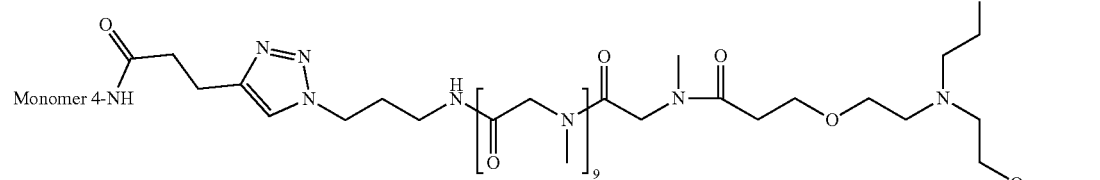
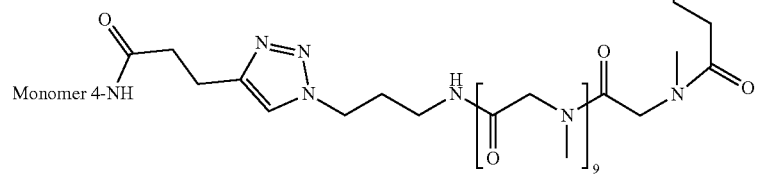

-continued
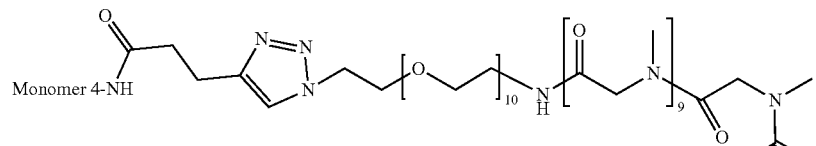
BCY9573
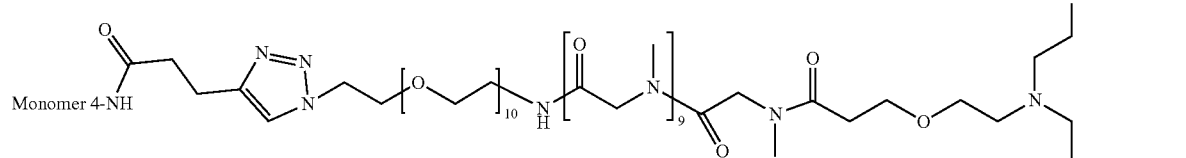
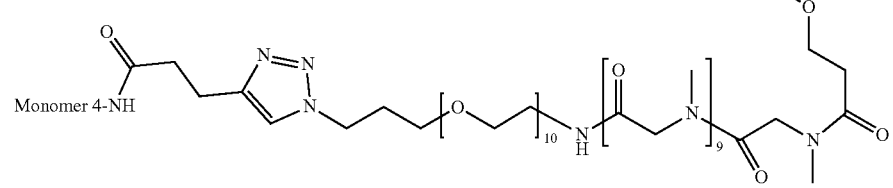
BCY9595
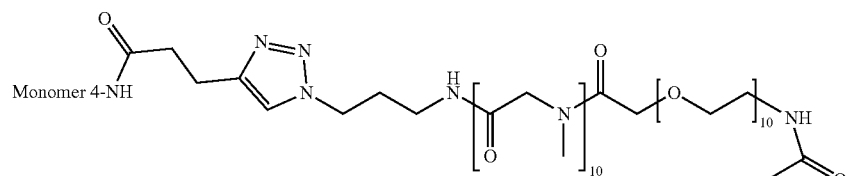
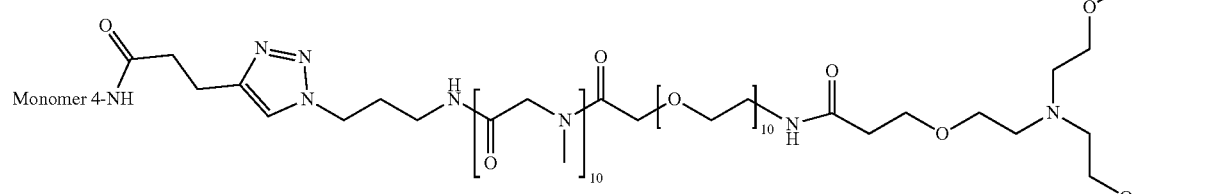
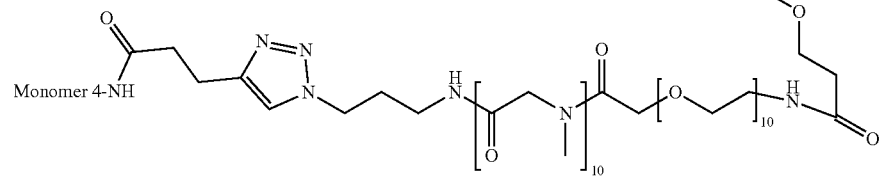
BCY11382
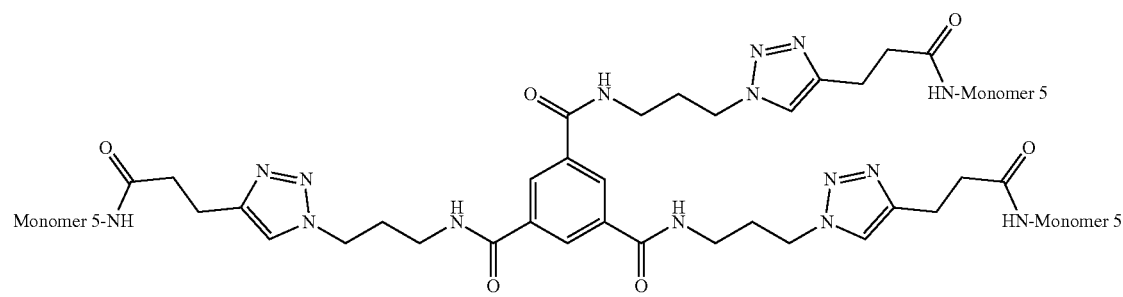

-continued
BCY9775
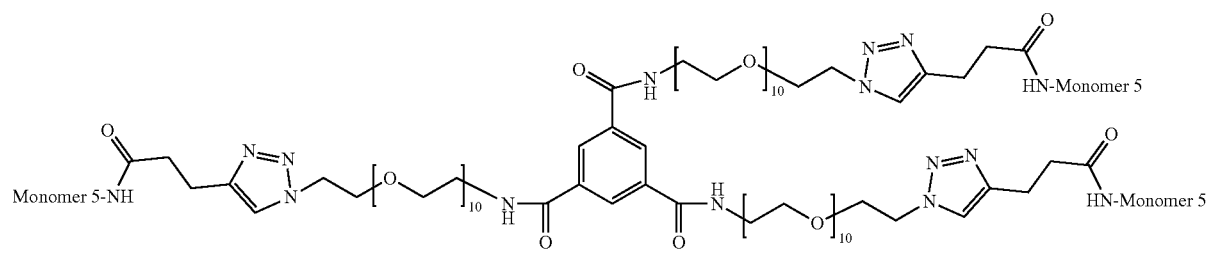
BCY9776
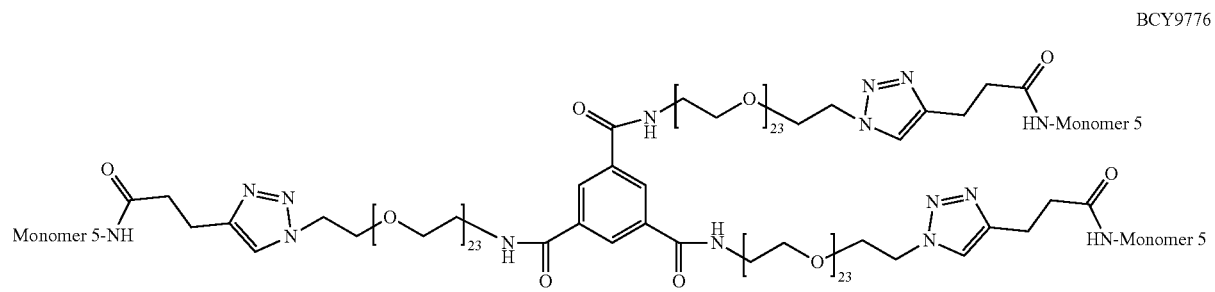
BCY11383
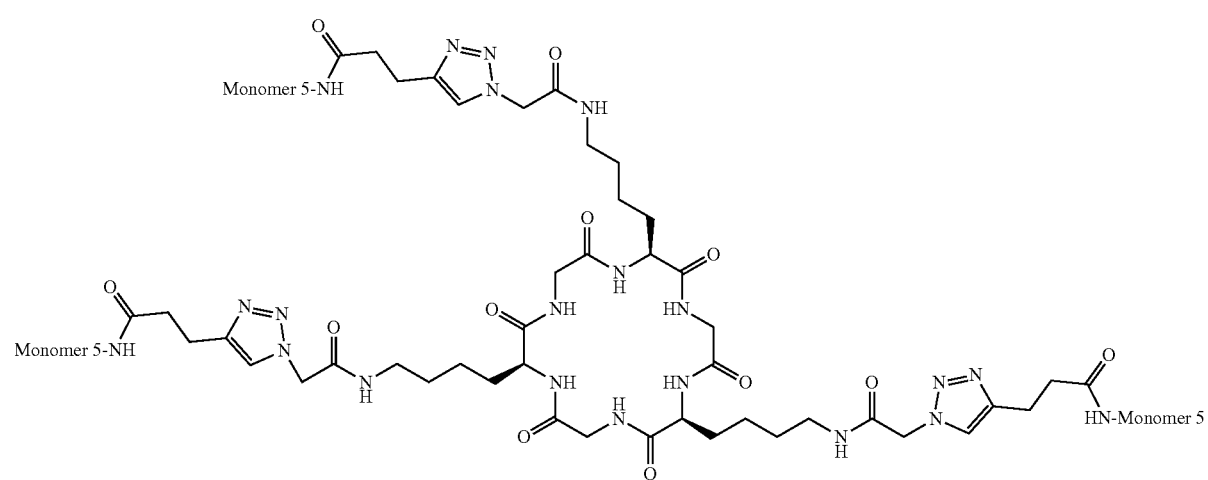
BCY10046
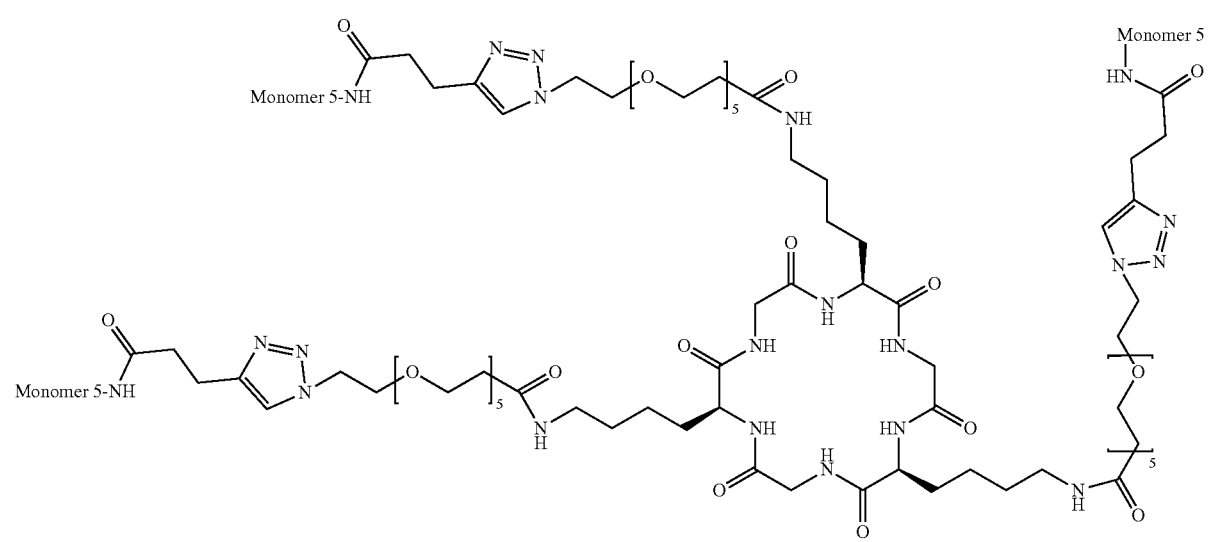

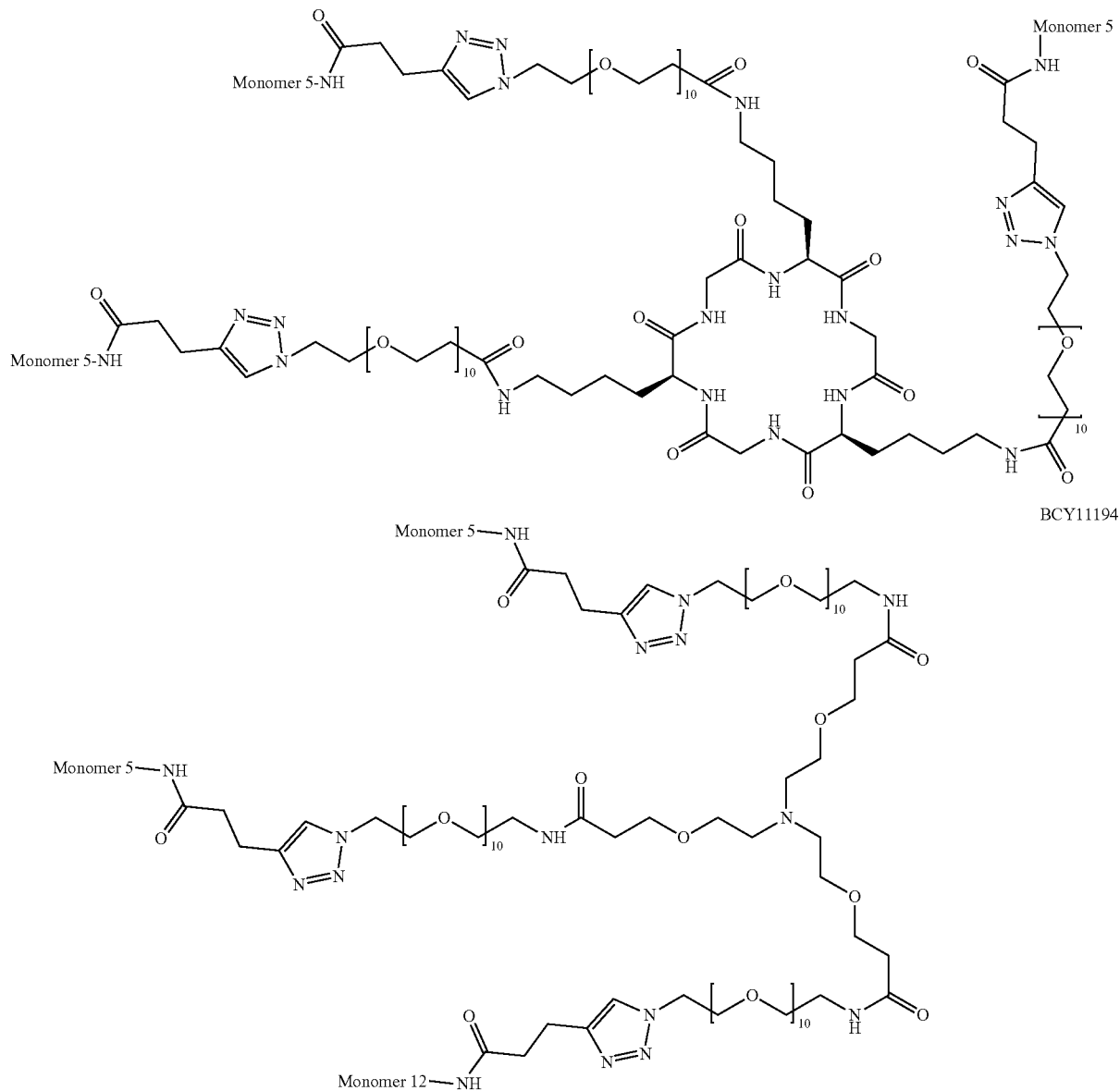

BCY7827:

To a solution of compound 11A (4 mg, 2.12 μmol, 1 eq) and Monomer 1A (28.2 mg, 12.69 μmol, 6.0 eq) in DMF (1 mL) was added a solution of $CuSO_4$ (0.8 M, 23.79 μL, 9.0 eq) and (2R)-2-[(1S)-1, 2-dihydroxyethyl]-3, 4-dihydroxy-2H-furan-5-one (0.8 M, 158.63 μL, 60 eq). The mixture was stirred at 25-30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7827 (9.1 mg, 0.96 μmol, 45.37% yield, 90.3% purity) as a white solid.

BCY7828:

To a solution of compound 11B (4 mg, 1.11 μmol, 1 eq) and Monomer 1A (15 mg, 6.74 μmol, 6.08 eq) in DMF (1 mL) was added a solution of $CuSO_4$ (0.8 M, 12.47 μL, 9.0 eq) and (2R)-2-[(1S)-1, 2-dihydroxyethyl]-3, 4-dihydroxy-2H-furan-5-one (0.8 M, 83.12 μL, 60 eq). The mixture was stirred at 25-30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7828 (5.7 mg, 5.05e-1 μmol, 45.60% yield, 91.17% purity) as a white solid.

BCY7750:

To a solution of compound 11A (4 mg, 2.12 μmol, 1 eq) and Monomer 2A (30 mg, 13.15 μmol, 6.22 eq) in DMF (1 mL) was added CuI (6.00 mg, 31.73 μmol, 15 eq). The mixture was stirred at 25-30° C. for 1 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7750 (7.3 mg, 6.85e-1 μmol, 32.41% yield, 82.02% purity) as a white solid.

BCY7749:

To a solution of compound 11B (48 mg, 13.30 µmol, 1 eq) and Monomer 2A (136.54 mg, 59.85 µmol, 4.5 eq) in DMF (6 mL) was added CuI (38.0 mg, 199.49 µmol, 15 eq). The mixture was stirred at 25-30° C. for 1 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7749 (22.4 mg, 1.39 µmol, 10.43% yield, 64.72% purity) as a white solid.

BCY7831:

To a solution of compound 11A (4 mg, 2.12 µmol, 1 eq) and Monomer 3A (21.56 mg, 9.52 µmol, 4.5 eq) in DMF (1 mL) was added CuI (6.00 mg, 31.73 µmol, 15 eq). The mixture was stirred at 25-30° C. for 2 hrs under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7831 (1.4 mg, 1.48e-1 µmol, 6.98% yield, 91.6% purity) as a white solid.

BCY7832:

To a solution of compound 11B (4 mg, 1.11 µmol, 1 eq) and Monomer 3A (11.30 mg, 4.99 µmol, 4.5 eq) in DMF (1 mL) was added CuI (3.17 mg, 16.62 µmol, 15 eq). The mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7832 (1.5 mg, 9.40e-2 µmol, 8.49% yield, 65.24% purity) as a white solid.

BCY7835:

To a solution of compound 11A (32 mg, 16.92 µmol, 1 eq) and Monomer 4A (172.51 mg, 76.14 µmol, 4.5 eq) in DMF (4 mL) was added CuI (48.34 mg, 253.81 µmol, 15 eq). The mixture was stirred at 25-30° C. for 2 hrs under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7835 (19.8 mg, 2.08 µmol, 12.28% yield, 91.16% purity) as a white solid.

BCY7836:

To a solution of compound 11B (4 mg, 1.11 µmol, 1 eq) and Monomer 4A (15.07 mg, 6.65 µmol, 6.0 eq) in DMF (1 mL) was added a solution of $CuSO_4$ (0.8 M, 12.47 µL, 9.0 eq) and (2R)-2-[(1S)-1, 2-dihydroxyethyl]-3, 4-dihydroxy-2H-furan-5-one (0.8 M, 83.12 µL, 60 eq). The mixture was stirred at 25-30° C. for 2 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7836 (2 mg, 1.15e-1 µmol, 10.40% yield, 59.97% purity) as a white solid.

BCY7839:

A mixture of compound 11A (0.2 g, 105.75 µmol, 1 eq.), Monomer 5A (750 mg, 320.8 µmol, 3.03 eq.), and THPTA (0.4 M, 264.4 µL, 1 eq.) was dissolved in t-BuOH/H2O (1:1, 12 mL, pre-degassed and purged with $N_2$ for 3 times), and then $CuSO_4$ (0.4 M, 265 µL, 1 eq.) and VcNa (0.4 M, 529 µL, 2 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed compound 11A was consumed completely and one main peak with desired m/z [MW: 8904.11, observed m/z: 1271.92 ([M/7+H+]), 1113.07 ([M/8+H+]), and 989.65 ([M/9+H+])] was detected. The reaction mixture was directly purified by prep-HPLC (TFA condition). BCY7839 (283.7 mg, 30.40 µmol, 28.74% yield, 95.40% purity) was obtained as a white solid.

BCY7840:

To a solution of compound 11B (4 mg, 1.11 µmol, 1 eq) and Monomer 5A (11.66 mg, 4.99 µmol, 4.5 eq) in DMF (0.5 mL) was added CuI (3.17 mg, 16.62 µmol, 15 eq). The mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7840 (2.9 mg, 2.54e-1 µmol, 22.91% yield, 93.00% purity) as a white solid.

BCY7743:

To a solution of compound 11A (4 mg, 2.12 µmol, 1 eq) and Monomer 6A (19.18 mg, 8.46 µmol, 4.5 eq) in DMF (1 mL) was added CuI (6.04 mg, 31.73 µmol, 15 eq). The mixture was stirred at 25-30° C. for 2 hrs under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7743 (4 mg, 3.85e-1 µmol, 18.19% yield, 83.56% purity) as a white solid.

BCY7744:

To a solution of compound 11B (4 mg, 1.11 µmol, 1 eq) and Monomer 6A (11.30 mg, 4.99 µmol, 4.5 eq) in DMF (1 mL) was added CuI (3.17 mg, 16.62 µmol, 15 eq). The mixture was stirred at 25-30° C. for 1 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7744 (4.2 mg, 1.79e-1 µmol, 16.17% yield, 44.40% purity) as a white solid.

BCY7847:

To a solution of compound 11A (4 mg, 2.12 µmol, 1 eq) and Monomer 7A (28.52 mg, 12.69 µmol, 6 eq) in DMF (1 mL) was added a solution of $CuSO_4$ (0.8 M, 23.79 µL, 9.0 eq) and (2R)-2-[(1S)-1, 2-dihydroxyethyl]-3, 4-dihydroxy-2H-furan-5-one (0.8 M, 158.63 µL, 60 eq). The mixture was stirred at 25-30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7847 (1.3 mg, 5.63e-2 µmol, 2.66% yield, 37.4% purity) as a white solid.

BCY7848:

To a solution of compound 11B (4 mg, 1.11 µmol, 1 eq) and Monomer 7A (14.95 mg, 6.65 µmol, 6.0 eq) in DMF (1 mL) was added a solution of $CuSO_4$ (0.8 M, 12.47 µL, 9.0 eq) and (2R)-2-[(1S)-1, 2-dihydroxyethyl]-3, 4-dihydroxy-2H-furan-5-one (0.8 M, 83.12 µL, 60 eq). The mixture was stirred at 25-30° C. for 1 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7848 (2.7 mg, 2.46e-1 µmol, 22.23% yield, 94.47% purity) as a white solid.

BCY7851:

To a solution of compound 11A (4 mg, 2.12 µmol, 1 eq) and Monomer 8A (21.87 mg, 9.52 µmol, 4.5 eq) in DMF (1 mL) was added CuI (6.0 mg, 31.73 µmol, 15 eq). The mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7851 (2.5 mg, 8.64e-2 µmol, 4.08% yield, 30.35% purity) as a white solid.

BCY7852:

To a solution of compound 11B (4 mg, 1.11 µmol, 1 eq) and Monomer 8A (15.28 mg, 6.65 µmol, 6.0 eq) in DMF (1 mL) was added a solution of $CuSO_4$ (0.8 M, 12.47 µL, 9.0 eq) and (2R)-2-[(1S)-1, 2-dihydroxyethyl]-3, 4-dihydroxy-2H-furan-5-one (0.8 M, 83.12 µL, 60 eq). The mixture was stirred at 25-30° C. for 1 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7852 (1.2 mg, 9.85e-2 µmol, 8.89% yield, 86.2% purity) as a white solid.

BCY7855:

To a solution of compound 11A (4 mg, 2.12 µmol, 1 eq) and Monomer 9A (21.72 mg, 9.52 µmol, 4.5 eq) in DMF (1 mL) was added CuI (6.04 mg, 31.73 µmol, 15 eq). The mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7855 (3.8 mg, 0.28 µmol, 13.25% yield, 64.45% purity) as a white solid.

BCY7856:

To a solution of compound 11B (4 mg, 1.11 µmol, 1 eq) and Monomer 9A (15.17 mg, 6.65 µmol, 6.0 eq) in DMF (1 mL) was added a solution of $CuSO_4$ (0.8 M, 12.47 µL, 9.0 eq) and (2R)-2-[(1S)-1, 2-dihydroxyethyl]-3,4-dihydroxy-2H-furan-5-one (0.8 M, 83.12 µL, 60 eq). The mixture was stirred at 25-30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7856 (5.7 mg, 5.05e-1 µmol, 45.60% yield, 91.17% purity) as a white solid.

BCY8958 (15.8 mg, 93.9% purity, 22.7% yield), BCY8957 (15.1 mg, 90.4% purity, 18 yield), BCY8961 (3.1 mg, 93.3% purity, 5.4% yield), BCY8962 (12.8 mg, 89.6% purity, 20.6% yield), BCY8965 (17.8 mg, 92.9% purity, 41.4% yield), BCY9573 (6.2 mg, 92.50% purity, 5.50% yield), BCY9595 (5.4 mg, 95.50% purity, 6.60% yield), BCY11382 (81 mg, 89.04% purity, 26.1% yield), BCY9775 (55.1 mg, 95.01% purity, 51.93% yield), BCY9776 (11.5 mg, 99.70% purity, 18.92% yield), BCY11383 (5.1 mg, 85.46% purity, 8.97% yield), BCY10046 (12.6 mg, 95.10% purity, 10.59% yield), BCY10047 (19.5 mg, 94.69% purity, 25.65% yield) were each synthesized in an analogous manner to that described above for BCY7839 using one of Compounds 11A, 11B, 11C, 11D, 11E, 11F, 11G, 11H, 11I, 11J, 11K, 11 L, 11M, 11N and 11O; and one of Monomer 4A, Monomer 5A; and $CuSO_4$, (2R)-2-[(1S)-1, 2-dihydroxyethyl]-3,4-dihydroxy-2H-furan-5-one and THPTA.

BCY11194:

A mixture of Compound 11A (30 mg, 15.86 µmol, 1 eq), Monomer 12A (31.6 mg, 14.28 µmol, 0.9 eq), and THPTA (8.0 mg, 1 eq) was dissolved in $t-BuOH/H_2O$ (1:1, 2 mL, pre-degassed and purged with $N_2$ for 3 times), followed by addition of $CuSO_4$ (0.4 M, 40.0 µL, 1 eq) and VcNa (0.4 M, 80.0 µL, 2 eq) under $N_2$. The pH of this solution was adjusted to 8 by dropwise addition of 0.2 M $NH_4HCO_3$ (in 1:1 $t-BuOH/H_2O$), and the solution turned to light yellow. The reaction mixture was stirred at 25° C. for 4 hr under $N_2$ atmosphere. LC-MS showed Monomer 12A was consumed completely and one main peak with desired m/z (MS: 4108.77, observed m/z: 1369.8 ($[M/3+H]^+$)) was detected. The reaction mixture was filtered and concentrated under reduced pressure to give a residue. The crude product was purified by prep-HPLC (TFA condition), and desired fractions were combine and lyophilized, resulting in Intermediate 1 (9.2 mg, 2.16 µmol, 13.63% yield, 96.56% purity) as a white solid. A mixture of Intermediate 1 (5 mg, 1.22 µmol, 1 eq), Monomer 5A (5.7 mg, 2.43 µmol, 2 eq), and THPTA (1.1 mg, 2 eq) was dissolved in $t-BuOH/H_2O$ (1:1, 2 mL, pre-degassed and purged with $N_2$ for 3 times), and then $CuSO_4$ (0.4 M, 6.1 µL, 2 eq) and VcNa (0.4 M, 12.2 µL, 4 eq) were added under $N_2$. The pH of this solution was adjusted to 8 by dropwise addition of 0.2 M $NH_4HCO_3$ (in 1:1 $t-BuOH/H_2O$), and the solution turned to light yellow. The reaction mixture was stirred at 25° C. for 4 hr under $N_2$ atmosphere. LC-MS showed Monomer 5A was consumed completely and one main peak with desired m/z (calculated MW: 8784.05, observed m/z: 1236.5 ($[M/7-H_2O+H]^+$), 1077.8 ($[M/8-H_2O+H^+]$)) was detected. The reaction mixture was filtered and concentrated under reduced pressure to give a residue. The crude product was purified by prep-HPLC (TFA condition). BCY11194 (3.4 mg, 29.01% yield, 91.2% purity) was obtained as a white solid.

General Procedure for Preparation of Compound 15

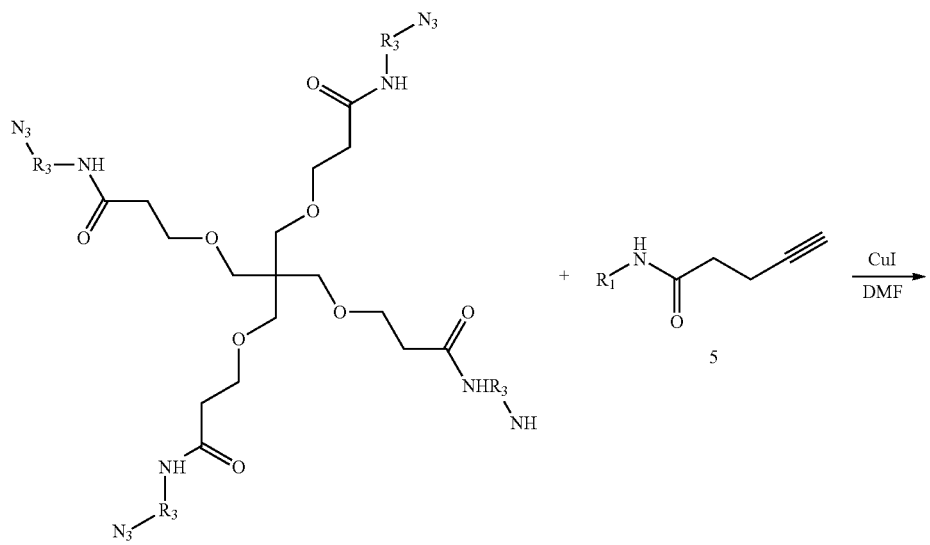

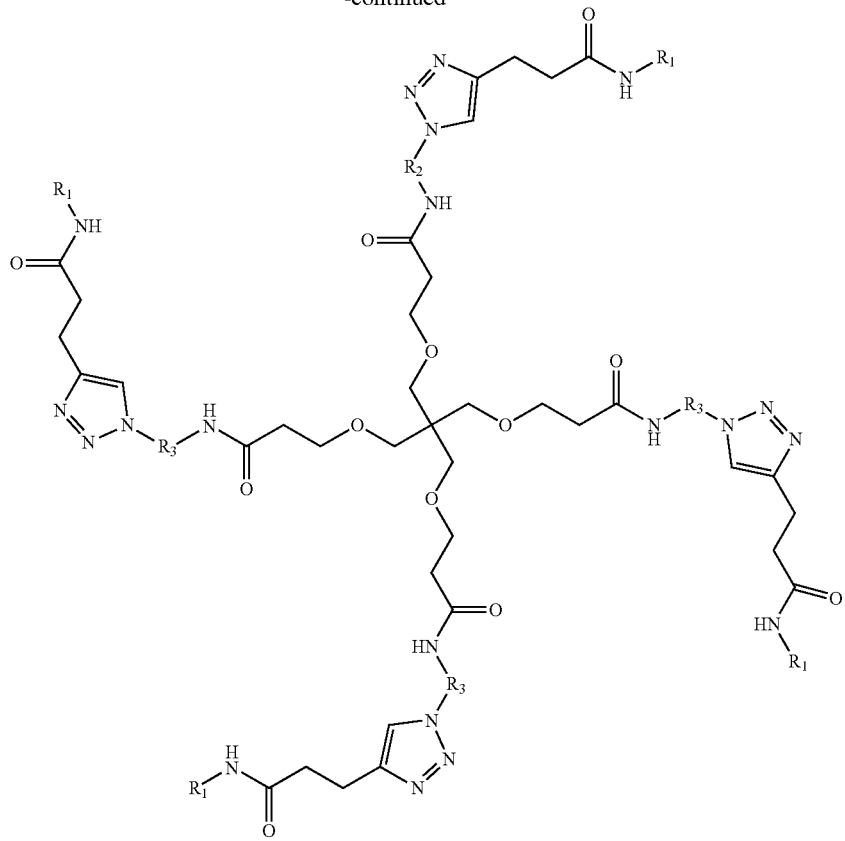
15
Compound 14:
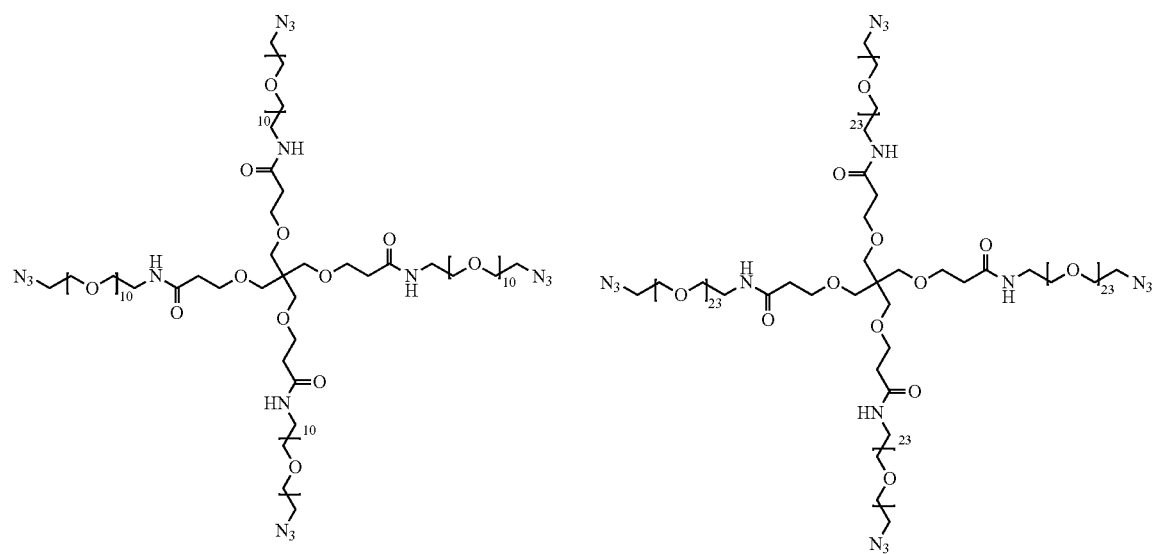

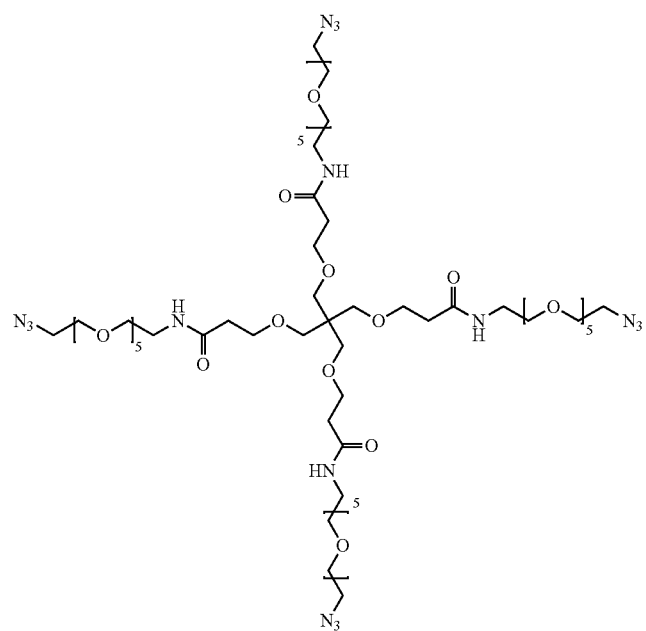
14C
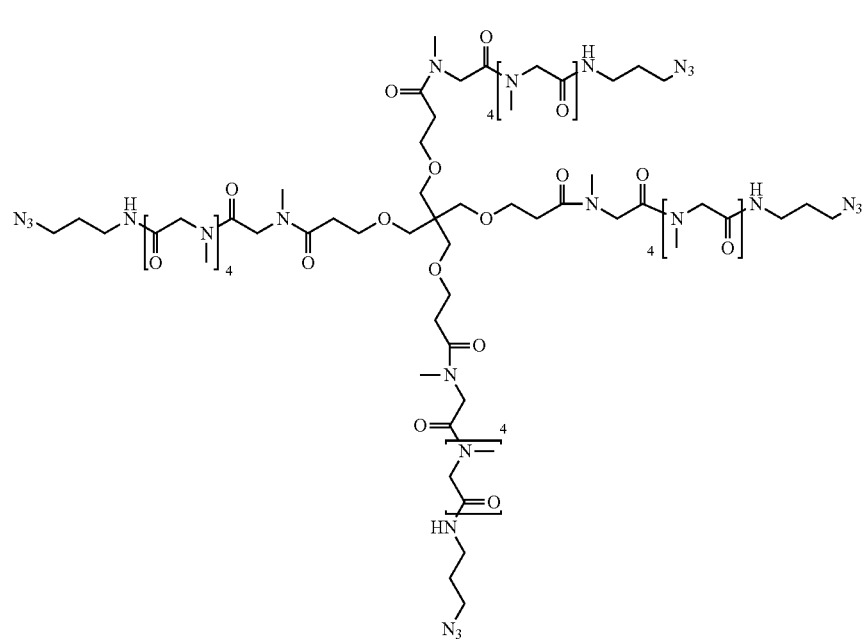
14D

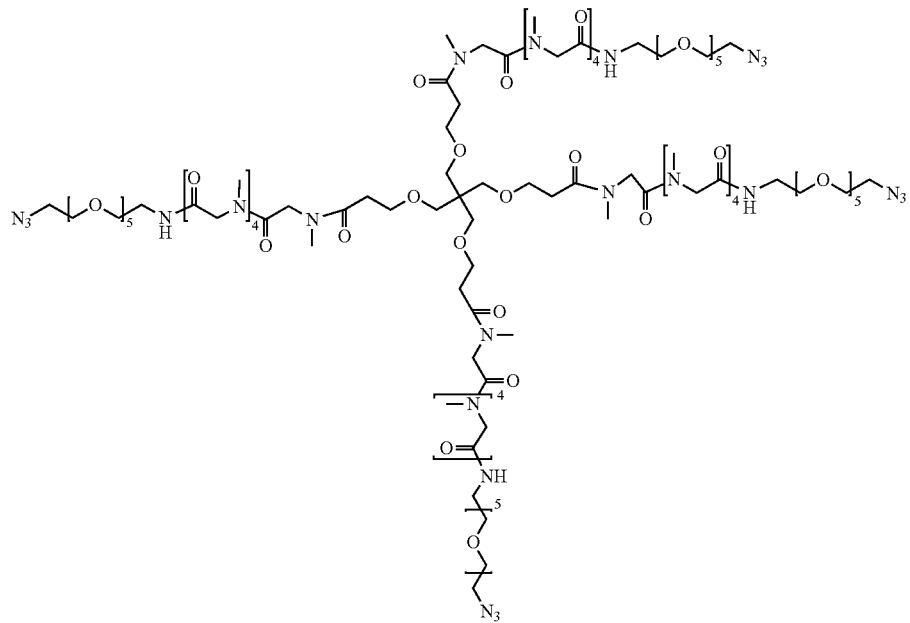
14E
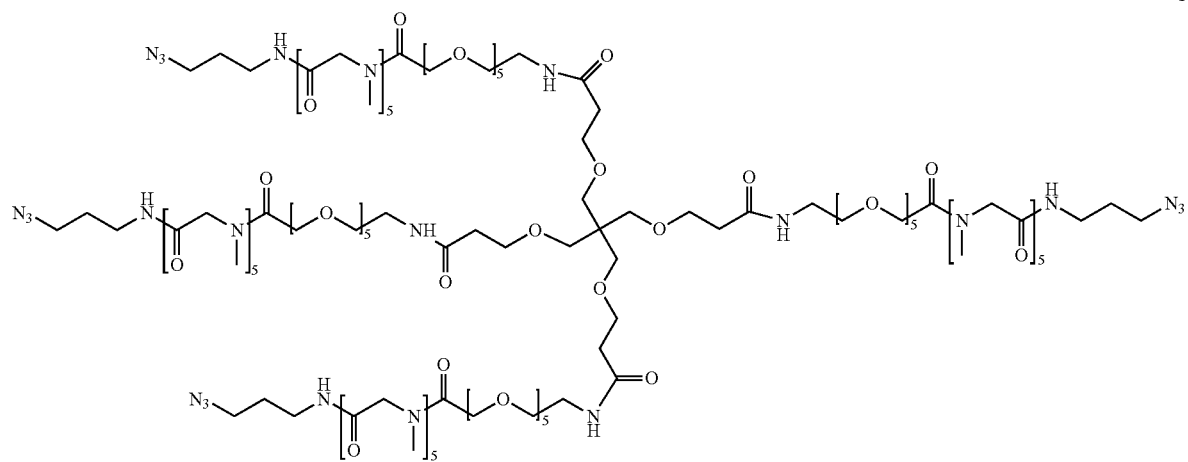
14F
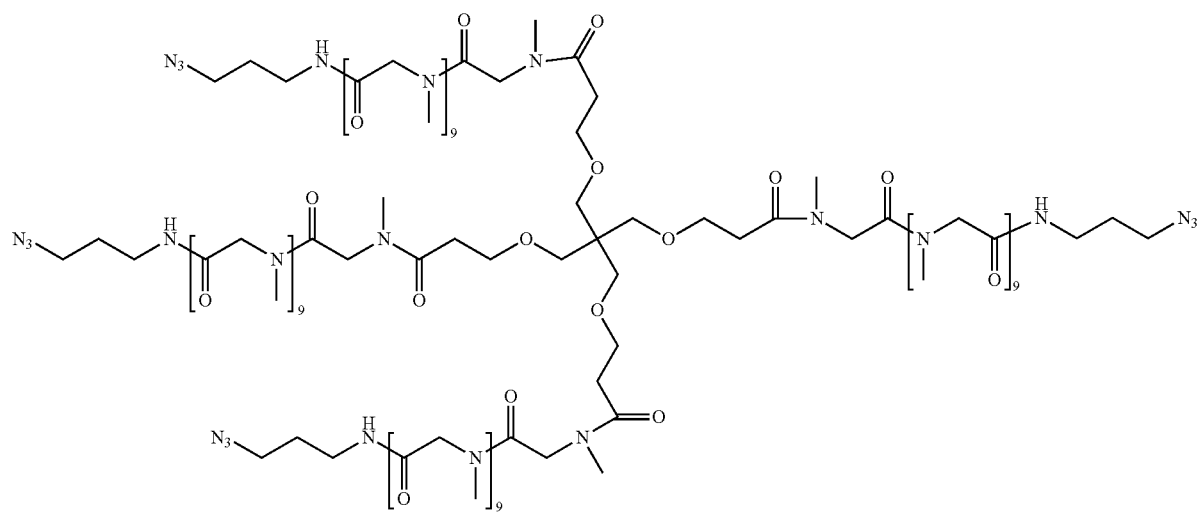
14G

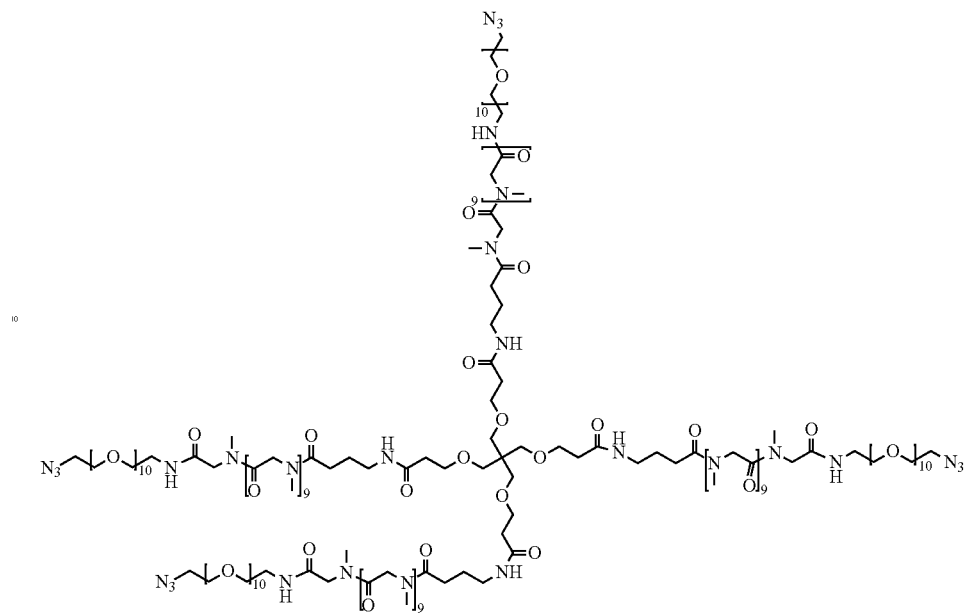
Compound 5:
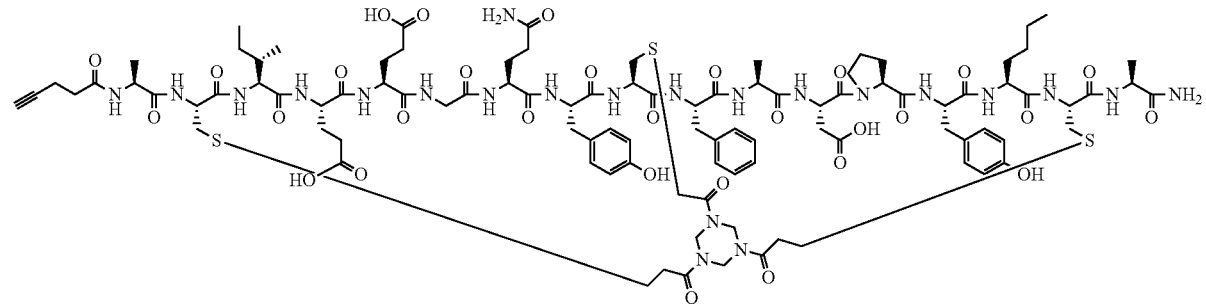
Monomer 1A
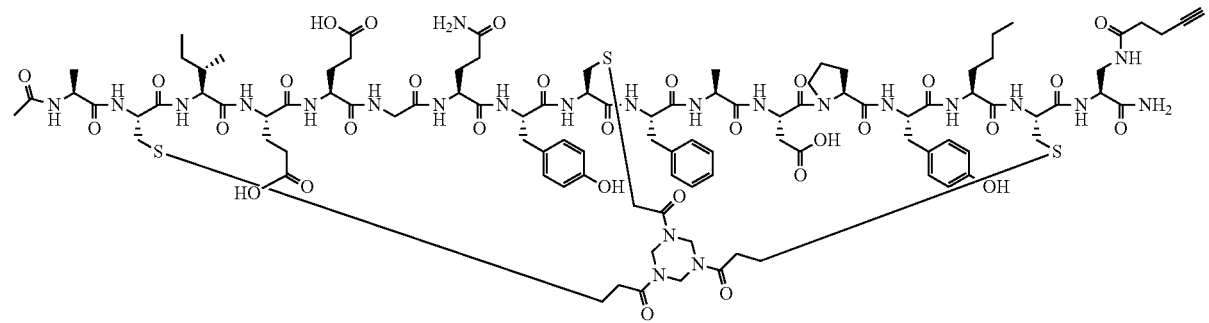
Monomer 2A

Monomer 3A
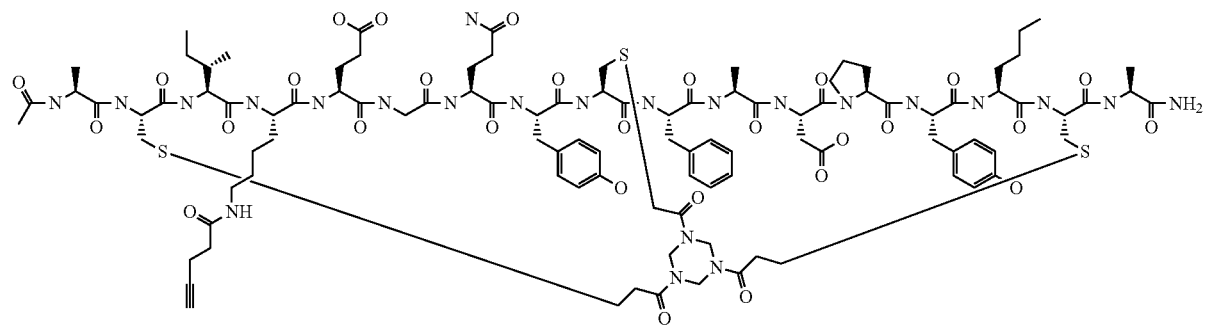
Monomer 4A
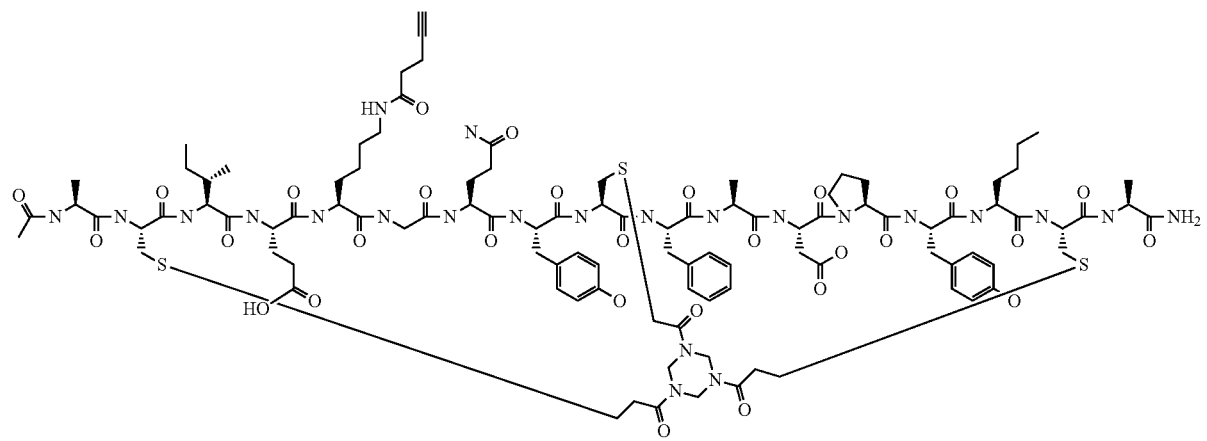
Monomer 5A
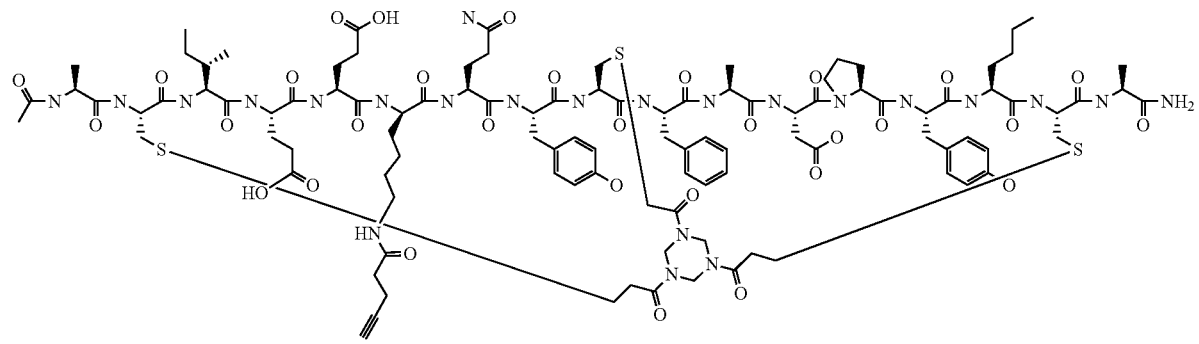
Monomer 6A
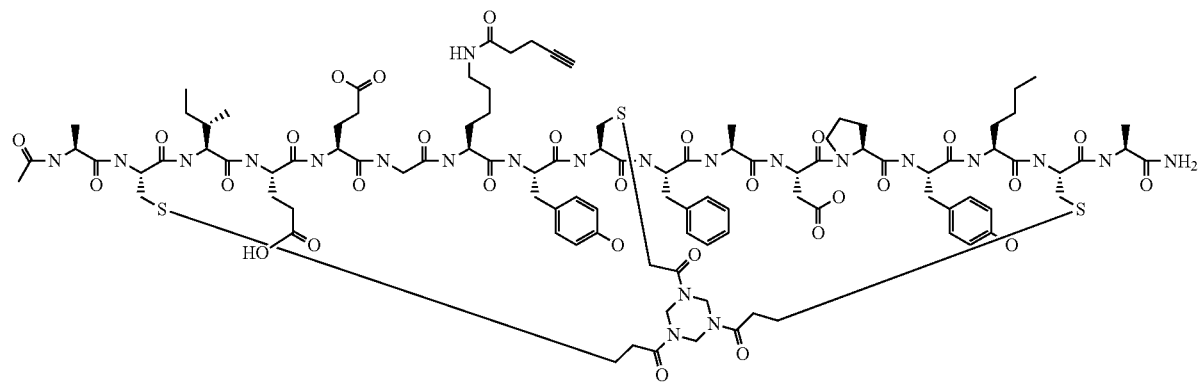

Monomer 7A
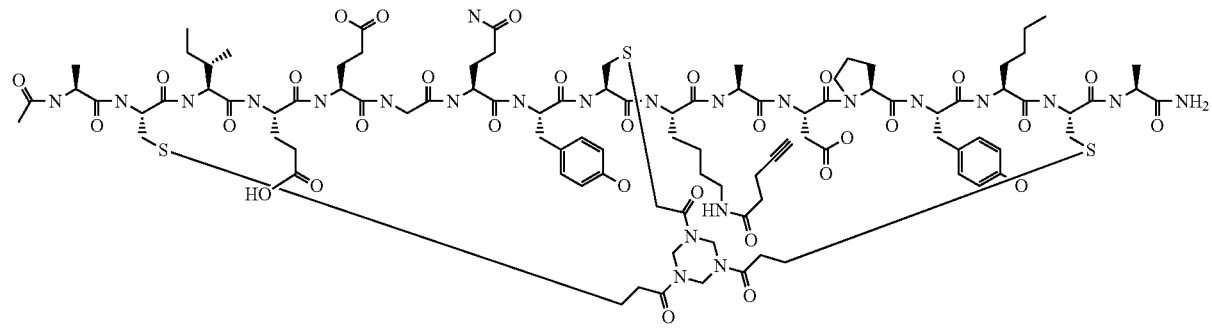
Monomer 8A
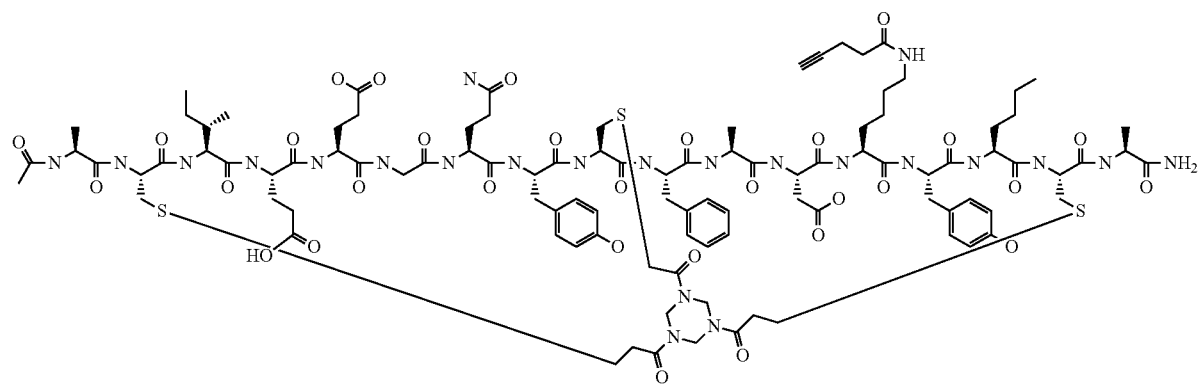
Monomer 9A
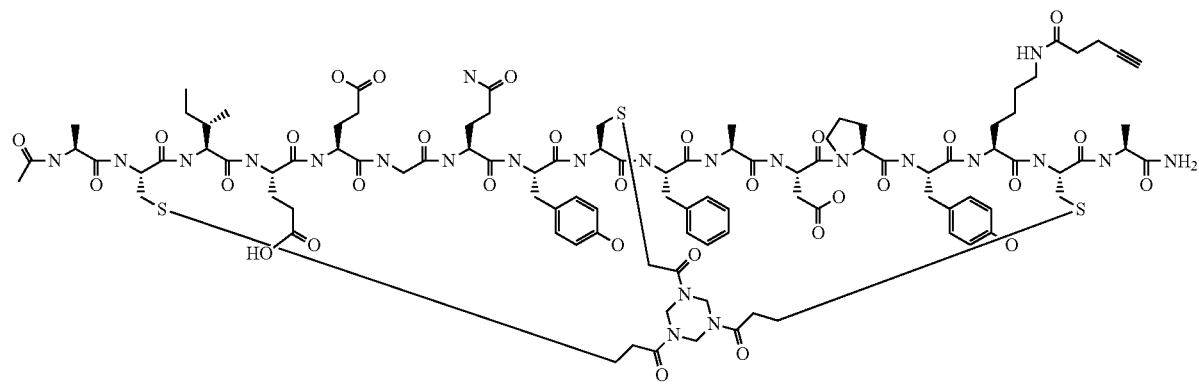
Monomer 10A
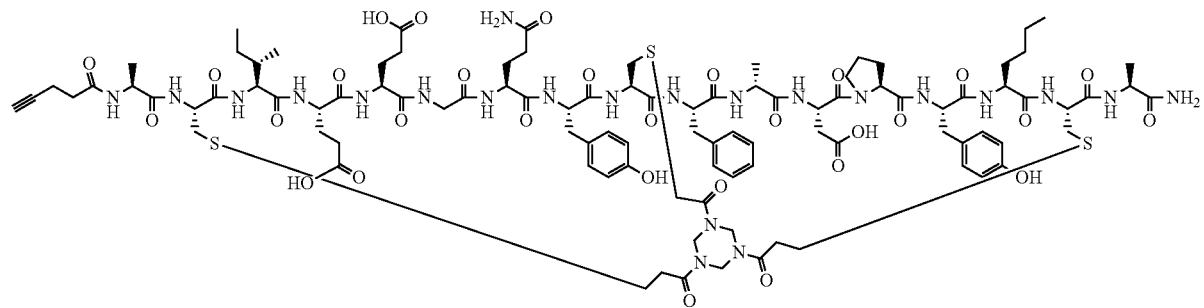

Monomer 11A
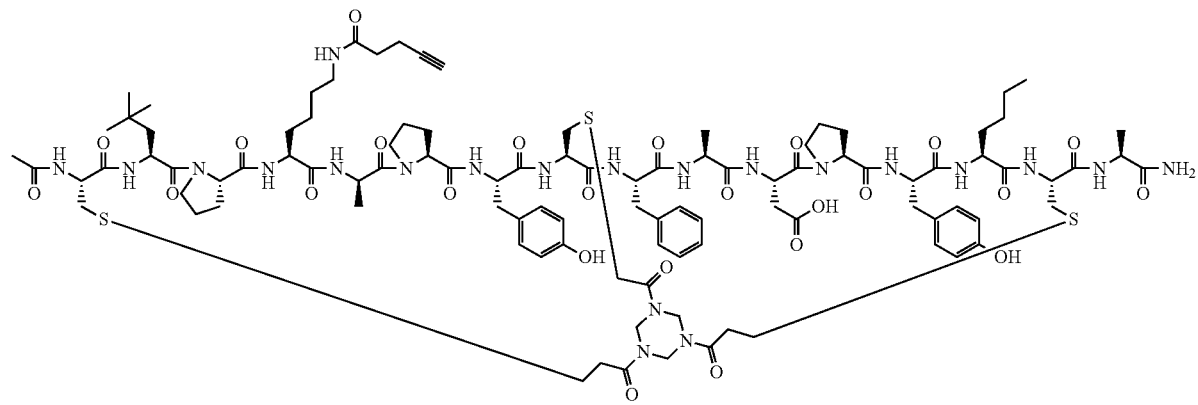
Monomer 12A
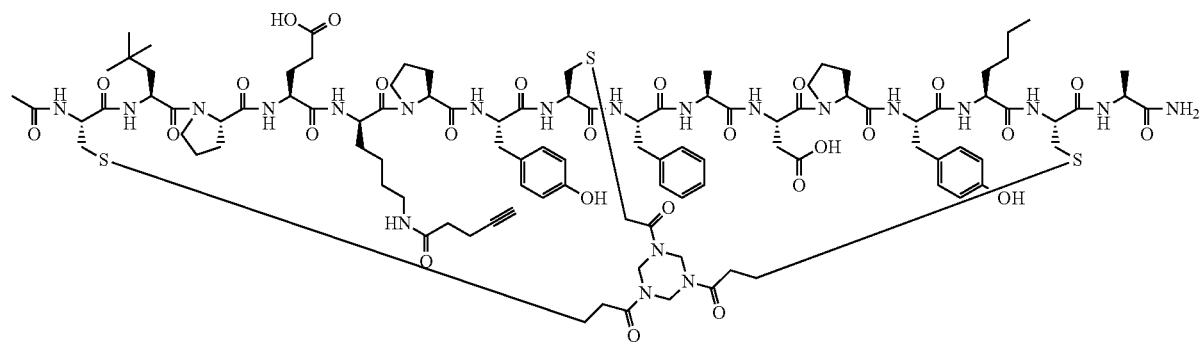
Monomer 13A
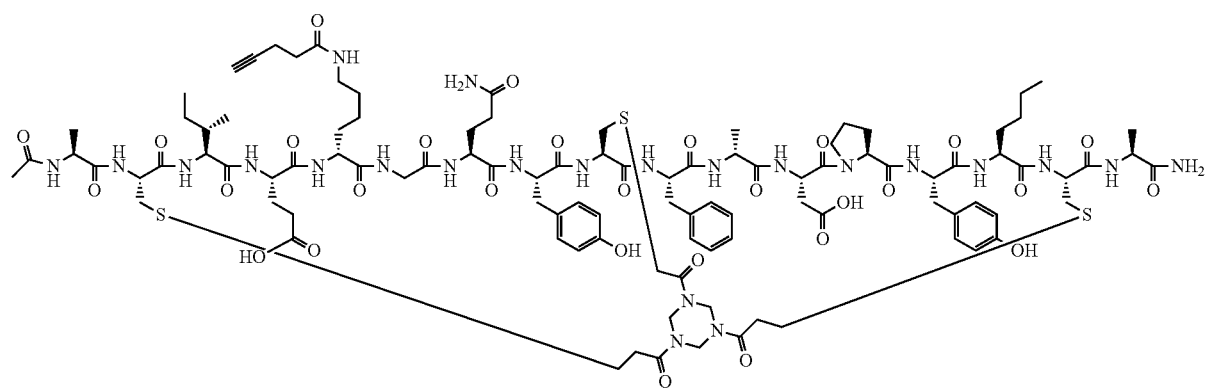
Monomer 14A
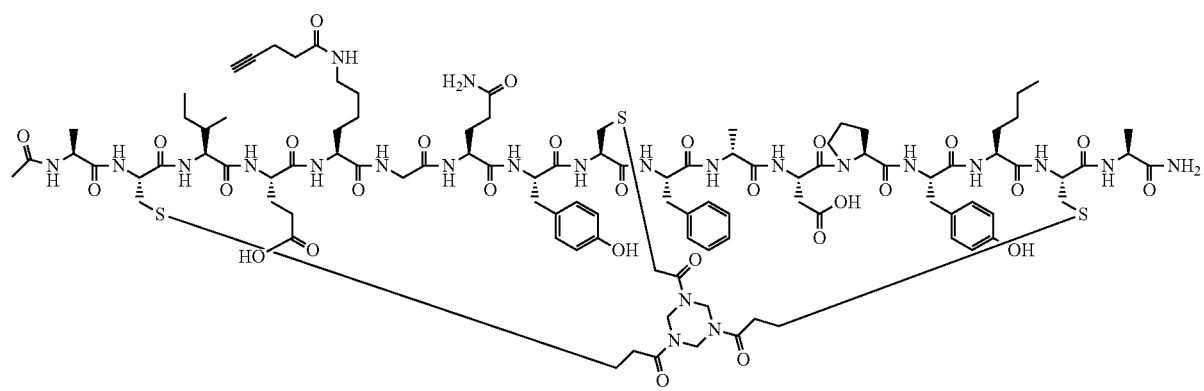

-continued
Monomer 15A
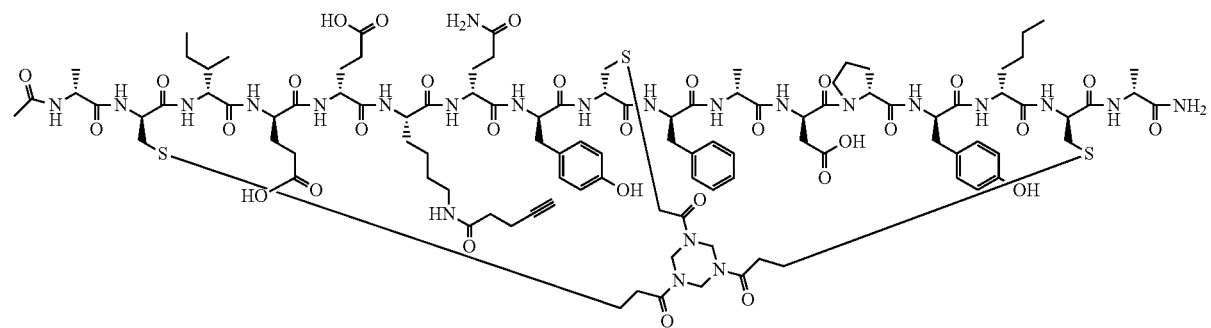
Compound 15:

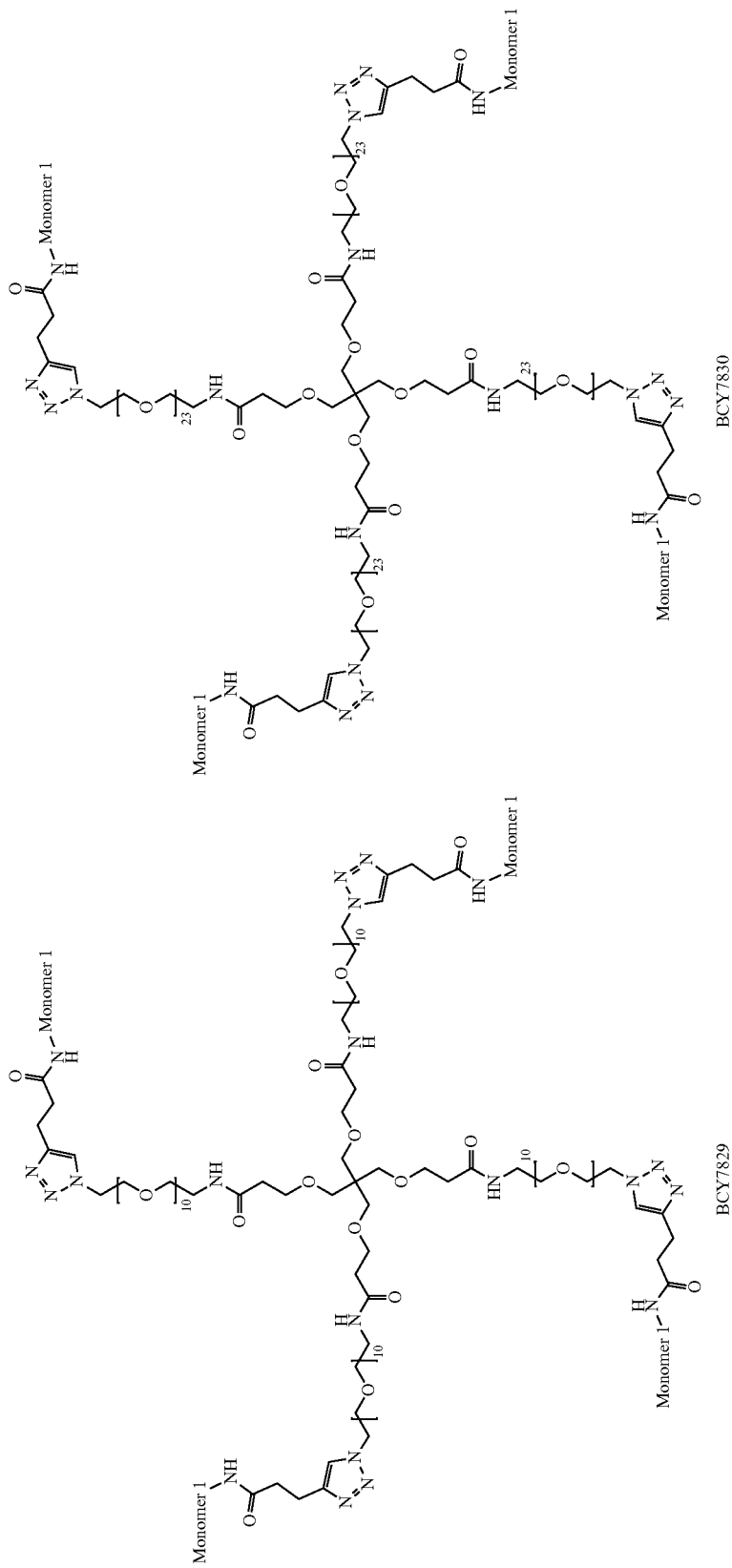

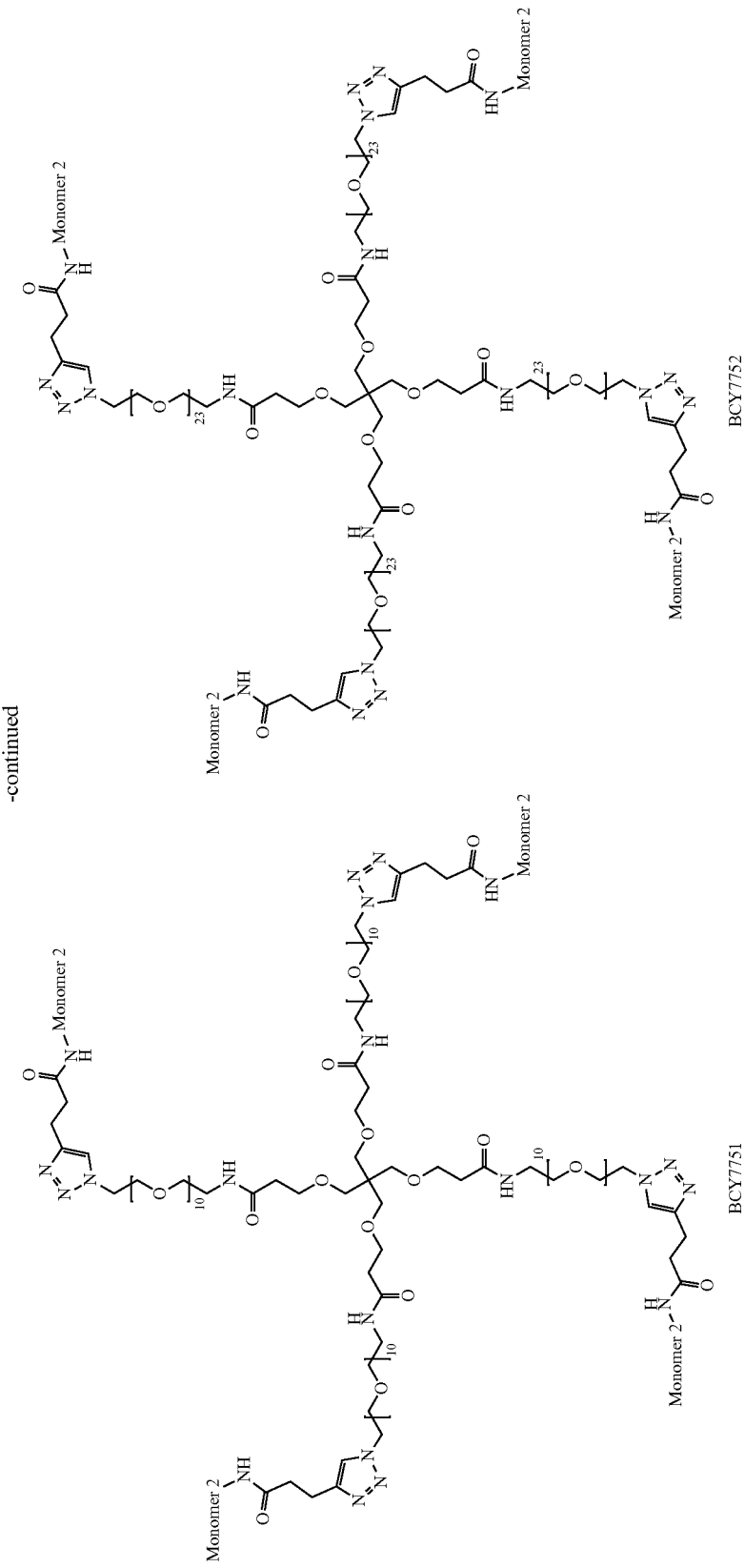

-continued
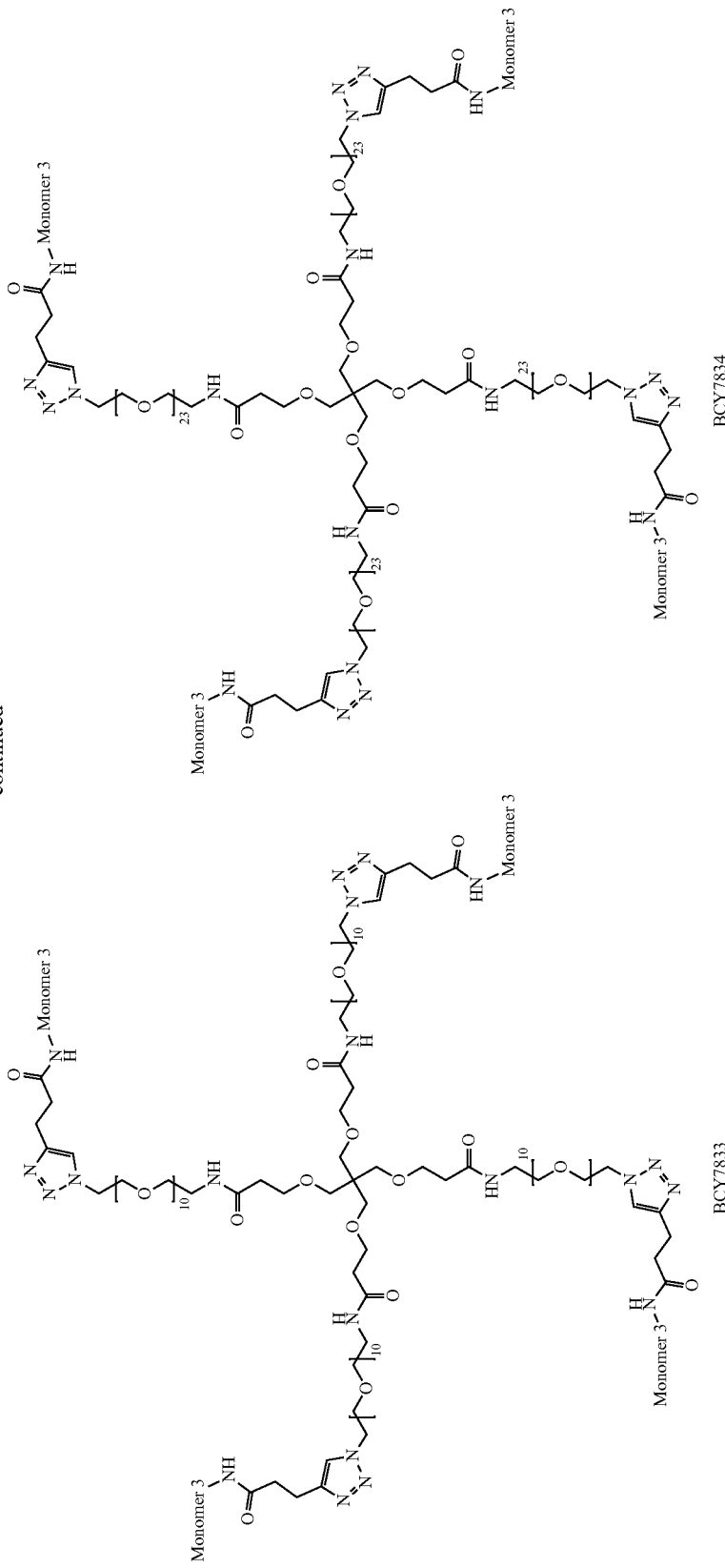

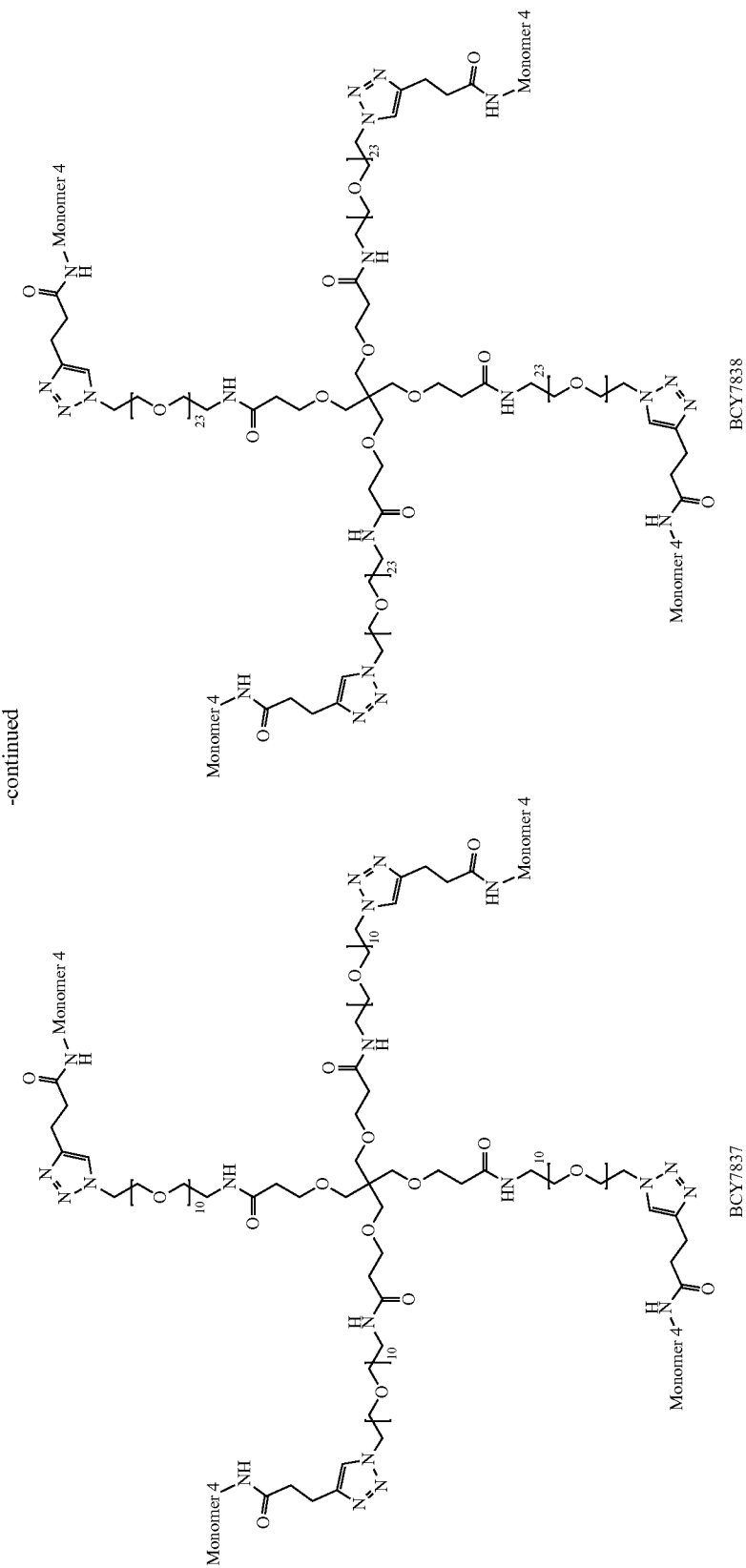

-continued
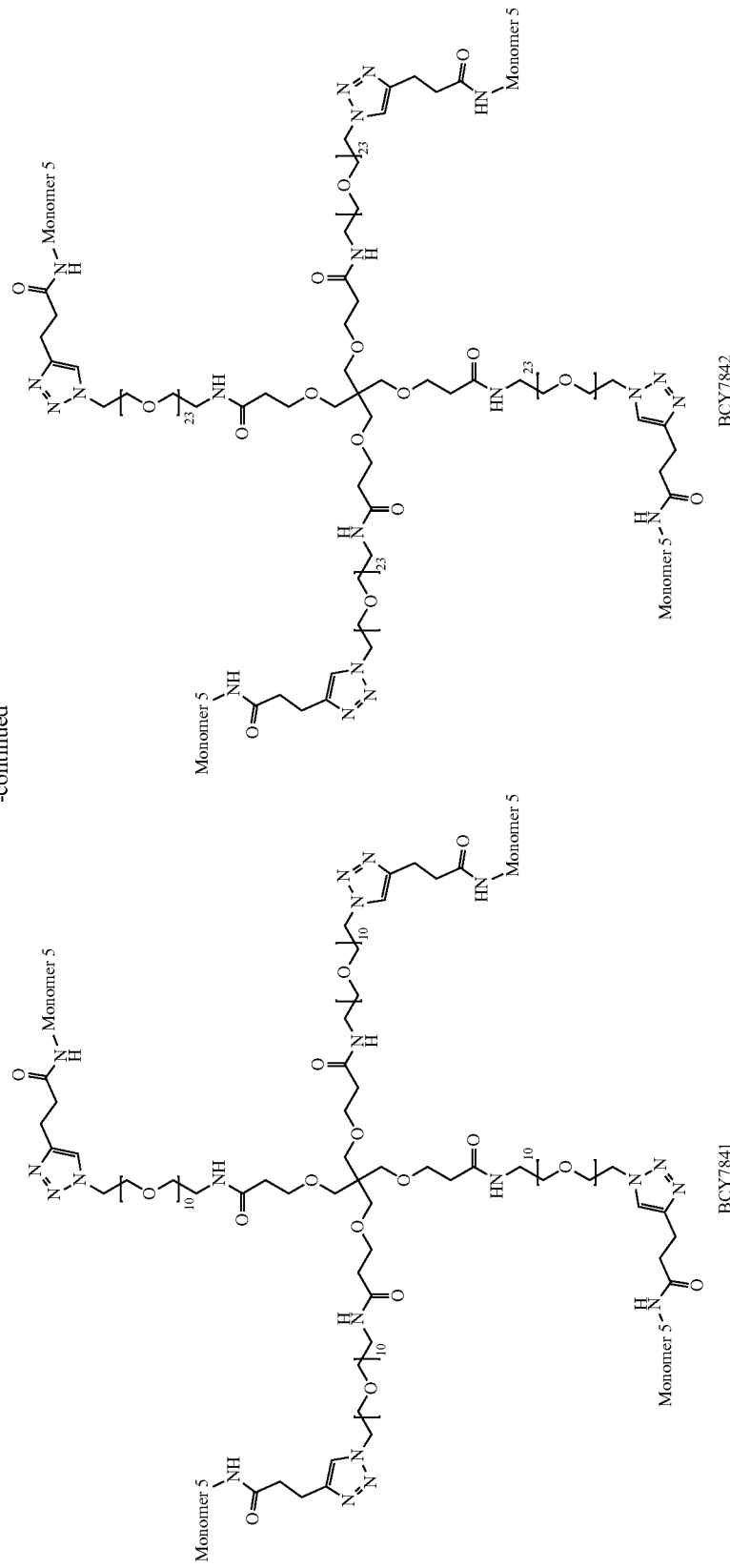

-continued
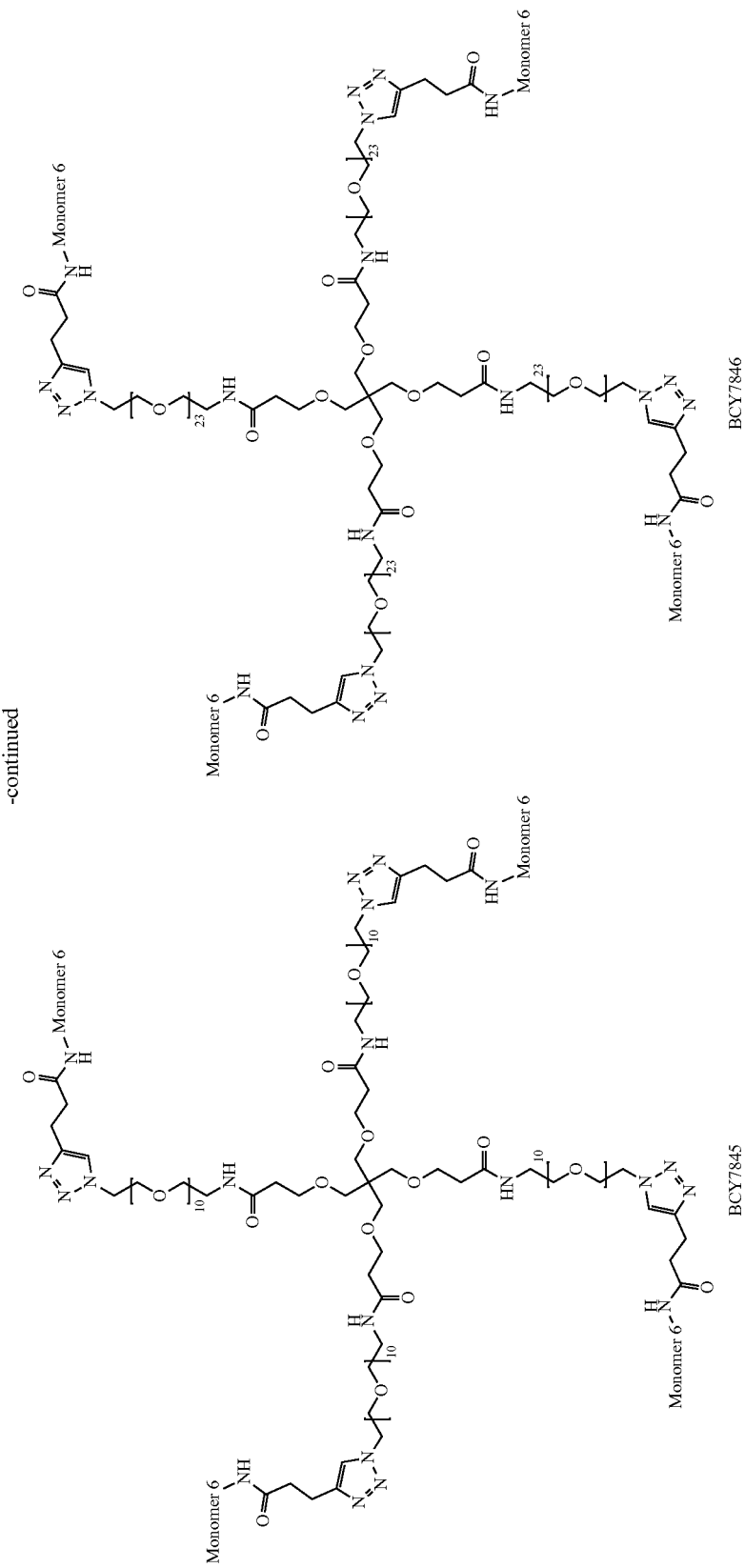

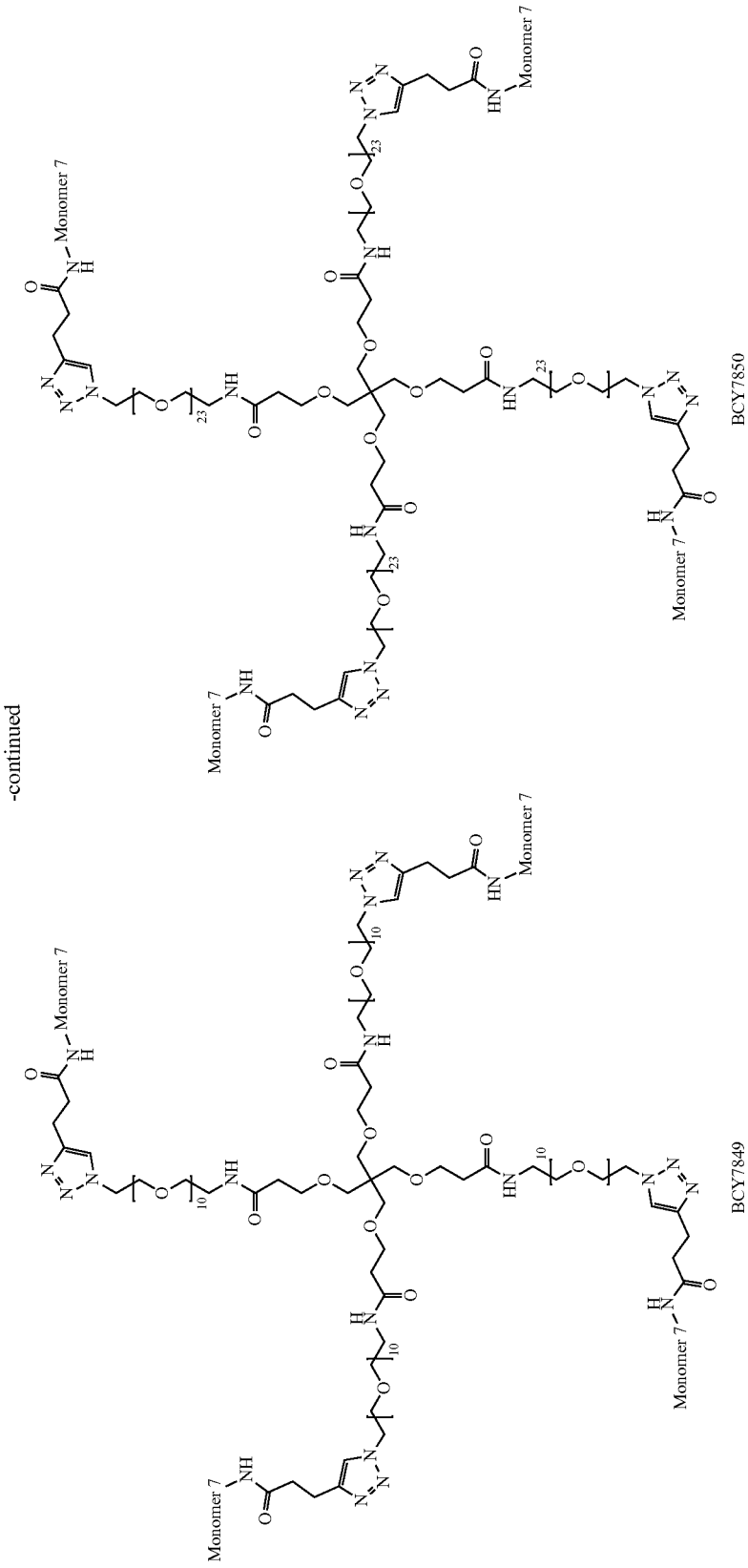

-continued
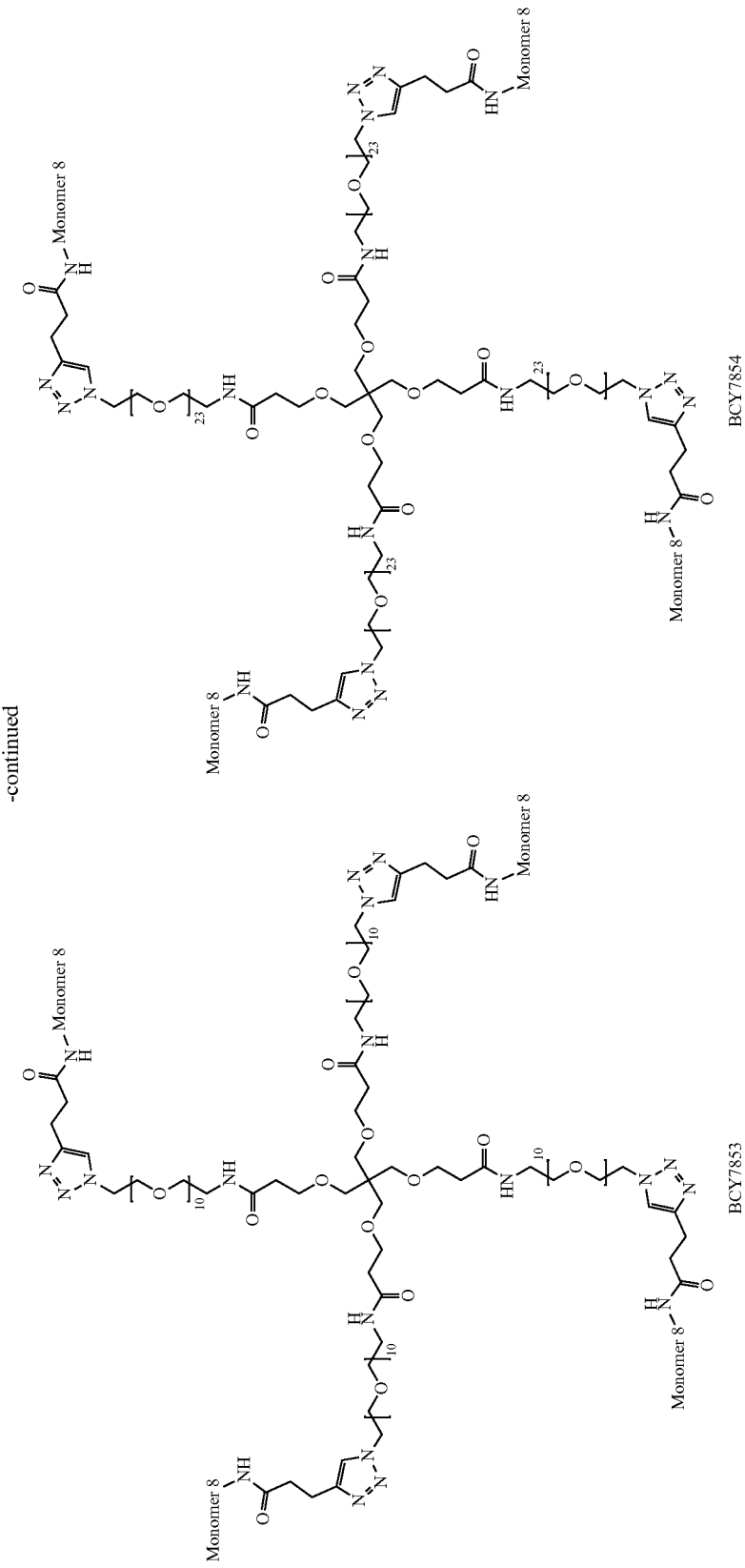

-continued
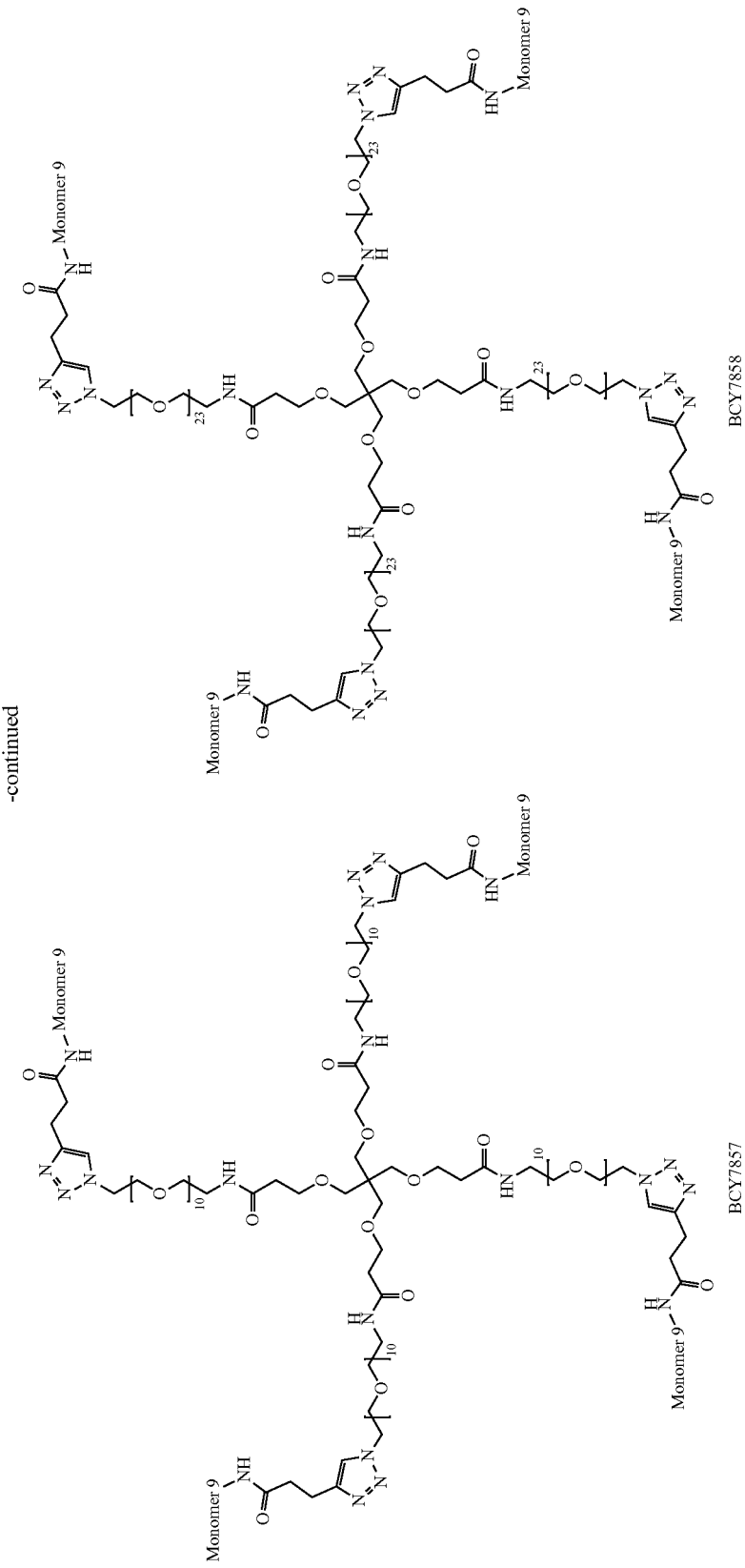

-continued
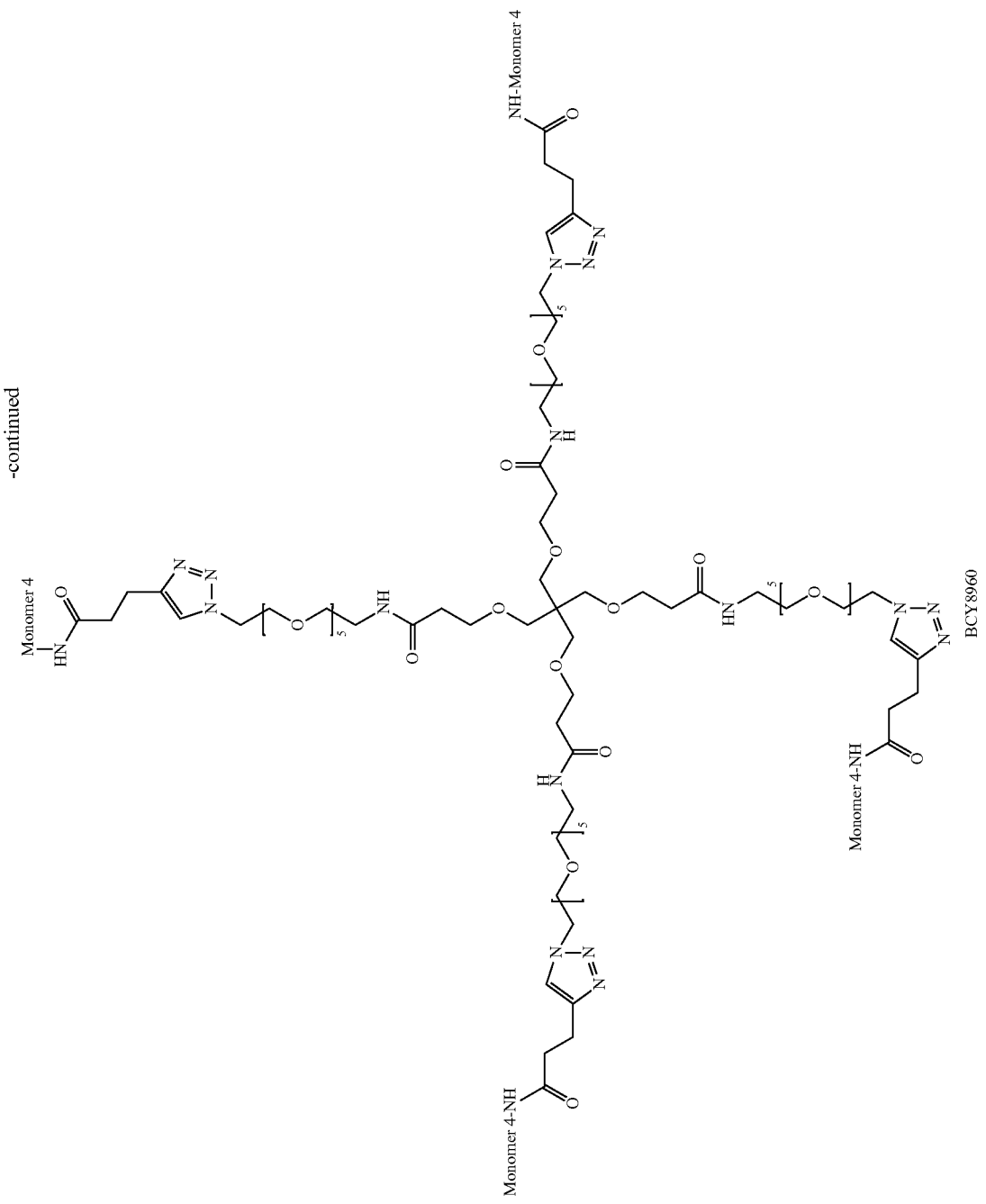
BCY8960

-continued
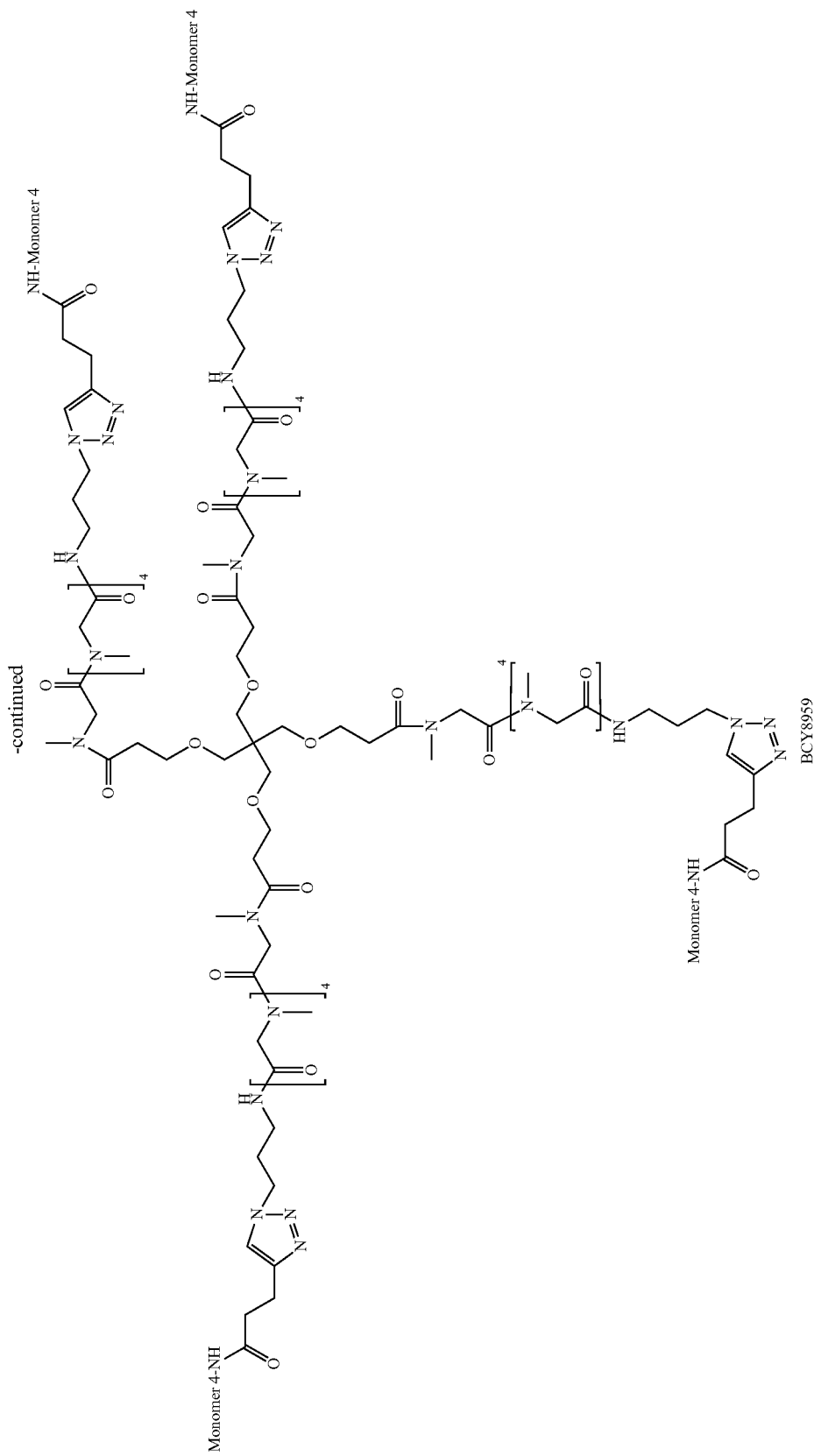

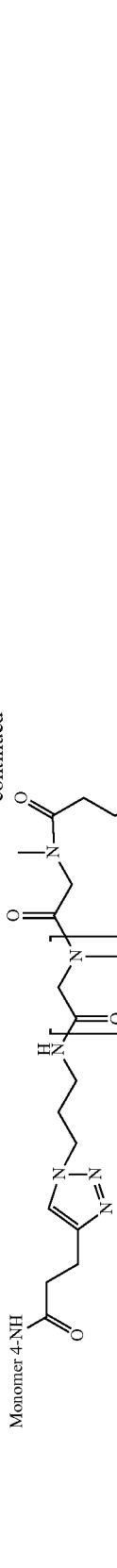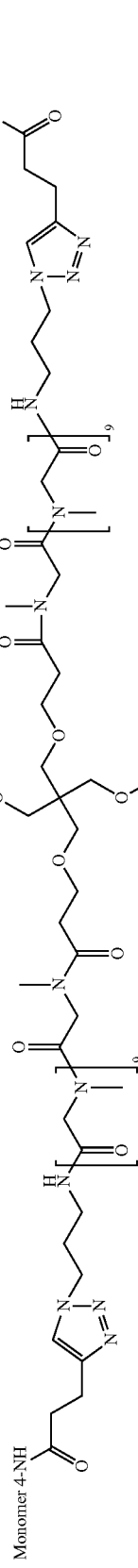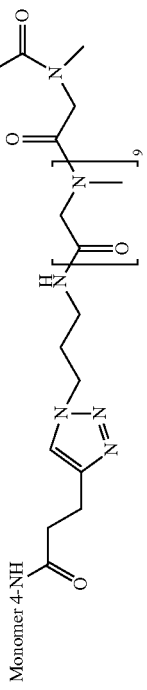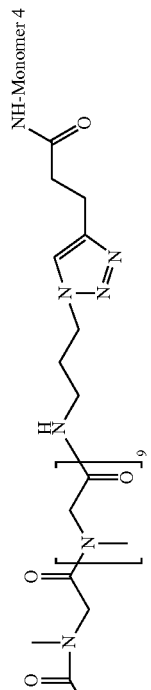

-continued
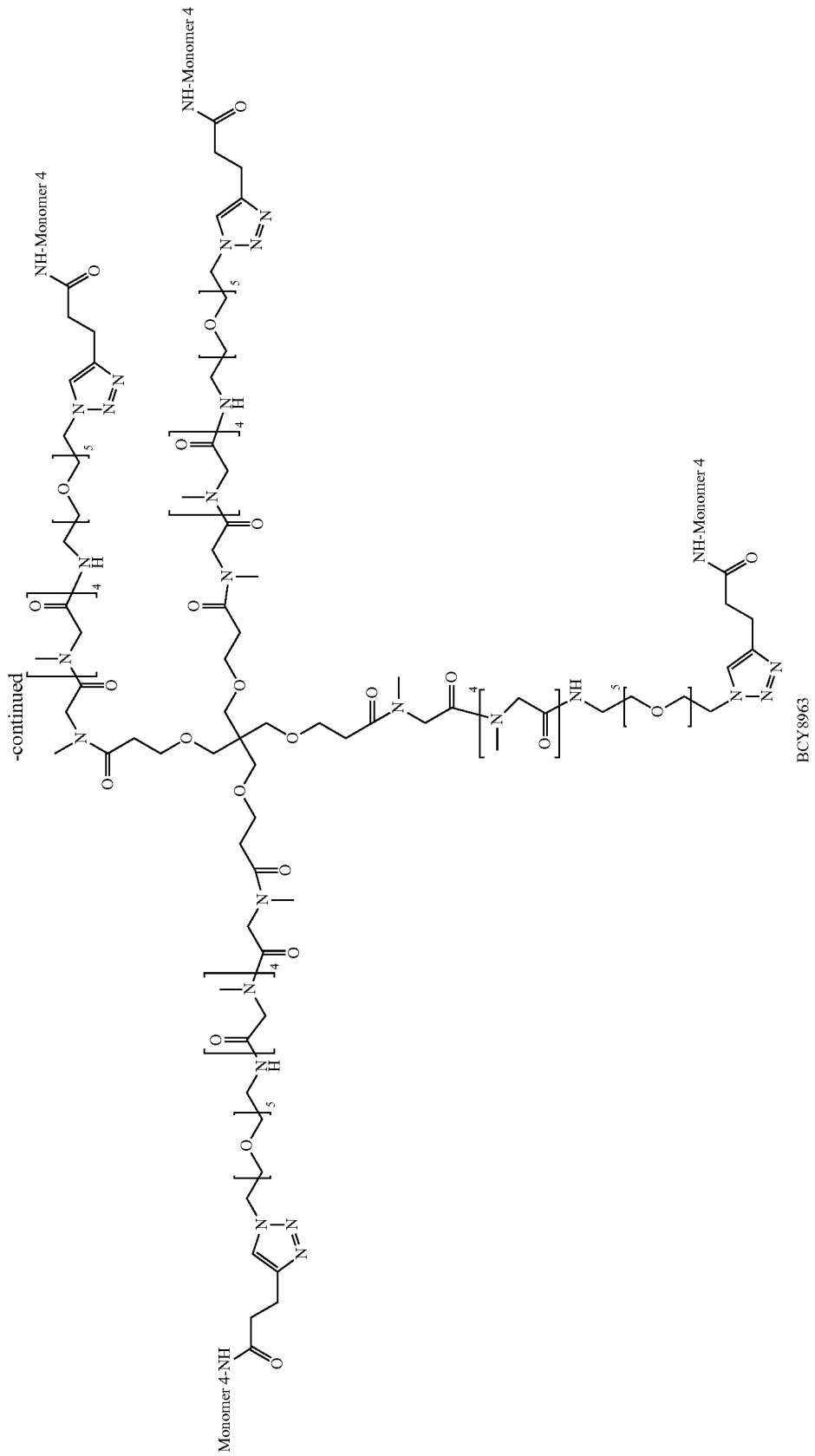
BCY8963

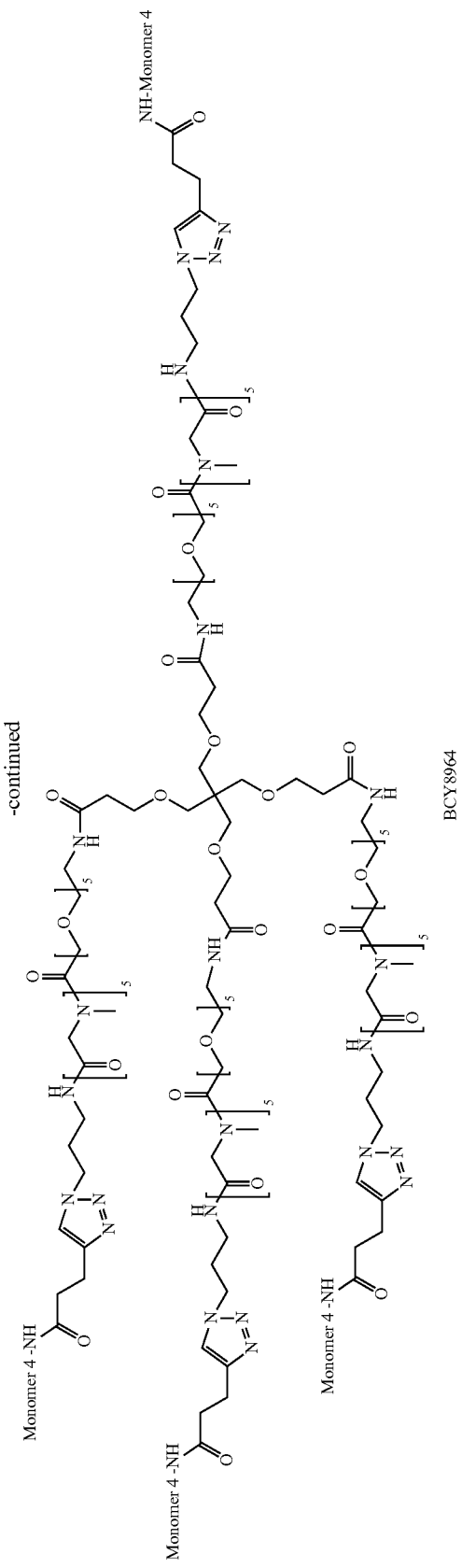

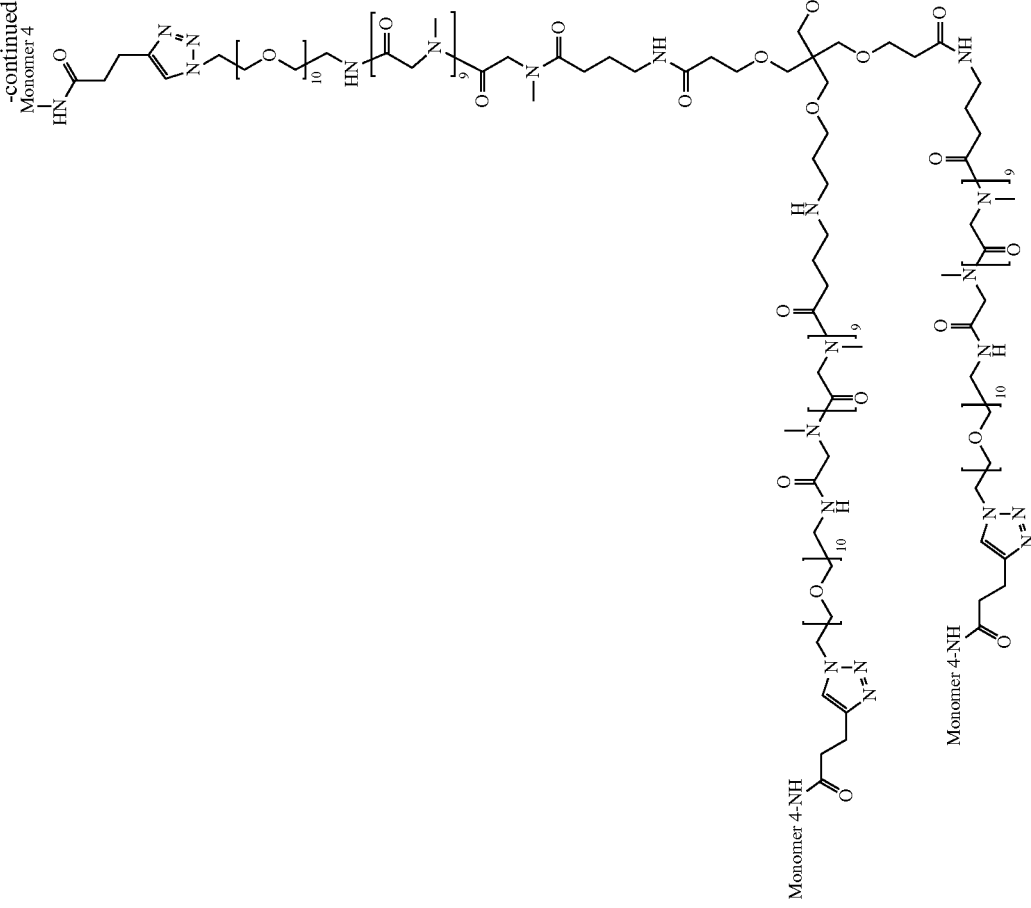

BCY7829:

A mixture of compound 14A (24 mg, 9.76 µmol, 1 eq), Monomer 1A (130.28 mg, 58.56 µmol, 6 eq), CuI (37.18 mg, 195.22 µmol, 20 eq) in DMF (3 mL) was degassed and purged with $N_2$ for 3 times, and then the mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7829 (39.4 mg, 3.19 µmol, 32.64% yield, 91.83% purity) as a white solid.

BCY7830:

To a solution of compound 14B (4 mg, 8.42e-1 µmol, 1 eq) and Monomer 1A (14.99 mg, 6.74 µmol, 8 eq) in DMF (1 mL) was added $CuSO_4.5H_2O$ (0.8 M, 12.63 µL, 12 eq) and ascorbic acid (0.8 M, 84.22 µL, 80 eq) under $N_2$ atmosphere. The mixture was stirred at 30° C. for 1 hr. LC-MS and HPLC showed Reactant 1 was consumed completely. The reaction mixture was filtered and concentrated under reduced pressure to give a residue. The residue was purified by prep-HPLC (TFA condition) to give BCY7830 (6 mg, 3.69e-1 µmol, 36.79% yield, 70.48% purity) as a white solid.

BCY7751:

To a mixture of compound 14A (4 mg, 1.63 µmol, 1 eq), Monomer 2A (29.67 mg, 13.00 µmol, 7.99 eq) in DMF (0.5 mL) was added CuI (6.2 mg, 32.6 µmol, 20 eq) and the mixture was degassed and purged with $N_2$ for 3 times, and then the mixture was stirred at 25-30° C. for 1 hr under $N_2$ atmosphere. LC-MS showed Reactant 1 was consumed completely. The reaction mixture was filtered and concentrated under reduced pressure to give a residue.

The residue was purified by prep-HPLC (TFA condition) to give BCY7751 (5 mg, 1.74e-1 µmol, 22.85% yield, 86.1% purity) as a white solid.

BCY7752:

A mixture of compound 14B (24 mg, 5.05 µmol, 1 eq), Monomer 2A (69.17 mg, 30.32 µmol, 6 eq), CuI (11.55 mg, 60.64 µmol, 12 eq) in DMF (3 mL) was degassed and purged with $N_2$ for 3 times, and then the mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7752 (21.7 mg, 1.41 µmol, 27.97% yield, 90.38% purity) as a white solid.

BCY7833:

To a mixture of compound 14A (4 mg, 1.63 µmol, 1 eq), Monomer 3A (44.23 mg, 19.52 µmol, 12.0 eq) in DMF (1 mL) was added a solution of $CuSO_4$ (0.4 M, 48.80 µL, 12.0 eq) and (2R)-2-[(1S)-1,2-dihydroxyethyl]-3,4-dihydroxy-2H-furan-5-one (0.4 M, 162.68 µL, 40.0 eq) and the mixture was degassed and purged with $N_2$ for 3 times, and then the mixture was stirred at 25-30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7833 (4.2 mg, 1.86e-1 µmol, 11.43% yield, 51.00% purity) as a white solid.

BCY7834:

To a mixture of compound 14B (4 mg, 8.42e-1 µmol, 1 eq), Monomer 3A (22.90 mg, 10.11 µmol, 12.0 eq) in DMF (1 mL) was added a solution of $CuSO_4.5H_2O$ (0.4 M, 18.95 µL, 9.0 eq) and (2R)-2-[(1S)-1,2-dihydroxyethyl]-3,4-dihydroxy-2H-furan-5-one (0.4 M, 84.22 µL, 40 eq) in $H_2O$ (0.11 mL) and the mixture was degassed and purged with $N_2$ for 3 times, and then the mixture was stirred at 25-30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7834 (2.3 mg, 1.40e-1 µmol, 16.64% yield, 84.14% purity) as a white solid.

BCY7837:

To a mixture of compound 14A (4 mg, 1.63 µmol, 1 eq), Monomer 4A (22.11 mg, 9.76 µmol, 6 eq) in DMF (1 mL) was added CuI (6.20 mg, 32.54 µmol, 20 eq) and the mixture was degassed and purged with $N_2$ for 3 times, and then the mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7837 (11.4 mg, 6.16e-1 µmol, 37.86% yield, 62.25% purity) as a white solid.

BCY7838:

A mixture of compound 14B (40 mg, 8.42 µmol, 1 eq), Monomer 4A (114.48 mg, 50.53 µmol, 6 eq), CuI (32.08 mg, 168.44 µmol, 20 eq) in DMF (5 mL) was degassed and purged with $N_2$ for 3 times, and then the mixture was stirred at 25-30° C. for 2 hrs under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7838 (51 mg, 3.33 µmol, 39.49% yield, 90.08% purity) as a white solid.

BCY7841:

A mixture of compound 14A (4 mg, 1.63 µmol, 1 eq), Monomer 5A (23 mg, 9.84 µmol, 6.05 eq), CuI (309.82 µg, 1.63 µmol, 1 eq) in DMF (0.5 mL) was degassed and purged with $N_2$ for 3 times, and then the mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7841 (8.3 mg, 4.47e-1 µmol, 27.45% yield, 63.54% purity) as a white solid.

BCY7842:

The click reaction was performed in 3 containers in parallel. In each reaction container, a mixture of compound 14B (170.0 mg, 35.8 µmol, 1.0 eq), Monomer 5A (340.0 mg, 145.4 µmol, 4.06 eq), and THPTA (0.4 M, 89.5 µL, 1.0 eq) was dissolved in t-BuOH/H2O (1:1, 6 mL, pre-degassed and purged with $N_2$ for 3 times), and then $CuSO_4$ (0.4 M, 89.5 µL, 1.0 eq) and VcNa (0.4 M, 179.0 µL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 16 hr under $N_2$ atmosphere. LC-MS showed compound 14B was consumed completely and one main peak with desired m/z (MW: 14100.11, observed m/z: 1007.5400 ([M/14+H+])) was detected. The reaction mixture was combined, filtered, and concentrated under reduced pressure to give a residue. The crude product was then purified by prep-HPLC (TFA condition), resulting in BCY7842 (1.03 g, 69.25 µmol, 64.49% yield, 94.34% purity) was obtained as a white solid.

BCY7845:

A mixture of compound 14A (40 mg, 16.27 µmol, 1 eq), Monomer 6A (221.23 mg, 97.61 µmol, 6 eq), CuI (62 mg, 325.36 µmol, 20 eq) in DMF (4 mL) was degassed and purged with $N_2$ for 3 times, and then the mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7845 (49 mg, 3.02 μmol, 18.57% yield, 71.06% purity) as a white solid.

BCY7846:

To a solution of compound 14B (4 mg, 8.42e-1 μmol, 1 eq) and Monomer 6A (15.27 mg, 6.74 μmol, 8.0 eq) in DMF (1 mL) was added $CuSO_4·5H_2O$ (0.8 M, 12.63 μL, 12 eq) and ascorbic acid (0.8 M, 84.22 μL, 80 eq). The mixture was degassed and purged with $N_2$ for 3 times, and then the mixture was stirred at 30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7846 (4.8 mg, 1.52e-1 μmol, 18.03% yield, 43.7% purity) as a white solid.

BCY7849:

To a solution of compound 14A (4 mg, 1.63 μmol, 1 eq) and Monomer 7A (29.25 mg, 13.01 μmol, 8 eq) in DMF (1 mL) was added $CuSO_4$ (0.8 M, 24.40 μL, 12 eq) and (2R)-2-[(1S)-1,2-dihydroxyethyl]-3,4-dihydroxy-2H-furan-5-one (0.8 M, 81.34 μL, 40 eq). The mixture was stirred at 30° C. for 1 hrs. LC-MS showed Reactant 1 was consumed completely. The reaction mixture was filtered and concentrated under reduced pressure to give a residue. The residue was purified by prep-HPLC (TFA condition) to give BCY7849 (8.5 mg, 4.72e-1 μmol, 29.03% yield, 63.6% purity) as a white solid.

BCY7850:

To a solution of compound 14B (4 mg, 8.42e-1 μmol, 1 eq) and Monomer 7A (15.14 mg, 6.74 μmol, 8 eq) in DMF (1 mL) was added $CuSO_4·5H_2O$ (0.8 M, 12.63 μL, 12 eq) and ascorbic acid (0.8 M, 84.22 μL, 80 eq) under $N_2$ atmosphere. The mixture was stirred at 30° C. for 1 hr. LC-MS and HPLC showed Reactant 1 was consumed completely. The reaction mixture was filtered and concentrated under reduced pressure to give a residue. The residue was purified by prep-HPLC (TFA condition) to give BCY7850 (2.5 mg, 0.18 μmol, 21.41% yield, 99.09% purity) as a white solid.

BCY7853:

To a solution of compound 14A (4 mg, 1.63 μmol, 1 eq) and Monomer 8A (29.90 mg, 13.01 μmol, 8 eq) in DMF (1 mL) was added $CuSO_4$ (0.8 M, 24.40 μL, 12 eq) and (2R)-2-[(1S)-1, 2-dihydroxyethyl]-3, 4-dihydroxy-2H-furan-5-one (0.8 M, 81.34 μL, 40 eq). The mixture was stirred at 30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7853 (0.7 mg, 4.20e-2 μmol, 2.58% yield, 69.882% purity) as a white solid.

BCY7854:

To a solution of compound 14B (4 mg, 8.42e-1 μmol, 1 eq) and Monomer 8A (15.48 mg, 6.74 μmol, 8 eq) in DMF (1 mL) was added $CuSO_4$ (0.8 M, 12.63 μL, 12 eq) and ascorbic acid (0.8 M, 84.22 μL, 80 eq). The mixture was stirred at 30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7854 (0.6 mg, 3.02e-2 μmol, 3.59% yield, 70.227% purity) as a white solid.

BCY7857:

To a solution of compound 14A (4 mg, 1.63 μmol, 1 eq) and Monomer 9A (22.27 mg, 9.76 μmol, 6 eq) in DMF (1 mL) was added CuI (6.20 mg, 32.54 μmol, 20 eq). The mixture was stirred at 25-30° C. for 1 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7857 (1.3 mg, 8.28e-2 μmol, 5.09% yield, 73.80% purity) as a white solid.

BCY7858:

To a solution of compound 14B (4 mg, 8.42e-1 μmol, 1 eq) and Monomer 9A (15.37 mg, 6.74 μmol, 8 eq) in DMF (1 mL) was added $CuSO_4$ (0.8 M, 12.63 μL, 12 eq) and ascorbic acid (0.8 M, 84.22 μL, 80 eq) under $N_2$ atmosphere. The mixture was stirred at 30° C. for 1 hr. LC-MS and HPLC showed Reactant 1 was consumed completely. The reaction mixture was filtered and concentrated under reduced pressure to give a residue. The residue was purified by prep-HPLC (TFA condition) to give BCY7858 (2.0 mg, 1.19e-1 μmol, 14.13% yield, 82.55% purity) as a white solid.

BCY8945:

A mixture of compound 14B (105 mg, 22.11 μmol, 1 eq.), Monomer 11A (200 mg, 92.61 μmol, 4.2 eq.), and THPTA (9.6 mg, 1 eq.) was dissolved in t-BuOH/$H_2O$ (1:1, 6 mL, pre-degassed and purged with $N_2$ for 3 times), and then $CuSO_4$ (0.4 M, 55 μL, 1 eq.) and VcNa (0.4 M, 110 μL, 2 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25° C. for 2 hr under $N_2$ atmosphere. LC-MS showed compound 14B was consumed completely and one main peak with desired m/z (MS: 13378.66, observed m/z: 1030.6 ([M/13+H+]), 956.9 ([M/14+H+])) was detected. The reaction mixture was filtered and concentrated under reduced pressure to give a residue. The crude product was purified by prep-HPLC (TFA condition). BCY8945 (120 mg, 8.37 μmol, 37.86% yield, 91.11% purity) was obtained as a white solid.

BCY8947:

To a solution of compound 14A (150.0 mg, 61.0 μmol, 1.0 eq), Monomer 12A (543.8 mg, 245.2 μmol, 4.02 eq), and THPTA (26.5 mg, 61.0 μmol, 1.0 eq) was dissolved in t-BuOH/H2O (1:1, 6 mL, pre-degassed and purged with $N_2$ for 3 times), and then CuSO4 (9.8 mg, 61.0 μmol, 1.0 eq) and VcNa (24.2 mg, 122.0 μmol, 2.0 eq) were added under $N_2$. The pH of this solution was adjusted to 8 by dropwise addition of 0.2 M NH4HCO3 (in 1:1 t-BuOH/H2O), and the solution turned to light yellow. The reaction mixture was stirred at 40° C. for 16 hr under $N_2$ atmosphere. LC-MS showed compound 14A was consumed completely and one main peak with desired m/z (calculated MW: 11329.12, observed m/z: 1133.6 ([M/10+H+]), 1029.2 ([M/11+H+]), m/z=1109 corresponds to extra compound 4) was detected. The reaction mixture was filtered and concentrated under reduced pressure to give a residue. The crude product was purified by prep-HPLC (TFA condition), resulting in BCY8947 (230 mg, 18.28 μmol, 29.96% yield, 95.82% purity) was obtained as a white solid. Furthermore, 200 mg was subjected to sodium salt exchange, and 150.3 mg (97.16% purity) was obtained.

BCY8960 (122.1 mg, 91.90% purity, 16.80% yield), BCY8959 (21.3 mg, 91.49% purity, 25.14% yield), BCY8966 (20.5 mg, 90.04% purity, 45.90% yield), BCY8963 (17.1 mg, 96.70% purity, 9.4% yield), BCY8964 (27.8 mg, 90.41% purity, 11.5% yield) and BCY9767 (6.1 mg, 89.40% purity, 6.12% yield) were synthesized in an analogous manner to that described above for BCY8945 using one of Compounds 14C, 14D, 14E, 14F, 14G or 14H;

monomer 4A; and CuSO$_4$, (2R)-2-[(1S)-1, 2-dihydroxyethyl]-3,4-dihydroxy-2H-furan-5-one and THPTA.

Production of CD137 Monoclonal Antibody Agonist:

The sequence of the CD137 monoclonal antibody agonist that was used for comparison to CD137 multimers in the experiments presented herein was disclosed in U.S. Pat. No. 7,288,638. The IgG4 isotype antibody was expressed using the ExpiCHO Expression System (Thermo Fisher Scientific) following transient transfection of the DNA expression construct. The antibody was purified by Protein A affinity chromatography and formulated in phosphate-buffered solution (PBS) pH 7.2. Purity analysis using HPLC-SEC (column GF-250, Agilent) indicated that the monomer rate of CD137 monoclonal antibody is approximately 95%. Binding activity analysis indicated that the CD137 monoclonal antibody with a concentration higher than 1 μg/ml can bind to CHO cells expressing CD137. Endotoxin analysis using the ToxinSensor™ Chromogenic LAL Endotoxin Assay Kit (Genscript) indicated that the CD137 monoclonal antibody preparation contained <7 EU/mg of endotoxin.

Biological Data

1. CD137 Biacore Experimental Description

Biacore experiments were performed to determine $k_a$ (M$^{-1}$ s$^{-1}$), $k_d$ (s$^{-1}$), $K_D$ (nM) values of monomeric peptides binding to human CD137 protein. Recombinant human CD137 (R&D systems) was resuspended in PBS and biotinylated using EZ-Link™ Sulfo-NHS-LC-LC-Biotin reagent (Thermo Fisher) as per the manufacturer's suggested protocol. The protein was desalted to remove uncoupled biotin using spin columns into PBS.

For analysis of peptide binding, a Biacore T200 or a Biacore 3000 instrument was used with a XanTec CMD500D chip. Streptavidin was immobilized on the chip using standard amine-coupling chemistry at 25° C. with HBS-N (10 mM HEPES, 0.15 M NaCl, pH 7.4) as the running buffer. Briefly, the carboxymethyl dextran surface was activated with a 7 min injection of a 1:1 ratio of 0.4 M 1-ethyl-3-(3-dimethylaminopropyl) carbodiimide hydrochloride (EDC)/0.1 M N-hy dr oxy succinimide (NHS) at a flow rate of 10 μl/min. For capture of streptavidin, the protein was diluted to 0.2 mg/ml in 10 mM sodium acetate (pH 4.5) and captured by injecting 120 μl of onto the activated chip surface. Residual activated groups were blocked with a 7 min injection of 1 M ethanolamine (pH 8.5) and biotinylated CD137 captured to a level of 270-1500 RU. Buffer was changed to PBS/0.05% Tween 20 and a dilution series of the peptides was prepared in this buffer with a final DMSO concentration of 0.5%. The top peptide concentration was 500 nM with 6 further 2-fold or 3-fold dilutions. The SPR analysis was run at 25° C. at a flow rate of 90 μl/min with 60 seconds association and 900 seconds dissociation. After each cycle a regeneration step (10 μl of 10 mM glycine pH 2) was employed. Data were corrected for DMSO excluded volume effects as needed. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

Certain monomeric peptides were tested in this assay and the results are shown in Table 3:

TABLE 3

CD137 Biacore Assay Data with Monomeric Peptides

| Monomer Number | Kd (nM) |
|---|---|
| BCY3814 | 33.3 |
| BCY7740 | 88 |
| BCY7741 | 122 |
| BCY7742 | 855 |
| BCY7743 | 101 |
| BCY7744 | 92 |
| BCY7745 | 63.1 |
| BCY7746 | 260 |
| BCY7747 | 361 |
| BCY7748 | 264 |
| BCY8935 | NB |
| BCY8927 | 12.3 |
| BCY8928 | 11.4 |
| BCY8925 | NB |
| BCY8926 | NB |
| BCY8141 | 57.8 |
| BCY8095 | 0.685 |
| BCY8142 | 321 |
| BCY8096 | 26 |
| BCY8143 | 112 |
| BCY8144 | 66.7 |
| BCY8097 | 99.4 |

NB: No binding up to 5 μM

2. CD137 Promega Assay Experimental Description

CD137 binding multimers were evaluated for CD137 using a Reporter cell activity assay that uses NF-κB luciferase luminescence as a read-out of CD137 activation in Jurkat cells. Medium was prepared by thawing FBS and adding 1% FBS to RPMI-1640 (Promega kit CS196005). Samples were diluted at concentration expected to give the maximum fold induction and then titrated down in ⅓ dilution series or 1/10 dilution series in a sterile 96 well-plate. CD137 Jurkat cells were thawed in a water-bath and then 500 μl cells were added to 9.5 ml pre-warmed 1% FBS RPMI-1640 medium. 50 μl cells were added per well to white cell culture plates. 25 μl of samples were added as duplicate samples or 1% FBS RPMI-1640 alone as background control.

Cells were co-incubated together with agonists for 6 h at 37° C., 5% CO$_2$. After 6 h Bio-Glo™ was thawed and the assay developed at room-temperature. 75 ul Bio-Glo™ was added per well and incubated for 5-10 min. Luciferase signal was read on a Pherastar plate-reader using MARS program. Data was analysed by transforming the data to x=log (X), then plotting log (agonist) vs. response variable slope (4 parameters) to calculate EC$_{50}$ values.

Figure 2:
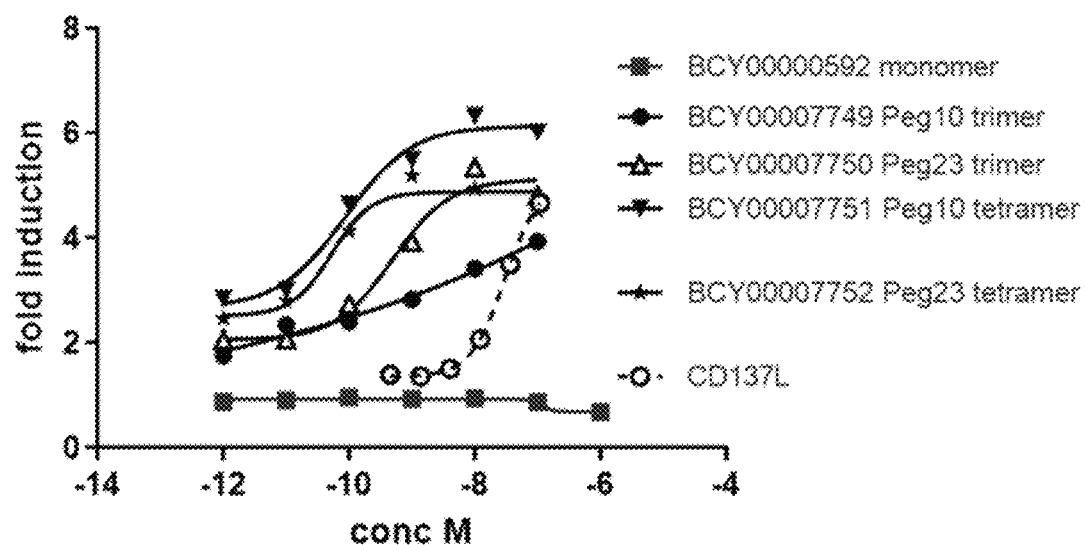
FIG. 2: Reporter cell activity assay data obtained for trimers BCY7749 and BCY7750 and tetramers BCY7751 and BCY7752 compared with monomer BCY592 and the CD137 ligand.
Figure 3:
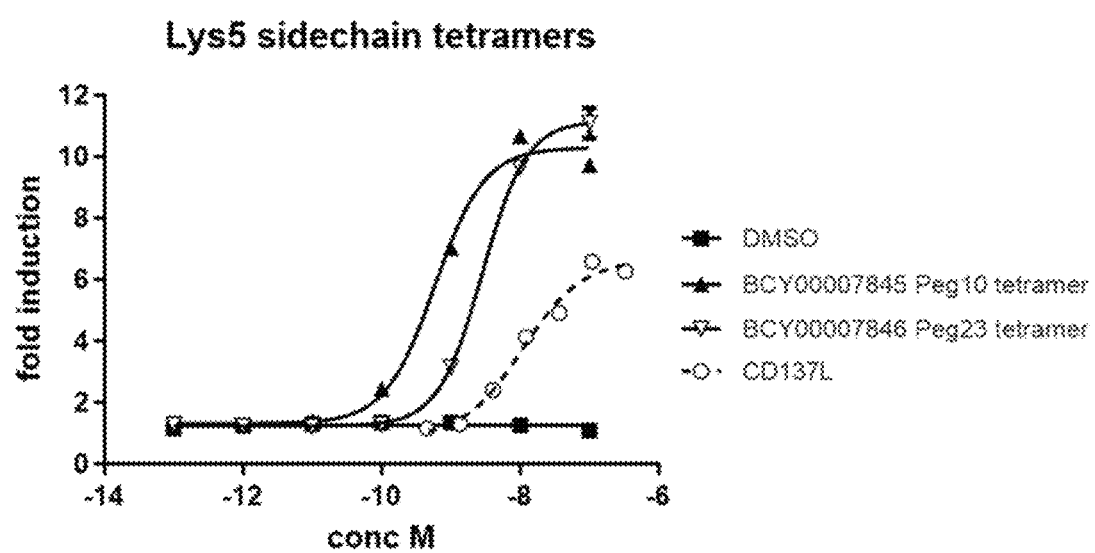
FIG. 3: Reporter cell activity assay data obtained for tetramers BCY7845 and BCY7846 compared with DMSO control and the CD137 ligand.

Data is presented in FIGS. 1 to 3 which shows that the multivalent CD137 bicyclic peptides exhibit a range of properties when compared to the natural ligand (CD137L) for activation of CD137. In FIG. 1, N and C-terminal conjugated trimers and tetramers are compared. A monomeric CD137 binding bicycle peptide (ACIEEGQYCFADPYMCA (SEQ ID NO: 56); BCY592) is included and has no detectable activity in the assay. In FIG. 2, activity for multimers with different PEG chain lengths are compared. Various attachment points for the multimers were explored and FIG. 3 shows the activation data for Lys5 conjugated tetramers as compared to CD137L. DMSO control is included to demonstrate that the inclusion of DMSO in the sample stocks has no influence on the observed activity. Table 4 details the average fold induction and fold improvement in EC50 for each multimer relative to CD137L.

TABLE 4A

CD137 Promega Assay Data with Multimeric Binding Peptides

| Multimer Number | Average Fold EC50 Improvement relative to CD137L* | Average Relative Fold Induction relative to CD137L** |
|---|---|---|
| BCY7750 | 16.13 | 0.90 |
| BCY7749 | 2.08 | 0.88 |
| BCY7827 | 10.86 | 0.76 |
| BCY7828 | 9.72 | 0.65 |
| BCY7831 | 0.56 | 1.01 |
| BCY7832 | 0.15 | 0.68 |
| BCY7835 | 0.50 | 1.04 |
| BCY7836 | 3.18 | 0.32 |
| BCY7839 | 188.19 | 0.56 |
| BCY7840 | 1.58 | 0.55 |
| BCY7843 | 47.73 | 0.68 |
| BCY7844 | 43.07 | 0.57 |
| BCY7847 | 2.91 | 0.59 |
| BCY7848 | 6.60 | 0.55 |
| BCY7851 | 1.43 | 0.64 |
| BCY7852 | 1.36 | 0.58 |
| BCY7855 | 0.66 | 1.12 |
| BCY7856 | 1.07 | 0.67 |
| BCY8102 | 41.27 | 0.91 |
| BCY8103 | 188.34 | 0.91 |
| BCY8106 | 1.26 | 0.94 |
| BCY8107 | 64.33 | 0.64 |
| BCY8145 | 5.93 | 0.95 |
| BCY8146 | 5.11 | 0.83 |
| BCY8151 | 213.05 | 0.49 |
| BCY7751 | 120.52 | 1.32 |
| BCY7752 | 177.8 | 1.18 |
| BCY7829 | 186.8 | 1.12 |
| BCY7830 | 31.31 | 1.48 |
| BCY7833 | 0.07 | 1.03 |
| BCY7837 | 28.99 | 0.97 |
| BCY7838 | 0.73 | 2.19 |
| BCY7841 | 306.76 | 1.14 |
| BCY7842 | 237.56 | 1.22 |
| BCY7845 | 17.78 | 1.54 |
| BCY7846 | 3.39 | 1.92 |
| BCY7849 | 4.91 | 1.50 |
| BCY7850 | 6.35 | 1.21 |
| BCY7853 | 3.46 | 1.02 |
| BCY7854 | 2.35 | 1.16 |
| BCY7857 | 6.66 | 0.86 |
| BCY7858 | 0.60 | 0.91 |
| BCY8104 | 103.27 | 1.65 |
| BCY8105 | 296.56 | 1.09 |
| BCY8108 | 34.03 | 0.79 |
| BCY8147 | 50.58 | 1.04 |
| BCY8148 | 18.71 | 1.20 |
| BCY8149 | 140.06 | 0.93 |
| BCY8150 | 4.14 | 0.77 |
| BCY8581 | — | <2 Fold induction over background at up to 1μM |
| BCY8582 | — | <2 Fold induction over background at up to 1μM |
| BCY8583 | 0.031 | 3.14 |
| BCY8584 | — | <2 Fold induction over background at up to 1μM |
| BCY8937 | — | <2 Fold induction over background at up to 1μM |

*Average EC50 for CD137L = 14.2 nM
**Average fold induction for CD137L = 4.0

Table 4B

CD137 Promega Assay Data with Multimeric Binding Peptides

| Multimer Number | Average Fold EC50 Improvement relative to BCY7845* | Average Relative Fold Induction relative to BCY7845** |
|---|---|---|
| BCY8948 | — | <2 Fold Induction over Background at concentrations up to 100 nM |
| BCY8957 | — | <2 Fold Induction over Background at concentrations up to 100 nM |
| BCY8958 | 0.96 | 0.39 |
| BCY8961 | — | <2 Fold Induction over Background at concentrations up to 100 nM |
| BCY8962 | — | <2 Fold Induction over Background at concentrations up to 100 nM |
| BCY8965 | — | <2 Fold Induction over Background at concentrations up to 100 nM |
| BCY9573 | 0.01 | 0.57 |
| BCY9595 | 0.03 | 0.52 |
| BCY9775 | 0.89 | 0.45 |
| BCY9776 | 0.13 | 0.87 |
| BCY10046 | 0.41 | 0.63 |
| BCY10047 | 0.52 | 0.53 |
| BCY8945 | 0.13 | 1.23 |
| BCY8946 | 5.22 | 0.41 |
| BCY8947 | 1.33 | 0.62 |
| BCY8959 | — | <2 Fold Induction over Background at concentrations up to 100 nM |
| BCY8960 | 0.41 | 0.68 |
| BCY8963 | 1.61 | 0.84 |
| BCY8964 | 2.37 | 1.13 |
| BCY8966 | 5.88 | 0.56 |
| BCY9113 | — | <2 Fold Induction over Background at concentrations up to 100 nM |
| BCY9767 | 0.02 | 0.74 |

*Average EC50 for BCY7845 = 0.57 nM
**Average fold induction for BCY7845 = 6.3
ND: Not determined

3. Plasma Stability Analysis

Multimer stability in plasma was assessed in human, cyno, rat and mouse plasma as follows. Plasma Sources

TABLE 5

| Species / Matrix | Minimum No. of Individuals | Anticoagulant Used | Vendor | Cat# | Batch |
|---|---|---|---|---|---|
| CD-1 Mouse Plasma | 20 Male | EDTA-K2 | Bioreclamation IVT | MSEPLEDTA2-M | MSE261221 |
| SD Rat Plasma | 10 Male | EDTA-K2 | Bioreclamation IVT | RATPLEDTA2-M | RAT326207 |
| Cynomolgus Monkey Plasma | 10 Male | EDTA-K2 | Suzhou Research | CYNOMOLGUS MONKEY PLASMA | SZ20170317 |
| Human Plasma | 3 Male & 3 Female | EDTA-K2 | Bioreclamation IVT | HMPLEDTA2 | BRH1412539 |

Propantheline bromide was used as reference compound in this assay.

Experimental

The pooled frozen plasma was thawed in a water bath at 37° C. prior to experiment. Plasma was centrifuged at 4000 rpm for 5 min and the clots were removed if any. The pH was be adjusted to 7.4±0.1 if required. 1 mM intermediate solutions of test compounds was prepared with DMSO. For positive control Propantheline: a 1 mM intermediate solution was prepared by diluting 5 µL of the stock solution with 45 µL ultra pure water. 100 µM dosing solution was prepared by diluting 20 µL of the intermediate solution (1 mM) with 180 µL DMSO. For positive control Propantheline: 100 µM intermediate solution was prepared by diluting 20 µL of the stock solution with 180 µL 45% MeOH/$H_2O$. 196 µL of blank plasma was spiked with 4 µL of dosing solution (100 µM) to achieve 2 µM of the final concentration in duplicate and samples were Incubated at 37° C. in a water bath. At each time point (0, 1, 2, 4, 6 and 24 hr), 800 µL of stop solution (100 ng/mL tolbutamide, Labetalol, Dexamethasone, propranolol, Diclofenac, Celecoxib in 100% MeOH) was added to precipitate protein and mixed thoroughly. Sample plates were centrifuged at 4,000 rpm for 10 min. An aliquot of supernatant (200 µL) was transferred from each well before submitting to LC-MS/MS analysis.

Data Analysis:

The % remaining of test compound after incubation in plasma was calculated using following equation:

% Remaining=100×(PAR at appointed incubation time/PAR at T0 time)

where PAR is the peak area ratio of analyte versus internal standard (IS)

The appointed incubation time points are T0 (0 hr), Tn (n=0, 1, 2, 4, 6, 24 hr)

Figure 4:
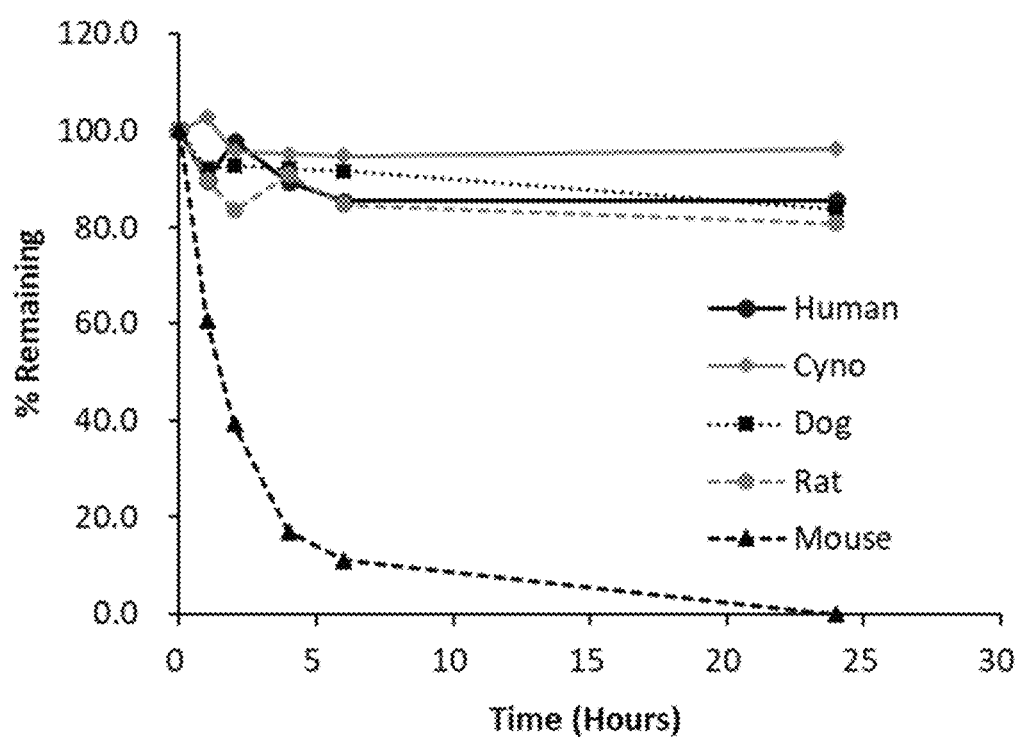
FIG. 4: Data showing plasma stability of BCY7829.

FIG. 4 shows the stability to human, cyno, rat and mouse plasma of BCY7829.

Figure 6:
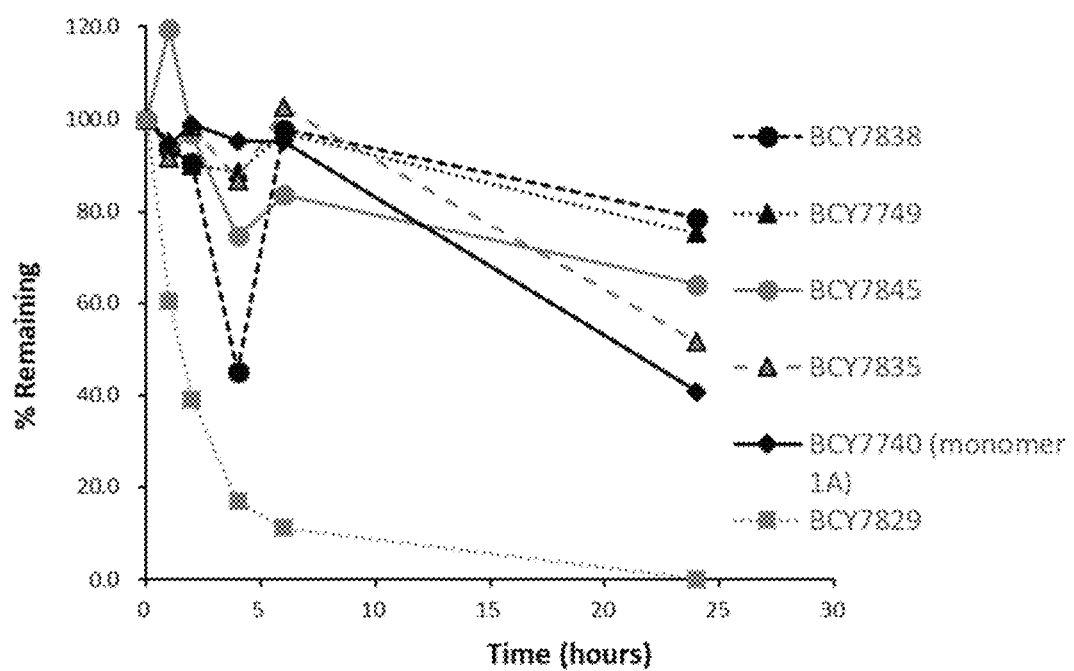
FIG. 6: Data showing stability of CD137 multimers in mouse plasma.

FIG. 6 shows the stability of several multimers and monomer 1A (BCY 7741) to mouse plasma.

4. In Vivo Efficacy Test of Bicycle Multimers Targeting CD137 in Treatment of MC38 Syngeneic Tumors in C57BL/6J B-h4-1BB Humanized Mice Experimental Methods and Procedures The MC38 murine colon carcinoma cell line was purchased from Shunran Shanghai Biological Technology Co., Ltd. The cells will be maintained in vitro as monolayer culture in Dulbecco's Modified Eagle's medium (DMEM) supplemented with 10% heat inactivated fetal calf serum, 100 U/mL penicillin and 100 µg/mL streptomycin at 37° C. in an atmosphere of 5% $CO_2$. The tumor cells will be routinely subcultured twice weekly by trypsin-EDTA treatment. Cells growing in an exponential growth phase will be harvested and counted for tumor inoculation. 6-8 week old female C57BL/6J B-h4-1BB humanized mice were subcutaneously injected (in the flank) with MC38 tumor cells ($5\times10^3$) with 0.1 mL PBS for tumor development. Tumor-bearing animals were randomly enrolled into six study groups when the mean tumor size reached approximately 113 $mm^3$ (Study 1) or 107 $mm^3$ (Study 2). The test and positive control articles were administrated to the tumor-bearing mice according to predetermined regimens as shown below.

Test articles were formulated in aqueous vehicle (25 mM Histidine, 10% sucrose pH=7) and administered intravenously or intraperitoneally. CD137 monoclonal antibody agonist was administered by intraperitoneal injection in 0.9% saline.

Tumor volume was measured three times a week in two dimensions using a caliper, and the volume was expressed in mm3 using the formula: V=0.5 a×b2 where a and b were the long and short diameters of the tumor, respectively. Results are represented by mean and the standard deviation (Mean±SD).

In study 2, mice were sacrificed 21 days after treatment initiation and tumors were harvested for T-cell analysis by flow cytometry. Tumor were cut into small pieces and filtered through a 70 micrometer filter. Lymphocytes were isolated using Histopaque 1083 and resuspended in RPMI 1640 supplemented with 10% fetal bovine serum. Lymphocytes were stained with a cell viability dye (Zombie NIR, Biolegend, #423106) and a panel of antibodies including anti-mouse CD45 (Biolegend, #103138), anti-mouse CD3 (Biolegend, #100328), anti-mouse CD4 (Biolegend, #100438), anti-mouse CD8 (Biolegend, #100759). Stained cells were analysed by Attune NxT Flow Cytometer. T-cell results are expressed as % of CD3+ cells among CD45+ cells. CD8+ T-cell results are expressed as % of CD8+ cells among CD45+CD3+ cells. CD4+ T-cell results are expressed as % of CD4+ cells among CD45+CD3+ cells. Results are represented by mean and the standard deviation (Mean±SD) and the individual values.

Statistical analysis: Data was analyzed using 2 way ANOVA or ordinary One-way ANOVA with Dunnett's test for multiple comparisons, and P<0.05 was considered to be statistically significant. Both statistical analysis and biological observations are taken into consideration. *p<0.001, p<0.01, *p<0.05.

Experimental Design

TABLE 6

Dosing Regimen

| Study | No. Of Animals | Treatment | Dosages (mg/kg) | Dosing Route | Schedule |
|---|---|---|---|---|---|
| 1 | 5 | BCY7829 | 20 | i.v. | QAD × 6 |
| 1 | 5 | BCY7835 | 20 | i.v. | QAD × 6 |
| 1 | 5 | BCY7838 | 30 | i.v. | QAD × 6 |
| 1 | 5 | Anti-CD137 mAb Agonist | 3 | i.p. | BIW × 4 |
| 1 | 5 | Vehicle | — | i.v. | QAD × 6 |
| 2 | 5 | Vehicle | — | i.v. | QD × 20 |
| 2 | 5 | Anti-CD137 mAb Agonist | 3 | i.p. | BIW × 6 |
| 2 | 5 | BCY8945 | 30 | i.p. | QD × 20 |
| 2 | 5 | BCY8945 | 30 | s.c. | QD × 20 |
| 2 | 5 | BCY8947 | 30 | i.p. | QD × 20 |
| 2 | 5 | BCY7842 | 30 | i.p. | QD × 20 |

Notes:
Dosing volume was adjusted based on body weight (10 µL/g).
QAD refers to every other days,
BIW refers to twice per week,
QD refers to once a day.
i.v. refers to intravenous injection.
i.p. refers to intraperitoneal injection.
s.c. refers to subcutaneous injection.

Figure 7:
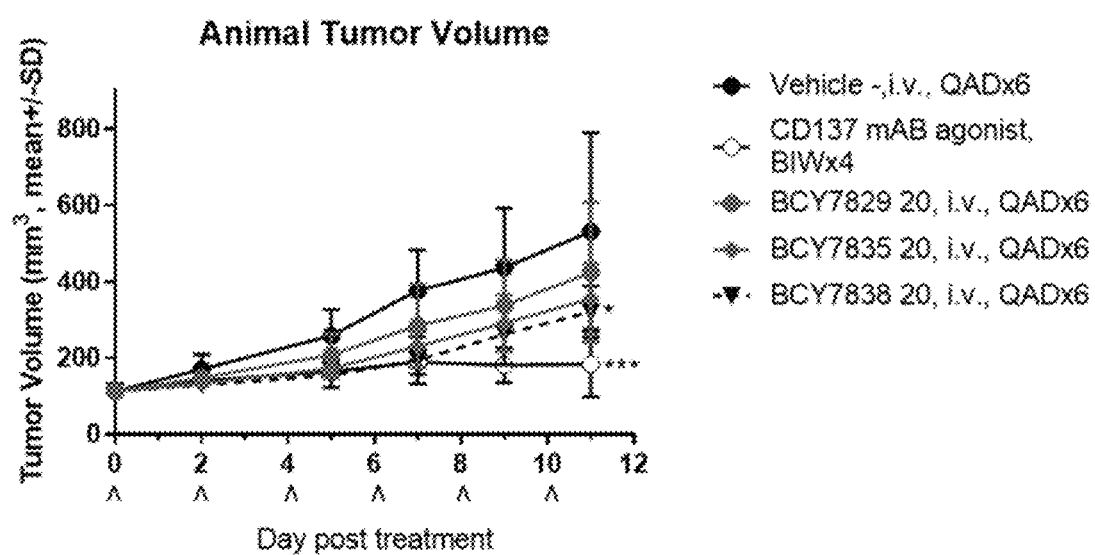
FIG. 7: Tumor volume trace after administering CD137 multimers to C57BL/6J B-h4-1BB humanized mice bearing MC38 syngeneic tumors. Data points represent group mean tumor volumes. Error bars represent standard deviation (SD).
Figure 8:
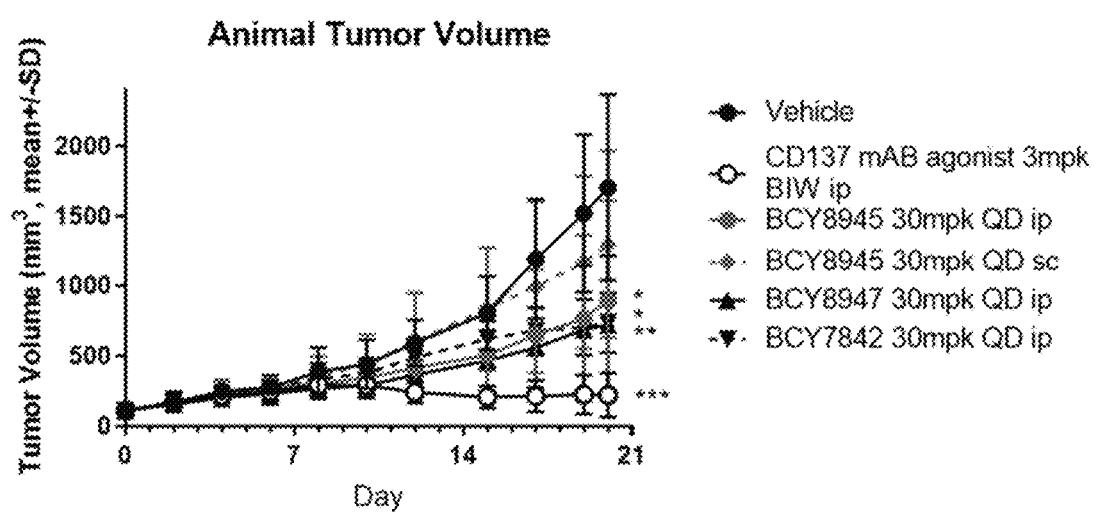
FIG. 8: Tumor volume trace after administering multimeric bicyclic peptides to C57BL/6J B-h4-1BB humanized mice bearing MC38 syngeneic tumors. Data points represent group mean tumor volumes. Error bars represent standard deviation (SD). *$p<0.001$, $p<0.01$, *$p<0.05$, 2 way ANOVA with Dunnett's test for multiple comparisons.
Figure 9:
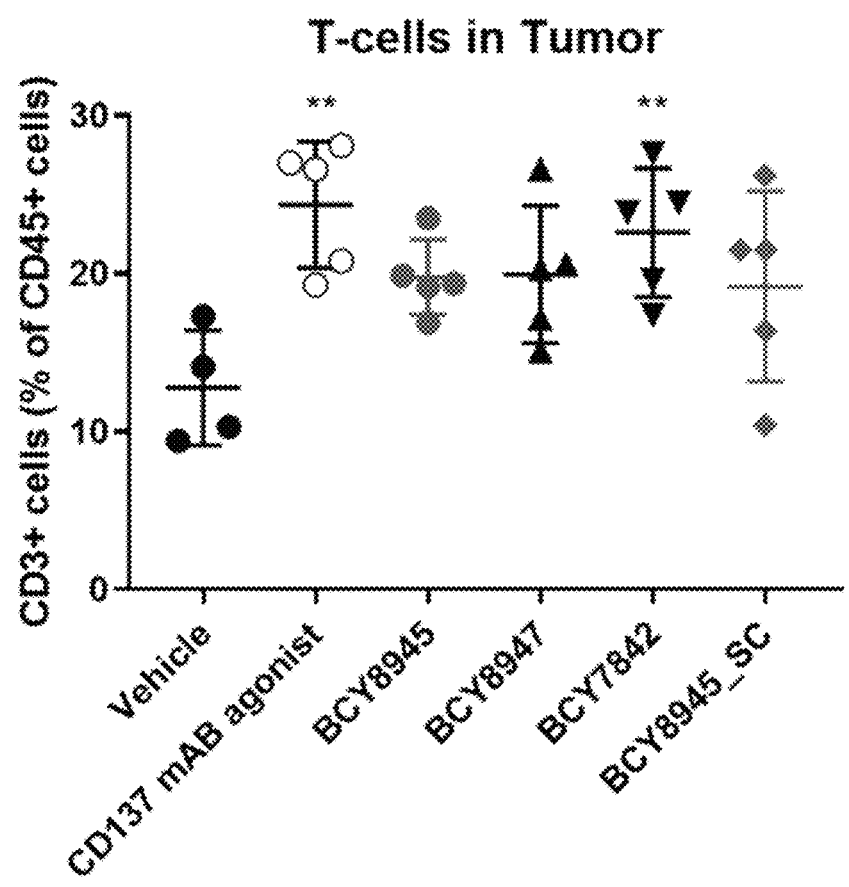
FIG. 9: Percentage of CD3+ cells among CD45+ cells in the tumor tissue after administering multimeric bicyclic peptides to C57BL/6J B-h4-1BB humanized mice bearing MC38 syngeneic tumors for a treatment period of 21 days. Data points represent cell population percentage from individual mice and line and error bars represent mean and standard deviation (SD). **$p<0.01$, one-way ANOVA with Dunnett's test for multiple comparisons.
Figure 10:
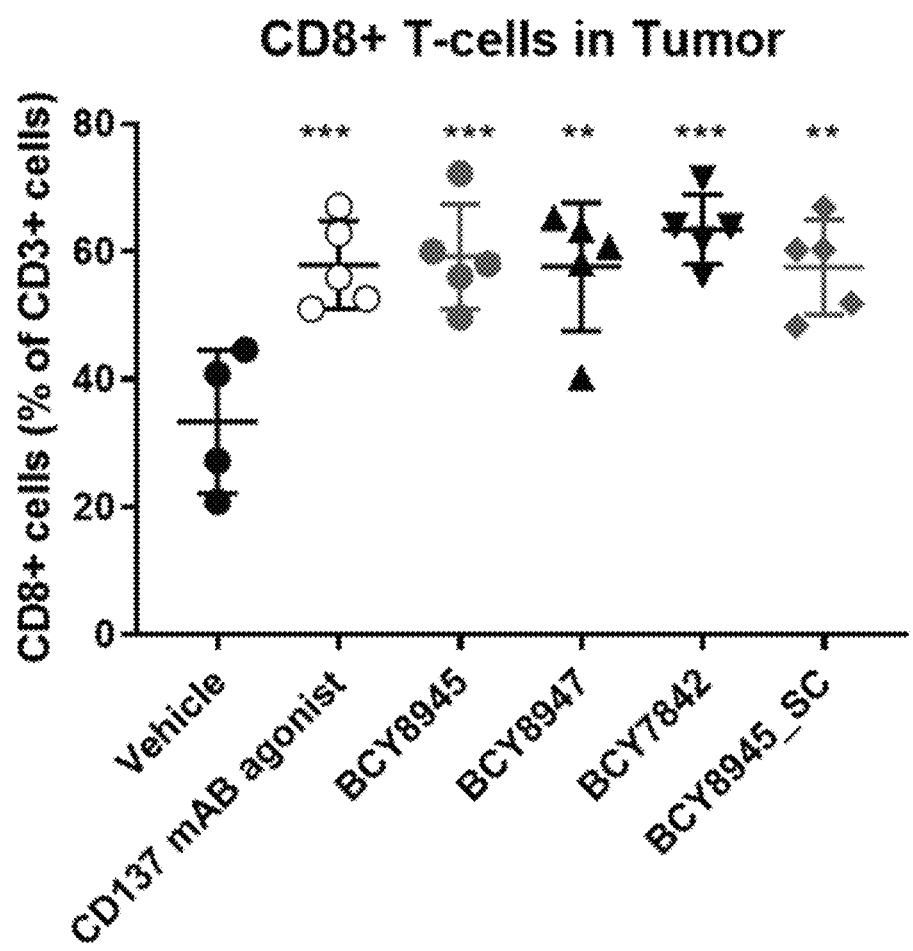
FIG. 10: Percentage of CD8+ cells among CD45+CD3+ cells in the tumor tissue after administering multimeric bicyclic peptides to C57BL/6J B-h4-1BB humanized mice bearing MC38 syngeneic tumors for a treatment period of 21 days. Data points represent cell population percentage from individual mice and line and error bars represent mean and standard deviation (SD). *$p<0.001$, $p<0.01$, one-way ANOVA with Dunnett's test for multiple comparisons.
Figure 11:
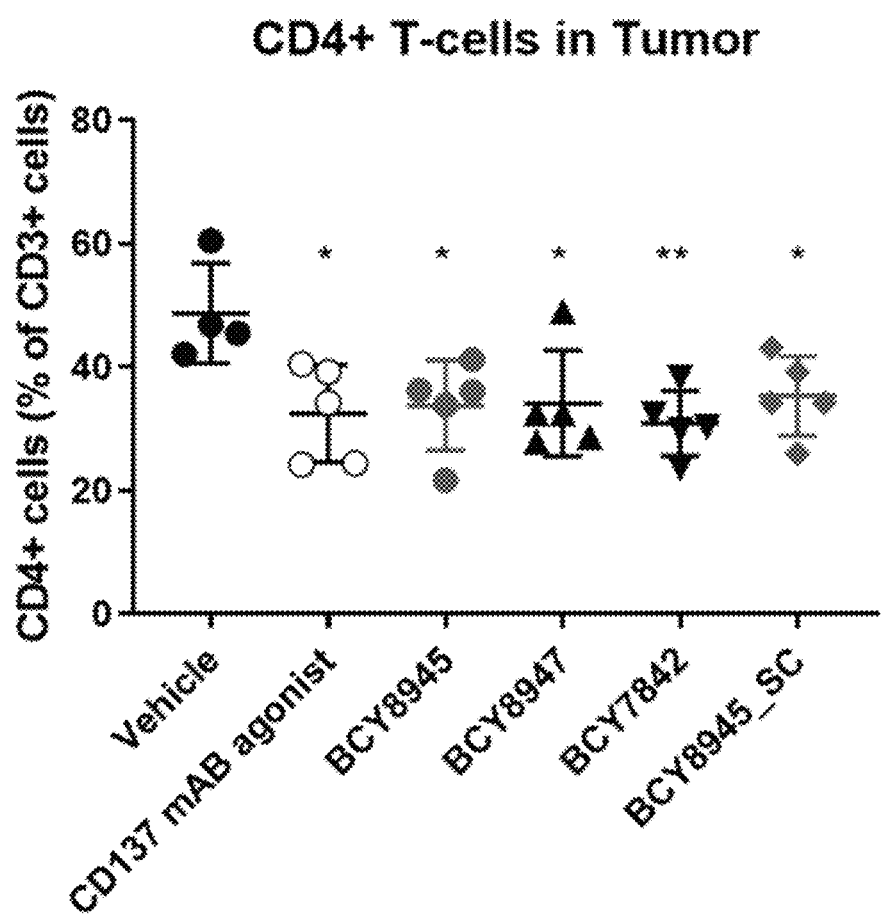
FIG. 11: Percentage of CD4+ cells among CD45+CD3+ cells in the tumor tissue after administering multimeric bicyclic peptides to C57BL/6J B-h4-1BB humanized mice bearing MC38 syngeneic tumors for a treatment period of 21 days. Data points represent cell population percentage from individual mice and line and error bars represent mean and standard deviation (SD). **$p<0.01$, *$p<0.05$, one-way ANOVA with Dunnett's test for multiple comparisons.

The results from Study 1 are shown in FIG. 7 wherein it can be seen that the multimeric bicyclic peptides elicit a range of anti-tumor activities as compared to the CD137 monoclonal antibody agonist. The results from Study 2 are shown in FIG. 8 wherein it can be seen that the multimeric bicyclic peptides elicit a range of anti-tumor activities as compared to the CD137 monoclonal antibody agonist. The results of Tumor T-cell analysis from Study 2 are shown in FIG. 9 wherein it can be seen that the multimeric bicyclic peptides elicit a range of increase in T-cell percentage in the tumor tissue as compared to the CD137 monoclonal antibody agonist. The results of CD8+ Tumor T-cell analysis from Study 2 are shown in FIG. 10 wherein it can be seen that the multimeric bicyclic peptides elicit a range of increase in CD8+ T-cell percentage in the tumor tissue as compared to the CD137 monoclonal antibody agonist. The results of CD4+ Tumor T-cell analysis from Study 2 are shown in FIG. 11 wherein it can be seen that the multimeric bicyclic peptides elicit a range of decease in T-cell percentage in the tumor tissue as compared to the CD137 monoclonal antibody agonist that has previously been shown to elicit a CD137 dependent anti-tumour activity.

5. Pharmacokinetics of Bicycle Multimers in CD-1 Mice

Male CD-1 mice were dosed with 5 mg/kg of each Bicycle multimer formulated in 25 mM Histidine HCl, 10% sucrose pH 7 via tail vein injection. Serial bleeding (about 80 µL blood/time point) was performed via submadibular or saphenous vein at each time point. All blood samples were immediately transferred into prechilled microcentrifuge tubes containing 2 µL K2-EDTA (0.5M) as anti-coagulant and placed on wet ice. Blood samples were immediately processed for plasma by centrifugation at approximately 4° C., 3000 g. The precipitant including internal standard was immediately added into the plasma, mixed well and centrifuged at 12,000 rpm, 4° C. for 10 minutes. The supernatant was transferred into pre-labeled polypropylene microcentrifuge tubes, and then quick-frozen over dry ice. The samples were stored at 70° C. or below as needed until analysis. 7.5 µL of the supernatant samples were directly injected for LC-MS/MS analysis using an Orbitrap Q Exactive in positive ion mode to determine the concentrations of Bicycle multimer. Plasma concentration versus time data were analyzed by non-compartmental approaches using the Phoenix WinNonlin 6.3 software program. $C_0$, Cl, $Vd_{ss}$, $T_{1/2}$, $AUC_{(0-last)}$, $AUC_{(0-inf)}$, $MRT_{(0-last)}$, $MRT_{(0-inf)}$ and graphs of plasma concentration versus time profile were reported.

Figure 5:
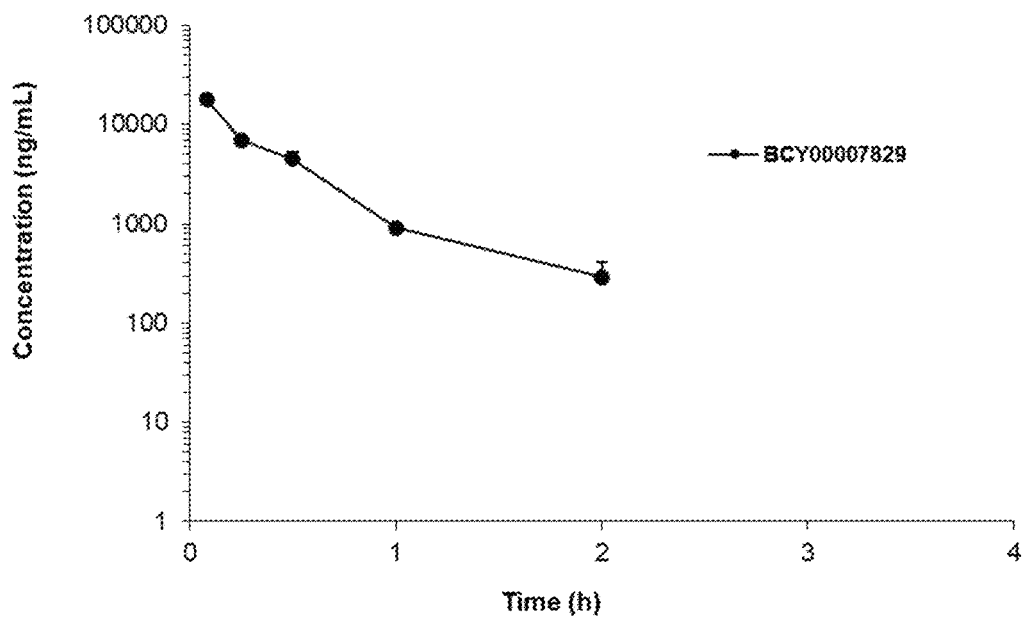
FIG. 5: (A): Data showing mean plasma concentration of BCY7829 after IV Dosing 5 mg/kg (6.35 mg/kg measured) in CD-1 mice; (B): Data showing mean plasma concentration of BCY7835 and BCY7838 after IV Dosing in CD-1 mice.
Figure 5:
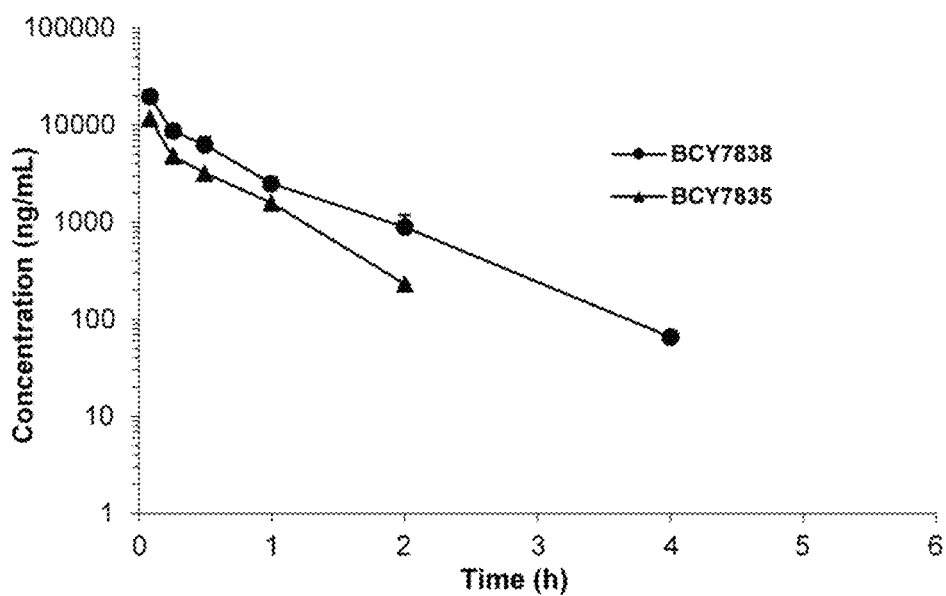

The results of the plasma concentration analysis in male CD-1 mice is shown in FIGS. 5A and 5B where it can be seen that the pharmacokinetic data show that the multimeric bicycle conjugates (in particular BCY7829, BCY7835 and BCY7838) retain the property of rapid systemic elimination characteristic of monomeric bicyclic peptides and bicyclic peptide drug conjugates (BDCs).

6. Ex Vivo Human Tumour Cell Kill Assay

Two frozen, dissociated melanoma patient tumour samples were purchased from Folio Conversant. Cells were thawed quickly at 37° C. and pipetted into 10 mL of Wash Medium [DMEM/F12+1× Penicillin/Streptomycin+50 µg/mL Gentamycin+100 µg/mL G418+100 µg/mL Hygromycin+1× Insulin-Transferrin-Selenium (ITS)+10 mM HEPES] with 1 mg/mL DNaseI added fresh. Cell counts were performed using a haemocytometer and a 1:2 dilution with 0.04% Trypan blue. Cells were spun down and resuspended in Growth Medium [EmbryoMax DMEM+10% heat-inactivated FBS+1× Penicillin/Streptomycin+50 µg/mL Gentamycin+1× GlutaMAX+1 mM Sodium pyruvate+1×ITS+0.4% BSA+4.5 g/L glucose+2.3 g/L sodium bicarbonate+10 mM HEPES+10 ng/mL basic fibroblast growth factor (bFGF)+20 ng/mL epidermal growth factor (EGF)] at $5 \times 10^5$ cells/mL. Cells were magnetized as described in the N3D Biosciences manufacturer's protocol. Briefly, NanoShuttle (NS) is added at 1 µL to $1 \times 10^4$ cells and mixed in by pipetting. Cells and NS are spun down at 100×g for 5 minutes, mixed by pipetting, and spun down again until the cell pellet acquires an even brown colour—approximately 3 to 5 cycles of spinning and mixing. Cells were then added to a cell-repellent 96-well plate at 50,000 cells/well in 100 µL of Growth Medium—one aliquot of 50,000 cells were reserved for a Day 0 flow cytometry panel. CD137 multimers (BCY7838, BCY7839 and BCY7842) and control compounds were added in 100 µL of 2× final concentration also in Growth Medium to the plated cells. The cell-repellent dish was then placed on top of the magnetic spheroid plate and incubated at 37° C. for 48 hours. At the end of 48 hours, cells were harvested, stained with the appropriate flow cytometry antibodies and a fixable viability stain (BD), and fixed in 2% paraformaldehyde before being run on the BD FACS Celesta. Data analysis was performed using FlowJo, Microsoft Excel, and GraphPad Prism software. Flow cytometry panels used in this experiment analysed the number of lymphocytes and tumour cells present on Days 0 and 2. Tumour cell killing was determined by the decrease in the number of CD45 negative cells in the treated wells versus the untreated control (FIG. 12)—significance was calculated using a 2-way ANOVA.

The data presented in FIG. 12 demonstrates significant tumour cell death in response to CD137 multimer treatment (BCY7838, BCY7839 and BCY7842) in one melanoma patient sample, but not the other (FIG. 12A). Though cell numbers changed from Day 0 to Day 2 (data not shown), there was no significant difference between treatments on lymphocyte numbers (FIG. 12B).

7. CD137 Reporter Cell Activity Washout Assay

Jurkat cells engineered to overexpress CD137 and express a luciferase gene under the NF-κB promoter were purchased from Promega. The reporter cells were incubated with 10 nM of CD137 agonists for the indicated times at 37° C. in RPM11640 media with 1% FBS. After either 30, 60, or 120 minutes, cells were washed in an excess of culture media and resuspended in 75 µL of fresh media. A no washout condition was also included. All washout conditions were performed in duplicate. Cells then continued to incubate for a total of 6 hours (an additional 5.5, 5, or 4 hours respective to exposure times). After incubation, 75 µL of Bio-Glo reagent (Promega) was added to each well and allowed to equilibrate for 10 minutes at room temperature. Luminescence was read on the Clariostar plate reader (BMG LabTech). Fold induction was calculated by dividing the luminescence signal by background wells (reporter cells with no agonist added). The percent of the maximum fold induction was calculated by dividing the fold induction of the washout time by the fold induction of the no washout condition and multiplying by 100. Data was graphed in Prism and is displayed as a bar graph of the means or replicates with standard deviation error bars.

Figure 13:
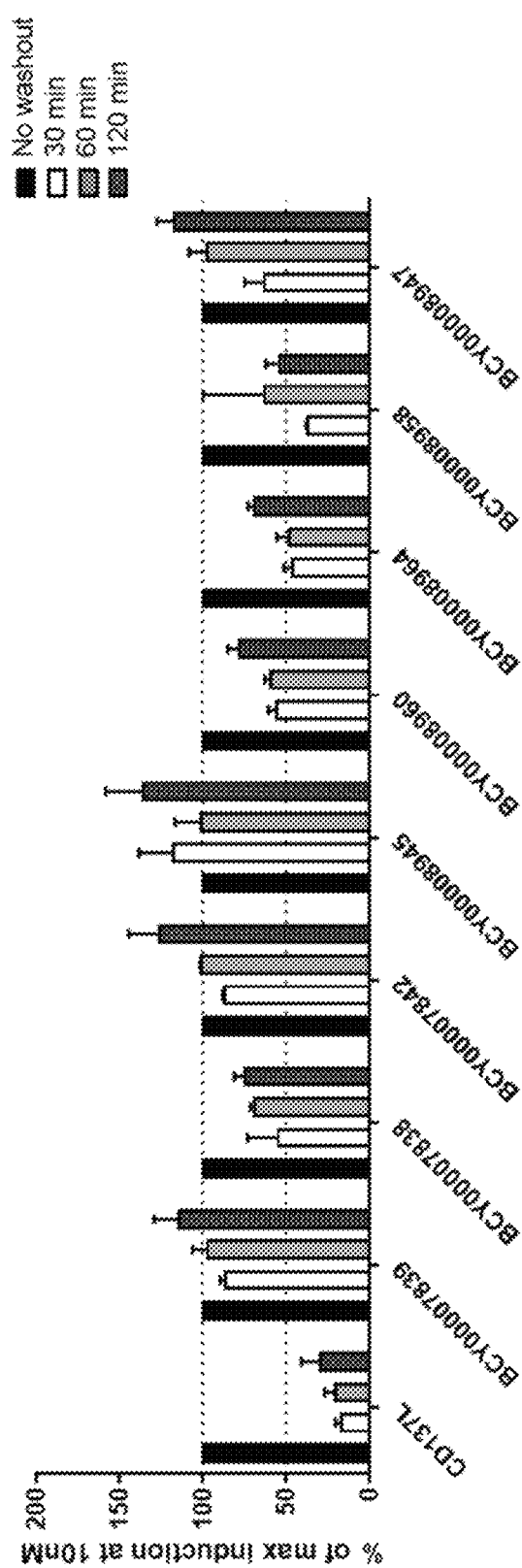
FIG. 13: CD137 multimers maintain activity after washout. CD137 reporter cells are exposed to compound for 30, 60, or 120 minutes prior to washout of the compound and activity is measured 5.5, 5, or 4 hours later, respectively. In the 'no washout' conditions, cells are exposed to the compound for the full 6 hour incubation.

The data presented in FIG. 13 demonstrates that CD137 multimers (BCY7838, BCY7839 and BCY7842) maintain cell activity after washout consistent with high avidity to the trimeric CD137 receptor complex.

8. T-cell Cytokine Release Assay

Healthy human buffy coat was purchased from the Sylvan N. Goldman Oklahoma Blood Institute and shipped fresh. Peripheral blood mononuclear cells (PBMCs) were isolated by Ficoll density gradient centrifugation. Red blood cells were lysed with ACK (Ammonium-Chloride-Potassium) lysis buffer. Pan T-cells were then isolated from total PBMCs using negative magnetic bead selection (Miltenyi MACS human Pan-T cell isolation kit). Pan T-cells were then plated on anti-CD3 coated 96-well plates (0.5 µg/mL) in culture media (RPM11640 with 10% FBS) plus or minus compounds. Supernatant from cultures was collected after 24 and 48 hours. Cytokine [i.e., interleukin-2 (IL-2), interferon gamma (IFNγ)] release in supernatant was measured by HTRF assay (CisBio) according to the kit's instructions. HTRF assay plates were read on a Clariostar plate reader (BMG Labtech) at 665 nm and 620 nm. Data was analyzed and extrapolated to a standard curve according to the HTRF kit instruction in Prism and Excel. Cytokine release fold change was calculated by dividing the µg/mL of cytokine detected by background cytokine released (CD3 stimulation alone). Data was graphed in Prism as the mean of replicates with standard deviation error bars.

Figure 14:
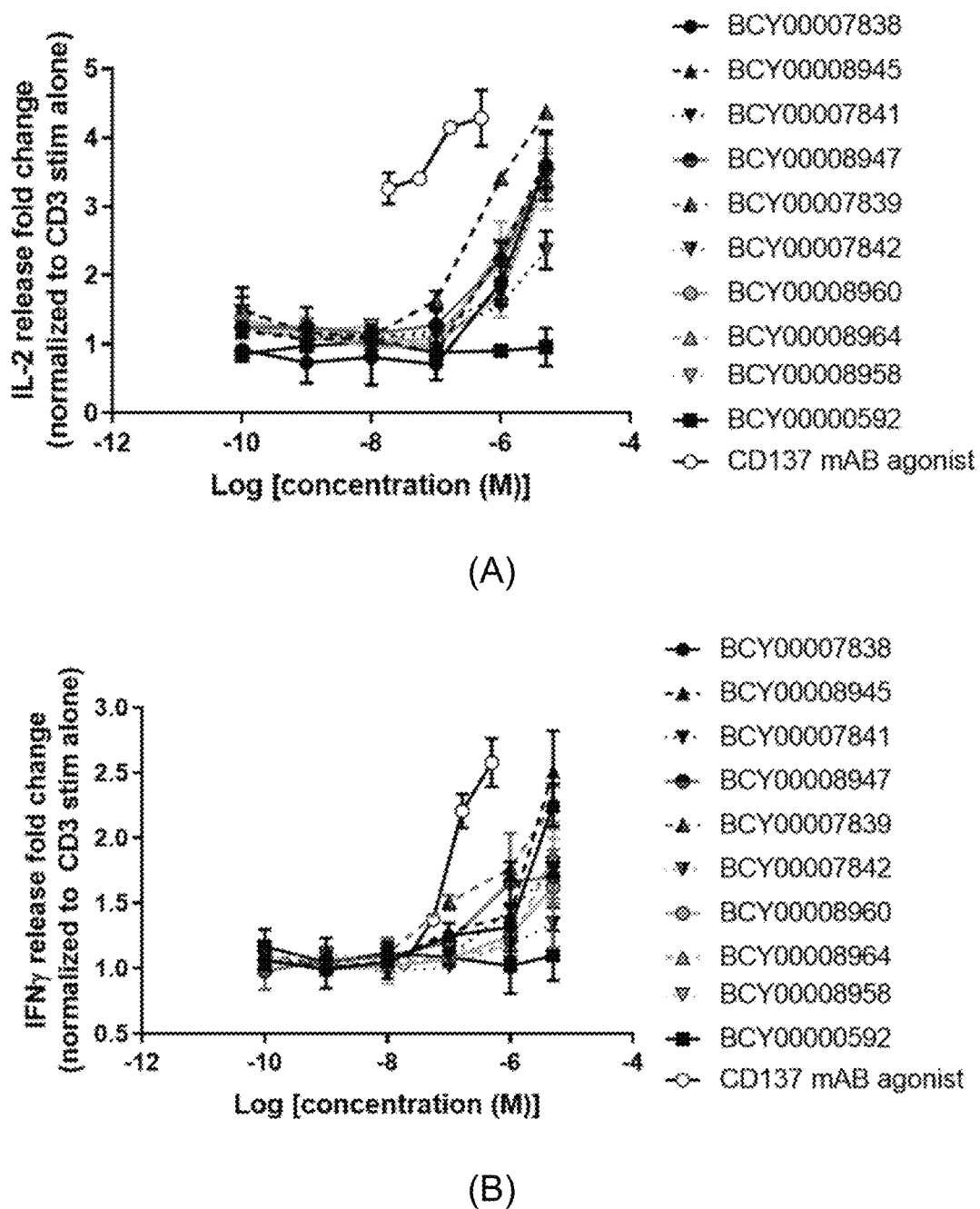
FIG. 14: CD137 multimers lead to increased cytokine secretion in a primary T cell assay. CD137 expression is induced in T cells (isolated from human PBMCs) using anti-CD3 antibody. T cells are then treated with CD137 multimers, CD137 monomer (negative control), or a CD137 monoclonal antibody agonist for 48 hours and IL-2 levels (A) and IFNγ (B) were measured in the supernatant using a HTRF assay.
Figure 15:
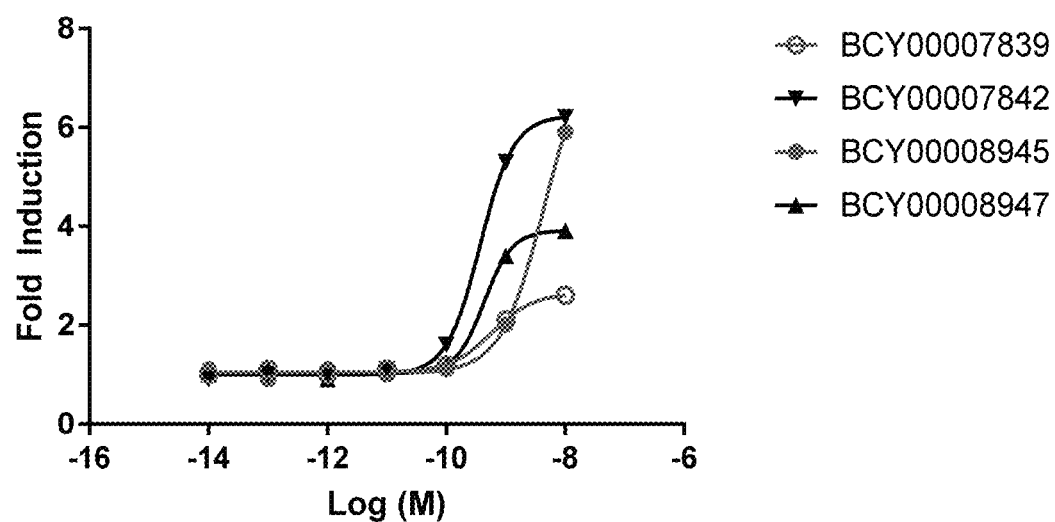
FIG. 15: Reporter cell activity assay data obtained for BCY7839, BCY7842, BCY8945 and BCY8947.

The data presented in FIG. 14 demonstrates that T-cells secrete pro-inflammatory cytokines in response to CD137 multimers BCY7838, BCY8945, BCY7841, BCY8947, BCY7839, BCY7842, BCY8960, BCY8964 and BCY8958 but not with monomer control BCY0592.

The invention claimed is:

1. A multimeric binding complex which comprises at least two bicyclic peptide ligands, wherein said peptide ligands may be the same or different, each of which comprises a polypeptide comprising at least three reactive groups, separated by at least two loop sequences, and a molecular scaffold which forms covalent bonds with the reactive groups of the polypeptide such that at least two polypeptide loops are formed on the molecular scaffold, wherein said at least two bicyclic peptide ligands are specific for CD137, and wherein each of said bicyclic peptide ligands comprises a core amino acid sequence selected from:

$C_i$IEEGQYC$_{ii}$FADPY(Nle)C$_{iii}$; (SEQ ID NO: 23)

$C_i$IKEGQYC$_{ii}$FADPY(Nle)C$_{iii}$; (SEQ ID NO: 24)

$C_i$EKGQYC$_{ii}$FADPY(Nle)C$_{iii}$; (SEQ ID NO: 25)

$C_i$IEE(D-K)QYC$_{ii}$FADPY(Nle)C$_{iii}$; (SEQ ID NO: 26)

$C_i$IEEGKYC$_{ii}$FADPY(Nle)C$_{iii}$; (SEQ ID NO: 27)

$C_i$IEEGQYC$_{ii}$KADPY(Nle)C$_{iii}$; (SEQ ID NO: 28)

$C_i$IEEGQYC$_{ii}$FADKY(Nle)C$_{iii}$; and (SEQ ID NO: 29)

$C_i$IEEGQYC$_{ii}$FADPYKC$_{iii}$; (SEQ ID NO: 30)

wherein $C_i$, $C_{ii}$ and $C_{iii}$ represent first, second and third cysteine residues, respectively and Nle represents norleucine, or a pharmaceutically acceptable salt thereof.

2. The multimeric binding complex as defined in claim 1, wherein each bicyclic peptide ligand is connected to a central hinge moiety by a spacer group.

3. The multimeric binding complex as defined in claim 1, which comprises a compound of formula (I):

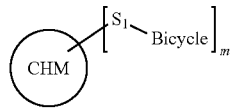

(I)

wherein CHM represents a central hinge moiety;

$S_1$ represents a spacer group;

Bicycle represents a bicyclic peptide ligand as defined in claim 1; and m represents an integer selected from 2 to 10.

4. The multimeric binding complex as defined in claim 3, wherein m represents 4 and CHM is a motif of formula (A):

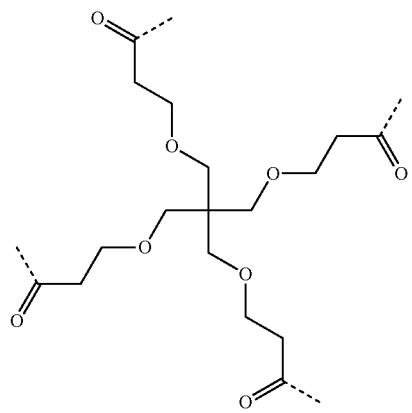

(A)

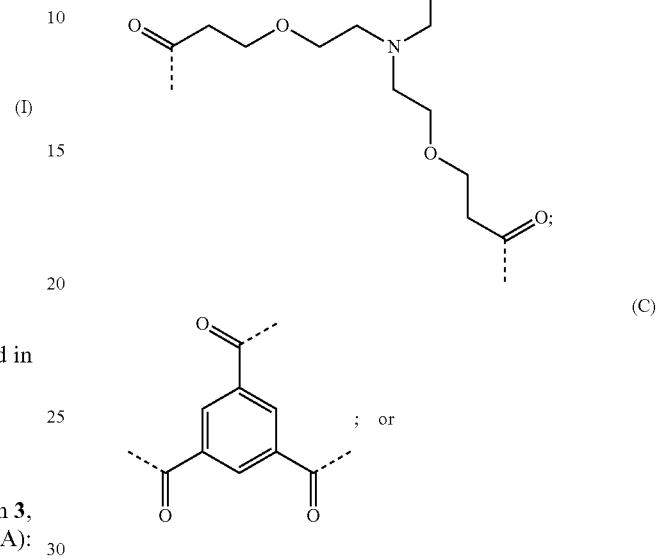

(B)

(C)

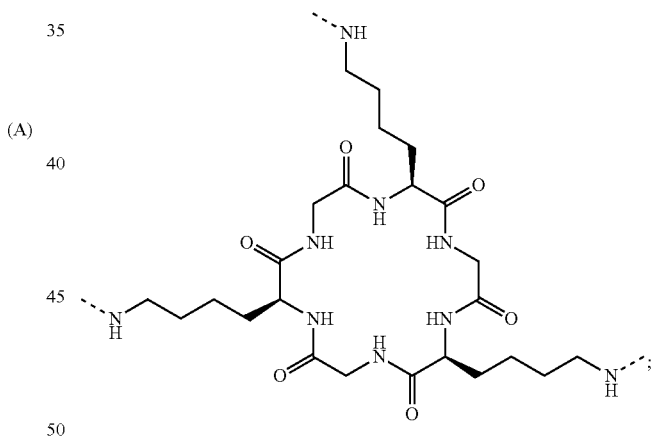

(D)

wherein "-----" represents the point of attachment to each $S_1$ group.

6. The multimeric binding complex as defined in claim 3, wherein the spacer ($S_1$) is selected from any one of spacers $S_1A$, $S_1B$, $S_1C$, $S_1D$, $S_1E$, $S_1F$, $S_1G$ and $S_1H$:

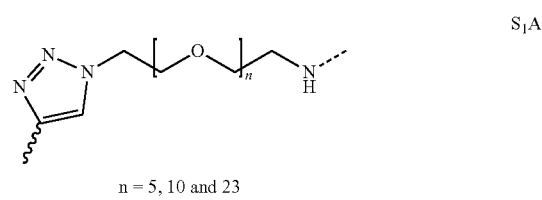

$S_1A$ n = 5, 10 and 23 wherein "-----" represents the point of attachment to each $S_1$ group.

5. The multimeric binding complex as defined in claim 3, wherein m represents 3 and CHM is selected from a motif of formula (B), (C) or (D):

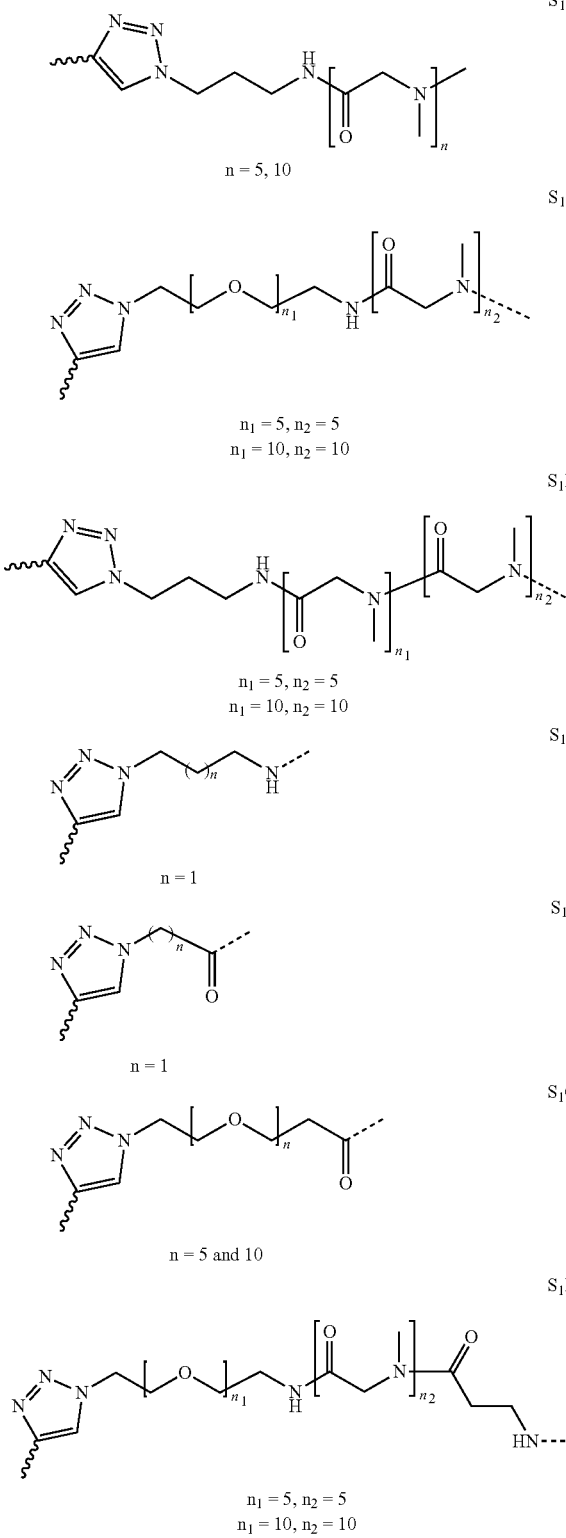

wherein "-----" represents the point of attachment to the CHM group; and

"〜〜〜" represents the point of attachment to the Bicycle group.

7. The multimeric binding complex as defined in claim 6, wherein the spacer ($S_1$) is $S_1A$:

and n=5, 10, or 23.

8. The multimeric binding complex as defined in claim 1, wherein said at least two bicyclic peptide ligands are identical.

9. The multimeric binding complex as defined in claim 1, said at least two bicyclic peptide ligands are different.

10. The multimeric binding complex as defined in claim 1, wherein each of said bicyclic peptide ligands comprises N and C terminal modifications and comprises an amino acid sequence selected from:

```
A-C_iIEEGQYC_iiFADPY(Nle)C_iii-A;                    (SEQ ID NO: 31)

Ac-A-C_iIEEGQYC_iiFADPY(Nle)C_iii-Dap;               (SEQ ID NO: 32)

Ac-A-C_iIKEGQYC_iiFADPY(Nle)C_iii-A;                 (SEQ ID NO: 33)

Ac-A-C_iIEKGQYC_iiFADPY(Nle)C_iii-A;                 (SEQ ID NO: 34)

Ac-A-C_iIEE(D-K)QYC_iiFADPY(Nle)_iii-A;              (SEQ ID NO: 35)

Ac-A-C_iIEEGKYC_iiFADPY(Nle)C_iii-A;                 (SEQ ID NO: 36)

Ac-A-C_iIEEGQYC_iiKADPY(Nle)C_iii-A;                 (SEQ ID NO: 37)

Ac-A-C_iIEEGQYC_iiFADKY(Nle)C_iii-A;                 (SEQ ID NO: 38)

Ac-A-C_iIEEGQYC_iiFADPYKC_iii-A;                     (SEQ ID NO: 39)

A-C_iIEEGQYC_iiF[D-A]DPY[Nle]C_iii-A;                (SEQ ID NO: 58)

Ac-C_i[tBuAla]PK[D-A]PYC_iiFADPY[Nle]C_iii-A;        (SEQ ID NO: 59)

Ac-C_i[tBuAla]PE[D-K]PYC_iiFADPY[Nle]C_iii-A;        (SEQ ID NO: 60)

Ac-A-C_iIE[D-K]GQYC_iiF[D-A]DPY[Nle]C_iii-A;         (SEQ ID NO: 61)

Ac-A-C_iIE[D-K]GQYC_iiF[D-A]DPY[Nle]C_iii-A;         (SEQ ID NO: 62)
and (SEQ ID NO: 63)
[Ac]-[D-A]-[D-C_i][D-I][D-E][D-E]K[D-Q][D-Y][D-C_ii]
[D-F][D-A][D-D][D-P][D-Y][D-Nle][D-C_iii][D-A];
``` wherein $C_i$, $C_{ii}$ and $C_{iii}$ represent first, second and third cysteine residues, respectively, Ac represents an N-terminal acetyl group, Dap represents diaminopropionic acid, tBuAla represents t-butyl-alanine and Nle represents norleucine, or a pharmaceutically acceptable salt thereof.

11. The multimeric binding complex as defined in claim 1, wherein each of said bicyclic peptide ligands comprises attachment of a PYA moiety at the N-terminus, C-terminus or Lysine residues within said sequence and comprises an amino acid sequence selected from:

```
                                              (SEQ ID NO: 40)
(PYA)-A-C_iIEEGQYC_iiFADPY(Nle)C_iii-A;

(SEQ ID NO: 41)
Ac-A-C_iIEEGQYC_iiFADPY(Nle)C_iii-Dap(PYA);

(SEQ ID NO: 42)
Ac-A-C_iIK(PYA)EGQYC_iiFADPY(Nle)C_iii-A;

(SEQ ID NO: 43)
Ac-A-C_iIEK(PYA)GQYC_iiFADPY(Nle)C_iii-A;

(SEQ ID NO: 44)
Ac-A-C_iIEE(D-K)(PYA)QYC_iiFADPY(Nle)C_iii-A;

(SEQ ID NO: 45)
Ac-A-C_iIEEGK(PYA)YC_iiFADPY(Nle)C_iii-A;

(SEQ ID NO: 46)
Ac-A-C_iIEEGQYC_iiK(PYA)ADPY(Nle)C_iii-A;

(SEQ ID NO: 47)
Ac-A-C_iIEEGQYC_iiFADK(PYA)Y(Nle)C_iii-A;

(SEQ ID NO: 48)
Ac-A-C_iIEEGQYC_iiFADPYK(PYA)C_iii-A;

(SEQ ID NO: 64)
(PYA)-A-C_iIEEGQYC_iiF[D-A]DPY[Nle]C_iii-A;

(SEQ ID NO: 65)
Ac-C_i[tBuAla]PK(PYA)[D-A]PYC_iiFADPY[Nle]C_iii-A;

(SEQ ID NO: 66)
Ac-C_i[tBuAla]PE[D-K(PYA)]PYC_iiFADPY[Nle]C_iii-A;

(SEQ ID NO: 67)
Ac-A-CiIE[D-K(PYA)]GQYC_iiF[D-A]DPY[Nle]C_iii-A;

(SEQ ID NO: 68)
Ac-A-CiIE[K(PYA)]GQYC_iiF[D-A]DPY[Nle]C_iii-A;
and
                                              (SEQ ID NO: 69)
[Ac]-[D-A][D-C_i][D-I][D-E][D-E][K(PYA)][D-Q][D-Y]
[D-C_ii][D-F][D-A][D-D][D-P][D-Y][D-Nle][D-C_iii][D-A];
``` wherein $C_i$, $C_{ii}$ and $C_{iii}$ represent first, second and third cysteine residues, respectively, Ac represents an N-terminal acetyl group, Dap represents diaminopropionic acid, PYA represents propargyl-acid, tBuAla represents t-butyl-alanine and Nle represents norleucine, or a pharmaceutically acceptable salt thereof.

12. The multimeric binding complex as defined in claim 1, wherein each of said bicyclic peptide ligands comprises attachment of a BCN moiety at the N-terminus or Lysine residues within said sequence and comprises an amino acid sequence selected from:

```
                                              (SEQ ID NO: 49)
(BCN)-A-C_iIEEGQYC_iiFADPY(Nle)C_iii-A;

(SEQ ID NO: 50)
Ac-A-C_iIK(BCN)EGQYC_iiFADPY(Nle)C_iii-A;

(SEQ ID NO: 51)
Ac-A-C_iIEK(BCN)GQYC_iiFADPY(Nle)C_iii-A;

(SEQ ID NO: 52)
Ac-A-C_iIEE[(D-K)(BCN)]QYC_iiFADPY(Nle)C_iii-A;

(SEQ ID NO: 53)
Ac-A-C_iIEEGK(BCN)YC_iiFADPY(Nle)C_iii-A;

(SEQ ID NO: 54)
Ac-A-C_iIEEGQYC_iiK(BCN)ADPY(Nle)C_iii-A;
and
                                              (SEQ ID NO: 55)
Ac-A-C_iIEEGQYC_iiFADPYK(BCN)C_iii-A;
``` wherein $C_i$, $C_{ii}$ and $C_{iii}$ represent first, second and third cysteine residues, respectively, Ac represents an N-terminal acetyl group, Nle represents norleucine and BCN represents:

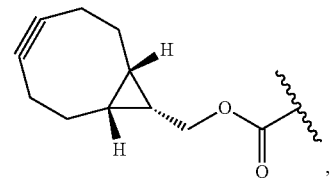 [SMILES: *C(=O)OC[C@@H]1[C@@H]2CCC#CCC[C@@H]21]

or a pharmaceutically acceptable salt thereof.

13. The multimeric binding complex as defined in claim 1, wherein said molecular scaffold is 1,1',1"-(1,3,5-triazinane-1,3,5-triyl)triprop-2-en-1-one (TATA).

14. The multimeric binding complex as defined in claim 1, wherein the pharmaceutically acceptable salt is selected from the free acid or the sodium, potassium, calcium, or ammonium salt.

15. A drug conjugate comprising the multimeric binding complex as defined in claim 1, conjugated to one or more effector and/or functional groups.

16. A pharmaceutical composition which comprises the multimeric binding complex of claim 1 or the drug conjugate of claim 15, in combination with one or more pharmaceutically acceptable excipients.

17. The multimeric binding complex as defined in claim 3, wherein each of said bicyclic peptide ligands comprises N and C terminal modifications and comprises an amino acid sequence selected from:

```
                                              (SEQ ID NO: 31)
A-C_iIEEGQYC_iiFADPY(Nle)C_iii-A;

(SEQ ID NO: 32)
Ac-A-C_iIEEGQYC_iiFADPY(Nle)C_iii-Dap;

(SEQ ID NO: 33)
Ac-A-C_iIKEGQYC_iiFADPY(Nle)C_iii-A;

(SEQ ID NO: 34)
Ac-A-C_iIEKGQYC_iiFADPY(Nle)C_iii-A;

(SEQ ID NO: 35)
Ac-A-C_iIEE(D-K)QYC_iiFADPY(Nle)C_iii-A;

(SEQ ID NO: 36)
Ac-A-C_iIEEGKYC_iiFADPY(Nle)C_iii-A;

(SEQ ID NO: 37)
Ac-A-C_iIEEGQYC_iiKADPY(Nle)C_iii-A;

(SEQ ID NO: 38)
Ac-A-C_iIEEGQYC_iiFADKY(Nle)C_iii-A;

(SEQ ID NO: 39)
Ac-A-C_iIEEGQYC_iiFADPYKC_iii-A;

(SEQ ID NO: 58)
A-C_iIEEGQYC_iiF[D-A]DPY[Nle]C_iii-A;
```

```
                                                (SEQ ID NO: 59)
Ac-C_i[tBuAla]PK[D-A]PYC_{ii}FADPY[Nle]C_{iii}-A;

(SEQ ID NO: 60)
Ac-C_i[tBuAla]PE[D-K]PYC_{ii}FADPY[Nle]C_{iii}-A;

(SEQ ID NO: 61)
Ac-A-C_iE[D-K]GQYC_{ii}F[D-A]DPY[Nle]C_{iii}-A;

(SEQ ID NO: 62)
Ac-A-C_iE[D-K]GQYC_{ii}F[D-A]DPY[Nle]C_{iii}-A;
and (SEQ ID NO: 63)
[Ac]-[D-A]-[D-C_i][D-I][D-E][D-E]K[D-Q][D-Y][D-C_{ii}][D-
F][D-A][D-D][D-P][D-Y][D-Nle][D-C_{iii}]-[D-A];
``` wherein $C_i$, $C_{ii}$ and $C_{iii}$ represent first, second and third cysteine residues, respectively, Ac represents an N-terminal acetyl group, Dap represents diaminopropionic acid, tBuAla represents t-butyl-alanine and Nle represents norleucine, or a pharmaceutically acceptable salt thereof.

18. The multimeric binding complex as defined in claim 3, wherein each of said bicyclic peptide ligands comprises attachment of a PYA moiety at the N-terminus, C-terminus or Lysine residues within said sequence and comprises an amino acid sequence selected from:

```
                                                (SEQ ID NO: 40)
(PYA)-A-C_iIEEGQYC_{ii}FADPY(Nle)C_{iii}-A;

(SEQ ID NO: 41)
Ac-A-C_iIEEGQYC_{ii}FADPY(Nle)C_{iii}-Dap(PYA);

(SEQ ID NO: 42)
Ac-A-C_iIK(PYA)EGQYC_{ii}FADPY(Nle)C_{iii}-A;

(SEQ ID NO: 43)
Ac-A-C_iIEK(PYA)GQYC_{ii}FADPY(Nle)C_{iii}-A;

(SEQ ID NO: 44)
Ac-A-C_iIEE(D-K)(PYA)QYC_{ii}FADPY(Nle)C_{iii}-A;

(SEQ ID NO: 45)
Ac-A-C_iIEEGK(PYA)YC_{ii}FADPY(Nle)C_{iii}-A;

(SEQ ID NO: 46)
Ac-A-C_iIEEGQYC_{ii}K(PYA)ADPY(Nle)C_{iii}-A;

(SEQ ID NO: 47)
Ac-A-C_iIEEGQYC_{ii}FADK(PYA)Y(Nle)C_{iii}-A;

(SEQ ID NO: 48)
Ac-A-C_iIEEGQYC_{ii}FADPYK(PYA)C_{iii}-A;

(SEQ ID NO: 64)
(PYA)-A-C_iIEEGQYC_{ii}F[D-A]DPY[Nle]C_{iii}-A;

(SEQ ID NO: 65)
Ac-C_i[tBuAla]PK(PYA)[D-A]PYC_{ii}FADPY[Nle]C_{iii}-A;

(SEQ ID NO: 66)
Ac-C_i[tBuAla]PE[D-K(PYA)]PYC_{ii}FADPY[Nle]C_{iii}-A;

(SEQ ID NO: 67)
Ac-A-C_iIE[D-K(PYA)]GQYC_{ii}F[D-A]DPY[Nle]C_{iii}-A;

(SEQ ID NO: 68)
Ac-A-C_iIE[K(PYA)]GQYC_{ii}F[D-A]DPY[Nle]C_{iii}-A;
and (SEQ ID NO: 69)
[Ac]-[D-A]-[D-C_i][D-I][D-E][D-E][K(PYA)][D-Q][D-
Y][D-C_{ii}][D-F][D-A][D-D][D-P][D-Y][D-Nle][D-C_{iii}]-
[D-A];
``` wherein $C_i$, $C_{ii}$ and $C_{iii}$ represent first, second and third cysteine residues, respectively, Ac represents an N-terminal acetyl group, Dap represents diaminopropionic acid, PYA represents propargyl-acid, tBuAla represents t-butyl-alanine and Nle represents norleucine, or a pharmaceutically acceptable salt thereof.

19. The multimeric binding complex as defined in claim 3, wherein each of said bicyclic peptide ligands comprises attachment of a BCN moiety at the N-terminus or Lysine residues within said sequence and comprises an amino acid sequence selected from:

```
                                                (SEQ ID NO: 49)
(BCN)-A-C_iIEEGQYC_{ii}FADPY(Nle)C_{iii}-A;

(SEQ ID NO: 50)
Ac-A-C_iIK(BCN)EGQYC_{ii}FADPY(Nle)C_{iii}-A;

(SEQ ID NO: 51)
Ac-A-C_iIEK(BCN)GQYC_{ii}FADPY(Nle)C_{iii}-A;

(SEQ ID NO: 52)
Ac-A-C_iIEE[D-K)(BCN)]QYC_{ii}FADPY(Nle)C_{iii}-A;

(SEQ ID NO: 53)
Ac-A-C_iIEEGK(BCN)YC_{ii}FADPY(Nle)C_{iii}-A;

(SEQ ID NO: 54)
Ac-A-C_iIEEGQYC_{ii}K(BCN)ADPY(Nle)C_{iii}-A;
and (SEQ ID NO: 55)
Ac-A-C_iIEEGQYC_{ii}FADPYK(BCN)C_{iii}-A;
``` wherein $C_i$, $C_{ii}$ and $C_{iii}$ represent first, second and third cysteine residues, respectively, Ac represents an N-terminal acetyl group, Nle represents norleucine and BCN represents:

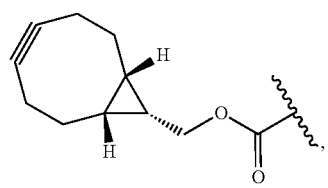 [SMILES: *C(=O)OC[C@@H]1[C@@H]2CCC#CCC[C@@H]21]

or a pharmaceutically acceptable salt thereof.

20. The multimeric binding complex as defined in claim 17, wherein m represents 4 and CHM is a motif of formula (A):

(A)

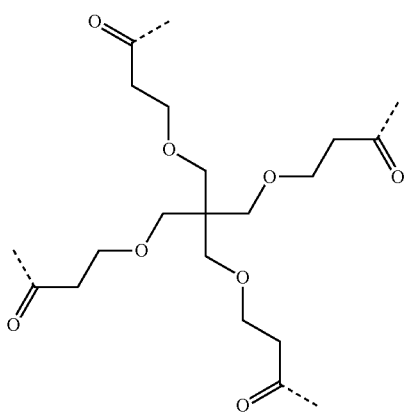

wherein "-----" represents the point of attachment to each $S_1$ group.

21. The multimeric binding complex as defined in claim 17, wherein m represents 3 and CHM is selected from a motif of formula (B), (C) or (D):

(B)

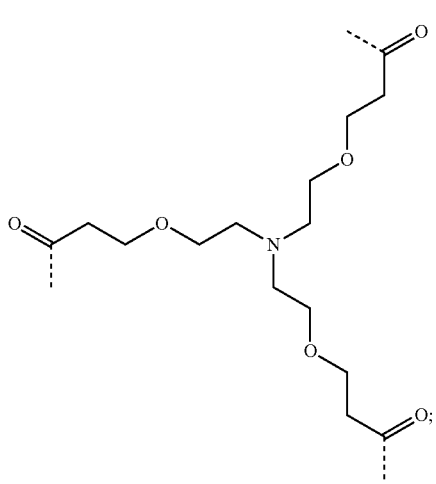

(C)

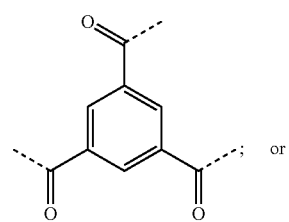

or (D)

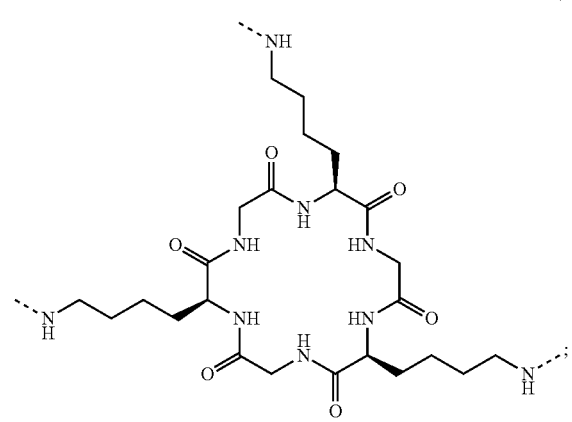

wherein "-----" represents the point of attachment to each $S_1$ group.

22. The multimeric binding complex as defined in claim 17, wherein the spacer ($S_1$) is selected from any one of spacers $S_1A$, $S_1B$, $S_1C$, $S_1D$, $S_1E$, $S_1F$, $S_1G$ and $S_1H$:

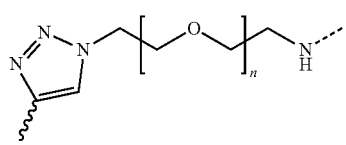

$S_1A$ n = 5, 10 or 23

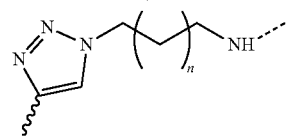

$S_1E$ n = 1

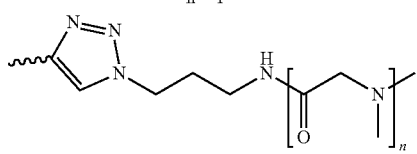

$S_1B$ n = 5, or 10

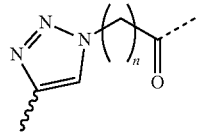

$S_1F$ n = 1

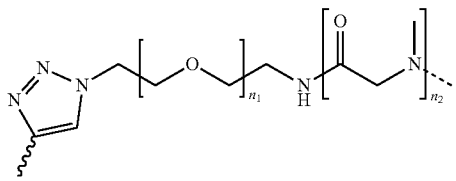

$S_1C$ $n_1 = 5, n_2 = 5$; or
$n_1 = 10, n_2 = 10$

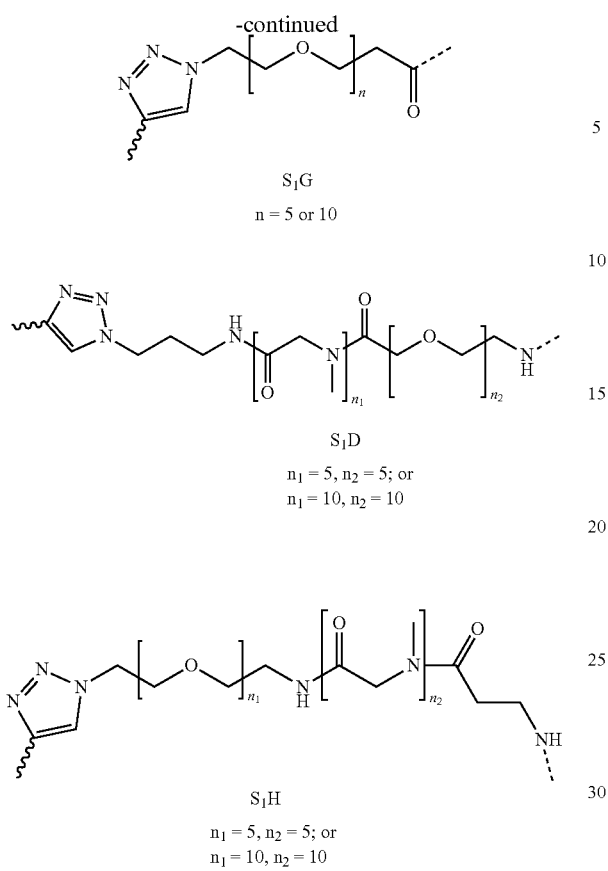

S₁G
n = 5 or 10

S₁D
n₁ = 5, n₂ = 5; or
n₁ = 10, n₂ = 10

S₁H
n₁ = 5, n₂ = 5; or
n₁ = 10, n₂ = 10 wherein "-----" represents the point of attachment to the CHM group; and

"∼∼∼" represents the point of attachment to the Bicycle group.

23. The multimeric binding complex as defined in claim 18, wherein m represents 4 and CHM is a motif of formula (A):

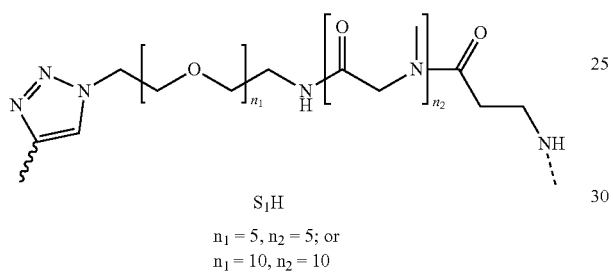

(A)

wherein "-----" represents the point of attachment to each S₁ group.

24. The multimeric binding complex as defined in claim 18, wherein m represents 3 and CHM is selected from a motif of formula (B), (C) or (D):

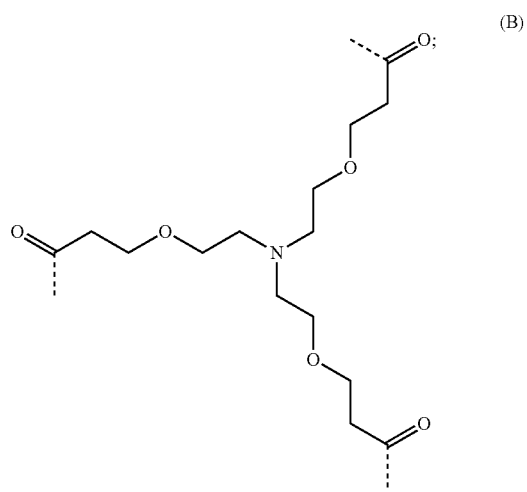

(B)

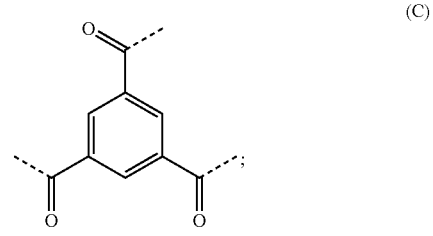

(C)

or

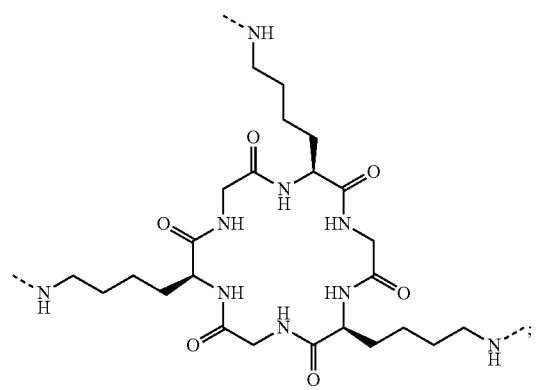

(D)

wherein "-----" represents the point of attachment to each S₁ group.

25. The multimeric binding complex as defined in claim 18, wherein the spacer (S₁) is selected from any one of spacers S₁A, S₁B, S₁C, S₁D, S₁E, S₁F, S₁G and S₁H:

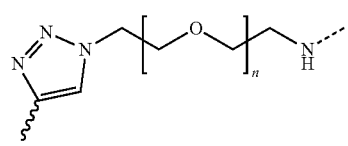

S₁A
n = 5, 10 or 23

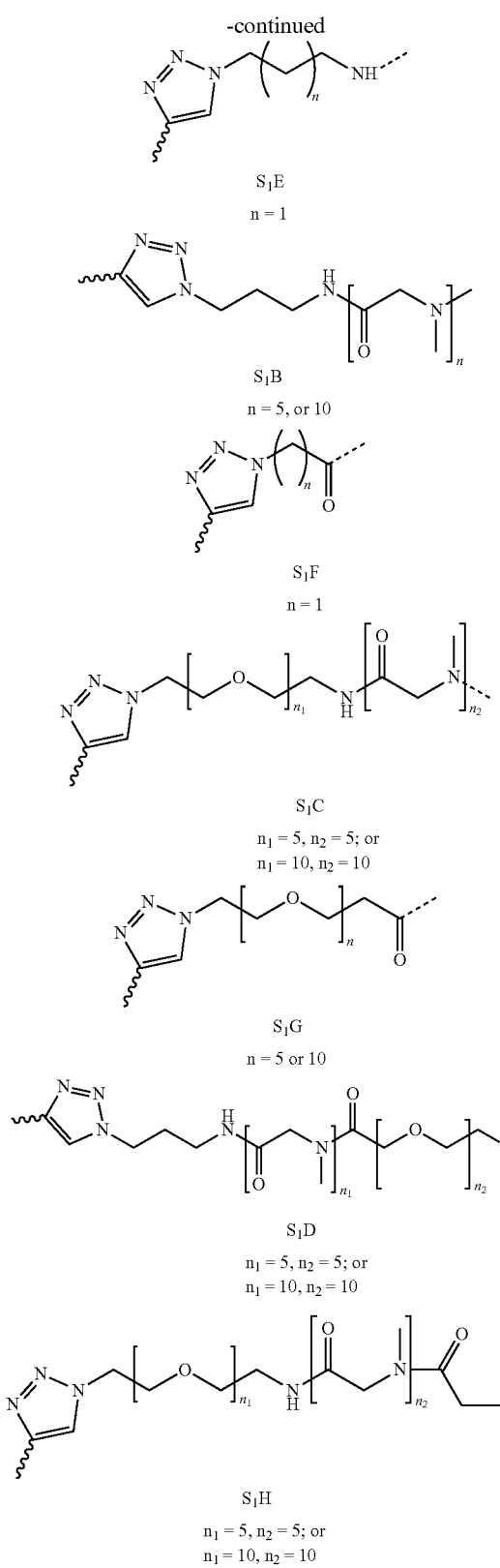

S₁E
n = 1

S₁B
n = 5, or 10

S₁F
n = 1

S₁C
n₁ = 5, n₂ = 5; or
n₁ = 10, n₂ = 10

S₁G
n = 5 or 10

S₁D
n₁ = 5, n₂ = 5; or
n₁ = 10, n₂ = 10

S₁H
n₁ = 5, n₂ = 5; or
n₁ = 10, n₂ = 10 wherein "-----" represents the point of attachment to the CHM group; and

" ~~~ " represents the point of attachment to the Bicycle group.

26. The multimeric binding complex as defined in claim 19, wherein m represents 4 and CHM is a motif of formula (A):

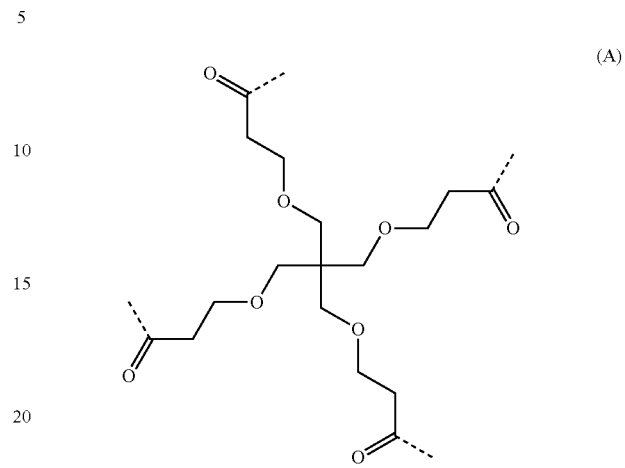

(A)

wherein "-----" represents the point of attachment to each S₁ group.

27. The multimeric binding complex as defined in claim 19, wherein m represents 3 and CHM is selected from a motif of formula (B), (C) or (D):

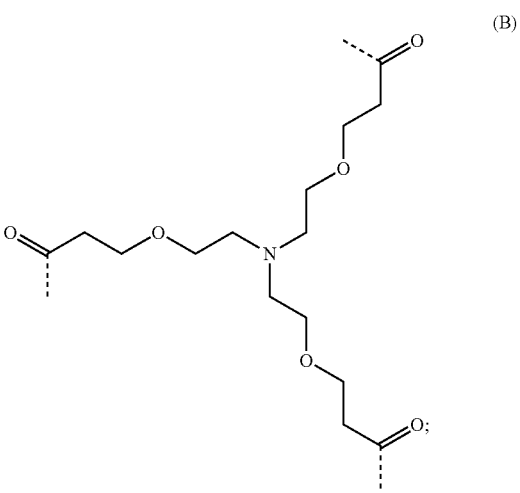

(B)

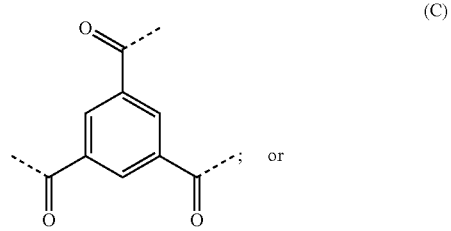

(C)

or

-continued (D)

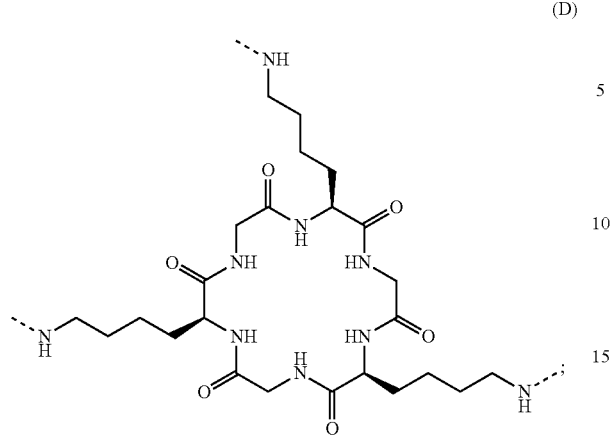

wherein "-----" represents the point of attachment to each $S_1$ group.

28. The multimeric binding complex as defined in claim 19, wherein the spacer ($S_1$) is selected from any one of spacers $S_1A$, $S_1B$, $S_1C$, $S_1D$, $S_1E$, $S_1F$, $S_1G$ and $S_1H$:

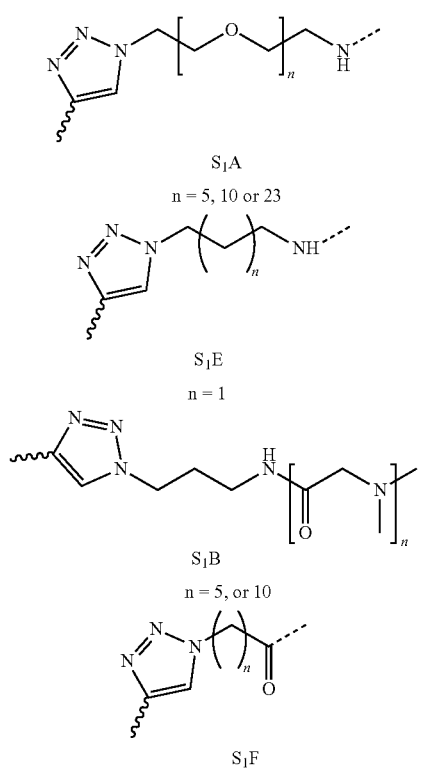

-continued

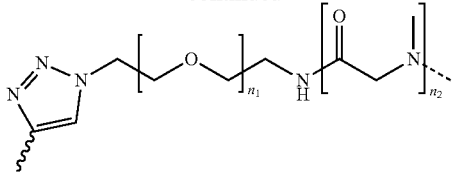

$S_1C$ $n_1 = 5, n_2 = 5$; or
$n_1 = 10, n_2 = 10$

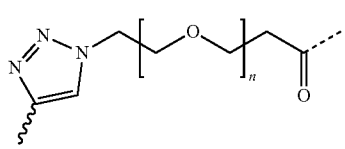

$S_1G$ $n = 5$ or $10$

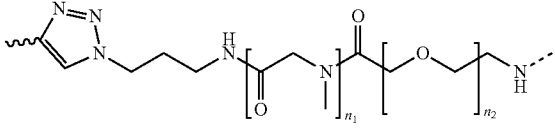

$S_1D$ $n_1 = 5, n_2 = 5$; or
$n_1 = 10, n_2 = 10$

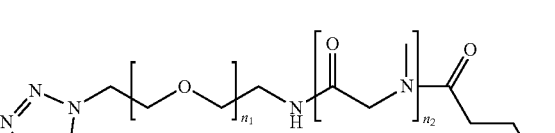

$S_1H$ $n_1 = 5, n_2 = 5$; or
$n_1 = 10, n_2 = 10$ wherein "-----" represents the point of attachment to the CHM group; and
"∿∿∿" represents the point of attachment to the Bicycle group.

29. A drug conjugate comprising the multimeric binding complex as defined in claim 3, conjugated to one or more effector and/or functional groups.

* * * * *

SEQUENCE LISTING

```
<160> NUMBER OF SEQ ID NOS: 69

<210> SEQ ID NO 1
<211> LENGTH: 15
<212> TYPE: PRT
<213> ORGANISM: Artificial
<220> FEATURE:
<223> OTHER INFORMATION: Synthetic peptide

<400> SEQUENCE: 1

Cys Ile Glu Glu Gly Gln Tyr Cys Tyr Arg Asp Met Tyr Met Cys
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic peptide

<400> SEQUENCE: 2

Cys Ile Glu Glu Gly Gln Tyr Cys Tyr Ala Asp Pro Tyr Met Cys
1               5                   10                  15

<210> SEQ ID NO 3
<211> LENGTH: 15
<212> TYPE: PRT
<213> ORGANISM: Artificial
<220> FEATURE:
<223> OTHER INFORMATION: Synthetic peptide

<400> SEQUENCE: 3

Cys Ile Glu Glu Gly Gln Tyr Cys Tyr Ala Asp Pro Tyr Tyr Cys
1               5                   10                  15

<210> SEQ ID NO 4
<211> LENGTH: 15
<212> TYPE: PRT
<213> ORGANISM: Artificial
<220> FEATURE:
```

```
<223> OTHER INFORMATION: Synthetic peptide

<400> SEQUENCE: 4

Cys Ile Glu Glu Gly Gln Tyr Cys Tyr Ser Asp Pro Tyr Tyr Cys
1               5                   10                  15

<210> SEQ ID NO 5
<211> LENGTH: 15
<212> TYPE: PRT
<213> ORGANISM: Artificial
<220> FEATURE:
<223> OTHER INFORMATION: Synthetic peptide

<400> SEQUENCE: 5

Cys Ile Glu Glu Gly Gln Tyr Cys Phe Ala Asp Pro Tyr Met Cys
1               5                   10                  15

<210> SEQ ID NO 6
<211> LENGTH: 15
<212> TYPE: PRT
<213> ORGANISM: Artificial
<220> FEATURE:
<223> OTHER INFORMATION: Synthetic peptide

<400> SEQUENCE: 6

Cys Ile Glu Glu Gly Gln Tyr Cys Tyr Ala Asp His Gln Leu Cys
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic peptide

<400> SEQUENCE: 7

Cys Ile Glu Glu Gly Gln Tyr Cys His Ala Asp Pro Tyr Tyr Cys
1               5                   10                  15

<210> SEQ ID NO 8
<211> LENGTH: 15
<212> TYPE: PRT
<213> ORGANISM: Artificial
<220> FEATURE:
<223> OTHER INFORMATION: Synthetic peptide

<400> SEQUENCE: 8

Cys Ile Glu Glu Gly Gln Tyr Cys His Ala Asp Pro Tyr Phe Cys
1               5                   10                  15

<210> SEQ ID NO 9
<211> LENGTH: 15
<212> TYPE: PRT
<213> ORGANISM: Artificial
<220> FEATURE:
<223> OTHER INFORMATION: Synthetic peptide

<400> SEQUENCE: 9

Cys Ile Glu Glu Gly Gln Tyr Cys Tyr Ala Asp His Tyr Met Cys
1               5                   10                  15

<210> SEQ ID NO 10
<211> LENGTH: 15
<212> TYPE: PRT
<213> ORGANISM: Artificial
<220> FEATURE:
<223> OTHER INFORMATION: Synthetic peptide
```

<400> SEQUENCE: 10

Cys Ile Glu Glu Gly Gln Tyr Cys Tyr Ala Asp Pro Tyr Leu Cys
1               5                   10                  15

<210> SEQ ID NO 11
<211> LENGTH: 15
<212> TYPE: PRT
<213> ORGANISM: Artificial
<220> FEATURE:
<223> OTHER INFORMATION: Synthetic peptide

<400> SEQUENCE: 11

Cys Ile Glu Glu Gly Gln Tyr Cys Tyr Ser Asp Pro Tyr Leu Cys
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthetic peptide

<400> SEQUENCE: 12

Cys Ile Glu Glu Gly Gln Tyr Cys Phe Ala Asp Pro Tyr Leu Cys
1               5                   10                  15

<210> SEQ ID NO 13
<211> LENGTH: 15
<212> TYPE: PRT
<213> ORGANISM: Artificial
<220> FEATURE:
<223> OTHER INFORMATION: Synthetic peptide

<400> SEQUENCE: 13

Cys Ile Glu Glu Gly Gln Tyr Cys His Ala Asp Pro Tyr Met Cys
1               5                   10                  15

<210> SEQ ID NO 14
<211> LENGTH: 15
<212> TYPE: PRT
<213> ORGANISM: Artificial
<220> FEATURE:
<223> OTHER INFORMATION: Synthetic peptide

<400> SEQUENCE: 14

Cys Ile Glu Glu Gly Gln Tyr Cys His Ala Asp Pro Gln Met Cys
1               5                   10                  15

<210> SEQ ID NO 15
<211> LENGTH: 15
<212> TYPE: PRT
<213> ORGANISM: Artificial
<220> FEATURE:
<223> OTHER INFORMATION: Synthetic peptide

<400> SEQUENCE: 15

Cys Asp Ile Gly Pro Pro Tyr Cys Tyr Arg Asp Met Tyr Met Cys
1               5                   10                  15

<210> SEQ ID NO 16
<211> LENGTH: 15
<212> TYPE: PRT
<213> ORGANISM: Artificial
<220> FEATURE:
<223> OTHER INFORMATION: Synthetic peptide

```
<400> SEQUENCE: 16

Cys Asp Ile Gly Pro Pro Tyr Cys Tyr Ala Asp Pro Tyr Met Cys
1               5                   10                  15

<210> SEQ ID NO 17
<211> LENGTH: 14
<212> TYPE: PRT
<213> ORGANISM: Artificial
<220> FEATURE:
<223> OTHER INFORMATION: Synthetic peptide

<400> SEQUENCE: 17

Cys Asp Glu Trp Gly Leu Phe Cys Ile Pro His Ser Asp Cys
1               5                   10

<210> SEQ ID NO 18
<211> LENGTH: 14
<212> TYPE: PRT
<213> ORGANISM: Artificial
<220> FEATURE:
<223> OTHER INFORMATION: Synthetic peptide

<400> SEQUENCE: 18

Cys Asp Glu Trp Gly Leu Tyr Cys Phe Ala His Pro Asp Cys
1               5                   10

<210> SEQ ID NO 19
<211> LENGTH: 15
<212> TYPE: PRT
<213> ORGANISM: Artificial
<220> FEATURE:
<223> OTHER INFORMATION: Synthetic peptide

<400> SEQUENCE: 19

Cys Ile Glu Pro Gly Pro Phe Cys Tyr Ala Asp Pro Tyr Met Cys
1               5                   10                  15

<210> SEQ ID NO 20
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (9)..(10)
<223> OTHER INFORMATION: Xaa is any amino acid residue
<220> FEATURE:
<221> NAME/KEY: Xaa
<222> LOCATION: (12)..(12)
<223> OTHER INFORMATION: Xaa is any amino acid residue
<220> FEATURE:
<221> NAME/KEY: Xaa
<222> LOCATION: (13)..(13)
<223> OTHER INFORMATION: Xaa is Y or Q
<220> FEATURE:
<221> NAME/KEY: Xaa
<222> LOCATION: (14)..(14)
<223> OTHER INFORMATION: Xaa is any amino acid residue

<400> SEQUENCE: 20

Cys Ile Glu Glu Gly Gln Tyr Cys Xaa Xaa Asp Xaa Xaa Xaa Cys
1               5                   10                  15

<210> SEQ ID NO 21
<211> LENGTH: 15
<212> TYPE: PRT
<213> ORGANISM: Artificial
<220> FEATURE:
```

```
<223> OTHER INFORMATION: Synthetic peptide
<220> FEATURE:
<221> NAME/KEY: Xaa
<222> LOCATION: (10)..(10)
<223> OTHER INFORMATION: Xaa is R or A
<220> FEATURE:
<221> NAME/KEY: Xaa
<222> LOCATION: (12)..(12)
<223> OTHER INFORMATION: Xaa is M or P

<400> SEQUENCE: 21

Cys Asp Ile Gly Pro Pro Tyr Cys Tyr Xaa Asp Xaa Tyr Met Cys
1               5                   10                  15

<210> SEQ ID NO 22
<211> LENGTH: 14
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is F or Y
<220> FEATURE:
<221> NAME/KEY: Xaa
<222> LOCATION: (9)..(9)
<223> OTHER INFORMATION: Xaa is I or F
<220> FEATURE:
<221> NAME/KEY: Xaa
<222> LOCATION: (10)..(10)
<223> OTHER INFORMATION: Xaa is P or A
<220> FEATURE:
<221> NAME/KEY: Xaa
<222> LOCATION: (12)..(12)
<223> OTHER INFORMATION: Xaa is S or P

<400> SEQUENCE: 22

Cys Asp Glu Trp Gly Leu Xaa Cys Xaa Xaa His Xaa Asp Cys
1               5                   10

<210> SEQ ID NO 23
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is Nle

<400> SEQUENCE: 23

Cys Ile Glu Glu Gly Gln Tyr Cys Phe Ala Asp Pro Tyr Xaa Cys
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is Nle

<400> SEQUENCE: 24

Cys Ile Lys Glu Gly Gln Tyr Cys Phe Ala Asp Pro Tyr Xaa Cys
1               5                   10                  15
```

```
<210> SEQ ID NO 25
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is Nle

<400> SEQUENCE: 25

Cys Ile Glu Lys Gly Gln Tyr Cys Phe Ala Asp Pro Tyr Xaa Cys
1               5                   10                  15

<210> SEQ ID NO 26
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is D-K
<220> FEATURE:
<221> NAME/KEY: Xaa
<222> LOCATION: (14)..(14)
<223> OTHER INFORMATION: Xaa is Nle

<400> SEQUENCE: 26

Cys Ile Glu Glu Xaa Gln Tyr Cys Phe Ala Asp Pro Tyr Xaa Cys
1               5                   10                  15

<210> SEQ ID NO 27
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is Nle

<400> SEQUENCE: 27

Cys Ile Glu Glu Gly Lys Tyr Cys Phe Ala Asp Pro Tyr Xaa Cys
1               5                   10                  15

<210> SEQ ID NO 28
<211> LENGTH: 15
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (14)..(14)
<223> OTHER INFORMATION: Xaa is Nle

<400> SEQUENCE: 28

Cys Ile Glu Glu Gly Gln Tyr Cys Lys Ala Asp Pro Tyr Xaa Cys
1               5                   10                  15

<210> SEQ ID NO 29
<211> LENGTH: 15
<212> TYPE: PRT
<213> ORGANISM: Artificial
<220> FEATURE:
<223> OTHER INFORMATION: Synthetic peptide
<220> FEATURE:
```

```
<221> NAME/KEY: Xaa
<222> LOCATION: (14)..(14)
<223> OTHER INFORMATION: Xaa is Nle

<400> SEQUENCE: 29

Cys Ile Glu Glu Gly Gln Tyr Cys Phe Ala Asp Lys Tyr Xaa Cys
1               5                   10                  15

<210> SEQ ID NO 30
<211> LENGTH: 15
<212> TYPE: PRT
<213> ORGANISM: Artificial
<220> FEATURE:
<223> OTHER INFORMATION: Synthetic peptide

<400> SEQUENCE: 30

Cys Ile Glu Glu Gly Gln Tyr Cys Phe Ala Asp Pro Tyr Lys Cys
1               5                   10                  15

<210> SEQ ID NO 31
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle

<400> SEQUENCE: 31

Ala Cys Ile Glu Glu Gly Gln Tyr Cys Phe Ala Asp Pro Tyr Xaa Cys
1               5                   10                  15

Ala

<210> SEQ ID NO 32
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle
<220> FEATURE:
<221> NAME/KEY: Xaa
<222> LOCATION: (17)..(17)
<223> OTHER INFORMATION: Xaa is Dap

<400> SEQUENCE: 32

Ala Cys Ile Glu Glu Gly Gln Tyr Cys Phe Ala Asp Pro Tyr Xaa Cys
1               5                   10                  15

Xaa

<210> SEQ ID NO 33
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle

<400> SEQUENCE: 33

Ala Cys Ile Lys Glu Gly Gln Tyr Cys Phe Ala Asp Pro Tyr Xaa Cys
```

```
1               5                   10                  15
Ala

<210> SEQ ID NO 34
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle

<400> SEQUENCE: 34

Ala Cys Ile Glu Lys Gly Gln Tyr Cys Phe Ala Asp Pro Tyr Xaa Cys
1               5                   10                  15
Ala

<210> SEQ ID NO 35
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa is D-K
<220> FEATURE:
<221> NAME/KEY: Xaa
<222> LOCATION: (15)..(15)
<223> OTHER INFORMATION: Xaa is Nle

<400> SEQUENCE: 35

Ala Cys Ile Glu Glu Xaa Gln Tyr Cys Phe Ala Asp Pro Tyr Xaa Cys
1               5                   10                  15
Ala

<210> SEQ ID NO 36
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle

<400> SEQUENCE: 36

Ala Cys Ile Glu Glu Gly Lys Tyr Cys Phe Ala Asp Pro Tyr Xaa Cys
1               5                   10                  15
Ala

<210> SEQ ID NO 37
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle

<400> SEQUENCE: 37
```

Ala Cys Ile Glu Glu Gly Gln Tyr Cys Lys Ala Asp Pro Tyr Xaa Cys
1               5                   10                  15

Ala

<210> SEQ ID NO 38
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle

<400> SEQUENCE: 38

Ala Cys Ile Glu Glu Gly Gln Tyr Cys Phe Ala Asp Lys Tyr Xaa Cys
1               5                   10                  15

Ala

<210> SEQ ID NO 39
<211> LENGTH: 17
<212> TYPE: PRT
<213> ORGANISM: Artificial
<220> FEATURE:
<223> OTHER INFORMATION: Synthetic peptide

<400> SEQUENCE: 39

Ala Cys Ile Glu Glu Gly Gln Tyr Cys Phe Ala Asp Pro Tyr Lys Cys
1               5                   10                  15

Ala

<210> SEQ ID NO 40
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (1)..(1)
<223> OTHER INFORMATION: Xaa is PYA
<220> FEATURE:
<221> NAME/KEY: Xaa
<222> LOCATION: (16)..(16)
<223> OTHER INFORMATION: Xaa is Nle

<400> SEQUENCE: 40

Xaa Ala Cys Ile Glu Glu Gly Gln Tyr Cys Phe Ala Asp Pro Tyr Xaa
1               5                   10                  15

Cys Ala

<210> SEQ ID NO 41
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle
<220> FEATURE:
<221> NAME/KEY: Xaa
<222> LOCATION: (17)..(17)
<223> OTHER INFORMATION: Xaa is Dap(PYA)

<400> SEQUENCE: 41

```
Ala Cys Ile Glu Glu Gly Gln Tyr Cys Phe Ala Asp Pro Tyr Xaa Cys
1               5                   10                  15

Xaa

<210> SEQ ID NO 42
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is K(PYA)
<220> FEATURE:
<221> NAME/KEY: Xaa
<222> LOCATION: (15)..(15)
<223> OTHER INFORMATION: Xaa is Nle

<400> SEQUENCE: 42

Ala Cys Ile Xaa Glu Gly Gln Tyr Cys Phe Ala Asp Pro Tyr Xaa Cys
1               5                   10                  15

Ala

<210> SEQ ID NO 43
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is K(PYA)
<220> FEATURE:
<221> NAME/KEY: Xaa
<222> LOCATION: (15)..(15)
<223> OTHER INFORMATION: Xaa is Nle

<400> SEQUENCE: 43

Ala Cys Ile Glu Xaa Gly Gln Tyr Cys Phe Ala Asp Pro Tyr Xaa Cys
1               5                   10                  15

Ala

<210> SEQ ID NO 44
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa is (D-K)(PYA)
<220> FEATURE:
<221> NAME/KEY: Xaa
<222> LOCATION: (15)..(15)
<223> OTHER INFORMATION: Xaa is Nle

<400> SEQUENCE: 44

Ala Cys Ile Glu Glu Xaa Gln Tyr Cys Phe Ala Asp Pro Tyr Xaa Cys
1               5                   10                  15

Ala

<210> SEQ ID NO 45
<211> LENGTH: 17
<212> TYPE: PRT
```

```
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is K(PYA)
<220> FEATURE:
<221> NAME/KEY: Xaa
<222> LOCATION: (15)..(15)
<223> OTHER INFORMATION: Xaa is Nle

<400> SEQUENCE: 45

Ala Cys Ile Glu Glu Gly Xaa Tyr Cys Phe Ala Asp Pro Tyr Xaa Cys
1               5                   10                  15
Ala

<210> SEQ ID NO 46
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (10)..(10)
<223> OTHER INFORMATION: Xaa is K(PYA)
<220> FEATURE:
<221> NAME/KEY: Xaa
<222> LOCATION: (15)..(15)
<223> OTHER INFORMATION: Xaa is Nle

<400> SEQUENCE: 46

Ala Cys Ile Glu Glu Gly Gln Tyr Cys Xaa Ala Asp Pro Tyr Xaa Cys
1               5                   10                  15
Ala

<210> SEQ ID NO 47
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (13)..(13)
<223> OTHER INFORMATION: Xaa is K(PYA)
<220> FEATURE:
<221> NAME/KEY: Xaa
<222> LOCATION: (15)..(15)
<223> OTHER INFORMATION: Xaa is Nle

<400> SEQUENCE: 47

Ala Cys Ile Glu Glu Gly Gln Tyr Cys Phe Ala Asp Xaa Tyr Xaa Cys
1               5                   10                  15
Ala

<210> SEQ ID NO 48
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is K(PYA)

<400> SEQUENCE: 48
```

Ala Cys Ile Glu Glu Gly Gln Tyr Cys Phe Ala Asp Pro Tyr Xaa Cys
1               5                   10                  15

Ala

<210> SEQ ID NO 49
<211> LENGTH: 18
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (1)..(1)
<223> OTHER INFORMATION: Xaa is BCN
<220> FEATURE:
<221> NAME/KEY: Xaa
<222> LOCATION: (16)..(16)
<223> OTHER INFORMATION: Xaa is Nle

<400> SEQUENCE: 49

Xaa Ala Cys Ile Glu Glu Gly Gln Tyr Cys Phe Ala Asp Pro Tyr Xaa
1               5                   10                  15

Cys Ala

<210> SEQ ID NO 50
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (4)..(4)
<223> OTHER INFORMATION: Xaa is K(BCN)
<220> FEATURE:
<221> NAME/KEY: Xaa
<222> LOCATION: (15)..(15)
<223> OTHER INFORMATION: Xaa is Nle

<400> SEQUENCE: 50

Ala Cys Ile Xaa Glu Gly Gln Tyr Cys Phe Ala Asp Pro Tyr Xaa Cys
1               5                   10                  15

Ala

<210> SEQ ID NO 51
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is K(BCN)
<220> FEATURE:
<221> NAME/KEY: Xaa
<222> LOCATION: (15)..(15)
<223> OTHER INFORMATION: Xaa is Nle

<400> SEQUENCE: 51

Ala Cys Ile Glu Xaa Gly Gln Tyr Cys Phe Ala Asp Pro Tyr Xaa Cys
1               5                   10                  15

Ala

<210> SEQ ID NO 52
<211> LENGTH: 17
<212> TYPE: PRT
<213> ORGANISM: Artificial

```
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa is (D-K)(BCN)
<220> FEATURE:
<221> NAME/KEY: Xaa
<222> LOCATION: (15)..(15)
<223> OTHER INFORMATION: Xaa is Nle

<400> SEQUENCE: 52

Ala Cys Ile Glu Glu Xaa Gln Tyr Cys Phe Ala Asp Pro Tyr Xaa Cys
1               5                   10                  15

Ala

<210> SEQ ID NO 53
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (7)..(7)
<223> OTHER INFORMATION: Xaa is K(BCN)
<220> FEATURE:
<221> NAME/KEY: Xaa
<222> LOCATION: (15)..(15)
<223> OTHER INFORMATION: Xaa is Nle

<400> SEQUENCE: 53

Ala Cys Ile Glu Glu Gly Xaa Tyr Cys Phe Ala Asp Pro Tyr Xaa Cys
1               5                   10                  15

Ala

<210> SEQ ID NO 54
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (10)..(10)
<223> OTHER INFORMATION: Xaa is K(BCN)
<220> FEATURE:
<221> NAME/KEY: Xaa
<222> LOCATION: (15)..(15)
<223> OTHER INFORMATION: Xaa is Nle

<400> SEQUENCE: 54

Ala Cys Ile Glu Glu Gly Gln Tyr Cys Xaa Ala Asp Pro Tyr Xaa Cys
1               5                   10                  15

Ala

<210> SEQ ID NO 55
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is K(BCN)

<400> SEQUENCE: 55

Ala Cys Ile Glu Glu Gly Gln Tyr Cys Phe Ala Asp Pro Tyr Xaa Cys
```

<210> SEQ ID NO 56
<211> LENGTH: 17
<212> TYPE: PRT
<213> ORGANISM: Artificial
<220> FEATURE:
<223> OTHER INFORMATION: Synthetic peptide

<400> SEQUENCE: 56

Ala Cys Ile Glu Glu Gly Gln Tyr Cys Phe Ala Asp Pro Tyr Met Cys
1               5                   10                  15
Ala

<210> SEQ ID NO 57
<211> LENGTH: 6
<212> TYPE: PRT
<213> ORGANISM: Artificial
<220> FEATURE:
<223> OTHER INFORMATION: Synthetic peptide

<400> SEQUENCE: 57

Lys Gly Lys Gly Lys Gly
1               5

<210> SEQ ID NO 58
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle

<400> SEQUENCE: 58

Ala Cys Ile Glu Glu Gly Gln Tyr Cys Phe Ala Asp Pro Tyr Xaa Cys
1               5                   10                  15
Ala

<210> SEQ ID NO 59
<211> LENGTH: 16
<212> TYPE: PRT
<213> ORGANISM: Artificial
<220> FEATURE:
<223> OTHER INFORMATION: Synthetic Peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 59

Cys Xaa Pro Lys Ala Pro Tyr Cys Phe Ala Asp Pro Tyr Xaa Cys Ala
1               5                   10                  15

<210> SEQ ID NO 60
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (14)..(14)
<223> OTHER INFORMATION: Xaa is Nle

<400> SEQUENCE: 60

Cys Xaa Pro Glu Lys Pro Tyr Cys Phe Ala Asp Pro Tyr Xaa Cys Ala
1               5                   10                  15

<210> SEQ ID NO 61
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle

<400> SEQUENCE: 61

Ala Cys Ile Glu Lys Gly Gln Tyr Cys Phe Ala Asp Pro Tyr Xaa Cys
1               5                   10                  15

Ala

<210> SEQ ID NO 62
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle

<400> SEQUENCE: 62

Ala Cys Ile Glu Lys Gly Gln Tyr Cys Phe Ala Asp Pro Tyr Xaa Cys
1               5                   10                  15

Ala

<210> SEQ ID NO 63
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (15)..(15)
<223> OTHER INFORMATION: Xaa is Nle

<400> SEQUENCE: 63

Ala Cys Ile Glu Glu Lys Gln Tyr Cys Phe Ala Asp Pro Tyr Xaa Cys
1               5                   10                  15

Ala

<210> SEQ ID NO 64
<211> LENGTH: 18
<212> TYPE: PRT
<213> ORGANISM: Artificial
<220> FEATURE:
<223> OTHER INFORMATION: Synthetic peptide
<220> FEATURE:

```
<221> NAME/KEY: Xaa
<222> LOCATION: (1)..(1)
<223> OTHER INFORMATION: Xaa is PYA
<220> FEATURE:
<221> NAME/KEY: Xaa
<222> LOCATION: (16)..(16)
<223> OTHER INFORMATION: Xaa is Nle

<400> SEQUENCE: 64

Xaa Ala Cys Ile Glu Glu Gly Gln Tyr Cys Phe Ala Asp Pro Tyr Xaa
1               5                   10                  15

Cys Ala

<210> SEQ ID NO 65
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (4)..(4)
<223> OTHER INFORMATION: Xaa is K(PYA)
<220> FEATURE:
<221> NAME/KEY: Xaa
<222> LOCATION: (14)..(14)
<223> OTHER INFORMATION: Xaa is Nle

<400> SEQUENCE: 65

Cys Xaa Pro Xaa Ala Pro Tyr Cys Phe Ala Asp Pro Tyr Xaa Cys Ala
1               5                   10                  15

<210> SEQ ID NO 66
<211> LENGTH: 16
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (2)..(2)
<223> OTHER INFORMATION: Xaa is tBuAla
<220> FEATURE:
<221> NAME/KEY: Xaa
<222> LOCATION: (5)..(5)
<223> OTHER INFORMATION: Xaa is D-Lys(PYA)
<220> FEATURE:
<221> NAME/KEY: Xaa
<222> LOCATION: (14)..(14)
<223> OTHER INFORMATION: Xaa is Nle

<400> SEQUENCE: 66

Cys Xaa Pro Glu Xaa Pro Tyr Cys Phe Ala Asp Pro Tyr Xaa Cys Ala
1               5                   10                  15

<210> SEQ ID NO 67
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is d-K(PYA)
<220> FEATURE:
<221> NAME/KEY: Xaa
<222> LOCATION: (15)..(15)
```

```
<223> OTHER INFORMATION: Xaa is Nle

<400> SEQUENCE: 67

Ala Cys Ile Glu Xaa Gly Gln Tyr Cys Phe Ala Asp Pro Tyr Xaa Cys
 1               5                  10                  15
Ala

<210> SEQ ID NO 68
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (5)..(5)
<223> OTHER INFORMATION: Xaa is K(PYA)
<220> FEATURE:
<221> NAME/KEY: Xaa
<222> LOCATION: (15)..(15)
<223> OTHER INFORMATION: Xaa is Nle

<400> SEQUENCE: 68

Ala Cys Ile Glu Xaa Gly Gln Tyr Cys Phe Ala Asp Pro Tyr Xaa Cys
 1               5                  10                  15
Ala

<210> SEQ ID NO 69
<211> LENGTH: 17
<212> TYPE: PRT
<213> ORGANISM: Artificial
<220> FEATURE:
<223> OTHER INFORMATION: Synthetic peptide
<220> FEATURE:
<221> NAME/KEY: Xaa
<222> LOCATION: (6)..(6)
<223> OTHER INFORMATION: Xaa is K(PYA)
<220> FEATURE:
<221> NAME/KEY: Xaa
<222> LOCATION: (15)..(15)
<223> OTHER INFORMATION: Xaa is Nle

<400> SEQUENCE: 69

Ala Cys Ile Glu Glu Xaa Gln Tyr Cys Phe Ala Asp Pro Tyr Xaa Cys
 1               5                  10                  15
Ala
```